US012686858B2

(12) United States Patent　　　　　(10) Patent No.:　US 12,686,858 B2
Peng et al.　　　　　　　　　　　　　　(45) **Date of Patent:　*Jul. 21, 2026**

(54) RECOMBINANT HUMAN SIALIDASES, SIALIDASE FUSION PROTEINS, AND METHODS OF USING THE SAME

(71) Applicant: Palleon Pharmaceuticals Inc., Waltham, MA (US)

(72) Inventors: Li Peng, Lexington, MA (US); Lizhi Cao, Stoneham, MA (US); Lihui Xu, Chestnut Hill, MA (US)

(73) Assignee: Palleon Pharmaceuticals Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/597,204

(22) Filed: Mar. 6, 2024

(65) Prior Publication Data

US 2024/0344046 A1　　Oct. 17, 2024

Related U.S. Application Data

(63) Continuation of application No. 16/958,914, filed as application No. PCT/US2019/012207 on Jan. 3, 2019, now Pat. No. 11,965,188.

(60) Provisional application No. 62/755,279, filed on Nov. 2, 2018, provisional application No. 62/613,363, filed on Jan. 3, 2018.

(51) Int. Cl.
| | |
|---|---|
| *C12N 9/24* | (2006.01) |
| *A61K 47/68* | (2017.01) |
| *A61P 35/00* | (2006.01) |
| *C07K 16/28* | (2006.01) |
| *C07K 16/32* | (2006.01) |
| *A61K 39/00* | (2006.01) |

(52) U.S. Cl.
CPC ........ *C12N 9/2402* (2013.01); *A61K 47/6815* (2017.08); *A61K 47/6855* (2017.08); *A61P 35/00* (2018.01); *C07K 16/2863* (2013.01); *C07K 16/32* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 4,510,129 A | 4/1985 | Knop et al. | |
| 4,975,278 A | 12/1990 | Senter et al. | |
| 6,877,169 B2 | 4/2005 | Acquaviva | |
| 6,977,169 B2 | 12/2005 | Kline | |
| 7,645,448 B2 | 1/2010 | Fang et al. | |
| 7,745,391 B2 * | 6/2010 | Mintz ..................... | A61P 37/00 |
| | | | 514/19.3 |
| 7,807,174 B2 | 10/2010 | Fang et al. | |
| 8,012,733 B2 | 9/2011 | Van Dijk et al. | |
| 8,084,036 B2 | 12/2011 | Yu et al. | |
| 8,114,412 B2 | 2/2012 | Chuenkova et al. | |
| 8,187,591 B2 | 5/2012 | Marth et al. | |
| 8,217,149 B2 | 7/2012 | Irving et al. | |
| 8,329,195 B2 | 12/2012 | Briles et al. | |
| 8,398,971 B2 | 3/2013 | Fang et al. | |
| 8,512,710 B2 | 8/2013 | Fang et al. | |
| 8,623,419 B2 | 1/2014 | Malakhov et al. | |
| 8,722,869 B2 | 5/2014 | Fang et al. | |
| 8,999,705 B2 | 4/2015 | Mills et al. | |
| 9,132,179 B2 | 9/2015 | Van Ginkel et al. | |
| 9,212,353 B2 | 12/2015 | Fang et al. | |
| 9,764,007 B2 | 9/2017 | Fang et al. | |
| 10,081,801 B2 | 9/2018 | Mikkelsen et al. | |
| 10,280,191 B2 | 5/2019 | Deamer et al. | |
| 10,300,116 B2 | 5/2019 | Moss | |
| 10,328,128 B2 | 6/2019 | Moss | |
| 10,351,828 B2 | 7/2019 | Hawley | |
| 10,428,318 B2 | 10/2019 | Vogel et al. | |
| 10,525,109 B2 | 1/2020 | Fang et al. | |
| 10,918,736 B2 | 2/2021 | Kim et al. | |
| 10,940,185 B2 | 3/2021 | Yasukawa et al. | |
| 11,459,398 B2 | 10/2022 | Woods et al. | |
| 11,965,188 B2 | 4/2024 | Peng et al. | |
| 2003/0219433 A1 | 11/2003 | Hansen et al. | |
| 2007/0231333 A1 | 10/2007 | Boghaert et al. | |
| 2011/0135570 A1 | 6/2011 | Janatpour et al. | |

(Continued)

FOREIGN PATENT DOCUMENTS

| | | |
|---|---|---|
| CN | 111763259 B | 12/2020 |
| WO | WO-1994/026908 A1 | 11/1994 |

(Continued)

OTHER PUBLICATIONS

Shevchenko et al., Russian Journal of Bioorganic Chemistry, (Jul. 2011) vol. 37, No. 4, pp. 421-427.*
"Trastuzumab Product Approval Information—Licensing Action Sep. 25, 1998". U.S. Food and Drug Administration (FDA). Dec. 18, 2015. Archived from the original on Jan. 28, 2017. Retrieved Jun. 7, 2021 (Year: 1998).
Albohy et al. (2010) "Insight into substrate recognition and catalysis by the human neuraminidase 3 (NEU3) through molecular modeling and site-directed mutagenesis," Glycobiology 20(9): 1127-1138.
Alley et al. (1977) "Effectiveness of Neuraminidase in Experimental Immunotherapy of Two Murine Pulmonary Carcinomas," Cancer Research, 37: 95-101.

(Continued)

*Primary Examiner* — Richard G Hutson
(74) *Attorney, Agent, or Firm* — Goodwin Procter LLP

(57) ABSTRACT

The invention relates generally to recombinant human sialidases and recombinant sialidase fusion proteins, wherein the sialidase optionally contains one or more mutations compared to wild-type human sialidase, e.g., a substitution, deletion, or addition of at least one amino acid. The invention also provides antibody conjugates including a sialidase and an antibody or a portion thereof. The invention further relates to methods of using the sialidase fusion proteins or antibody conjugates for treating cancer.

20 Claims, 34 Drawing Sheets

Specification includes a Sequence Listing.

(56) References Cited

U.S. PATENT DOCUMENTS

| | | |
|---|---|---|
| 2011/0142912 A1 | 6/2011 | Moser et al. |
| 2011/0171132 A1 | 7/2011 | Fang et al. |
| 2012/0213705 A1 | 8/2012 | Dimasi et al. |
| 2013/0189293 A1 | 7/2013 | Yang et al. |
| 2013/0287802 A1 | 10/2013 | Govindappa et al. |
| 2014/0271462 A1 | 9/2014 | Ho et al. |
| 2015/0152187 A1 | 6/2015 | Sun et al. |
| 2015/0355184 A1 | 12/2015 | Pierce et al. |
| 2016/0076013 A1 | 3/2016 | Mikkelsen et al. |
| 2016/0184407 A1 | 6/2016 | Fang et al. |
| 2017/0119859 A1 | 5/2017 | Moss |
| 2017/0165334 A1 | 6/2017 | Wang |
| 2017/0354720 A1 | 12/2017 | Fang et al. |
| 2018/0200345 A1 | 7/2018 | Schmitt |
| 2018/0271997 A1 | 9/2018 | Wang |
| 2019/0037899 A1 | 2/2019 | Juge et al. |
| 2019/0125859 A1 | 5/2019 | Palese et al. |
| 2019/0177416 A1 | 6/2019 | Ting et al. |
| 2019/0192691 A1 | 6/2019 | Barrett et al. |
| 2019/0211099 A1 | 7/2019 | Burchell et al. |
| 2019/0247460 A1 | 8/2019 | Connaris et al. |
| 2019/0248919 A1 | 8/2019 | Woods et al. |
| 2019/0352420 A1 | 11/2019 | Hofmann et al. |
| 2020/0164049 A1 | 5/2020 | Moss |
| 2020/0222511 A1 | 7/2020 | Moss |
| 2020/0230253 A1 | 7/2020 | Kim et al. |
| 2020/0231677 A1 | 7/2020 | West et al. |
| 2020/0332009 A1 | 10/2020 | Miao et al. |
| 2020/0339968 A1 | 10/2020 | Peng et al. |
| 2020/0369765 A1 | 11/2020 | Cornen et al. |
| 2020/0386770 A1 | 12/2020 | Lou et al. |
| 2022/0105179 A1 | 4/2022 | Anthony et al. |
| 2022/0169724 A1 | 6/2022 | Woods et al. |
| 2022/0356457 A1 | 11/2022 | Peng et al. |
| 2022/0362351 A1 | 11/2022 | Peng et al. |
| 2022/0372458 A1 | 11/2022 | Peng et al. |
| 2022/0380742 A1 | 12/2022 | Peng et al. |
| 2022/0387616 A1 | 12/2022 | Peng et al. |
| 2023/0265406 A1 | 8/2023 | Peng et al. |
| 2023/0287140 A1 | 9/2023 | Woods et al. |
| 2024/0059773 A1 | 2/2024 | Peng et al. |
| 2024/0059792 A1 | 2/2024 | Peng et al. |
| 2024/0067729 A1 | 2/2024 | Peng et al. |
| 2025/0049846 A1 | 2/2025 | Alkhateeb et al. |

FOREIGN PATENT DOCUMENTS

| | | |
|---|---|---|
| WO | WO-2006/127966 A2 | 11/2006 |
| WO | WO-2007/108464 A1 | 9/2007 |
| WO | WO-2007/109376 A2 | 9/2007 |
| WO | WO-2007/115467 A1 | 10/2007 |
| WO | WO-2009/049234 A2 | 4/2009 |
| WO | WO-2009/049284 A2 | 4/2009 |
| WO | WO-2010/056765 A2 | 5/2010 |
| WO | WO-2013/137920 A1 | 9/2013 |
| WO | WO-2014/037785 A2 | 3/2014 |
| WO | WO-2014/113641 A1 | 7/2014 |
| WO | WO-2014/140103 A2 | 9/2014 |
| WO | WO-2016/038064 A1 | 3/2016 |
| WO | WO-2016/056913 A1 | 4/2016 |
| WO | WO-2016/102436 A1 | 6/2016 |
| WO | WO-2017/100467 A2 | 6/2017 |
| WO | WO-2017/100725 A1 | 6/2017 |
| WO | WO-2017/123745 A1 | 7/2017 |
| WO | WO-2018/006034 A1 | 1/2018 |
| WO | WO-2018/188672 A1 | 10/2018 |
| WO | WO-2018/215657 A1 | 11/2018 |
| WO | WO-2018/231661 A1 | 12/2018 |
| WO | WO-2018/237201 A1 | 12/2018 |
| WO | WO-2019/086554 A1 | 5/2019 |
| WO | WO-2019/136167 A1 | 7/2019 |
| WO | WO-2020/018996 A2 | 1/2020 |
| WO | WO-2020/142727 A1 | 7/2020 |
| WO | WO-2020/172072 A1 | 8/2020 |
| WO | WO-2020/223550 A1 | 11/2020 |
| WO | WO-2020/263830 A1 | 12/2020 |
| WO | WO-2021/003463 A1 | 1/2021 |
| WO | WO-2021/003464 A1 | 1/2021 |
| WO | WO-2021/003465 A1 | 1/2021 |
| WO | WO-2021/003468 A2 | 1/2021 |
| WO | WO-2021/003469 A2 | 1/2021 |
| WO | WO-2022/006492 A2 | 1/2022 |
| WO | WO-2022/150507 A1 | 7/2022 |
| WO | WO-2022/150516 A1 | 7/2022 |
| WO | WO-2022/150521 A1 | 7/2022 |

OTHER PUBLICATIONS

Basler et al. (1999) "Mutation of Neuraminidase Cysteine Residues Yields Temperature-Sensitive Influenza Viruses," Journal of Virology 73(10):8095-8103.

Bhat et al. (2014) "The next step in homogenous bioconjugate development: Optimizing payload placement and conjugate composition," Bio Process International, downloaded from https://bioprocessintl.com/manufacturing/monoclonal-antibodies/ next-step-homogenous-bioconjugate-development-optimizing-payload-placement-conjugate-composition/ on Jun. 7, 2021.

Bosch et al. (2013) "Drugs Targeting B-Cells in Autoimmune Diseases," Springer Science & Business Media. pp. 1-4.

Chavas et al. (2005) "Crystal Structure of the Human Cytosolic Sialidase Neu2," J. Bio. Chem., 280(1): 469-475.

Chu et al. (2006) "Lineage Determination of CD20-B-Cell Neoplasms: An Immunohistochemical Study," Am. J. Clin. Pathol. 126:534-544.

Database accession No. AWP96859, "Cricetulus griseus cytoplasmic sialidase (Neu2) protein, Seq Id No: 5.", XP093091928, retrieved from EBI accession No. GSP:AWP96859, Jan. 19, 2012 (Jan. 19, 2012).

Database accession No. BG076176, Sep. 5, 2019 (Sep. 5, 2019) "Human neu2 protein mutant M1D/V6Y/I187K/C332A," XP093052179, retrieved from EBI accession No. GSP:BG076176 (1 page).

Database accession No. BHZ60027, Sep. 3, 2020 (Sep. 3, 2020) "Human Neu2 mutant/iggl Fc domain fusion protein, SEQ 149," XP093051773, retrieved from EBI accession No. gsp:bhz60027 (1 page).

Database Geneseq [Online] Feb. 8, 2018 (Feb. 8, 2018), "Human NEU2 protein, Seq Id 8.", XP093052599, retrieved from EBI accession No. GSP:BES28168, Database accession No. BES28168 (1 page).

Database Geneseq [Online], Sep. 1, 2011, "Human NEU4 sialidase protein, Seq Id No. 9 #2.", XP093053029, retrieved from EBI accession No. GSP:AZK51676, Database accession No. AZK51676 (1 pages).

Database GenPept [Online] Jan. 19, 2018 (Jan. 19, 2018), "Sialidase-2 [Pteropus vampyrus] —Protein—NCBI", XP093053007, retrieved from EBI accession No. XP_011379176 (2 pages).

Database UniProt [Online] Dec. 11, 2019 (Dec. 11, 2019), XP093179690, Neuraminidase 2, Database accession No. A0A0D9R225 (2 pages).

Database UniProt [Online] Dec. 14, 2011 (Dec. 14, 2011), "RecName: Full=Exo-alpha-sialidase [ECO:0000256\ARBA:ARBA00012733}; EC=3.2.1.18 [ECO:0000256|ARBA:ARBA00012733}; ", XP002804582, retrieved from EBI accession No. UniProt:G5BXG6 (1 page).

Database UniProt [Online] Jan. 9, 2013 (Jan. 9, 2013), "RecName: Full=Exo-alpha-sialidase {ECO:0000256!ARBA:ARBA00012733}; EC=3.2.1.18 {ECO:0000256 !ARBA:ARBA00012733};", XP002805932, retrieved from EBI accession No. UniProt:K7GDB1 (2 pages).

Database UniProtKB/TrEMBL [Online] May 8, 2018 (May 8, 2018), "Exo-alpha-sialidase Neu2 from Pan paniscus (Pygmy chimpanzee) (Bonobo)", retrieved from EBI accession No. A0A2R9BJ98, Database accession No. A0A2R9BJ98_PANPA (2 pages).

Fuster et al. (2005) "The sweet and sour of cancer: glycans as novel therapeutic targets," Nat. Rev. Cancer 5(7): 526-42.

(56)            References Cited

OTHER PUBLICATIONS

Gray et al. (2020) "Targeted glycan degradation potentiates the anticancer immune response in vivo," Nat. Chem. Biol., 16(12): 1376-1384.

Hausmann et al. (1997) "Biosynthesis, intracellular transport and enzymatic activity of an avian influenza A virus neuraminidase : role of unpaired cysteines and individual oligosaccharides," Journal of General Virology 78: 3233-3245.

He et al. (2004) "Alanine-scanning n1utagenesis of the (3-sheet region of phage T 4 1 ysozyn1e suggests that tertiary context has a don1inant effect on f3-sheet forn1ation," Protein Science, 13: 2716-2724.

Hudak et al. (2014) "Glycocalyx engineering reveals a Siglec-based mechanism for NK cell immunoevasion," Nat. Chem. Biol. 10: 69-75.

International Search Report for International Application No. PCT/US2017/040411, mailed Sep. 21, 2017 (4 pages).

International Search Report for International Application No. PCT/US2019/012207, mailed Apr. 10, 2019 (9 pages).

International Search Report for International Application No. PCT/US2020/040814, mailed Dec. 14, 2020 (5 pages).

International Search Report for International Application No. PCT/US2020/040815, mailed Dec. 15, 2020 (5 pages).

International Search Report for International Application No. PCT/US2020/040816, mailed Dec. 14, 2020 (5 pages).

International Search Report for International Application No. PCT/US2020/040827, mailed Dec. 18, 2020 (5 pages).

International Search Report for International Application No. PCT/US2020/040828, mailed Dec. 14, 2020 (5 pages).

International Search Report for International Application No. PCT/US2021/040240, mailed Jan. 6, 2022 (6 pages).

International Search Report for International Application No. PCT/US2022/011487, mailed May 3, 2022 (4 pages).

International Search Report for International Application No. PCT/US2022/011499, mailed Apr. 28, 2022 (4 pages).

International Search Report for International Application No. PCT/US2022/011504, mailed Jun. 15, 2022 (5 pages).

Ito et al. (2011) "Cysteine-to-serine shuffling using aexpression system improves protein secretion: case of a nonglycosylated mutant of miraculin, a taste-modifying protein," Biotechnology Letters 33(1): 103-107.

Itoh et al. (2002) "Novel missense mutations in the human lysosomal sialidase gene in sialidosis patients and prediction of structural alterations of mutant enzymes," J. Hum. Genet. 47(1): 29-37.

Jandus et al. (2014) "Interactions between Siglec-7/9 receptors and ligands influence NK cell-dependent tumor immunosurveillance," J. Clin. Invest. 124(4): 1810-1820.

Jonson et al. (2015) "Systematic Aß Analysis in *Drosophila* Reveals High Toxicity for the 1-42, 3-42 and 11-42 Peptides, and Emphasizes N- and C-Terminal Residues," PLoS One 10(7): e0133272.

Julien S. et al. (2015) "Sialic Acid and Cancer," Glycoscience: Biology and Medicine 1419-1424.

Jung et al. (2006) "The complete mitochondrial genome of the Korean soft-shelled turtle *Pelodiscus sinensis* (Testudines, Trionychidae)," DNA Sequence, 17(6): 471-483.

Kim et al. (2011) "Features and applications of bacterial sialidases," Appl. Microbiol. Biotechnol., 91: 1-15.

Kim et al. (2011) "Genome sequencing reveals insights into physiology and longevity of the naked mole rat," Nature 479, 223-227.

Kontermann (2011) "Strategies for extended serum half-life of protein therapeutics," Curr Opin Biotechnol, 22(6): 868-876.

Kruse et al. (1998) "Effect of cysteine modifications on the activity of the 'small' Clostridium perfringens sialidase," Glycoconjugate Journal 15: 769-775.

Läubli et al. (2014) "Engagement of myelomonocytic Siglecs by tumor-associated ligands modulates the innate immune response to cancer," Proc. Natl. Acad. Sci USA 111(39): 14211- 14216.

Lukong et al. (2000) "Characterization of the sialidase molecular defects in sialidosis patients suggests the structural organization of the lysosomal multienzyme complex," Human Molecular Genetics 9(7): 1075-1085.

Malakhov et al. (2006) "Sialidase Fusion Protein as a Novel Broad-Spectrum Inhibitor of Influenza Virus Infection," Antimicrobial Agents and Chemotherapy 50(4): 1470-1479.

McCombs et al. (2016) "Enhanced Cross-Linking of Diazirine-Modified Sialylated Glycoproteins Enabled through Profiling of Sialidase Specificities," ACS Chem. Biol., 11: 185-192.

Mitri et al. (2012) "The HER2 Receptor in Breast Cancer: Pathophysiology, Clinical Use, and New Advances in Therapy,"Chemotherapy Research and Practice vol. 2012, Article ID 743193, 7 pages.

Miyagi et al. (2012) "Mammalian sialidases: Physiological and pathological roles in cellular functions," Glycobiology 22(7): 880-896.

Monti et al. (1999) "Expression of a novel human sialidase encoded by the NEU2 gene," Glycobiology 9(12):1313-1321.

Monti et al. (2010) "Sialidases in vertebrates: a family of enzymes tailored for several cell functions," Adv Carbohydr Chemi Biochem, 64: 403-479.

Ngo et al. (1994) "Computational Complexity, Protein Structure Prediction, and the Levinthal Paradox," The Protein Folding Problem and Tertiary Structure Prediction, Merz et al. (ed.), Birkhauser, Boston, MA, pp. 433 and 492-495.

Notification of Transmittal of the International Search Report and the Written Opinion of the International Searching Authority issued in PCT/US2022/011487, mailed May 3, 2022.

Paris et al. (2001) "Probing molecular function of trypanosomal sialidases: single point mutations can change substrate specificity and increase hydrolytic activity," Glycobiology 11(4): 305-311.

PDBe entry 1SNT (Nov. 2004) (3 pages).

Predicted: sialidase-2 [Ceratotherium simum simum]; NCB! Reference Sequence: XP_004427750.1, Nov. 27, 2015, retreaved from <www.ncbi.nlm.nih.gov/protein/XP_004427750> on Jun. 27, 2024 (2 pages).

Rabuka et al. (2012) "Site-specific chemical protein conjugation using genetically encoded aldehyde tags," Nat. Protoc., 7(6): 1052-1067.

Rahman et al. (2013) "Inhibitory effects and specificity of synthetic sialyldendrimers toward recombinant human cytosolic sialidase 2 (NEU2)," Glycobiology, 23(4): 495-504.

Seid et al. (2017) "Cysteine mutagenesis improves the production without abrogating antigenicity of a recombinant protein vaccine candidate for human chagas disease," Human Vaccines & Immunotherapeutics 13(3): 621-633.

Stanczak et al. (2018) "Self-associated molecular patterns mediate cancer immune evasion by engaging Siglec on T cells," J. Clin. Invest., 128(11): 4912-4923.

Stanczak et al. (2018) "Targeting the sialoglycan/Siglec pathway in combination with checkpoint inhibitors for cancer immunotherapy," Journal of ImmunoTherapy of Cancer, 6(Suppl 1): 115 (1 page).

Stanczak et al. (2018) "Targeting tumor sialylation in combination with checkpoint inhibitors for cancer immunotherapy," Retrieved from the Internet: URL:https://palleonpharma.com/wp-content/uploads/SITC_2018_2.pdf (1 page).

Strohl (2015) "Fusion Proteins for Half-Life Extension of Biologics as a Strategy to Make Biobetters," BioDrugs 29(4): 215-239.

Tringali et al. (2007) "Expression of sialidase Neu2 in leukemic K562 cells induces apoptosis by impairing Bcr-Abl/Src kinases signaling," J. Biol. Chem., 282(19): 14364-14372.

Tseng et al. (2007) "Desialylation of human cancer cells leading apoptosis by treatment with purified and overexpressed nanl cloned from Clostridium perfringens ATCC 10543," Enzyme and Microbial Technology, 41(1-2): 5-12.

UniProt entry QY3R4—NEUR2_HUMAN (Release Mar. 2023) (12 pages).

Vahidi et al. (2018) "Reversible inhibition of the ClpP protease via an N-terminal conformational switch," Proc. Natl. Acad. Sci. USA 115(28): E6447-E6456.

Van Rooijen et al. (1992) "Monoclonal antibody mediated targeting of enzymes—A comparative study using the mouse spleen as a model system," J. Immunol. Methods, 151(1-2): 149-155.

(56)        References Cited

OTHER PUBLICATIONS

Written Opinion for International Application No. PCT/US2017/040411, mailed Sep. 21, 2017 (6 pages).
Written Opinion for International Application No. PCT/US2019/012207, mailed Apr. 10, 2019 (7 pages).
Written Opinion for International Application No. PCT/US2020/040814, mailed Dec. 14, 2020 (6 pages).
Written Opinion for International Application No. PCT/US2020/040815, mailed Dec. 15, 2020 (6 pages).
Written Opinion for International Application No. PCT/US2020/040816, mailed Dec. 14, 2020 (6 pages).
Written Opinion for International Application No. PCT/US2020/040827, mailed Dec. 18, 2020 (6 pages).
Written Opinion for International Application No. PCT/US2020/040828, mailed Dec. 14, 2020 (6 pages).
Written Opinion for International Application No. PCT/US2021/040240, mailed Jan. 6, 2022 (9 pages).
Written Opinion for International Application No. PCT/US2022/011487, mailed May 3, 2022 (4 pages).
Written Opinion for International Application No. PCT/US2022/011499, mailed Apr. 28, 2022 (4 pages).
Written Opinion for International Application No. PCT/US2022/011504, mailed Jun. 15, 2022 (7 pages).
Xiao et al. (2016) "Precision glycocalyx editing as a strategy for cancer immunotherapy," Proc. Natl. Acad. Sci. USA 113(37): 10304-9.
Yang et al. (2022) "Enhancing the anti-tumor efficacy of Bispecific T cell engagers via cell surface glycocalyx editing," bioRxiv, posted May 23, 2022; https://doi.org/10.1101/2022.05.22.492978 (23 pages).
4kaq—Rituximab Fab light chain. Protein Data Bank in Europe. Retrieved on Sep. 11, 2025 from <URL:https://www.ebi.ac.uk/pdbe/ entry/pdb/4kaq/protein/1 > (2 pages).

Bedouelle et al. (2006) "Diversity and junction residues as hotspots of binding energy in an antibody neutralizing the dengue virus," FEBS Journal, 273: 34-46.
Cao et al. (2019) "A Novel Therapeutic Modality of Inhibiting the Glyco-Immune Checkpoint Axis to Treat Cancer," Poster Presentation, Presented in March of 2019 at AACR Annual Meeting in Atlanta, GA (1 page).
Database UniProt [Online] Mar. 28, 2018, "RecName: Full=Exo-alpha-sialidase {ECO:0000256 !ARBA:ARBA00012733}", XP093341319, retrieved Oct. 8, 2025, Database accession No. A0A2K5IZX5 (1 page).
Edwards et al. (2003) "The Remarkable Flexibility of the Human Antibody Repertoire; Isolation of Over One Thousand Different Antibodies to a Single Protein, BLyS," J. Mol. Biol., 34: 103-118.
Johnson et al. (2003) "Variation in the Divalent Cation Requirements of Influenza A Virus N2 Neuraminidases," J. Biochem., 314: 345-352.
Magesh et al. (2006) "Homology modeling of human sialidase enzymes NEU1, NEU3 and NEU4 based on the crystal structure of NEU2: Hints for the design of selective NEU3 inhibitors," Journal of Molecular Graphics and Modelling, 25: 196-207.
Mozzi et al. (2012) "Molecular insight into substrate recognition by human cytosolic sialidase NEU2," Proteins, 80: 1123-1132.
Petrick et al. (1994) "Desialylation of metastatic human colorectal carcinoma cells facilitates binding to Kupffer cells," Clin. Exp. Metastasis, 12: 108-116.
Rudikoff et al. (1982) "Single amino acid substitution altering antigen-binding speficicity," Proc. Natl. Acad. Aci. USA, 79: 1979-1983.
Vajdos et al. (2002) "Comprehensive Functional Maps of the Antigen-binding site of an Anti-ErbB2 Antibody Obtained with Shotgun Scanning Mutagenesis," J. Mol. Biol., 320: 415-428.

* cited by examiner

WT Neu2 (yield 1 µg/ml, 7% monomer, 93% aggregate)

Mutant C332A + C352L (yield 2 µg/ml, 12% monomer, 88% aggregate)

WT Neu2 (yield 1 µg/ml, 7% monomer, 93% aggregate)

Mutant A2K (yield 4.4 µg/ml, 8% monomer, 92% aggregate)

Mutant A2K+V325 (yield 12 µg/ml, 17.4% monomer, 82.6% aggregate)

Km: 178 ± 17 uM at pH 5
   524 ± 23 uM at pH 7

[substrate] uM

• Near complete cleavage of α2,3 at pH5
• Substantial cleavage of α2,8 (colominic acid) at pH5

WT Neu2 (yield 1 μg/ml, 7% monomer, 93% aggregate)

Neu2 variant V6Y (yield ~10 μg/ml, 78% monomer, 21% aggregate)

RAPTOR

JANUS

LOBSTER

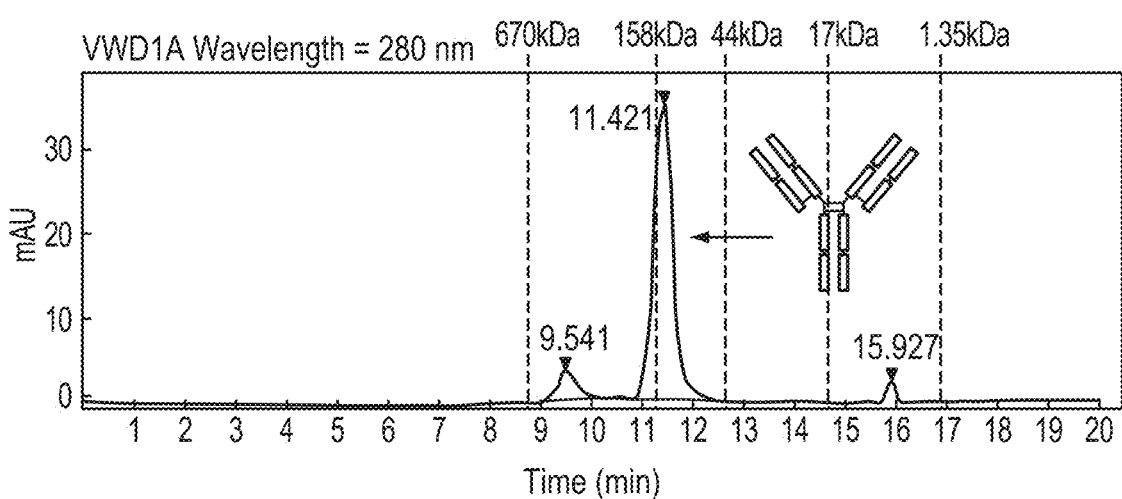
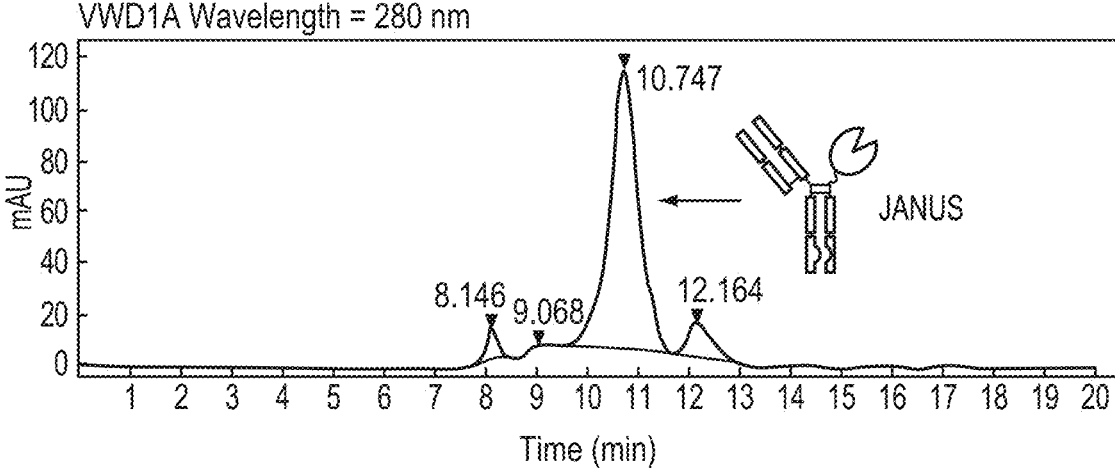
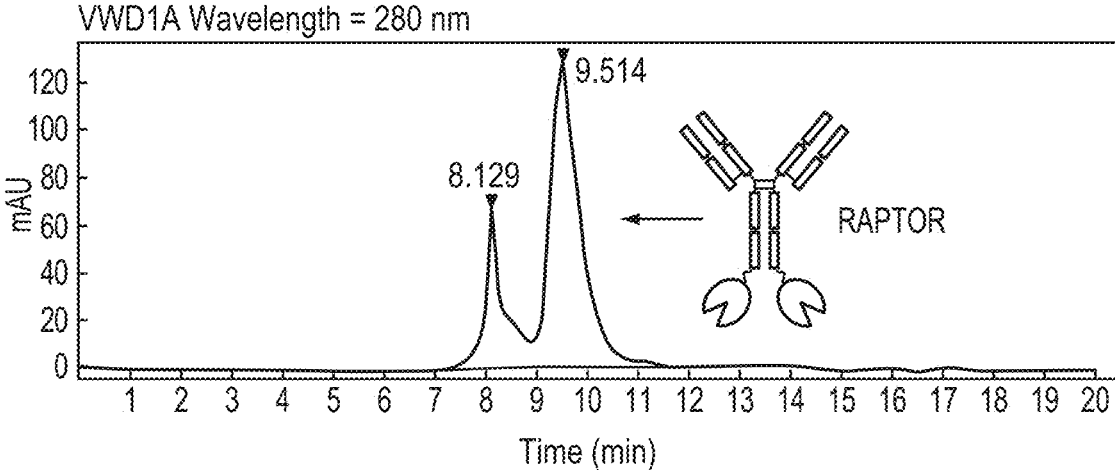
FIG. 11B

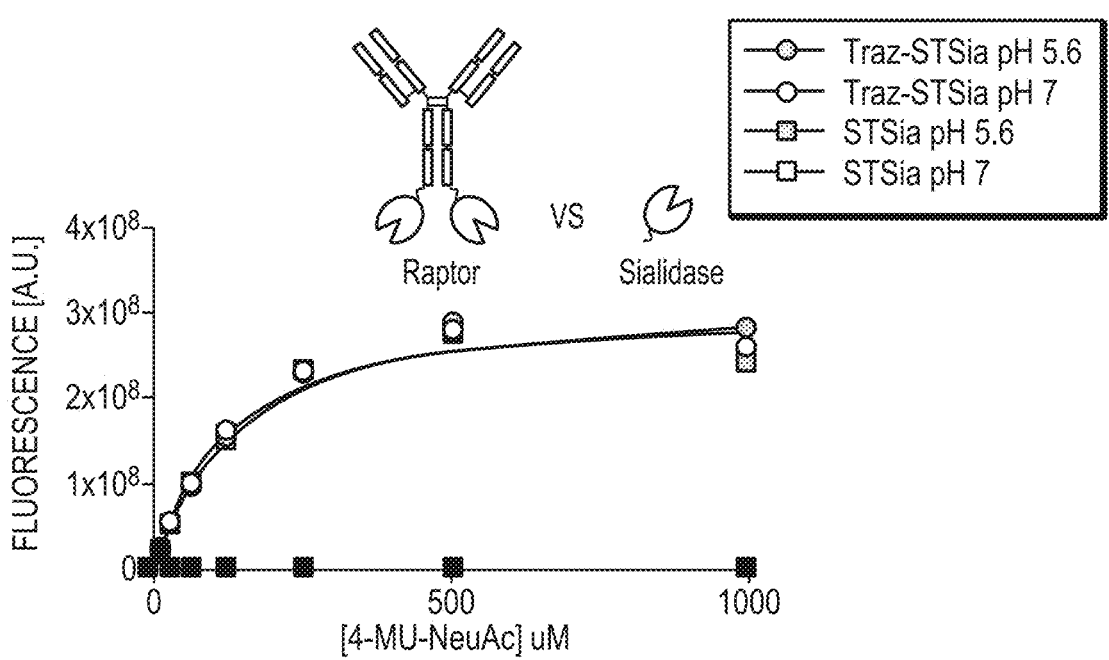
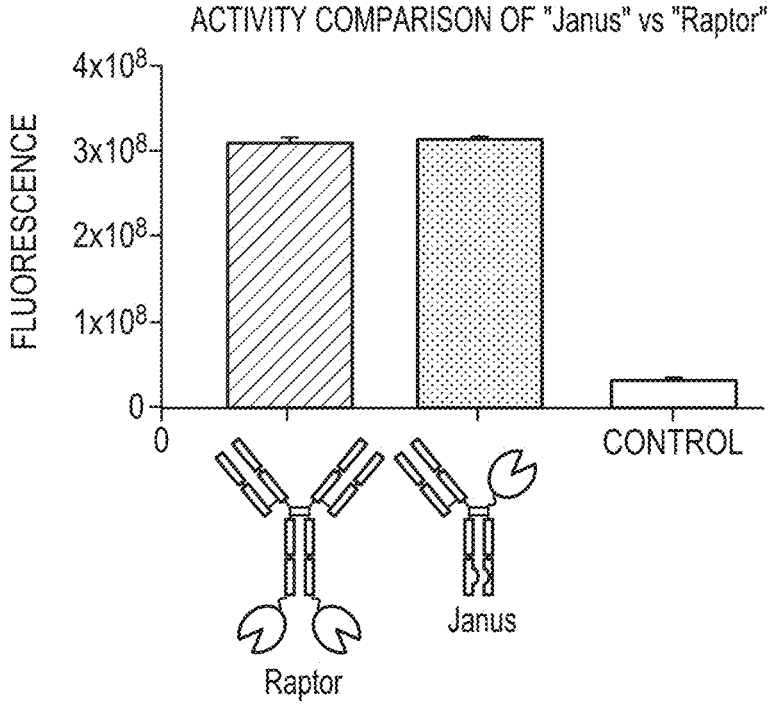
FIG. 12A

* ↓MAL II binding signals = ↓Sialic acids = De-sialylation
** ↑PNA binding signals = ↑Galactose Residues = De-sialylation

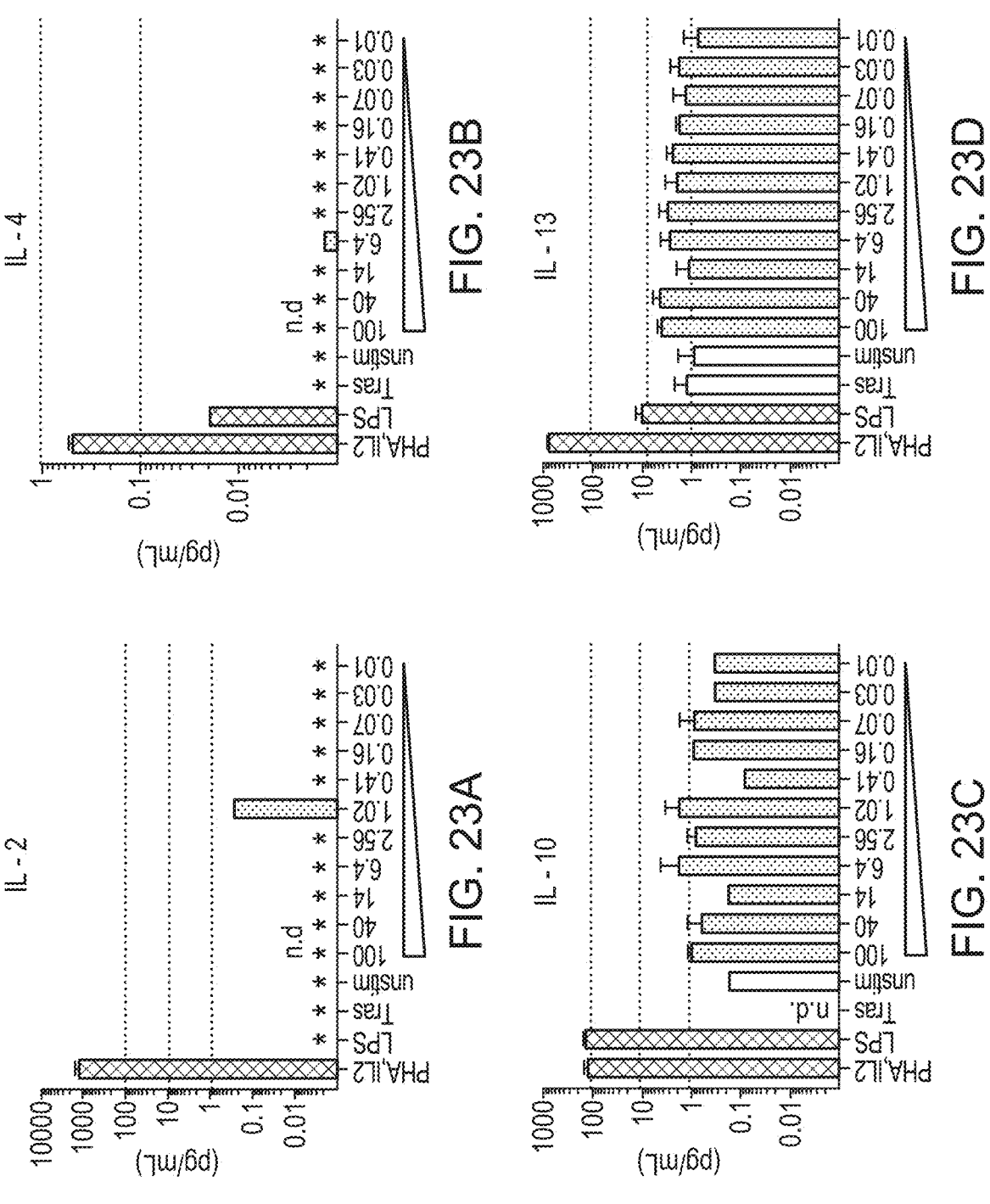

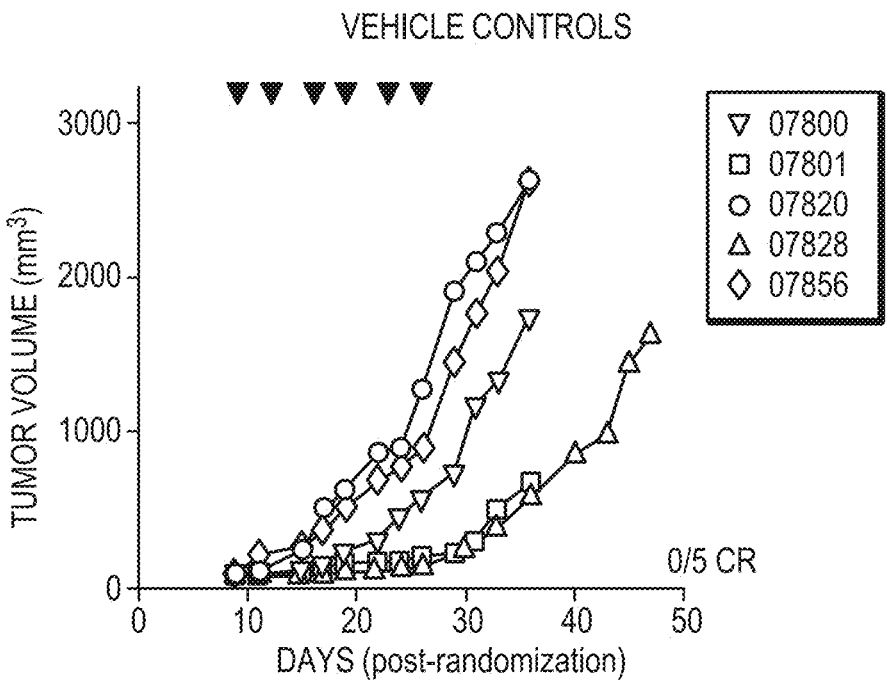
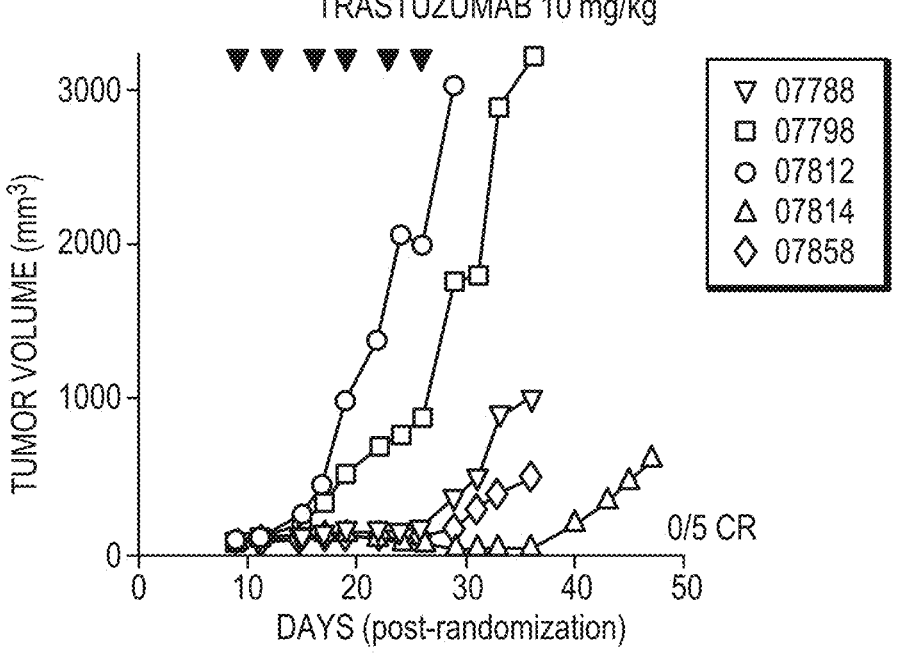
FIG. 27

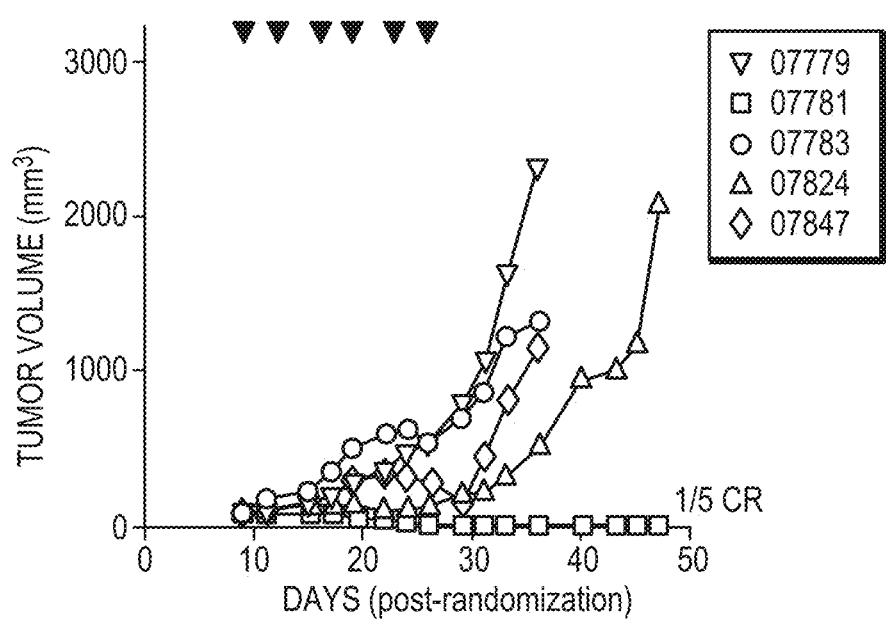
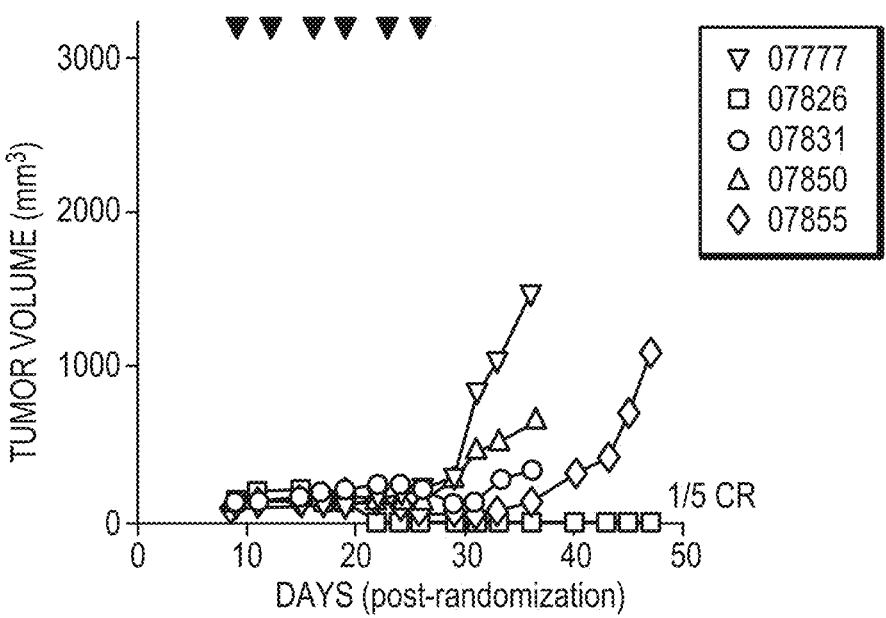
FIG. 27 (CONTD.)

RECOMBINANT HUMAN SIALIDASES, SIALIDASE FUSION PROTEINS, AND METHODS OF USING THE SAME

CROSS REFERENCE TO RELATED APPLICATIONS

This application is continuation of U.S. patent application Ser. No. 16/958,914, filed on Jun. 29, 2020, which is a § 371 National Stage of International (PCT) Patent Application No. PCT/US2019/012207, filed Jan. 3, 2019, which claims the benefit of, and priority to, U.S. Provisional Patent Application No. 62/613,363, filed Jan. 3, 2018 and U.S. Provisional Patent Application No. 62/755,279, filed Nov. 2, 2018, the entire disclosure of each of which is hereby incorporated by reference for all purposes.

SEQUENCE LISTING

The instant application contains a Sequence Listing which has been submitted electronically in XML format and is hereby incorporated by reference in its entirety. The XML copy, created on Mar. 5, 2024, is named PAL-009USC1_SL.xml and is 218.6 kilobytes in size.

FIELD OF THE INVENTION

The invention relates generally to recombinant human sialidases and recombinant sialidase fusion proteins, and their use in the treatment of cancer.

BACKGROUND

A growing body of evidence supports roles for glycans, and sialoglycans in particular, at various pathophysiological steps of tumor progression. Glycans regulate tumor proliferation, invasion, hematogenous metastasis and angiogenesis (Fuster et al. (2005) NAT. REV. CANCER 5 (7): 526-42). The sialylation of cell surface glycoconjugates is frequently altered in cancers, resulting in the expression of sialylated tumor-associated carbohydrate antigens. The expression of sialylated glycans by tumor cells is often associated with increased aggressiveness and metastatic potential of a tumor.

It has recently become apparent that Siglecs (sialic acid-binding immunoglobulin-like lectins), a family of sialic acid binding lectins, play a role in cancer immune suppression by binding to hypersialylated cancer cells and mediating the suppression of signals from activating NK cell receptors, thereby inhibiting NK cell-mediated killing of tumor cells (Jandus et al. (2014) J. CLIN. INVEST. 124:1810-1820; Läubli et al. (2014) PROC. NATL. ACAD. SCI. USA 111:14211-14216; Hudak et al. (2014) NAT. CHEM. BIOL. 10:69-75). Likewise, enzymatic removal of sialic acids by treatment with sialidase can enhance NK cell-mediated killing of tumor cells (Jandus, supra; Hudak, supra; Xiao et al. (2016) PROC. NATL. ACAD. SCI. USA 113 (37): 10304-9.)

Cancer immunotherapy with immune checkpoint inhibitors, including antibodies blocking the PD-1/PD-L1 pathway, has improved the outcome of many cancer patients. However, despite advances that have been made to date, many patients do not respond to currently available immune checkpoint inhibitors. Accordingly, there is still a need for effective interventions that overcome the immune suppressive tumor microenvironment and for treating cancers associated with hypersialylated cancer cells.

SUMMARY OF THE INVENTION

The invention is based, in part, upon the discovery that it is possible to produce recombinant mutant forms of human sialidase enzymes and fusion proteins and/or antibody conjugates containing such enzymes that have suitable substrate specificities and activities to be useful in removing sialic acid and/or sialic acid containing molecules from the surface of cancer cells and/or removing sialic acid and/or sialic acid containing molecules from the tumor microenvironment, and/or reducing the concentration of sialic acid and/or sialic acid containing molecules in the tumor microenvironment.

In one aspect, the invention provides a recombinant mutant human sialidase comprising a substitution of at least one wild-type amino acid residue, wherein the substitution increases at least one of the (a) expression, (b) stability, and (c) activity of the sialidase, or a combination of (a) and (b), combination of (a) and (c), a combination of (b) and (c), or a combination of (a), (b) and (c).

In another aspect, the invention provides a recombinant mutant human sialidase enzyme comprising an N-terminus and a C-terminus and comprising: (a) a substitution of at least one wild-type cysteine residue; (b) a substitution of at least one wild-type amino acid residue, wherein the substitution increases the isoelectric point (pI) of the sialidase and/or decreases the hydrophobicity of the sialidase relative to a sialidase without the substitution; (c) a peptide at least two amino acid residues in length covalently associated with an N-terminal amino acid at the N-terminus of the sialidase; (d) a substitution of at least one wild-type amino acid residue, wherein the substitution increases hydrophobic interactions and/or hydrogen bonding between the N- and C-termini of the sialidase relative to a sialidase without the substitution; or (e) a substitution or deletion of an N-terminal methionine at the N-terminus of the sialidase; or a combination of any of the foregoing. For example, the recombinant mutant sialidase enzyme may comprise a combination of the above-identified features, namely (a), (b), (c), (d), and (e), and may include, for example, a combination selected from: (a) and (b); (a) and (c); (a) and (d); (a) and (e); (b) and (c); (b) and (d); (b) and (e); (c) and (d); (c) and (e); (d) and (e); (a) and (b) and (c); (b) and (c) and (d); (a) and (c) and (d); (a) and (b) and (d); (a) and (b) and (e); (a) and (c) and (e); (a) and (d) and (e); (b) and (c) and (e); (b) and (d) and (e); (c) and (d) and (e); (a) and (b) and (c) and (d); (a) and (b) and (c) and (e); (a) and (c) and (d) and (e); (b) and (c) and (d) and (e); and (a) and (b) and (c) and (d) and (e). In certain embodiments, the sialidase is selected from Neu1, Neu2, Neu3, and Neu4, e.g., the sialidase is Neu2.

In certain embodiments, the sialidase comprises a substitution of at least one wild-type cysteine residue, e.g., a free cysteine residue. The cysteine residue may, for example, be substituted by serine, isoleucine, valine, phenylalanine, leucine, or alanine. In certain embodiments, the sialidase comprises a substitution of a cysteine residue at a position corresponding to position 332 of wild-type human Neu2 (SEQ ID NO: 1), e.g., the cysteine residue at a position corresponding to position 332 of wild-type human Neu2 is substituted by alanine (C332A). In certain embodiments, the sialidase comprises a substitution of a cysteine residue at a position corresponding to position 352 of wild-type human Neu2 (SEQ ID NO: 1), e.g., the cysteine residue at a position corresponding to position 352 of wild-type human Neu2 is substituted by leucine (C352L). In certain embodiments, the sialidase comprises both the C332A and C352L substitutions. In certain embodiments, the sialidase contains an amino acid substitution at 2, 3, 4, 5, or 6 cysteines typically present in a human sialidase, e.g., Neu2 or Neu3.

In certain embodiments, the sialidase comprises a substitution of at least one wild-type amino acid residue, e.g., a solvent exposed wild-type amino acid residue, wherein the substitution increases the isoelectric point (pI) of the sialidase and/or decreases the hydrophobicity of the sialidase relative to a sialidase without the substitution. In certain embodiments, the wild-type amino acid is substituted by lysine, arginine, or histidine, e.g., the wild-type amino acid is substituted by lysine. In certain embodiments, the sialidase comprises a substitution of an alanine residue at a position corresponding to position 2 of wild-type human Neu2 (SEQ ID NO: 1), e.g., the alanine residue at a position corresponding to position 2 of wild-type human Neu2 is substituted by lysine (A2K).

In certain embodiments, the sialidase comprises a peptide at least two amino acid residues in length fused to the N-terminus of the sialidase, e.g., fused to an N-terminal amino acid residue of the sialidase, e.g., by a peptide bond. In certain embodiments, the peptide is between 2 amino acid residues and 20 amino acid residues in length. In certain embodiments, the peptide is at least two, three, four or five amino acid residues in length. In certain embodiments, the peptide comprises an amino acid sequence derived from wild-type mouse thymus Neu2 (SEQ ID NO: 2), e.g., in certain embodiments the peptide comprises EDLRP (SEQ ID NO: 3) or MEDLRP (SEQ ID NO: 4).

In certain embodiments, the sialidase comprises a substitution of at least one wild-type amino acid residue, wherein the substitution increases hydrophobic interactions and/or hydrogen bonding between the N- and C-termini of the sialidase relative to a sialidase without the substitution. For example, in certain embodiments, the sialidase comprises a substitution of a valine residue at a position corresponding to position 6 of wild-type human Neu2 (SEQ ID NO: 1), e.g., the valine residue at a position corresponding to position 6 of wild-type human Neu2 is substituted by tyrosine (V6Y).

In certain embodiments, the sialidase comprises a substitution or deletion of an N-terminal methionine at the N-terminus of the sialidase. For example, in certain embodiments, the sialidase comprises a substitution of a methionine residue at a position corresponding to position 1 of wild-type human Neu2 (SEQ ID NO: 1), e.g., the methionine at a position corresponding to position 1 of wild-type human Neu2 is substituted by alanine (M1A) or aspartic acid (M1D).

In certain embodiments, the sialidase has a different substrate specificity than the corresponding wild-type sialidase. For example, in certain embodiments the sialidase can cleave α2,3, α2,6, and/or α2,8 linkages. In certain embodiments the sialidase can cleave α2,3 and α2,8 linkages.

In certain embodiments, the sialidase comprises SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

In another aspect, the invention provides a fusion protein comprising: (a) a sialidase enzyme; and (b) an immunoglobulin Fc domain and/or an immunoglobulin antigen-binding domain; wherein the sialidase and the Fc domain and/or the antigen-binding domain are linked by a peptide bond or an amino acid linker. In certain embodiments, the sialidase is a human sialidase, e.g., a recombinant mutant human sialidase disclosed herein. In certain embodiments, the fusion protein further comprises a linker, for example, an amino acid linker, connecting the sialidase enzyme and the Fc domain and/or an antigen-binding domain. In certain embodiments, the immunoglobulin antigen-binding domain is associated (for example, covalently or non-covalently associated) with a second immunoglobulin antigen-binding domain to produce an antigen-binding site.

In certain embodiments, the immunoglobulin Fc domain is derived from a human IgG1, IgG2, IgG3, IgG4, IgA1, IgA2, IgD, IgE, or IgM Fc domain, e.g., the immunoglobulin Fc domain is derived from a human IgG1, IgG2, IgG3, or IgG4 Fc domain, e.g., the immunoglobulin Fc domain is derived from a human IgG1 Fc domain.

In certain embodiments, the immunoglobulin antigen-binding domain is derived from an antibody selected from trastuzumab, cetuximab, daratumumab, girentuximab, panitumumab, ofatumumab, and rituximab. In certain embodiments, the immunoglobulin antigen-binding domain is derived from trastuzumab.

In certain embodiments, the fusion protein comprises SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 63, SEQ ID NO: 74, SEQ ID NO: 75, SEQ ID NO: 76, SEQ ID NO: 77, SEQ ID NO: 78, or SEQ ID NO: 79, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 63, SEQ ID NO: 74, SEQ ID NO: 75, SEQ ID NO: 76, SEQ ID NO: 77, SEQ ID NO: 78, or SEQ ID NO: 79.

In another aspect, the invention provides an antibody conjugate comprising any of the foregoing fusion proteins. In certain embodiments, the antibody conjugate comprises a single sialidase. In other embodiments, the antibody conjugate comprises two sialidases, which can be the same or different. In certain embodiments the antibody conjugate comprises two identical sialidases. In certain embodiments, the antibody conjugate comprises a single antigen-binding site. In other embodiments, the antibody conjugate comprises two antigen-binding sites, which can be the same or different. In certain embodiments, the antibody conjugate comprises two identical antigen-binding sites.

In certain embodiments, the antibody conjugate has a molecular weight from about 135 kDa to about 165 kDa, or the antibody conjugate has a molecular weight from about 215 kDa to about 245 kDa.

In certain embodiments, the antibody conjugate comprises: (a) a first polypeptide comprising an immunoglobulin light chain; (b) a second polypeptide comprising an immunoglobulin heavy chain; and (c) a third polypeptide comprising an immunoglobulin Fc domain and a sialidase; wherein the first and second polypeptides are covalently linked together and the second and third polypeptides are covalently linked together, and wherein the first polypeptide and the second polypeptide together define an antigen-binding site. The third polypeptide may, for example, comprise the sialidase and the immunoglobulin Fc domain in an N- to C-terminal orientation. The first polypeptide may, for example, comprise SEQ ID NO: 49, the second polypeptide may, for example, comprise SEQ ID NO: 50, and/or the third polypeptide may, for example, comprise SEQ ID NO: 51, SEQ ID NO: 52, SEQ ID NO: 53, SEQ ID NO: 54, SEQ ID NO: 76, SEQ ID NO: 77, SEQ ID NO: 78, or SEQ ID NO: 79.

In certain embodiments, the antibody conjugate comprises: (a) a first polypeptide comprising a first immunoglobulin light chain; (b) a second polypeptide comprising a first immunoglobulin heavy chain and a first sialidase; (c) a third polypeptide comprising a second immunoglobulin heavy chain and a second sialidase; and (d) a fourth polypeptide comprising a second immunoglobulin light chain;

wherein the first and second polypeptides are covalently linked together, the third and fourth polypeptides are covalently linked together, and the second and third polypeptides are covalently linked together, and wherein the first polypeptide and the second polypeptide together define a first antigen-binding site, and the third polypeptide and the fourth polypeptide together define a second antigen-binding site. The second and third polypeptides may, for example, comprise the first and second immunoglobulin heavy chain and the first and second sialidase, respectively, in an N- to C-terminal orientation.

In certain embodiments, the antibody conjugate comprises: (a) a first polypeptide comprising a first sialidase, a first immunoglobulin Fc domain, and a first single chain variable fragment (scFv); and (b) a second polypeptide comprising a second sialidase, a second immunoglobulin Fc domain, and an optional second single chain variable fragment (scFv); wherein the first and second polypeptides are covalently linked together, and wherein the first scFv defines a first antigen-binding site, and the second scFv, when present, defines a second antigen-binding site. The first polypeptide may, for example comprise the first sialidase, the first immunoglobulin Fc domain, and the first scFv in an N- to C-terminal orientation. The second polypeptide may, for example, comprise the second sialidase, the second immunoglobulin Fc domain, and the optional second scFv in an N- to C-terminal orientation. The first polypeptide may, for example, comprise SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, and/or the second polypeptide may, for example, comprise SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75.

In another aspect, the invention provides an isolated nucleic acid comprising a nucleotide sequence encoding any of the foregoing recombinant mutant human sialidases, any of the foregoing fusion proteins, or at least a portion of any of the foregoing antibody conjugates. In another aspect, the invention provides an expression vector comprising any of the foregoing nucleic acids. In another aspect, the invention provides a host cell comprising any of the foregoing expression vectors.

In another aspect, the invention provides a pharmaceutical composition comprising any of the foregoing recombinant mutant human sialidases, any of the foregoing fusion proteins, or any of the foregoing antibody conjugates.

In another aspect, the invention provides a method of treating cancer in a subject in need thereof. The method comprises administering to the subject an effective amount of any of the foregoing sialidases, any of the foregoing fusion proteins, any of the foregoing antibody conjugates, or any of the foregoing pharmaceutical compositions. In certain embodiments, the cancer is an epithelial cancer, e.g., endometrial cancer, ovarian cancer, cervical cancer, vulvar cancer, uterine cancer, fallopian tube cancer, breast cancer, prostate cancer, lung cancer, pancreatic cancer, urinary cancer, bladder cancer, head and neck cancer, oral cancer and liver cancer.

In another aspect, the invention provides a method of increasing expression of HLA-DR, CD86, CD83, IFNγ, IL-1b, IL-6, TNFα, IL-17A, IL-2, or IL-6 in a cell or tissue. The method comprises contacting the cell or tissue with an effective amount of any of the foregoing sialidases, any of the foregoing fusion proteins, any of the foregoing antibody conjugates, or any of the foregoing pharmaceutical compositions. In certain embodiments, the cell is selected from a dendritic cell and a peripheral blood mononuclear cell (PBMC).

These and other aspects and features of the invention are described in the following detailed description and claims.

DESCRIPTION OF THE DRAWINGS

The invention can be more completely understood with reference to the following drawings.

FIG. 11B is an SEC-HPLC trace of trastuzumab (top), and ASCs made using St-sialidase and trastuzumab in the Janus (middle) and Raptor (bottom) formats.

FIG. 12A is a line graph (top) and a bar graph (bottom) showing the enzymatic activity for St-sialidase and ASCs made using St-sialidase and trastuzumab in the Raptor and Janus formats.

FIG. 16D depicts the mean tumor volume with error bars of the indicated treatment groups from Example 8.

FIG. 17B depicts the rechallenge experiment of either the three mice treated with Janus from FIG. 17A with complete regressions of the original EMT6-Her2 tumors (cured mice) or naïve mice. Cured mice were inoculated with either EMT6-Her2 cells or parental EMT6 cells on the left and right lower flank region. Naïve mice were inoculated with EMT6-Her2 cells.

FIGS. 23A-D depict IL-2 (FIG. 23A), IL-4 (FIG. 23B), IL-10 (FIG. 23C), and IL-13 (FIG. 23D) release following treatment with a Janus ASC including human Neu2 with ΔM1, V6Y, I187K, and C332A mutations and trastuzumab. Freshly isolated human peripheral blood mononuclear cells (PBMCs) were incubated with Janus at the indicated concentrations (shown in μg/ml) for 24 hours. PHA-L with IL-2 or LPS were used as positive controls to stimulate cytokine release. Trastuzumab (Tras) was used as a negative control.

Figure 1:
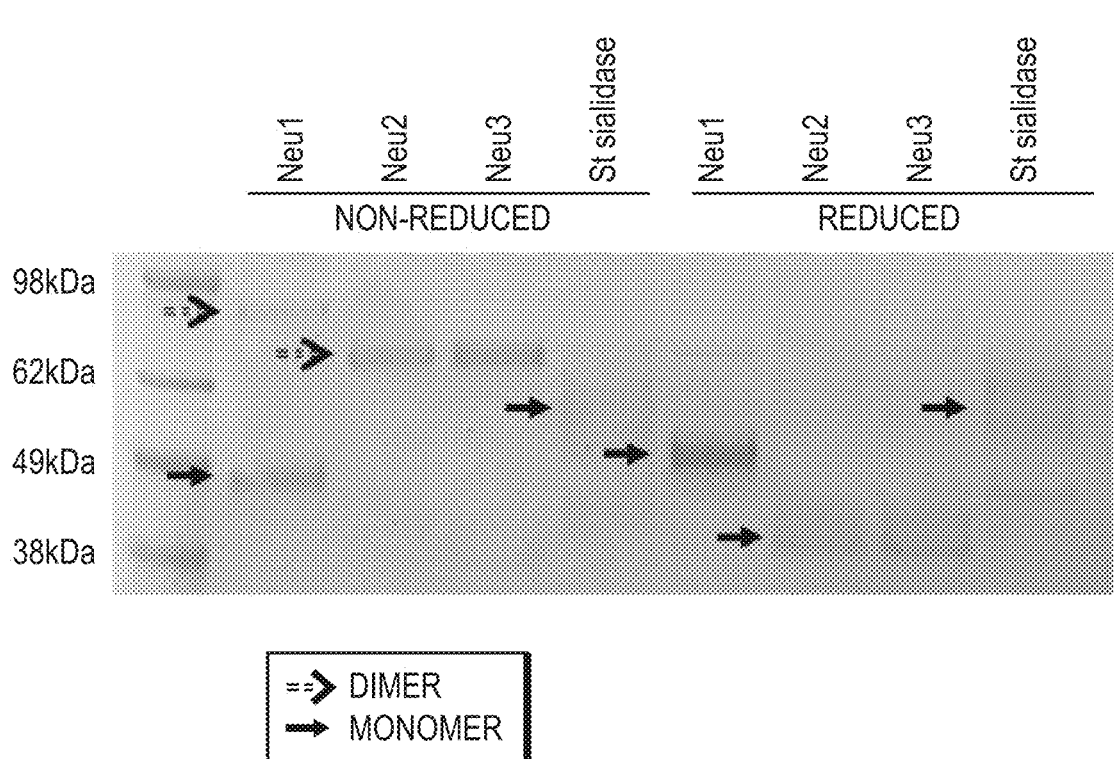
FIG. 1 depicts an SDS-PAGE gel showing recombinant human Neu1, Neu2, Neu3, and *Salmonella typhimurium* (St-sialidase) under non-reducing and reducing conditions. Monomer and dimer species are indicated.

Complete Responses (CR, defined as regression below the limit of palpation at any point during the study) are shown as well.

FIG. 27 depicts the testing of human Lobster antibody sialidase conjugates in a mouse syngeneic tumor model utilizing EMT6 mouse breast cancer cells engineered to express human Her2. Mice were treated via intraperitoneal injection of 10 mg/kg of trastuzumab, human Lobster 1, human Lobster 2, and vehicle on the days marked with black triangles (▼) and tumor volume (mm³) was recorded. Graphs show the individual mice for the indicated treatments. Complete Responses (CR, defined as regression below the limit of palpation at any point during the study) are shown as well.

DETAILED DESCRIPTION

Various features and aspects of the invention are discussed in more detail below. The invention provides a recombinant human sialidase that comprises at least one mutation relative to a wild-type human sialidase, e.g., a substitution, deletion, or addition (insertion) of at least one amino acid. The mutations, or combination of mutations, can improve the expression, activity or both the expression and activity of the sialidase to improve its use in cancer diagnosis and/or treatment.

The invention further relates to fusion proteins and/or antibody conjugates comprising a sialidase enzyme and an antibody or portion thereof, e.g., an immunoglobulin Fc domain and/or an antigen-binding domain. The sialidase enzyme portion of the fusion protein and/or antibody conjugate may comprise at least one mutation relative to a wild-type human sialidase.

The invention further relates to pharmaceutical compositions and methods of using fusion proteins and/or antibody conjugates to treat cancer, e.g., an epithelial cell cancer.

I. Recombinant Human Sialidases

As used herein, the term "sialidase" refers to any enzyme, or a functional fragment thereof, that cleaves a terminal sialic acid residue from a substrate, for example, a glycoprotein or a glycolipid. The term sialidase includes variants having one or more amino acid substitutions, deletions, or insertions relative to a wild-type sialidase sequence, and/or fusion proteins or conjugates including a sialidase. Sialidases are also called neuraminidases, and, unless indicated otherwise, the two terms are used interchangeably herein. As used herein, the term "functional fragment" of a sialidase refers to fragment of a full-length sialidase that retains, for example, at least 10%, at least 20%, at least 30%, at least 40%, at least 50%, at least 60%, at least 70%, at least 80%, at least 90%, or 100% of the enzymatic activity of the corresponding full-length, naturally occurring sialidase. Sialidase enzymatic activity may be assayed by any method known in the art, including, for example, by measuring the release of sialic acid from the fluorogenic substrate 4-methylumbelliferyl-N-acetylneuraminic acid (4MU-NeuAc). In certain embodiments, the functional fragment comprises at least 100, 150, 200, 250, 300, 310, 320, 330, 340, 350, 360, or 370 consecutive amino acids present in a full-length, naturally occurring sialidase.

Four sialidases have been found in the human genome and are referred to as Neu1, Neu2, Neu3 and Neu4.

Human Neu1 is a lysosomal neuraminidase enzyme which functions in a complex with beta-galactosidase and cathepsin A. The amino acid sequence of human Neu1 is depicted in SEQ ID NO: 7, and a nucleotide sequence encoding human Neu1 is depicted in SEQ ID NO: 23.

Human Neu2 is a cytosolic sialidase enzyme. The amino acid sequence of human Neu2 is depicted in SEQ ID NO: 1, and a nucleotide sequence encoding human Neu2 is depicted in SEQ ID NO: 24.

Human Neu3 is a plasma membrane sialidase with an activity specific for gangliosides. Human Neu3 has two isoforms: isoform 1 and isoform 2. The amino acid sequence of human Neu3, isoform 1 is depicted in SEQ ID NO: 8, and a nucleotide sequence encoding human Neu3, isoform 1 is depicted in SEQ ID NO: 25. The amino acid sequence of human Neu3, isoform 2 is depicted in SEQ ID NO: 9, and a nucleotide sequence encoding human Neu3, isoform 2 is depicted in SEQ ID NO: 34.

Human Neu4 has two isoforms: isoform 1 is a peripheral membrane protein and isoform 2 localizes to the lysosome lumen. The amino acid sequence of human Neu4, isoform 1 is depicted in SEQ ID NO: 10, and a nucleotide sequence encoding human Neu4, isoform 1 is depicted in SEQ ID NO: 26. The amino acid sequence of human Neu4, isoform 2 is depicted in SEQ ID NO: 11, and a nucleotide sequence encoding human Neu4, isoform 2 is depicted in SEQ ID NO: 35.

Four sialidases have also been found in the mouse genome and are referred to as Neu1, Neu2, Neu3 and Neu4. The amino acid sequence of mouse Neu1 is depicted in SEQ ID NO: 83, and a nucleotide sequence encoding mouse Neu1 is depicted in SEQ ID NO: 87. The amino acid sequence of mouse Neu2 is depicted in SEQ ID NO: 84 and a nucleotide sequence encoding mouse Neu2 is depicted in SEQ ID NO: 88. The amino acid sequence of mouse Neu3 is depicted in SEQ ID NO: 85, and a nucleotide sequence encoding mouse Neu3 is depicted in SEQ ID NO: 89. The amino acid sequence of mouse Neu4 is depicted in SEQ ID NO: 86, and a nucleotide sequence encoding mouse Neu4 is depicted in SEQ ID NO: 90.

Exemplary prokaryotic sialidases include sialidases from *Salmonella typhimurium* and *Vibrio cholera*. The amino acid sequence of *Salmonella typhimurium* sialidase (St-sialidase) is depicted in SEQ ID NO: 30, and a nucleotide sequence encoding *Salmonella typhimurium* sialidase is depicted in SEQ ID NO: 80. The amino acid sequence of *Vibrio cholera* sialidase is depicted in SEQ ID NO: 81, and a nucleotide sequence encoding *Vibrio cholera* sialidase is depicted in SEQ ID NO: 82.

In certain embodiments, a recombinant mutant human sialidase has about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100%, or more than 100% of the enzymatic activity of a corresponding (or template) wild-type human sialidase.

In certain embodiments, the recombinant mutant human sialidase has the same substrate specificity as the corresponding wild-type human sialidase. In other embodiments, the recombinant mutant human sialidase has a different substrate specificity than the corresponding wild-type human sialidase. For example, in certain embodiments the recombinant mutant human sialidase can cleave α2,3, α2,6, and/or α2,8 linkages. In certain embodiments the sialidase can cleave α2,3 and α2,8 linkages.

In certain embodiments, the expression yield of the recombinant mutant human sialidase in mammalian cells, e.g., HEK293 cells, CHO cells, murine myeloma cells (NS0, Sp2/0), or human fibrosarcoma cells (HT-1080), e.g., HEK293 cells, is greater than about 10%, about 20%, about 50%, about 75%, about 100%, about 150%, about 200%, about 250%, about 300%, about 400%, about 500%, about 600%, about 700%, about 800%, about 900%, or about 1,000% of the expression yield of the corresponding wild-type human sialidase.

In certain embodiments, the recombinant mutant human sialidase has about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100%, or more than 100% of the enzymatic activity of a corresponding wild-type human sialidase, and the expression yield of the recombinant mutant human sialidase in mammalian cells, e.g., HEK293 cells, is greater than about 10%, about 20%, about 50%, about 75%, about 100%, about 150%, about 200%, about 250%, about 300%, about 400%, about 500%, about 600%, about 700%, about 800%, about 900%, or about 1,000% of the expression yield of a corresponding wild-type human sialidase.

a. Substitution of Cysteine Residues

In certain embodiments, the recombinant mutant human sialidase comprises a substitution of at least one cysteine (cys, C) residue. It has been discovered that certain cysteine residues in sialidases may inhibit expression of functional protein as a result of protein aggregation. Accordingly, in certain embodiments, the recombinant mutant human sialidase contains at least one mutation of a free cysteine (e.g., for Neu1 (SEQ ID NO: 7), C111, C117, C171, C183, C218, C240, C242, and C252; for Neu2 (SEQ ID NO: 1), C125, C196, C219, C272, C332, and C352; for Neu3 (SEQ ID NO: 8), C7, C90, C99, C106, C127, C136, C189, C194, C226, C242, C250, C273, C279, C295, C356, C365, C368, C384, C383, C394, and C415; and for Neu4 (SEQ ID NO: 10), C88, C125, C126, C186, C191, C211, C223, C239, C276, C437, C453, C480, and C481). Free cysteines can be substituted with any amino acid. In certain embodiments, the free cysteine is substituted with serine (ser, S), isoleucine (iso, I), valine (val, V), phenylalanine (phe, F), leucine (leu, L), or alanine (ala, A). Exemplary cysteine substitutions in Neu2 include C125A, C125I, C125S, C125V, C196A, C196L, C196V, C272S, C272V, C332A, C332S, C332V, C352L, and C352V.

In certain embodiments, the recombinant mutant human sialidase comprises two or more cysteine substitutions. Exemplary double or triple substitutions in Neu2 include: C125S and C332S; C272V and C332A; C272V and C332S; C332A and C352L; C125S and C196L; C196L and C352L; C196L and C332A; C332A and C352L; and C196L, C332A and C352L.

In certain embodiments, the recombinant mutant human sialidase is a Neu2 sialidase and comprises the substitutions C322A and C352L (SEQ ID NO: 5).

In certain embodiments, the sialidase contains an amino acid substitution at 2, 3, 4, 5, or 6 cysteines typically present in a human sialidase, e.g., Neu2 or Neu3.

In certain embodiments, the recombinant mutant human sialidase comprises a substitution or combination of substitutions corresponding to a substitution or combination of substitutions listed in TABLE 2 herein below.

b. Substitutions of Residues to Increase pI and/or Decrease Hydrophobicity

The isoelectric point (pI) of a protein is the pH at which the net charge is zero. The pI also indicates the pH at which the protein is least soluble, which affects the ability to express and purify the protein. Generally, a protein has good solubility if its pI is greater than 2 units above the pH of the solution. Human Neu2 has a predicted pI of 7.5. Thus, human Neu2 is least soluble around neutral pH, which is undesirable because expression and physiological systems are at neutral pH. In contrast, the sialidase from *Salmonella typhimurium* (St-sialidase), which exhibits good solubility and recombinant expression, has a pI of 9.6. Accordingly, to increase expression of human Neu2 or the other human sialidases, a recombinant mutant human sialidase may be designed to contain one or more amino acid substitution(s) wherein the substitution(s) increase(s) the pI of the sialidase relative to a sialidase without the substitution. Additionally, decreasing the number of hydrophobic amino acids on the surface of a sialidase may improve expression of sialidase by, for example, reducing aggregation. Accordingly, to increase expression of human Neu2 or the other human sialidases, a recombinant mutant human sialidase may be designed to contain one or more amino acid substitution(s) wherein the substitution(s) decrease(s) the hydrophobicity of a surface of the sialidase relative to a sialidase without the substitution(s).

Accordingly, in certain embodiments, the recombinant mutant human sialidase comprises at least one amino acid substitution, wherein the substitution increases the isoelectric point (pI) of the sialidase and/or decreases the hydrophobicity of the sialidase relative to a sialidase without the substitution. This may be achieved by introducing one or more charged amino acids, for example, positively or negatively charged amino acids, into the recombinant sialidase. In certain embodiments, the amino acid substitution is to a charged amino acid, for example, a positively charged amino acid such as lysine (lys, K), histidine (his, H), or arginine (arg, R), or a negatively charged amino acid such as aspartic acid (asp, D) or glutamic acid (glu, E). In certain embodiments, the amino acid substitution is to a lysine residue. In certain embodiments, the substitution increases the pI of the sialidase to about 7.75, about 8, about 8.25, about 8.5, about 8.75, about 9, about 9.25, about 9.5, or about 9.75.

In certain embodiments, the amino acid substitution occurs at a surface exposed D or E amino acid, in a helix or loop, or in a position that has a K or R in the corresponding position of St-sialidase. In certain embodiments, the amino acid substitution occurs at an amino acid that is remote from the catalytic site or otherwise not involved in catalysis, an amino acid that is not conserved with the other human Neu proteins or with an St-Sialidase or *Clostridium* NanH, or an amino acid that is not located in a domain important for function (e.g., an Asp-box or beta strand).

Exemplary amino acid substitutions in Neu2 that increase the isoelectric point (pI) of the sialidase and/or decrease the hydrophobicity of the sialidase relative to a sialidase without the substitution include A2E, A2K, D215K, V325E, V325K, E257K, and E319K. In certain embodiments, the recombinant mutant human sialidase comprises two or more amino acid substitutions, including, for example, A2K and V325E, A2K and V325K, E257K and V325K, A2K and E257K, and E257K and A2K and V325K.

In certain embodiments, the recombinant mutant human sialidase comprises a substitution or combination of substitutions corresponding to a substitution or combination of substitutions listed in TABLE 3 herein below.

c. Addition of N-Terminal Peptides and N- or C-Terminal Substitutions

It has been discovered that the addition of a peptide sequence of two or more amino acids to the N-terminus of a human sialidase can improve expression and/or activity of the sialidase. In certain embodiments, the peptide is at least 2 amino acids in length, for example, from 2 to 20, from 2 to 10, from 2 to 5, or 2, 3, 4, 5, 6, 7, 8, 9, 10, 11, 12, 13, 14, 15, 16, 17, 18, 19, or 20 amino acids in length. In certain embodiments, the peptide may form, or have a propensity to form, an α-helix.

In mice, a Neu2 isoform (type B) found in thymus contains six amino acids not present in the canonical isoform of Neu2 found in skeletal muscle. In certain embodiments herein, the N-terminal six amino acids of the mouse thymus Neu2 isoform, MEDLRP (SEQ ID NO: 4), or variations thereof, can be added onto a human Nou, e.g., human Neu2. In certain embodiments, the recombinant mutant human sialidase comprises a peptide at least two amino acid residues in length covalently associated with an N-terminal amino acid of the sialidase. In certain embodiments the recombinant mutant human sialidase comprises the peptide MEDLRP (SEQ ID NO: 4) or EDLRP (SEQ ID NO: 3) covalently associated with an N-terminal amino acid of the sialidase. In certain embodiments, the sialidase may further comprise a cleavage site, e.g., a proteolytic cleavage site, located between the peptide, e.g., MEDLRP (SEQ ID NO: 4) or EDLRP (SEQ ID NO: 3), and the remainder of the sialidase. In certain embodiments, the peptide, e.g., MEDLRP (SEQ ID NO: 4) or EDLRP (SEQ ID NO: 3), may be post-translationally cleaved from the remainder of the sialidase.

Alternatively to, or in combination with, the N-terminal addition, 1-5 amino acids of the 12 amino acid N-terminal region of the recombinant mutant human sialidase may be removed, e.g., the N-terminal methionine can be removed. In certain embodiments, if the recombinant mutant human sialidase is Neu2, the N-terminal methionine can be removed, the first five amino acids (MASLP; SEQ ID NO: 12) can be removed, or the second through fourth amino acids (ASLP; SEQ ID NO: 13) can be removed.

In certain embodiments, 1-5 amino acids of the 12 amino acid N-terminal region of the recombinant mutant human sialidase are substituted with MEDLRP (SEQ ID NO: 4), EDLRP (SEQ ID NO: 3), or TVEKSVVF (SEQ ID NO: 14). For example, in certain embodiments, if the recombinant mutant human sialidase is Neu2, the amino acids MASLP (SEQ ID NO: 12), ASLP (SEQ ID NO: 13) or M are substituted with MEDLRP (SEQ ID NO: 4), EDLRP (SEQ ID NO: 3) or TVEKSVVF (SEQ ID NO: 14).

Human sialidases have a β-propeller structure, characterized by 6 blade-shaped β-sheets arranged toroidally around a central axis. Generally, hydrophobic interactions between the blades of a β-propeller, including between the N- and C-terminal blades, enhance stability. Accordingly, in order to increase expression of human Neu2 or the other human sialidases, a recombinant mutant human sialidase can be designed comprising an amino acid substitution that increases hydrophobic interactions and/or hydrogen bonding between the N- and C-terminal β-propeller blades of the sialidase.

Accordingly, in certain embodiments, the recombinant mutant human sialidase comprises a substitution of at least one wild-type amino acid residue, wherein the substitution increases hydrophobic interactions and/or hydrogen bonding between the N- and C-termini of the sialidase relative to a sialidase without the substitution. In certain embodiments, the wild-type amino acid is substituted with asparagine (asn, N), lysine (lys, K), tyrosine (tyr, Y), phenylalanine (phe, F), or tryptophan (trp, W). Exemplary substitutions in Neu2 that increase hydrophobic interactions and/or hydrogen bonding between the N- and C-termini include LAN, LAK, V6Y, L7N, LAN and L7N, L4N and V6Y and L7N, V12N, V12Y, V12L, V6Y, V6F, or V6W. In certain embodiments, the sialidase comprises the V6Y substitution.

In certain embodiments, the recombinant mutant human sialidase comprises a combination of the above substitutions. For example, a recombinant mutant human Neu2 sialidase can comprise the additional amino acids MEDLRP (SEQ ID NO: 4), EDLRP (SEQ ID NO: 3), or TVEKSVVF (SEQ ID NO: 14) at the N-terminus and, in combination, can comprise at least one LAN, LAK, V6Y, L7N, LAN and L7N, L4N and V6Y and L7N, V12N, V12Y, V12L, V6Y, V6F, or V6W substitution. In certain embodiments, the amino acids MASLP (SEQ ID NO: 12), ASLP (SEQ ID NO: 13) or M of a recombinant mutant human Neu2 sialidase are replaced with MEDLRP (SEQ ID NO: 4), EDLRP (SEQ ID NO: 3) or TVEKSVVF (SEQ ID NO: 14) and the recombinant mutant human Neu2 sialidase also comprises at least one L4N, LAK, V6Y, L7N, L4N and L7N, LAN and V6Y and L7N, V12N, V12Y, V12L, V6Y, V6F, or V6W substitution.

In certain embodiments, the recombinant mutant human sialidase comprises a substitution or combination of substitutions corresponding to a substitution or combination of substitutions listed in TABLES 4 or 5 herein below.

Additionally, in certain embodiments, the sialidase comprises a substitution or deletion of an N-terminal methionine at the N-terminus of the sialidase. For example, in certain embodiments, the sialidase comprises a substitution of a methionine residue at a position corresponding to position 1 of wild-type human Neu2 (SEQ ID NO: 1), e.g., the methionine at a position corresponding to position 1 of wild-type human Neu2 is substituted by alanine (MIA) or aspartic acid (MID). In other embodiments, the sialidase comprises a deletion of a methionine residue at a position corresponding to position 1 (ΔM1) of wild-type human Neu2 (SEQ ID NO: 1).

In certain embodiments, the recombinant mutant human sialidase comprises a substitution or combination of substitutions corresponding to a substitution or combination of substitutions listed in TABLE 6 herein below.

d. Other Substitutions and Combinations of Substitutions

The invention further provides a recombinant mutant human Neu2 sialidase comprising at least one of the following substitutions: I187K, A328E, K370N, or H210N. In certain embodiments, a recombinant mutant human Neu2 comprises the substitution of the amino acids GDYDAPTHQVQW (SEQ ID NO: 15) with the amino acids SMDQGSTW (SEQ ID NO: 16) or STDGGKTW (SEQ ID NO: 17). In certain embodiments, a recombinant mutant human Neu2 comprises the substitution of the amino acids PRPPAPEA (SEQ ID NO: 18) with the amino acids QTPLEAAC (SEQ ID NO: 19). In certain embodiments, a recombinant mutant human Neu2 comprises the substitution of the amino acids NPRPPAPEA (SEQ ID NO: 20) with the amino acids SQNDGES (SEQ ID NO: 21).

The invention further provides a recombinant mutant human Neu2 sialidase comprising at least one substitution at a position corresponding to V212, A213, Q214, D215, T216, L217, E218, C219, Q220, V221, A222, E223, V224, E225, or T225.

The invention further provides a recombinant mutant human Neu2 sialidase comprising a combination of any of the mutations contemplated herein. For example, the recombinant mutant sialidase enzyme may comprise a combination of 2, 3, 4, 5, 6, 7, 8, 9, 10, or more of the mutations contemplated herein. For example, the recombinant mutant sialidase enzyme may comprise a M1 deletion (ΔM1), MIA substitution, MID substitution, V6Y substitution, I187K substitution, C332A substitution, or a combination of any of the foregoing. For example, the recombinant mutant sialidase enzyme may comprise a combination of mutations selected from: M1A and V6Y; M1A and I187K; M1A and C332A; M1D and V6Y; M1D and I187K; M1D and C332A; ΔM1 and V6Y; ΔM1 and I187K; ΔM1 and C332A; V6Y and I187K; V6Y and C332A; I187K and C332A; M1A, V6Y, and I187K; M1A, V6Y, and C332A; M1A, I187K, and C332A; M1D, V6Y, and I187K; M1D, V6Y, and C332A; M1D, I187K, and C332A; ΔM1, V6Y, and I187K; ΔM1, V6Y, and C332A; ΔM1, I187K, and C332A; V6Y, I187K, and C332A; M1A, V6Y, I187K, and C332A; M1D, V6Y, I187K, and C332A; and ΔM1, V6Y, I187K, and C332A.

In certain embodiments, the recombinant mutant human sialidase comprises a substitution or combination of substitutions corresponding to a substitution or combination of substitutions listed in TABLE 7 herein below.

In certain embodiments, the recombinant mutant human sialidase comprises the amino acid sequence of SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73, or an amino acid sequence that has at least 85%, 90%, 95%, 96%, 97%, 98%, or 99% sequence identity to SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

In certain embodiments, the recombinant mutant human sialidase comprises the amino acid sequence of $X_1X_2SX_3PX_4LQKESVFQSGAHAYRIPALLYLPGQQSL$ LAFAEQRASKKDEHAELIVLRRGDYD APTHQVQWQAQEVVAQARLDGHRSMNPCPLYDAQ TGTLFLFFIAIPGQVTEQQQLQTRANVT $RLX_5QVTSTDHGRTWSSPRDLTDAAIGPAYREWSTFA$ VGPGHCLQLHDRARSLVVPAYAYRKL $HPX_6QRPIPSAFX_7FLSHDHGRTWARGHFVAQDTLEC$ QVAEVETGEQRVVTLNARSHLRARVQ $AQSTNDGLDFQX_8SQLVKKLVEPPPQGX_9QGSVISFPS$ PRSGPGSPAQWLLYTHPTHSWQRAD $LGAYLNPRPPAPEAWSEPX_{10}LLAKGSX_{11}AYSDLQSM$ $GTGPDGSPLFGX_{12}LYEANDYEEIVF$    LMFTLKQAF-PAEYLPQ (SEQ ID NO: 100), wherein $X_1$ is Ala, Arg, Asn, Asp, Gln, Glu, Gly, His, Leu, Lys, Met, Phe, Thr, Val, or not present, $X_2$ is Ala or Lys, $X_3$ is Asn or Leu, $X_4$ is Phe, Trp, Tyr or Val, $X_5$ is Ala, Cys, Ile, Ser, or Val, $X_6$ is Arg, Ile, or Lys, $X_7$ is Ala, Cys, Leu, or Val, $X_8$ is Glu or Lys, $X_9$ is Cys or Val, $X_{10}$ is Lys or Val, $X_{11}$ is Ala, Cys, Ser, or Val, and $X_{12}$ is Cys, Leu, or Val, and the sialidase comprises at least one mutation relative to wild-type human Neu2 (SEQ ID NO: 1).

In certain embodiments, the recombinant mutant human sialidase comprises the amino acid sequence of $X_1ASLPX_2LQKESVFQSGAHAYRIPALLYLPGQQSLLA$ FAEQRASKKDEHAELIVLRRGDYDA PTHQVQWQAQEVVAQARLDGHRSMNPCPLYDAQT GTLFLFFIAIPGQVTEQQQLQTRANVTR    LCQVT-STDHGRTWSSPRDLTDAAIGPAYREWS-TFAVGPGHCLQLHDRARSLVVPAYAYRKLH $PX_3QRPIPSAFCFLSHDHGRTWARGHFVAQDTLECQV$ AEVETGEQRVVTLNARSHLRARVQAQ    STNDG-LDFQESQLVKKLVEPPPQGCQGSVIS-FPSPRSGPGSPAQWLLYTHPTHSWQRADLGA $YLNPRPPAPEAWSEPVLLAKGSX_4AYSDLQSMGTGP$ GSPLFGCLYEANDYEEIVFLMFTLKQ AFPAEYLPQ (SEQ ID NO: 91), wherein $X_1$ is Ala, Arg, Asn, Asp, Gln, Glu, Gly, His, Leu, Lys, Met, Phe, Thr, Val, or not present, $X_2$ is Phe, Trp, Tyr or Val, $X_3$ is Arg, Ile, or Lys, and $X_4$ is Ala, Cys, Ser, or Val, and the sialidase comprises at least one mutation relative to wild-type human Neu2 (SEQ ID NO: 1). In certain embodiments, $X_1$ is Ala, Asp, Met, or not present, $X_2$ is Tyr or Val, $X_3$ is Ile or Lys, and $X_4$ is Ala or Cys.

In certain embodiments, the recombinant mutant human sialidase comprises a conservative substitution relative to a recombinant mutant human sialidase sequence disclosed herein. As used herein, the term "conservative substitution" refers to a substitution with a structurally similar amino acid. For example, conservative substitutions may include those within the following groups: Ser and Cys; Leu, Ile, and Val; Glu and Asp; Lys and Arg; Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLO-SUM 62 matrix), or the PAM substitution:p matrix (e.g., the PAM 250 matrix).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36:290-300; Altschul et al., (1997) Nucleic Acids Res. 25:3389-3402, incorporated by reference herein) are tailored for sequence similarity searching. For a discussion of basic issues in searching sequence databases see Altschul et al., (1994) Nature Genetics 6:119-129, which is fully incorporated by reference herein. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=−3; -r, reward for nucleotide match [Integer]: default=1; -e, expect value [Real]: default=10; -W, wordsize [Integer]: default=11 for nucleotides/28 for megablast/3 for proteins; -y, Dropoff (X) for blast extensions in bits: default=20 for blastn/7 for others; -X, X dropoff value for gapped alignment (in bits): default=15 for all programs, not applicable to blastn; and -Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50

(gap creation penalty) and LEN=3 (gap extension penalty). The equivalent settings in Bestfit protein comparisons are GAP=8 and LEN=2.

II. Fusion Proteins/Antibody Conjugates

To promote the selective removal of sialic acids on hypersialylated cancer cells and/or in the tumor microenvironment, it may be helpful to target a sialidase as described herein to such a cell or to such a tumor microenvironment. Additionally, in order to promote the removal of sialic acid by a sialidase in a subject, it may be helpful to extend the plasma half-life of the sialidase in the subject. These can be achieved by including the sialidase in a fusion protein and/or antibody conjugate (e.g., a chemically conjugated conjugate).

Accordingly, the invention further provides fusion proteins comprising a sialidase enzyme, or a functional fragment thereof, and a portion or fragment of an antibody, such as an immunoglobulin Fc domain (also referred to herein as an Fc domain), or an immunoglobulin antigen-binding domain (also referred to herein as an antigen-binding domain). In certain embodiments, the sialidase and antibody or portion thereof (e.g., immunoglobulin Fc domain or antigen-binding domain) are linked by a peptide bond or an amino acid linker.

As used herein, unless otherwise indicated, the term "fusion protein" is understood to refer to a single polypeptide chain comprising amino acid sequences based upon two or more separate proteins or polypeptide chains, where the two amino acid sequences may be fused together directly or via an intervening linker sequence, e.g., via an intervening amino acid linker. A nucleotide sequence encoding a fusion protein can, for example, be created using conventional recombinant DNA technologies.

In certain embodiments, the fusion protein comprises a tag, such as a Strep tag (e.g., a Strep II tag), a His tag (e.g., a 10× His tag (SEQ ID NO: 105)), a myc tag, or a FLAG tag. The tag can be located on the C-terminus or the N-terminus of the fusion protein. In certain embodiments, a fusion protein comprises a sialidase portion joined to a polypeptide comprising an immunoglobulin heavy chain in an N- to C-terminal orientation, wherein the sialidase portion comprises an N-terminal addition of MEDLRP (SEQ ID NO: 4), and a Strep II Tag is located on the C-terminus of the immunoglobulin heavy chain or the N-terminus of the sialidase portion.

a. Sialidase Portion

The sialidase portion of the fusion protein described herein can be any sialidase, e.g., a fungal, bacterial, non-human mammalian or human sialidase. In certain embodiments, the sialidase portion is a recombinant human sialidase comprising at least one mutation relative to a wild-type human sialidase, e.g., a substitution, deletion, or addition of at least one amino acid, as described above.

In certain embodiments, the sialidase is any recombinant mutant human sialidase disclosed herein, or a functional fragment thereof.

In certain embodiments, the sialidase portion comprises a C332A and C352L mutation. In certain embodiments, the sialidase comprises an N-terminal addition of MEDLRP (SEQ ID NO: 4) or EDLRP (SEQ ID NO: 3). In certain embodiments, the sialidase portion comprises a LSHSLST (SEQ ID NO: 22) peptide on the N-terminus. In certain embodiments, the sialidase portion comprises an N-terminal addition of MEDLRP (SEQ ID NO: 4) and an A2K substitution. In certain embodiments, the sialidase portion comprises an N-terminal addition of MEDLRP (SEQ ID NO: 4) and a C332A substitution. In certain embodiments, the sialidase portion comprises an N-terminal addition of MEDLRP (SEQ ID NO: 4), a C332A substitution, and a C352L substitution.

In certain embodiments, the sialidase portion comprises a M1 deletion (ΔM1), M1A substitution, M1D substitution, V6Y substitution, I187K substitution, C332A substitution, or a combination of any of the foregoing. For example, the sialidase portion may comprise a combination of mutations selected from: M1A and V6Y; M1A and I187K; M1A and C332A; M1D and V6Y; M1D and I187K; M1D and C332A; ΔM1 and V6Y; ΔM1 and I187K; ΔM1 and C332A; V6Y and I187K; V6Y and C332A; I187K and C332A; M1A, V6Y, and I187K; M1A, V6Y, and C332A; M1A, I187K, and C332A; M1D, V6Y, and I187K; M1D, V6Y, and C332A; M1D, I187K, and C332A; ΔM1, V6Y, and I187K; ΔM1, V6Y, and C332A; ΔM1, I187K, and C332A; V6Y, I187K, and C332A; M1A, V6Y, I187K, and C332A; M1D, V6Y, I187K, and C332A; and ΔM1, V6Y, I187K, and C332A.

In certain embodiments, the sialidase portion comprises the amino acid sequence of SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73, or an amino acid sequence that has at least 85%, 90%, 95%, 96%, 97%, 98%, or 99% sequence identity to SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

b. Antibody Portion

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. Examples of antigen-binding fragments include Fab, Fab', (Fab')$_2$, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

In certain embodiments, the fusion protein comprises an immunoglobulin Fc domain. As used herein, unless otherwise indicated, the term "immunoglobulin Fc domain" refers to a fragment of an immunoglobulin heavy chain constant region which, either alone or in combination with a second immunoglobulin Fc domain, is capable of binding to an Fc receptor. An immunoglobulin Fc domain may include, e.g., immunoglobulin CH2 and CH3 domains. An immunoglobulin Fc domain may include, e.g., immunoglobulin CH2 and CH3 domains and an immunoglobulin hinge region. Boundaries between immunoglobulin hinge regions, CH2, and CH3 domains are well known in the art, and can be found, e.g., in the PROSITE database (available on the world wide web at prosite.expasy.org).

In certain embodiments, the immunoglobulin Fc domain is derived from a human IgG1, IgG2, IgG3, IgG4, IgA1, IgA2, IgD, IgE, and IgM Fc domain. A single amino acid substitution (S228P according to Kabat numbering; designated IgG4Pro) may be introduced to abolish the heterogeneity observed in recombinant IgG4 antibody. Sec Angal, S. et al. (1993) MOL. IMMUNOL. 30:105-108.

In certain embodiments, the immunoglobulin Fc domain is derived from a human IgG1 isotype or another isotype that elicits antibody-dependent cell-mediated cytotoxicity (ADCC) and/or complement mediated cytotoxicity (CDC). In certain embodiments, the immunoglobulin Fc domain is derived from a human IgG1 isotype (e.g., SEQ ID NO: 31 or SEQ ID NO: 69).

In certain embodiments, the immunoglobulin Fc domain is derived from a human IgG4 isotype or another isotype that elicits little or no antibody-dependent cell-mediated cytotoxicity (ADCC) and/or complement mediated cytotoxicity (CDC). In certain embodiments, the immunoglobulin Fc domain is derived from a human IgG4 isotype.

In certain embodiments, the immunoglobulin Fc domain comprises either a "knob" mutation, e.g., T366Y or a "hole" mutation, e.g., Y407T for heterodimerization with a second polypeptide (residue numbers according to EU numbering, Kabat, E. A., et al. (1991) SEQUENCES OF PROTEINS OF IMMUNO-LOGICAL INTEREST, FIFTH EDITION, U.S. Department of Health and Human Services, NIH Publication No. 91-3242).

In certain embodiments, the fusion protein comprises an immunoglobulin antigen-binding domain. The inclusion of such a domain may improve targeting of a fusion protein to a sialylated cancer cell and/or to the tumor microenvironment. As used herein, unless otherwise indicated, the term "immunoglobulin antigen-binding domain" refers to a polypeptide that, alone or in combination with another immunoglobulin antigen-binding domain, defines an antigen-binding site. Exemplary immunoglobulin antigen-binding domains include, for example, immunoglobulin heavy chain variable region and an immunoglobulin light chain variable region, where the variable regions together define an antigen binding site.

The immunoglobulin antigen-binding domain and/or antigen binding site can be derived from an antibody selected from, for example, adecatumumab, ascrinvacumab, cixutumumab, conatumumab, daratumumab, drozitumab, duligotumab, durvalumab, dusigitumab, enfortumab, enoticumab, epratuzumab, figitumumab, ganitumab, glembatumumab, intetumumab, ipilimumab, iratumumab, icrucumab, lexatumumab, lucatumumab, mapatumumab, narnatumab, necitumumab, nesvacumab, ofatumumab, olaratumab, panitumumab, patritumab, pritumumab, radretumab, ramucirumab, rilotumumab, robatumumab, seribantumab, tarextumab, teprotumumab, tovetumab, vantictumab, vesencumab, votumumab, zalutumumab, flanvotumab, altumomab, anatumomab, arcitumomab, bectumomab, blinatumomab, detumomab, ibritumomab, minretumomab, mitumomab, moxetumomab, naptumomab, nofetumomab, pemtumomab, pintumomab, racotumomab, satumomab, solitomab, taplitumomab, tenatumomab, tositumomab, tremelimumab, abagovomab, atezolizumab, durvalumab, avelumab, igovomab, oregovomab, capromab, edrecolomab, nacolomab, amatuximab, bavituximab, brentuximab, cetuximab, derlotuximab, dinutuximab, ensituximab, futuximab, girentuximab, indatuximab, isatuximab, margetuximab, rituximab, siltuximab, ublituximab, ecromeximab, abituzumab, alemtuzumab, bevacizumab, bivatuzumab, brontictuzumab, cantuzumab, cantuzumab, citatuzumab, clivatuzumab, dacetuzumab, demcizumab, dalotuzumab, denintuzumab, elotuzumab, emactuzumab, emibetuzumab, enoblituzumab, etaracizumab, farletuzumab, ficlatuzumab, gemtuzumab, imgatuzumab, inotuzumab, labetuzumab, lifastuzumab, lintuzumab, lirilumab, lorvotuzumab, lumretuzumab, matuzumab, milatuzumab, moxetumomab, nimotuzumab, obinutuzumab, ocaratuzumab, otlertuzumab, onartuzumab, oportuzumab, parsatuzumab, pertuzumab, pidilizumab, pinatuzumab, polatuzumab, sibrotuzumab, simtuzumab, tacatuzumab, tigatuzumab, trastuzumab, tucotuzumab, urelumab, vandortuzumab, vanucizumab, veltuzumab, vorsetuzumab, sofituzumab, catumaxomab, ertumaxomab, depatuxizumab, ontuxizumab, blontuvetmab, tamtuvetmab, nivolumab, pembrolizumab, epratuzumab, MEDI9447, urelumab, utomilumab, hu3F8, hu14.18-IL-2, 3F8/OKT3BsAb, lirilumab, BMS-986016 pidilizumab, AMP-224, AMP-514, BMS-936559, atezolizumab, and avelumab. In certain embodiments, the immunoglobulin antigen-binding domain can be derived from an antibody selected from trastuzumab, cetuximab, daratumumab, girentuximab, panitumumab, ofatumumab, and rituximab.

In certain embodiments, the immunoglobulin antigen-binding domain is derived from trastuzumab. The trastuzumab heavy chain amino acid sequence is depicted in SEQ ID NO: 40, and the trastuzumab light chain amino acid sequence is depicted in SEQ ID NO: 41. The amino acid sequence of an exemplary scFv derived from trastuzumab is depicted in SEQ ID NO: 42.

The immunoglobulin antigen-binding domain and/or antigen binding site can be derived from an antibody that binds a cancer antigen selected from, for example, adenosine A2a receptor (A2aR), A kinase anchor protein 4 (AKAP4), B melanoma antigen (BAGE), brother of the regulator of imprinted sites (BORIS), breakpoint cluster region Abelson tyrosine kinase (BCR/ABL), CA125, CAIX, CD19, CD20, CD22, CD30, CD33, CD52, CD73, CD137, carcinoembryonic antigen (CEA), CS1, cytotoxic T-lymphocyte-associated antigen 4 (CTLA-4), estrogen receptor binding site associated antigen 9 (EBAG9), epidermal growth factor (EGF), epidermal growth factor receptor (EGFR), EGF-like module receptor 2 (EMR2), epithelial cell adhesion molecule (EpCAM) (17-1A), FR-alpha, G antigen (GAGE), disialoganglioside GD2 (GD2), glycoprotein 100 (gp100), human epidermal growth factor receptor 2 (Her2), hepatocyte growth factor (HGF), human papillomavirus 16 (HPV-16), heat-shock protein 105 (HSP105), isocitrate dehydrogenase type 1 (IDH1), idiotype (NeuGcGM3), indoleamine-2,3-dioxygenase 1 (IDO1), IGF-1, IGF1R, IGG1K, killer cell immunoglobulin-like receptor (KIR), lymphocyte activation gene 3 (LAG-3), lymphocyte antigen 6 complex K (LY6K), Matrix-metalloproteinase-16 (MMP16), melanotransferrin (MFI2), melanoma antigen 3 (MAGE-A3), melanoma antigen C2 (MAGE-C2), melanoma antigen D4 (MAGE-D4), melanoma antigen recognized by T-cells 1 (Melan-A/MART-1), N-methyl-N'-nitroso-guanidine human osteosarcoma transforming gene (MET), mucin 1 (MUC1), mucin 4 (MUC4), mucin 16 (MUC16), New York esophageal squamous cell carcinoma 1 (NY-ESO-1), prostatic acid phosphatase (PAP), programmed cell death receptor 1 (PD-1), programmed cell death receptor ligand 1 (PD-L1), phosphatidylserine, preferentially expressed antigen of melanoma (PRAME), prostate specific antigen (PSA), protein tyrosine kinase 7 (PTK7, also known as colon carcinoma kinase 4 (CCK4)), receptor tyrosine kinase orphan receptor 1 (ROR1), scatter factor receptor kinase, sialyl-Tn, sperm-associated antigen 9 (SPAG-9), synovial sarcoma X-chromosome breakpoint 1 (SSX1), survivin, telomerase, T-cell immunoglobulin domain and mucin domain-3 (TIM-3), vascular endothelial growth factor (VEGF) (e.g., VEGF-A), vascular endothelial growth factor Receptor 2 (VEGFR2), V-domain immunoglobulin-containing suppressor of T-cell activation (VISTA), Wilms' Tumor-1 (WT1), X chromosome antigen 1b (XAGE-1b), 5T4, Mesothelin, Glypican 3

(GPC3), Folate Receptor α (FRα), Prostate Specific Membrane Antigen (PSMA), cMET, CD38, B Cell Maturation Antigen (BCMA), CD123, CLDN6, CLDN9, LRRC15, PRLR (Prolactin Receptor), RING finger protein 43 (RNF43), Uroplakin-1 B (UPK1 B), tumor necrosis factor superfamily member 9 (TNFSF9), tumor necrosis factor receptor superfamily member 21 (TNFSRF21), bone morphogenetic protein receptor type-1B (BMPR1B), Kringle domain-containing transmembrane protein 2 (KREMEN2), Delta-like protein 3 (DLL3), Siglec7 and Siglec9. Additional exemplary cancer antigens include those found on cancer stem cells, e.g., SSEA3, SSEA4, TRA-1-60, TRA-1-81, SSEA1, CD133 (AC133), CD90 (Thy-1), CD326 (Ep-CAM), Cripto-1 (TDGF1), PODXL-1 (Podocalyxin-like protein 1), ABCG2, CD24, CD49f (Integrin α6), Notch2, CD146 (MCAM), CD10 (Neprilysin), CD117 (c-KIT), CD26 (DPP-4), CXCR4, CD34, CD271, CD13 (Alanine aminopeptidase), CD56 (NCAM), CD105 (Endoglin), LGR5, CD114 (CSF3R), CD54 (ICAM-1), CXCR1, 2, TIM-3 (HAVCR2), CD55 (DAF), DLL4 (Delta-like ligand 4), CD20 (MS4A1), and CD96.

The invention further provides antibody conjugates containing one or more of the fusion proteins disclosed herein. As used herein, unless otherwise indicated, the term "antibody conjugate" is understood to refer to an antibody, or a functional fragment thereof, that comprises antigen-binding activity and/or Fc receptor-binding activity, conjugated (e.g., covalently coupled) to an additional functional moiety. In certain embodiments, the antibody or functional antibody fragment is conjugated to a sialidase enzyme, e.g., a recombinant mutant human sialidase enzyme disclosed herein. In certain embodiments, an antibody conjugate comprises a single polypeptide chain. In certain embodiments, an antibody conjugate comprises two, three, four, or more polypeptide chains that are covalently or non-covalently associated together to produce a multimeric complex, e.g., a dimeric, trimeric or tetrameric complex.

TABLE 1 shows antibodies and antibody-drug conjugates suitable for use in accordance with the present invention, the antigen bound by the antibody or antibody-drug conjugate, and for certain antibodies, the type of cancer targeted by the antibody or antibody-drug conjugate.

TABLE 1

| Antibody or antibody-drug conjugate | Cancer Antigen | Cancer Type |
|---|---|---|
| oregovomab | CA125 | |
| girentuximab | CAIX | |
| obinutuzumab | CD20 | |
| ofatumumab | CD20 | |
| rituximab | CD20 | |
| alemtuzumab | CD52 | |
| Ipilimumab | cytotoxic T-lymphocyte-associated antigen 4 (CTLA-4) | |
| tremelimumab | CTLA-4 | |
| Cetuximab | epidermal growth factor receptor (EGFR) | |
| necitumumab | EGFR | |
| panitumumab | EGFR | |
| zalutumumab | EGFR | |
| edrecolomab | epithelial cell adhesion molecule (EpCAM) (17-1A) | |
| farletuzumab | FR-alpha | |
| Pertuzumab | human epidermal growth factor receptor 2 (Her2) | |
| trastuzumab | Her2 | |
| rilotumumab | HGF | |
| figitumumab | IGF-1 | |
| Ganitumab | IGF1R | |
| durvalumab | IGG1K | |
| bavituximab | Phosphatidylserine | |
| onartuzumab | scatter factor receptor kinase | |
| bevacizumab | vascular endothelial growth factor-A (VEGF-A) | |
| ramucirumab | vascular endothelial growth factor Receptor 2 (VEGFR2) | |
| blinatumomab | CD19 | acute lymphoblastic leukemia (ALL) |
| Rituximab; ofatumumab, ibritumomab (e.g., $^{90}$Y-ibritumomab; tositumomab (e.g., $^{131}$I-tositumomab | CD20 | non-Hodgkin's lymphoma (NHL), chronic lymphocytic leukemia (CLL) B-cell NHL pre-B ALL |
| brentuximab (e.g., brentuximab vedotin | CD30 | Hodgkin's lymphoma |
| gemtuzumab (e.g., gemtuzumab ozogamicin | CD33 | acute myelogenous leukemia (AML) |
| Alemtuzumab | CD52 | CLL |
| Ipilimumab | cytotoxic T-lymphocyte-associated antigen 4 (CTLA-4) | Unresectable or metastatic melanoma |
| cetuximab; panitumumab | epidermal growth factor receptor (EGFR) | colorectal cancer (CRC) Head and Neck |
| Catumaxomab | epithelial cell adhesion molecule (EpCAM) | Malignant ascites |
| trastuzumab; | human epidermal growth factor | Breast |

TABLE 1-continued

| Antibody or antibody-drug conjugate | Cancer Antigen | Cancer Type |
|---|---|---|
| pertuzumab | receptor 2 (HER2) | |
| nivolumab, pembrolizumab | programmed cell death receptor 1 (PD-1) | Metastatic melanoma, non-small cell lung cancer (NSCLC) |
| Bevacizumab | vascular endothelial growth factor (VEGF) | Breast, Cervical CRC, NSCLC renal cell carcinoma (RCC), Ovarian Glioblastoma |
| Ramucirumab | vascular endothelial growth factor receptor 2 (VEGF-R2) | Gastric NSCLC |
| Epratuzumab; moxetumomab; inotuzumab (e.g., inotuzumab ozogamicin) | CD22 | acute lymphoblastic leukemia (ALL) |
| MEDI9447 | CD73 | Advanced solid tumors |
| Urelumab; utomilumab (PF-05082566) | CD137 | Advanced solid tumors |
| Elotuzumab | CD2 subset 1 (CS1) | Multiple myeloma |
| Tremelimumab | cytotoxic T-lymphocyte-associated antigen 4 (CTLA-4) | Malignant mesothelioma |
| Necitumumab | epidermal growth factor receptor (EGFR) | non-small cell lung cancer (NSCLC) |
| dinutuximab, hu3F8; hu14.18-IL-2; 3F8/OKT3BsAb | disialoganglioside GD2 (GD2) | Neuroblastoma Retinoblastoma Melanoma other solid tumors |
| Racotumomab | Idiotype (NeuGcGM3) | NSCLC, Breast Melanoma |
| Lirilumab | killer cell immunoglobulin-like receptor (KIR) | Lymphoma |
| BMS-986016 | lymphocyte activation gene 3 (LAG-3) | Breast, Hematological, Advanced solid tumors |
| Onartuzumab | N-methyl-N'-nitroso-guanidine human osteosarcoma transforming gene (MET) | NSCLC |
| abagovomab; oregovomab | mucin 16 (MUC16) | Ovarian |
| pidilizumab; AMP-224; AMP-514 | programmed cell death receptor 1 (PD-1) | B-cell lymphoma Melanoma, CRC |
| BMS-936559; atezolizumab; durvalumab; avelumab | programmed cell death receptor ligand 1 (PD-L1) | NSCLC, renal cell carcinoma (RCC) Bladder, Breast Melanoma, squamous cell carcinoma of the head and neck (SCCHN) |
| naptumomab (e.g., naptumomab estafenatox) | 5T4 | RCC, CRC Prostate | c. Linker

In certain embodiments, the sialidase portion of the fusion protein can be linked or fused directly to the antibody portion (e.g., immunoglobulin Fc domain and/or immunoglobulin antigen-binding domain) of the fusion protein. In other embodiments, the sialidase portion can be covalently bound to the antibody portion by a linker.

The linker may couple, with one or more natural amino acids, the sialidase, or functional fragment thereof, and the antibody portions or fragments, where the amino acid (for example, a cysteine amino acid) may be introduced by site-directed mutagenesis. The linker may include one or more unnatural amino acids. It is contemplated that, in certain circumstances, a linker containing for example, one or more sulfhydryl reactive groups (e.g., a maleimide) may covalently link a cysteine in the sialidase portion or the antibody portion that is a naturally occurring cysteine residue or is the product of site-specific mutagenesis.

The linker may be a cleavable linker or a non-cleavable linker. Optionally or in addition, the linker may be a flexible linker or an inflexible linker.

The linker should be a length sufficiently long to allow the sialidase and the antibody portions to be linked without steric hindrance from one another and sufficiently short to retain the intended activity of the fusion protein. The linker preferably is sufficiently hydrophilic to avoid or minimize instability of the fusion protein. The linker preferably is sufficiently hydrophilic to avoid or minimize insolubility of the fusion protein. The linker should be sufficiently stable in vivo (e.g., it is not cleaved by serum, enzymes, etc.) to permit the fusion protein to be operative in vivo.

The linker may be from about 1 angstroms (Å) to about 150 Å in length, or from about 1 Å to about 120 Å in length, or from about 5 Å to about 110 Å in length, or from about 10 Å to about 100 Å in length. The linker may be greater than about 2, 3, 4, 5, 6, 7, 8, 9, 10, 11, 12, 13, 14, 15, 16, 17, 18, 19, 20, 25, 27, 30 or greater angstroms in length and/or less than about 110, 100, 90, 85, 80, 75, 70, 65, 60, 55, 50, 45, 43, 42, 41, 40, 39, 38, 37, 36, 35, 34, 33, 32, 31, or fewer Å in length. Furthermore, the linker may be about 5, 10, 15, 20, 25, 30, 35, 40, 45, 50, 55, 60, 65, 70, 75, 80, 85, 90, 95, 100, 110, and 120 Å in length.

In certain embodiments, the linker comprises a polypeptide linker that connects or fuses the sialidase portion of the fusion protein to the antibody portion (e.g., immunoglobulin Fc domain and/or immunoglobulin antigen-binding domain) of the fusion protein. For example, it is contemplated that a gene encoding a sialidase portion linked directly or indirectly (for example, via an amino acid containing linker) to an antibody portion can be created and expressed using conventional recombinant DNA technologies. For example, the amino terminus of a sialidase portion can be linked to the carboxy terminus of either the light or the heavy chain of an antibody portion. For example, for a Fab fragment, the amino terminus or carboxy terminus of the sialidase can be linked to the first constant domain of the heavy antibody chain (CH1). When a linker is employed, the linker may comprise hydrophilic amino acid residues, such as Gln, Ser, Gly, Glu, Pro, His and Arg. In certain embodiments, the linker is a peptide containing 1-25 amino acid residues, 1-20 amino acid residues, 2-15 amino acid residues, 3-10 amino acid residues, 3-7 amino acid residues, 4-25 amino acid residues, 4-20 amino acid residues, 4-15 amino acid residues, 4-10 amino acid residues, 5-25 amino acid residues, 5-20 amino acid residues, 5-15 amino acid residues, or 5-10 amino acid residues. Exemplary linkers include glycine and serine-rich linkers, e.g., (GlyGlyPro)$_n$ (SEQ ID NO: 106), or (GlyGlyGlyGlySer)$_n$ (SEQ ID NO: 107), where n is 1-5. In certain embodiments, the linker is (Gly$_4$Ser)$_2$ (SEQ ID NO: 108). Additional exemplary linker sequences are disclosed, e.g., in George et al. (2003) PROTEIN ENGINEERING 15:871-879, and U.S. Pat. Nos. 5,482,858 and 5,525,491.

d. Antibody Conjugates

The invention further provides antibody conjugates comprising a fusion protein disclosed herein. The antibody conjugate may comprise a single polypeptide chain (i.e., a fusion protein disclosed herein) or, the antibody conjugate may comprise additional polypeptide chains (e.g., one, two, or three additional polypeptide chains). For example, an antibody conjugate may comprise a first polypeptide (fusion protein) comprising a recombinant mutant human sialidase enzyme and an immunoglobulin heavy chain, and a second polypeptide comprising an immunoglobulin light chain, where, for example, the immunoglobulin heavy and light chains together define a single antigen-binding site.

In certain embodiments, the antibody conjugate can include a single sialidase. In other embodiments, the antibody conjugate can include more than one (e.g., two) sialidases. If more than one sialidase is included, the sialidases can be the same or different. In certain embodiments, the antibody conjugate can include a single antigen-binding site. In other embodiments, the antibody conjugate can include more than one (e.g., two) antigen-binding sites. If two antigen-binding sites are used, they can be the same or different. In certain embodiments, the antibody conjugate comprises an immunoglobulin Fc fragment.

In certain embodiments, the antibody conjugate comprises one or two immunoglobulin heavy chains, or a functional fragment thereof. In certain embodiments, the antibody conjugate comprises one or two immunoglobulin light chains, or a functional fragment thereof. In certain embodiments, the antibody conjugate comprises a sialidase fused to the N- or C-terminus of an immunoglobulin heavy chain or an immunoglobulin light chain.

FIG. 9 depicts exemplary antibody conjugate constructs containing one or more sialidase enzymes. For example, in FIG. 9A, a first antigen-binding site is depicted as 10, a second antigen-binding site is depicted as 20, a sialidase is depicted as 30, and a Fab is depicted as 40. In each of the constructs depicted in FIGS. 9A-9I it is understood that the Fc may optionally be modified in some manner, e.g. using Knobs-into-Holes type technology, e.g., as depicted by 50 in FIG. 9B. Throughout FIG. 9 similar structures are depicted by similar schematic representations.

Figures 9A, 9B:
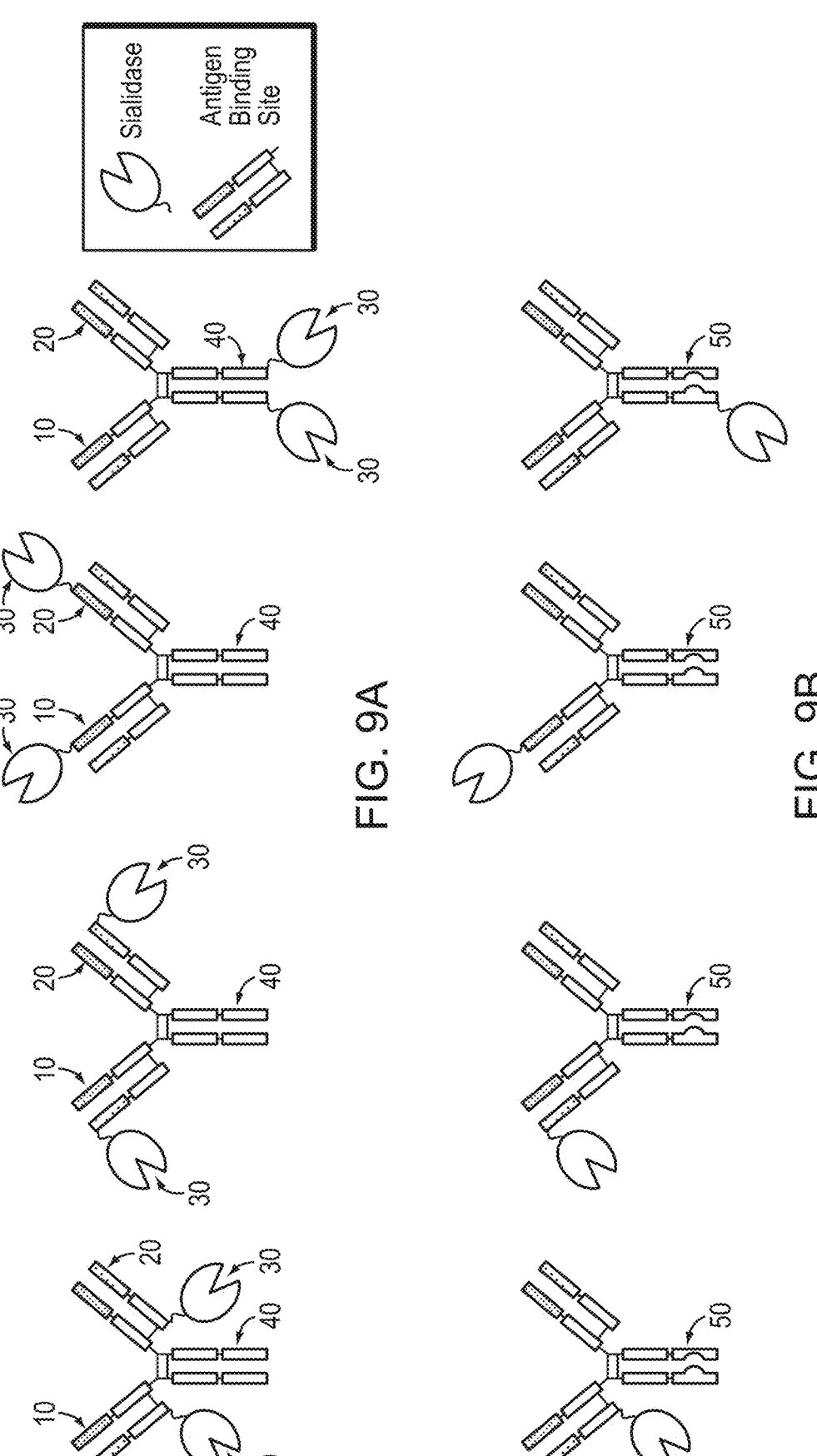
FIGS. 9A-9I depict schematic representations of certain antibody conjugate constructs containing a sialidase enzyme, e.g., a human sialidase enzyme, and an antigen binding site. For each antibody conjugate construct that contains more than one (e.g., two) sialidase, each sialidase may be the same or different. For each antibody conjugate construct that contains more than one (e.g., two) antigen binding site, each antigen binding site may be the same or different.

FIG. 9A depicts antibody conjugate constructs comprising a first polypeptide comprising a first immunoglobulin light chain; a second polypeptide comprising a first immunoglobulin heavy chain; a third polypeptide comprising a second immunoglobulin heavy chain; and a fourth polypeptide comprising a second immunoglobulin light chain. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site as depicted as 10, and the third polypeptide and the fourth polypeptide together define a second antigen-binding site as depicted as 20. A sialidase enzyme as depicted as 30 can be conjugated to the N- or C-terminus of the first and second immunoglobulin light chain or the first and second immunoglobulin heavy chain.

FIG. 9B depicts antibody conjugate constructs comprising a first polypeptide comprising a first immunoglobulin light chain; a second polypeptide comprising a first immunoglobulin heavy chain; a third polypeptide comprising a second immunoglobulin heavy chain; and a fourth polypeptide comprising a second immunoglobulin light chain. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site, and the third polypeptide and the fourth polypeptide together define a second antigen-binding site. A sialidase enzyme can be conjugated to the N- or C-terminus of the first immunoglobulin light chain or the first immunoglobulin heavy chain.

Figures 9C, 9D, 9E, 9F:
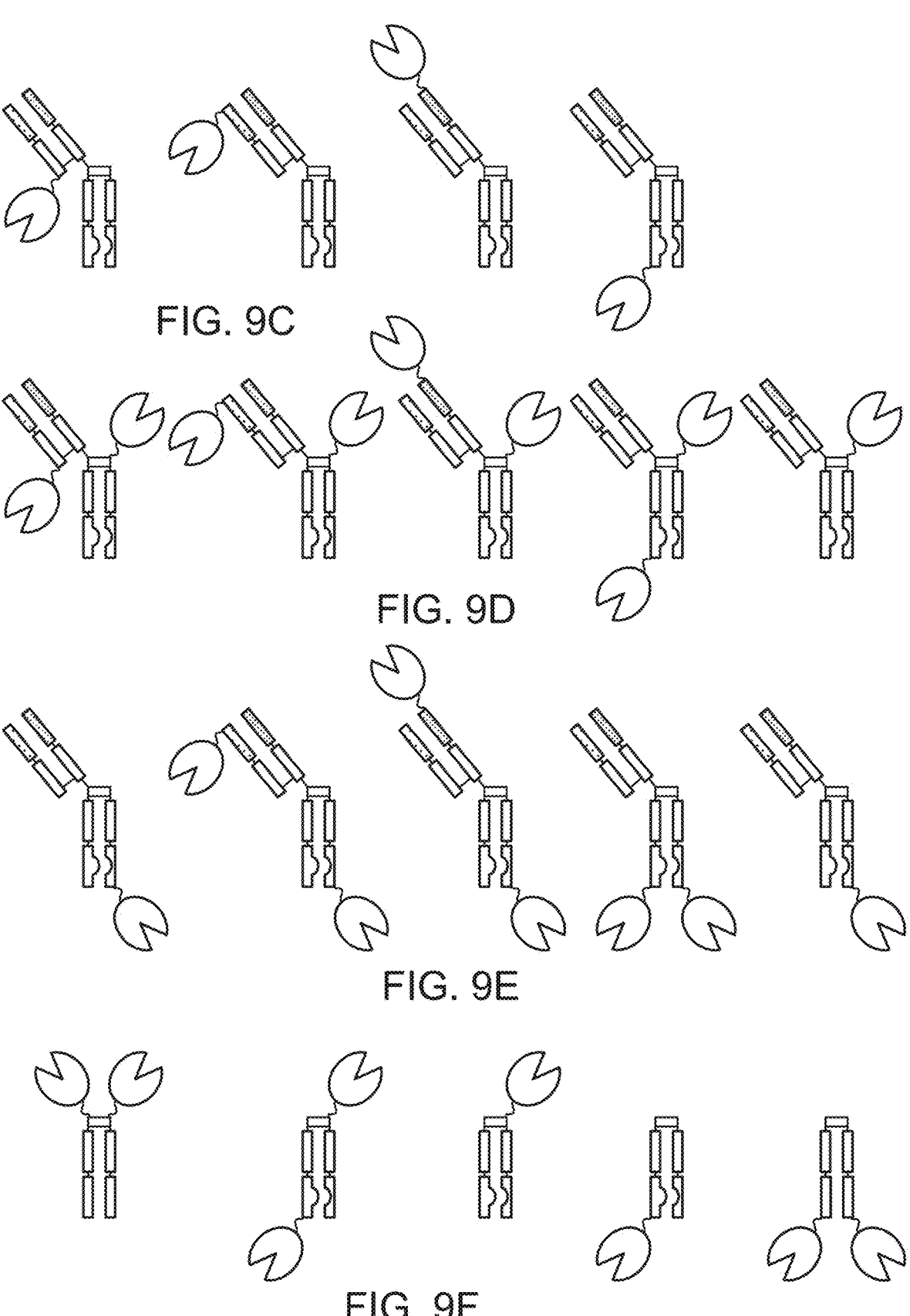

FIG. 9C depicts antibody conjugate constructs comprising a first polypeptide comprising an immunoglobulin light chain; a second polypeptide comprising an immunoglobulin heavy chain; and a third polypeptide comprising an immunoglobulin Fc domain. The first and second polypeptides can be covalently linked together and the second and third polypeptides can be covalently linked together. The covalent linkages can be disulfide bonds. In certain embodiments, the first polypeptide and the second polypeptide together define an antigen-binding site. A sialidase enzyme can be conjugated to the N- or C-terminus of the first immunoglobulin light chain or the first immunoglobulin heavy chain.

FIG. 9D depicts antibody conjugate constructs comprising a first polypeptide comprising an immunoglobulin light chain; a second polypeptide comprising an immunoglobulin heavy chain; and a third polypeptide comprising an immunoglobulin Fc domain and a first sialidase enzyme. The first and second polypeptides can be covalently linked together and the second and third polypeptides can be covalently linked together. The covalent linkages can be disulfide bonds. The third polypeptide comprises the sialidase and the immunoglobulin Fc domain in an N- to C-terminal orientation. In certain embodiments, the first polypeptide and the second polypeptide together define an antigen-binding site. An optional second sialidase enzyme can be conjugated to the N- or C-terminus of the first immunoglobulin light chain or the first immunoglobulin heavy chain.

FIG. 9E depicts antibody conjugate constructs comprising a first polypeptide comprising an immunoglobulin light chain; a second polypeptide comprising an immunoglobulin heavy chain; and a third polypeptide comprising an immunoglobulin Fc domain and a first sialidase enzyme. The first and second polypeptides can be covalently linked together and the second and third polypeptides can be covalently linked together. The covalent linkages can be disulfide bonds. The third polypeptide comprises the immunoglobulin Fc domain and the sialidase in an N- to C-terminal orientation. In certain embodiments, the first polypeptide and the second polypeptide together define an antigen-binding site. An optional second sialidase enzyme can be conjugated to the N- or C-terminus of the first immunoglobulin light chain or the first immunoglobulin heavy chain.

FIG. 9F depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N- or C-terminus of the first immunoglobulin Fc domain or to the N- or C-terminus of the second immunoglobulin Fc domain. An optional second sialidase enzyme can be conjugated to the N- or C-terminus of the first immunoglobulin Fc domain or to the N- or C-terminus of the second immunoglobulin Fc domain.

Figure 9G:
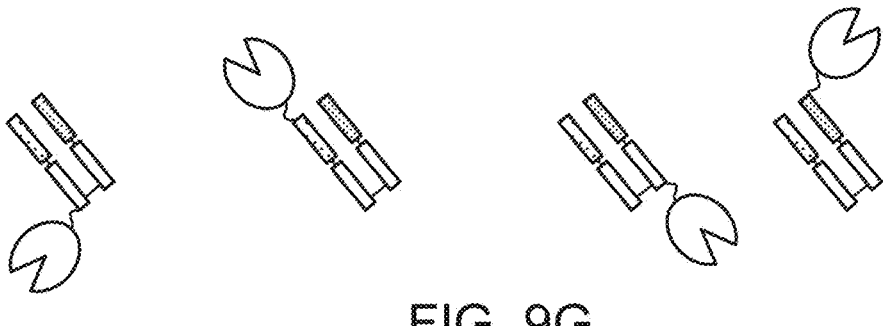

FIG. 9G depicts antibody conjugate constructs comprising a first polypeptide comprising an immunoglobulin light chain; and a second polypeptide comprising an immunoglobulin heavy chain variable region. The first and second polypeptides can be covalently linked together. The covalent linkages can be disulfide bonds. In certain embodiments, the first polypeptide and the second polypeptide together define an antigen-binding site. The sialidase enzyme can be conjugated to the N- or C-terminus of the immunoglobulin light chain or the immunoglobulin heavy chain variable region.

Figure 9H:
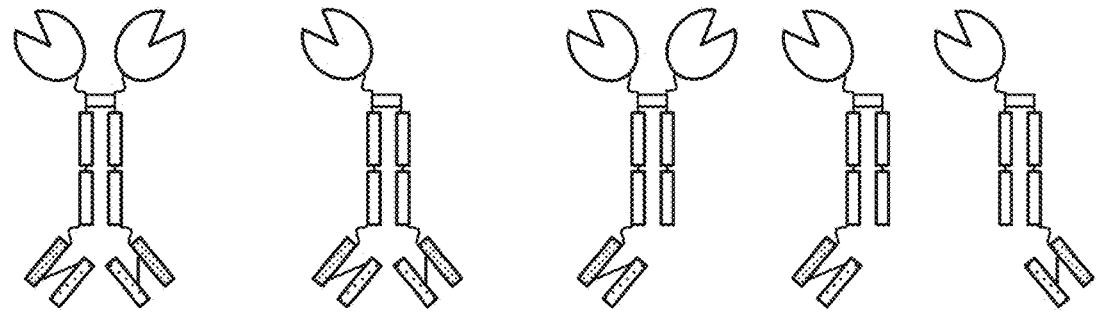

FIG. 9H depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N-terminus of the first immunoglobulin Fc domain or the second immunoglobulin Fc domain. An optional second sialidase enzyme can be conjugated to the N-terminus of the second immunoglobulin Fc domain or the first immunoglobulin Fc domain, respectively. A single chain variable fragment (scFv) can be conjugated to the C-terminus of the first immunoglobulin Fc domain or the second immunoglobulin Fc domain. An optional second single chain variable fragment (scFv) can be conjugated to the C-terminus of the first immunoglobulin Fc domain or the second immunoglobulin Fc domain, respectively.

Figure 9I:
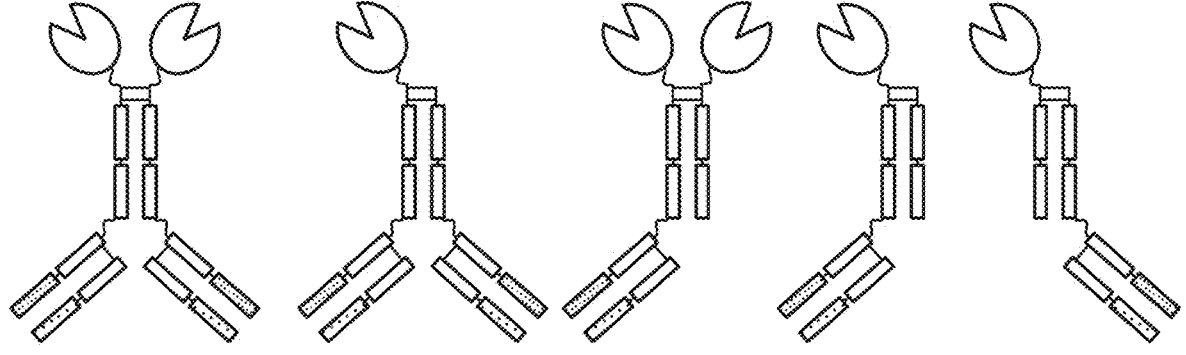

FIG. 9I depicts antibody conjugate constructs similar to those depicted in FIG. 9H except that each scFv is replaced with an immunoglobulin antigen binding fragment, e.g., an Fab. For example, FIG. 9I depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N-terminus of the first immunoglobulin Fc domain or the second immunoglobulin Fc domain. An optional second sialidase enzyme can be conjugated to the N-terminus of the second immunoglobulin Fc domain or the first immunoglobulin Fc domain, respectively. An antibody fragment (Fab) can be conjugated or fused to the C-terminus of the first immunoglobulin Fc domain or the second immunoglobulin Fc domain. An optional second antibody fragment (Fab) can be conjugated or fused to the C-terminus of the second immunoglobulin Fc domain or the first immunoglobulin Fc domain, respectively. In the case of a fusion, the C terminus of the Fc domain is linked (either by a bond or an amino acid linker) to a first polypeptide chain defining an immunoglobulin antigen binding fragment. In the case of antibodies that have an antigen binding site defined by a single variable region, then this may be sufficient to impart binding affinity to a target antigen. In other instances, e.g., in the case of a human antibody, the first polypeptide chain defining an immunoglobulin antigen binding fragment can be conjugated (e.g., covalently conjugated, e.g., via a disulfide bond) to a second polypeptide chain defining an immunoglobulin antigen binding fragment, there the two antigen binding fragments together define an antigen binding site for binding the target antigen.

Figures 10A, 10B, 10C:
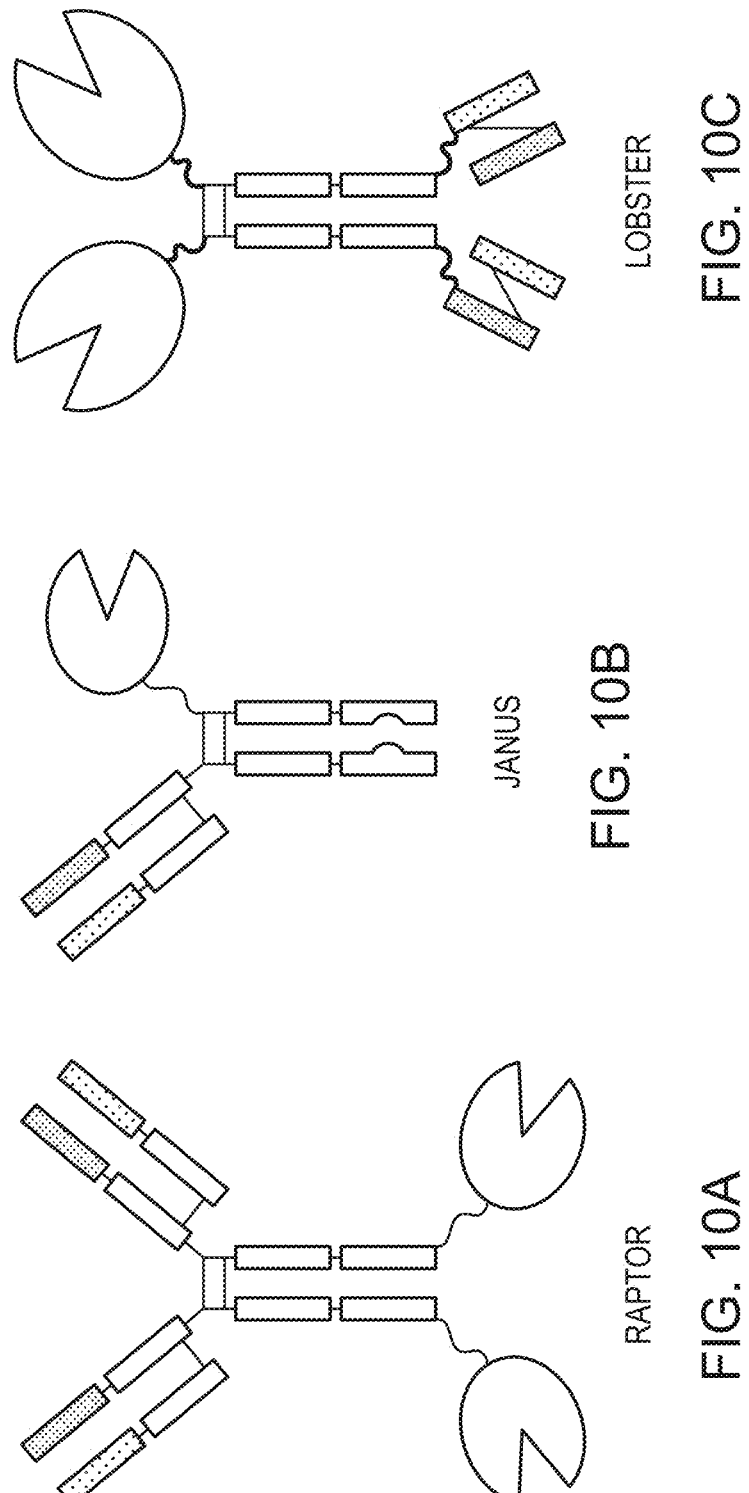
FIGS. 10A-C are schematic representations of fusion protein conjugates referred to as a Raptor antibody sialidase conjugate (FIG. 10A), a Janus antibody sialidase conjugate (FIG. 10B), and a Lobster antibody sialidase conjugate (FIG. 10C).

In certain embodiments, the antibody conjugate comprises a first polypeptide comprising a first immunoglobulin light chain; a second polypeptide comprising a first immunoglobulin heavy chain and a first sialidase; a third polypeptide comprising a second immunoglobulin heavy chain and a second sialidase; and a fourth polypeptide comprising a second immunoglobulin light chain. An example of this embodiment is shown in FIG. 10A. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site, and the third polypeptide and the fourth polypeptide together define a second antigen-binding site. In certain embodiments, the second and third polypeptides comprise the first and second immunoglobulin heavy chain and the first and second sialidase, respectively, in an N- to C-terminal orientation. In certain embodiments, the second and third polypeptides comprise the first and second sialidase and the first and second immunoglobulin heavy chain, respectively, in an N- to C-terminal orientation.

In certain embodiments, the antibody conjugate comprises a first polypeptide comprising an immunoglobulin light chain; a second polypeptide comprising an immunoglobulin heavy chain; and a third polypeptide comprising an immunoglobulin Fc domain and a sialidase. An example of this embodiment is shown in FIG. 10B. The first and second polypeptides can be covalently linked together and the second and third polypeptides can be covalently linked together. The covalent linkages can be disulfide bonds. In certain embodiments, the first polypeptide and the second polypeptide together define an antigen-binding site. In certain embodiments, the third polypeptide comprises the sialidase and the immunoglobulin Fc domain in an N- to C-terminal orientation or the immunoglobulin Fc domain and the sialidase in an N- to C-terminal orientation.

In certain embodiments, the first polypeptide comprises the amino acid sequence of SEQ ID NO: 49, or an amino acid sequence that has at least 85%, 90%, 95%, 96%, 97%, 98%, or 99% sequence identity to SEQ ID NO: 49. In certain embodiments, the second polypeptide comprises the amino acid sequence of SEQ ID NO: 50 or an amino acid sequence that has at least 85%, 90%, 95%, 96%, 97%, 98%, or 99% sequence identity to SEQ ID NO: 50. In certain embodiments, the third polypeptide comprises the amino acid sequence of SEQ ID NO: 51, SEQ ID NO: 52, SEQ ID NO: 53, SEQ ID NO: 54, SEQ ID NO: 63, SEQ ID NO: 76, SEQ ID NO: 77, SEQ ID NO: 78, or SEQ ID NO: 79, or an amino acid sequence that has at least 85%, 90%, 95%, 96%, 97%, 98%, or 99% sequence identity to SEQ ID NO: 51, SEQ ID NO: 52, SEQ ID NO: 53, SEQ ID NO: 54, SEQ ID NO: 63, SEQ ID NO: 76, SEQ ID NO: 77, SEQ ID NO: 78, or SEQ ID NO: 79.

In certain embodiments, the third polypeptide comprises the amino acid sequence of $X_1X_2SX_3PX_4$LOKESVFQSGAHAYRIPALLYLPGQQSLL AFAEQRASKKDEHAELIVLRRGDYD APTHQVQWQAQEVVAQARLDGHRSMNPCPLYDAQ TGTLFLFFIAIPGQVTEQQQLQTRANVT RLX$_5$QVTSTDHGRTWSSPRDLTDAAIGPAYREWSTFA GPGHCLQLHDRARSLVVPAYAYRKL HPX$_6$QRPIPSAFX$_7$FLSHDHGRTWARGHFVAQDTLEC QVAEVETGEQRVVTLNARSHLRARVQ AQSTNDGLDFQX$_8$SQLVKKLVEPPPQGX$_9$QGSVISFPS PRSGPGSPAQWLLYTHPTHSWQRAD LGAYLNPRPPAPEAWSEPX$_{10}$LLAKGSX$_{11}$AYSDLQSM GTGPDGSPLFGX$_{12}$LYEANDYEEIVF LMFTLKQAF- PAEYLPQGGGGSGGGGSDKTHTCPPCPA- PELLGGPSVFLFPPKPKDTLMISRT PEVTCVVVDVSHEDPE- VKFNWYVDGVEVHNAKTKPREEQYN- STYRVVSVLTVLHQDWLNGKE YKCKVSNKALPA- PIEKTISKAKGQPREPQVYTLPPSREEMTKNQVSLTC LVKGFYPSDIAVE WESNGQPEN- NYKTTPPVLDSDGSFFLTSK- LTVDKSRWQQGNVFSCSVMHEALHNHYTQKSLS LSPGK (SEQ ID NO: 101), wherein X$_1$ is Ala, Arg, Asn, Asp, Gln, Glu, Gly, His, Leu, Lys, Met, Phe, Thr, Val, or not present, X$_2$ is Ala or Lys, X$_3$ is Asn or Leu, X$_4$ is Phe, Trp, Tyr or Val, X$_5$ is Ala, Cys, Ile, Ser, or Val, X$_6$ is Arg, Ile, or Lys, X$_7$ is Ala, Cys, Leu, or Val, X$_8$ is Glu or Lys, X$_9$ is Cys or Val, X$_{10}$ is Lys or Val, X$_{11}$ is Ala, Cys, Ser, or Val, and X$_{12}$ is Cys, Leu, or Val.

In certain embodiments, the third polypeptide comprises the amino acid sequence of $X_1$ASLPX$_2$LQKESVFQSGAHAYRIPALLYLPGQQSLL AFAEQRASKKDEHAELIVLRRGDYDA PTHQVQWQAQEVVAQARLDGHRSMNPCPLYDAQT GTLFLFFIAIPGQVTEQQQLQTRANVTR LCQVT- STDHGRTWSSPRDLTDAAIGPAYREWS- TFAVGPGHCLQLHDRARSLVVPAYAYRKLH PX$_3$QRPIPSAFCFLSHDHGRTWARGHFVAQDTLECQV AEVETGEQRVVTLNARSHLRARVQAQ STNDG- LDFQESQLVKKLVEPPPQGCQGSVIS- FPSPRSGPGSPAQWLLYTHPTHSWQRADLGA YLNPRPPAPEAWSEPVLLAKGSX$_4$AYSDLQSMGTGPD GSPLFGCLYEANDYEEIVELMFTLKQ AFPAEY- LPQGGGGSGGGGSDKTHTCPPCPA- PELLGGPSVFLFPPKPKDTLMISRTPEVTCVV VDVSHEDPEVKFNWYVDGVEVHNAKTKPREEQYN- STYRVVSVLTVLHQDWLNGKEYKCKVSN KALPA- PIEKTISKAKGQPREPQVYTLPPSREEMTKNQVSLT- CLVKGFYPSDIAVEWESNGQP ENNYKTTPPVLDSDGSFFLTSK- LTVDKSRWQQGNVFSCSVMHEALHNHYTQKSLSL- SPGK (SEQ ID NO: 92), wherein X$_1$ is Ala, Arg, Asn, Asp, Gln, Glu, Gly, His, Leu, Lys, Met, Phe, Thr, Val, or not present, X$_2$ is Phe, Trp, Tyr or Val, X$_3$ is Arg, Ile, or Lys, and X$_4$ is Ala, Cys, Ser, or Val. In certain embodiments, X$_1$ is Ala, Asp, Met, or not present, X$_2$ is Tyr or Val, X$_3$ is Ile or Lys, and X$_4$ is Ala or Cys.

In certain embodiments, the first polypeptide comprises SEQ ID NO: 49, the second polypeptide comprises SEQ ID NO: 50, and the third polypeptide comprises SEQ ID NO: 51. In certain embodiments, the first polypeptide comprises SEQ ID NO: 49, the second polypeptide comprises SEQ ID NO: 50, and the third polypeptide comprises SEQ ID NO: 52. In certain embodiments, the first polypeptide comprises SEQ ID NO: 49, the second polypeptide comprises SEQ ID NO: 50, and the third polypeptide comprises SEQ ID NO: 53. In certain embodiments, the first polypeptide comprises SEQ ID NO: 49, the second polypeptide comprises SEQ ID NO: 50, and the third polypeptide comprises SEQ ID NO: 54. In certain embodiments, the first polypeptide comprises SEQ ID NO: 49, the second polypeptide comprises SEQ ID NO: 50, and the third polypeptide comprises SEQ ID NO: 63. In certain embodiments, the first polypeptide comprises SEQ ID NO: 49, the second polypeptide comprises SEQ ID NO: 50, and the third polypeptide comprises SEQ ID NO: 76. In certain embodiments, the first polypeptide comprises SEQ ID NO: 49, the second polypeptide comprises SEQ ID NO: 50, and the third polypeptide comprises SEQ ID NO: 77. In certain embodiments, the first polypeptide comprises SEQ ID NO: 49, the second polypeptide comprises SEQ ID NO: 50, and the third polypeptide comprises SEQ ID NO: 78. In certain embodiments, the first polypeptide comprises SEQ ID NO: 49, the second polypeptide comprises SEQ ID NO: 50, and the third polypeptide comprises SEQ ID NO: 79.

In certain embodiments, the antibody conjugate comprises a first polypeptide comprising a first sialidase, a first immunoglobulin Fc domain, and a first single chain variable fragment (scFv) (it is also understood that the scFv may be replaced by a first polypeptide chain of an immunoglobulin antigen binding fragment, e.g., Fab fragment); and a second polypeptide comprising a second sialidase, a second immunoglobulin Fc domain, and a second single chain variable fragment (scFv) (it is also understood that the scFv may be replaced by a second polypeptide chain of an immunoglobulin antigen binding fragment, e.g., Fab fragment). An example of this embodiment is shown in FIG. 10C. The first and second polypeptides can be covalently linked together. The covalent linkages can be disulfide bonds. In certain embodiments, the first scFv defines a first antigen-binding site, and the second scFv defines a second antigen-binding site. In certain embodiments, the first polypeptide comprises the first sialidase, the first immunoglobulin Fc domain, and the first scFv in an N- to C-terminal orientation. In certain embodiments, the first polypeptide comprises the first scFv, the first immunoglobulin Fc domain, and the first sialidase in an N- to C-terminal orientation. In certain embodiments, the second polypeptide comprises the second sialidase, the second immunoglobulin Fc domain, and the second scFv in an N- to C-terminal orientation. In certain embodiments, the second polypeptide comprises the second scFv, the second immunoglobulin Fc domain, and the second sialidase in an N- to C-terminal orientation.

In certain embodiments, the first polypeptide comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75. In certain embodiments, the second polypeptide comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75.

In certain embodiments, the first and/or second polypeptide comprises the amino acid sequence of $X_1X$-SX$_3$PX$_4$LOKESVFQSGAHAYRIPALLYLPGQQSLLAFA EQRASKKDEHAELIVLRRGDYD APTHQVQWQAQEVVAQARLDGHRSMNPCPLYDAQT GTLFLFFIAIPGQVTEQQQLQTRANVT RLX$_5$QVTSTDHGRTWSSPRDLTDAAIGPAYREWSTFA VGPGHCLQLHDRARSLVVPAYAYRKL HPX$_6$QRPIPSAFX$_7$FLSHDHGRTWARGHFVAQDTLEC QVAEVETGEQRVVTLNARSHLRARVQ AQSTNDGLDFQX$_8$SQLVKKLVEPPPQGX$_9$QGSVISFPS PRSGPGSPAQWLLYTHPTHSWQRAD LGAYLNPRPPAPEAWSEPX$_{10}$LLAKGSX$_{11}$AYSDLQSM GTGPDGSPLFGX$_{12}$LYEANDYEEIVF LMFTLKQAF-PAEYLPQGGGGSGGGGSDKTHTCPPCPA-PELLGGPSVFLFPPKPKDTLMISRT PEVTCVVVDVSHEDPE-VKFNWYVDGVEVHNAKTKPREEQYN-STYRVVSVLTVLHQDWLNGKE YKCKVSNKALPA-PIEKTISKAKGQPREPQVYTLPPSREEMTKNQVSLTCL VKGFYPSDIAVE WESNGQPEN-NYKTTPPVLDSDGSFFLYSK-LTVDKSRWQQGNVFSCSVMHEALHNHYTQKSLS LSPGKGGGGGGGGSGGGGSEVQLVESGG-GLVQPGGSLRLSCAASGFNIKDTYIHWVRQAPG KGLEWVARIYPTNGYTRYADSVKGRFTISADTSKN-TAYLQMNSLRAEDTAVYYCSRWGGDGF YAMDYWGQGTLVTVSSGGGGSGGGGSGGGGSDIQM TQSPSSLSASVGDRVTITCRASQDVNT AVAWYQQKPGKAPKLLIYSASFLY-SGVPSRFSGSRSGTDFTLTISSLQPEDFATYYCQQHYT TPPTFGQGTKVEIK (SEQ ID NO: 102), wherein $X_1$ is Ala, Arg, Asn, Asp, Gln, Glu, Gly, His, Leu, Lys, Met, Phe, Thr, Val, or not present, $X_2$ is Ala or Lys, $X_3$ is Asn or Leu, $X_4$ is Phe, Trp, Tyr or Val, $X_5$ is Ala, Cys, Ile, Ser, or Val, $X_6$ is Arg, Ile, or Lys, $X_7$ is Ala, Cys, Leu, or Val, $X_8$ is Glu or Lys, $X_9$ is Cys or Val, $X_{10}$ is Lys or Val, $X_{11}$ is Ala, Cys, Ser, or Val, and $X_{12}$ is Cys, Leu, or Val.

In certain embodiments, the first and/or second polypeptide comprises the amino acid sequence of $X_1$ASLPX$_2$LOKESVFQSGAHAYRIPALLYLPGQQSLLA FAEQRASKKDEHAELIVLRRGDYDA PTHQVQWQAQEVVAQARLDGHRSMNPCPLYDAQT GTLFLFFIAIPGQVTEQQQLQTRANVTR LCQVT-STDHGRTWSSPRDLTDAAIGPAYREWS-TFAVGPGHCLQLHDRARSLVVPAYAYRKLH PX$_3$QRPIPSAFCFLSHDHGRTWARGHFVAQDTLECQV AEVETGEQRVVTLNARSHLRARVQAQ STNDG-LDFQESQLVKKLVEPPPQGCOGSVIS-FPSPRSGPGSPAQWLLYTHPTHSWQRADLGA YLNPRPPAPEAWSEPVLLAKGSX$_4$AYSDLQSMGTGPD GSPLFGCLYEANDYEEIVELMFTLKQ AFPAEY-LPQGGGGSGGGGSDKTHTCPPCPA-PELLGGPSVFLFPPKPKDTLMISRTPEVTCVV VDVSHEDPEVKFNWYVDGVEVHNAKTKPREEQYN-STYRVVSVLTVLHQDWLNGKEYKCKVSN KALPA-PIEKTISKAKGQPREPQVYTLPPSREEMTKNQVSLT-CLVKGFYPSDIAVEWESNGQP ENNYKTTPPVLDSDGSFFLYSK- LTVDKSRWQQGNVFSCSVMHEALHNHYTQKSLSL-SPGKGG GGSGGGGSGGGGSEVQLVESGG-GLVQPGGSLRLSCAASGFNIKDTYIHWVRQAPGKGL EWVA RIYPTNGYTRYADSVKGRFTISADTSKNTAY-LQMNSLRAEDTAVYYCSRWGGDGFYAMDYWG QGTLVTVSSGGGGGGGGGSGGGGSDIQMTQSPSSL-SASVGDRVTITCRASQDVNTAVAWYQQ KPGKAPKLLIYSASFLY-SGVPSRFSGSRSGTDFTLTISSLQPEDFA-TYYCQQHYTTPPTFGQ GTKVEIK (SEQ ID NO: 93), wherein $X_1$ is Ala, Arg, Asn, Asp, Gln, Glu, Gly, His, Leu, Lys, Met, Phe, Thr, Val, or not present, $X_2$ is Phe, Trp, Tyr or Val, $X_3$ is Arg, Ile, or Lys, and $X_4$ is Ala, Cys, Ser, or Val. In certain embodiments, $X_1$ is Ala, Asp, Met, or not present, $X_2$ is Tyr or Val, $X_3$ is Ile or Lys, and $X_4$ is Ala or Cys.

In certain embodiments, the first and second polypeptide comprise SEQ ID NO: 43. In certain embodiments, the first and second polypeptide comprise SEQ ID NO: 44. In certain embodiments, the first and second polypeptide comprise SEQ ID NO: 45. In certain embodiments, the first and second polypeptide comprise SEQ ID NO: 46. In certain embodiments, the first and second polypeptide comprise SEQ ID NO: 47. In certain embodiments, the first and second polypeptide comprise SEQ ID NO: 48. In certain embodiments, the first and second polypeptide comprise SEQ ID NO: 74. In certain embodiments, the first and second polypeptide comprise SEQ ID NO: 75.

In certain embodiments, the antibody conjugate has a molecular weight from about 135 kDa to about 165 kDa, e.g., about 140 kDa. In other embodiments, the antibody conjugate has a molecular weight from about 215 kDa to about 245 kDa, e.g., about 230 kDa.

In certain embodiments, the antibody conjugate comprises two polypeptides that each comprise an immunoglobulin Fc domain, and the first polypeptide has either a "knob" mutation, e.g., T366Y, or a "hole" mutation, e.g., Y407T, for heterodimerization with the second polypeptide, and the second polypeptide has either a respective "knob" mutation, e.g., T366Y, or a "hole" mutation, e.g., Y407T, for heterodimerization with the first polypeptide (residue numbers according to EU numbering, Kabat, E. A., et al. (1991) supra). For example, in certain embodiments, the antibody comprises two polypeptides that each comprise an immunoglobulin Fc domain derived from human IgG1 Fc domain, and the first polypeptide comprises a Y407T mutation (e.g., the first polypeptide comprises SEQ ID NO: 32), and the second polypeptide comprises a T366Y mutation (e.g., the second polypeptide comprises SEQ ID NO: 33).

As used herein, the term "multispecific antibody" is understood to mean an antibody that specifically binds to at least two different antigens, i.e., an antibody that comprises at least two antigen-binding sites that bind to at least two different antigens. As used herein, the term "bispecific antibody" is understood to mean an antibody that specifically binds to two different antigens, i.e., an antibody that comprises two antigen-binding sites each of which bind to separate and distinct antigens. In other words, a first binding site binds a first antigen and a second binding site binds a second, different antigen. A multispecific or bispecific antibody may, for example, be a human or humanized antibody, and/or be a full length antibody or an antibody fragment (e.g., a F(ab')$_2$ bispecific antibody).

The present invention encompasses antibody conjugates comprising antibody fragments, which may be generated by traditional means, such as enzymatic digestion, or by recombinant techniques. For a review of certain antibody fragments, see Hudson et al. (2003) supra.

In certain embodiments, the antibody conjugate or fusion protein can be covalently or non-covalently associated with a biological modifier, wherein the biological modifier can be used to enhance the solubility of the antibody, increase binding specificity, decrease immunogenicity or toxicity or modify the pharmacokinetic profile of the antibody. For example, the biological modifier can be used to increase the molecular weight of the antibody to increase its circulating half-life.

It is contemplated that the antibody conjugate or fusion protein may be covalently bound to one or more (for example, 2, 3, 4, 5, 6, 8, 9, 10 or more) biological modifiers that may comprise linear or branched polymers. Exemplary biological modifiers may include, for example, a variety of polymers, such as those described in U.S. Pat. No. 7,842, 789. Particularly useful are polyalkylene ethers such as polyethylene glycol (PEG) and derivatives thereof (for example, alkoxy polyethylene glycol, for example, methoxypolyethylene glycol, ethoxypolyethylene glycol and the like); block copolymers of polyoxyethylene and polyoxypropylene (Pluronics); polymethacrylates; carbomers; and branched or unbranched polysaccharides which comprise the saccharide monomers such as D-mannose, D- and L-galactose, fucose, fructose, D-xylose, L-arabinose, and D-glucuronic acid.

In other embodiments, the biological modifier can be a hydrophilic polyvinyl polymer such as polyvinyl alcohol and polyvinylpyrrolidone (PVP)-type polymers. The biological modifier can be a functionalized polyvinylpyrrolidone, for example, carboxy or amine functionalized on one (or both) ends of the polymer (as available from Polymer-Source). Alternatively, the biological modifier can include Poly N-(2-hydroxypropyl) methacrylamide (HPMA), or functionalized HPMA (amine, carboxy, etc.), Poly(N-isopropylacrylamide) or functionalized poly(N-isopropylacrylamide). Alternatively, the biological modifier can include Poly N-(2-hydroxypropyl) methacrylamide (HPMA), or functionalized HPMA (amine, carboxy, etc.), Poly(N-isopropylacrylamide) or functionalized poly(N-isopropylacrylamide). The modifier prior to conjugation need not be, but preferably is, water soluble, but the final conjugate should be water soluble.

In general, the biological modifier may have a molecular weight from about 2 kDa to about 5 kDa, from about 2 kDa to about 10 kDa, from about 2 kDa to about 20 kDa, from about 2 kDa to about 30 kDa, from about 2 kDa to about 40 kDa, from about 2 kDa to about 50 kDa, from about 2 kDa to about 60 kDa, from about 2 kDa to about 70 kDa, from about 2 kDa to about 80 kDa, from about 2 kDa to about 90 kDa, from about 2 kDa to about 100 kDa, from about 2 kDa to about 150 kDa, from about 5 kDa to about 10 kDa, from about 5 kDa to about 20 kDa, from about 5 kDa to about 30 kDa, from about 5 kDa to about 40 kDa, from about 5 kDa to about 50 kDa, from about 5 kDa to about 60 kDa, from about 5 kDa to about 70 kDa, from about 5 kDa to about 80 kDa, from about 5 kDa to about 90 kDa, from about 5 kDa to about 100 kDa, from about 5 kDa to about 150 kDa, from about 10 kDa to about 20 kDa, from about 10 kDa to about 30 kDa, from about 10 kDa to about 40 kDa, from about 10 kDa to about 50 kDa, from about 10 kDa to about 60 kDa, from about 10 kDa to about 70 kDa, from about 10 kDa to about 80 kDa, from about 10 kDa to about 90 kDa, from about 10 kDa to about 100 kDa, from about 10 kDa to about 150 kDa, from about 20 kDa to about 30 kDa, from about 20 kDa to about 40 kDa, from about 20 kDa to about 50 kDa, from about 20 kDa to about 60 kDa, from about 20 kDa to about 70 kDa, from about 20 kDa to about 80 kDa, from about 20 kDa to about 90 kDa, from about 20 kDa to about 100 kDa, from about 20 kDa to about 150 kDa, from about 30 kDa to about 40 kDa, from about 30 kDa to about 50 kDa, from about 30 kDa to about 60 kDa, from about 30 kDa to about 70 kDa, from about 30 kDa to about 80 kDa, from about 30 kDa to about 90 kDa, from about 30 kDa to about 100 kDa, from about 30 kDa to about 150 kDa, from about 40 kDa to about 50 kDa, from about 40 kDa to about 60 kDa, from about 40 kDa to about 70 kDa, from about 40 kDa to about 80 kDa, from about 40 kDa to about 90 kDa, from about 40 kDa to about 100 kDa, from about 40 kDa to about 150 kDa, from about 50 kDa to about 60 kDa, from about 50 kDa to about 70 kDa, from about 50 kDa to about 80 kDa, from about 50 kDa to about 90 kDa, from about 50 kDa to about 100 kDa, from about 50 kDa to about 150 kDa, from about 60 kDa to about 70 kDa, from about 60 kDa to about 80 kDa, from about 60 kDa to about 90 kDa, from about 60 kDa to about 100 kDa, from about 60 kDa to about 150 kDa, from about 70 kDa to about 80 kDa, from about 70 kDa to about 90 kDa, from about 70 kDa to about 100 kDa, from about 70 kDa to about 150 kDa, from about 80 kDa to about 90 kDa, from about 80 kDa to about 100 kDa, from about 80 kDa to about 150 kDa, from about 90 kDa to about 100 kDa, from about 90 kDa to about 150 kDa, or from about 100 kDa to about 150 kDa.

It is contemplated that the antibody conjugate or fusion protein is attached to about 10 or fewer polymer molecules (e.g., 9, 8, 7, 6, 5, 4, 3, 2, or 1), each polymer molecule having a molecular weight of at least about 20,000 D, or at least about 30,000 D, or at least about 40,000 D.

Although a variety of polymers can be used as biological modifiers, it is contemplated that the antibody conjugates or fusion proteins described herein may be attached to polyethylene glycol (PEG) polymers. In one embodiment, the antibody conjugate or fusion protein described herein is covalently attached to at least one PEG having an actual MW of at least about 20,000 D. In another embodiment, the antibody conjugate or fusion protein described herein is covalently attached to at least one PEG having an actual MW of at least about 30,000 D. In another embodiment, the antibody conjugate or fusion protein described herein is covalently attached to at least one PEG having an actual MW of at least about 40,000 D. In certain embodiments, the PEG is methoxyPEG (5000)-succinimidylpropionate (mPEG-SPA), methoxyPEG (5000)-succinimidylsuccinate (mPEG-SS). Such PEGS are commercially available from Nektar Therapeutics or SunBiowest.

Attachment sites on an antibody conjugate or fusion protein for a biological modifier include the N-terminal amino group and epsilon amino groups found on lysine residues, as well as other amino, imino, carboxyl, sulfhydryl, hydroxyl or other hydrophilic groups. The polymer may be covalently bonded directly to the antibody conjugate or fusion protein with or without the known use of a multifunctional (ordinarily bifunctional) crosslinking agent using chemistries and used in the art. For example, sulfhydryl groups can be derivatized by coupling to maleimido-substituted PEG (e.g. alkoxy-PEG amine plus sulfosuccinimidyl 4-(N-maleimidomethyl)cyclohexane-1-carboxylate), or PEG-maleimide commercially available from Shearwater Polymers, Inc., Huntsville, Ala.).

III. Methods of Making a Recombinant Human Sialidase, Fusion Protein, or Antibody Conjugate Methods for producing recombinant human sialidases, fusion proteins, e.g., those disclosed herein, antibodies, or antibody conjugates, e.g., those disclosed herein, are known in the art. For example, DNA molecules encoding light chain variable regions and/or heavy chain variable regions can be synthesized chemically or by recombinant DNA methodologies. For example, the sequences of the antibodies can be cloned from hybridomas by conventional hybridization techniques or polymerase chain reaction (PCR) techniques, using the appropriate synthetic nucleic acid primers. The resulting DNA molecules encoding the variable regions of interest can be ligated to other appropriate nucleotide sequences, including, for example, constant region coding sequences, and expression control sequences, to produce conventional gene expression constructs (i.e., expression vectors) encoding the desired antibodies. Production of defined gene constructs is within routine skill in the art.

Nucleic acids encoding desired recombinant human sialidases, fusion proteins, and/or antibody conjugates can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The host cells express a recombinant human sialidase or a fusion protein and/or antibody conjugate comprising a sialidase and $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments involving fusion proteins and/or antibody conjugates, a host cell is transfected with a single vector expressing a polypeptide expressing a sialidase and an entire, or part of, a heavy chain (e.g., a heavy chain variable region) or a sialidase and a light chain (e.g., a light chain variable region), or a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain, wherein in (a) or in (b), the polypeptide may also comprise a sialidase. In some embodiments, a host cell is co-transfected with more than one expression vector (e.g., one expression vector expressing a polypeptide comprising an entire, or part of, a heavy chain or heavy chain variable region, optionally comprising a sialidase fused thereto, and another expression vector expressing a polypeptide comprising an entire, or part of, a light chain or light chain variable region, optionally comprising a sialidase fused thereto).

A polypeptide comprising a sialidase or a fusion protein, e.g., a fusion protein comprising an immunoglobulin heavy chain variable region or light chain variable region, can be produced by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

In embodiments in which a fusion protein and/or antibody conjugate is produced, a sialidase fused to a monoclonal antibody, Fc domain, or an antigen-binding domain of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The sialidase will be fused to one or more of the chains. The intact fusion protein and/or antibody conjugate can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

In certain embodiments, in order to express a protein, e.g., a recombinant human sialidase, as a secreted protein, a native N-terminal signal sequence of the protein is replaced, e.g., with MDMRVPAQLLGLLLLWLPGARC (SEQ ID NO: 28). In certain embodiments, to express a protein, e.g., a recombinant human sialidase, as a secreted protein, an N-terminal signal sequence, e.g., MDMRVPAQLLGLLLL-WLPGARC (SEQ ID NO: 28), is added. Additional exemplary N-terminal signal sequences include signal sequences from interleukin-2, CD-5, IgG kappa light chain, trypsinogen, serum albumin, and prolactin. In certain embodiments, in order to express a protein, e.g., a recombinant human sialidase, as a secreted protein, a C terminal lysosomal signal motif, e.g., YGTL (SEQ ID NO: 29) is removed.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions.

See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022, 500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332:323-327; Verhoeyen et al. (1988) SCIENCE 239:1534-1536; and Winter (1998) FEBS LETT 430:92-94.

In an approach called "SUPERHUMANIZATION™," human CDR sequences are chosen from human germline genes, based on the structural similarity of the human CDRs to those of the mouse antibody to be humanized. Sec, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." Sec, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains can be produced. Sec, e.g., U.S. Pat. No. 6,706,477 (Zauderer); U.S. Pat. No. 6,800,442 (Zauderer); and U.S. Pat. No. 6,872,518 (Zauderer). Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection. Another approach for modifying a mouse antibody into a form suitable for medical use in humans is HUMAN ENGINEERING™ technology, which is practiced commercially by XOMA (US) LLC. See, e.g., International (PCT) Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Fully human monoclonal antibodies can also be prepared and optimized from phage display libraries by techniques referenced in, e.g., Knappik et al., J. MOL. BIOL. 296:57-86, 2000; and Krebs et al., J. IMMUNOL. METH. 254:67-84 2001).

The present invention encompasses fusion proteins comprising antibody fragments, which may be generated by traditional means, such as enzymatic digestion, or by recombinant techniques. For a review of certain antibody fragments, see Hudson et al. (2003) NAT. MED. 9:129-134.

Various techniques have been developed for the production of antibody fragments. Traditionally, these fragments were derived via proteolytic digestion of intact antibodies (see, e.g., Morimoto et al. (1992) JOURNAL OF BIOCHEMICAL AND BIOPHYSICAL METHODS 24:107-117; and Brennan et al. (1985) SCIENCE 229:81). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries. Alternatively, Fab'-SH fragments can be directly recovered from E. coli and chemically coupled to form F(ab')$_2$ fragments (Carter et al. (1992) BIO/TECHNOLOGY 10:163-167). According to another approach, F(ab')$_2$ fragments can be isolated directly from recombinant host cell culture. Fab and F(ab')$_2$ fragments with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). Sec U.S. Pat. Nos. 5,571,894 and 5,587, 458.

Methods for making bispecific antibodies are known in the art. See Milstein and Cuello (1983) NATURE 305:537, International (PCT) Publication No. WO93/08829, and Traunecker et al. (1991) EMBO J., 10:3655. For further details of generating bispecific antibodies see, for example, Suresh et al. (1986) METHODS ENZYMOL. 121:210. Bispecific antibodies include cross-linked or "heteroconjugate" or "heterodimer" antibodies. For example, one of the antibodies in the heterodimer can be coupled to avidin, the other to biotin. Heterodimer antibodies may be made using any convenient cross-linking method. Suitable cross-linking agents are well known in the art, and are disclosed in U.S. Pat. No. 4,676,980, along with a number of cross-linking techniques.

Examples of heterodimeric or asymmetric IgG-like molecules include but are not limited to those obtained with the following technologies or using the following formats: Triomab/Quadroma, Knobs-into-Holes, CrossMabs, electrostatically-matched antibodies, LUZ-Y, Strand Exchange Engineered Domain body, Biclonic and DuoBody.

Advantages of using antibody fragments (e.g., F(ab) and F(ab')$_2$ fragments) include the elimination of non-specific binding between Fc portions of antibodies and Fc receptors on cells (such as macrophages, dendritic cells, neutrophils, NK cells and B cells). In addition, they may be able to penetrate tissues more efficiently due to their smaller size.

Heterodimeric antibodies, or asymmetric antibodies, allow for greater flexibility and new formats for attaching a variety of drugs to the antibody arms. One of the general formats for creating a heterodimeric antibody is the "knobsinto-holes" format. This format is specific to the heavy chain part of the constant region in antibodies. The "knobs" part is engineered by replacing a small amino acid with a larger one, which fits into a "hole", which is engineered by replacing a large amino acid with a smaller one. What connects the "knobs" to the "holes" are the disulfide bonds between each chain. The "knobs-into-holes" shape facilitates antibody dependent cell mediated cytotoxicity. Single chain variable fragments (scFv) are connected to the variable domain of the heavy and light chain via a short linker peptide. The linker is rich in glycine, which gives it more flexibility, and serine/threonine, which gives it specificity. Two different scFv fragments can be connected together, via a hinge region, to the constant domain of the heavy chain or the constant domain of the light chain. This gives the antibody bispecificity, allowing for the binding specificities of two different antigens. The "knobs-into-holes" format enhances heterodimer formation but doesn't suppress homodimer formation.

Several approaches to support heterodimerization have been described, for example in International (PCT) Publication Nos. WO96/27011, WO98/050431, WO2007/110205, WO2007/147901, WO2009/089004, WO2010/129304, WO2011/90754, WO2011/143545, WO2012/058768, WO2013/157954, and WO2013/096291, and European Patent Publication No. EP1870459. Typically, in the approaches known in the art, the $CH_3$ domain of the first heavy chain and the $CH_3$ domain of the second heavy chain are both engineered in a complementary manner so that the heavy chain comprising one engineered $CH_3$ domain can no longer homodimerize with another heavy chain of the same structure (e.g. a $CH_3$-engineered first heavy chain can no longer homodimerize with another $CH_3$-engineered first heavy chain; and a $CH_3$-engineered second heavy chain can no longer homodimerize with another $CH_3$-engineered second heavy chain). Thereby the heavy chain comprising one engineered $CH_3$ domain is forced to heterodimerize with another heavy chain comprising the $CH_3$ domain, which is engineered in a complementary manner. As a result, the $CH_3$ domain of the first heavy chain and the $CH_3$ domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g., for steric reasons).

IV. Pharmaceutical Compositions

For therapeutic use, a recombinant human sialidase or a fusion protein and/or antibody conjugate thereof preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, PA [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, *Remington's Pharmaceutical Sciences,* 18th ed. (Mack Publishing Company, 1990).

In certain embodiments, a pharmaceutical composition may contain nanoparticles, e.g., polymeric nanoparticles, liposomes, or micelles (See Anselmo et al. (2016) BIOENG. TRANSL. MED. 1:10-29).

In certain embodiments, a pharmaceutical composition may contain a sustained- or controlled-delivery formulation. Techniques for formulating sustained- or controlled-delivery means, such as liposome carriers, bio-erodible micropar ticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate, or poly-D (−)-3-hydroxybutyric acid. Sustained release compositions may also include liposomes that can be prepared by any of several methods known in the art.

Pharmaceutical compositions containing a recombinant human sialidase, a recombinant human sialidase fusion protein, or an antibody conjugate disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a recombinant human sialidase, a recombinant human sialidase fusion protein, or an antibody conjugate disclosed herein is administered by IV infusion. In certain embodiments, a recombinant human sialidase, a recombinant human sialidase fusion protein, or an antibody conjugate disclosed herein is administered by intratumoral injection. Useful formulations can be prepared by methods known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In a preferred embodiment, the pharmaceutical composition is administered subcutaneously and in an even more preferred embodiment intravenously. Preparations for parenteral administration include sterile aqueous or non-aqueous solutions, suspensions, and emulsions.

Generally, a therapeutically effective amount of active component, for example, a recombinant human sialidase or fusion protein and/or antibody conjugate thereof, is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the recombinant human sialidase or fusion protein and/or antibody conjugate thereof, and the disease being treated. Exemplary dosing frequencies are once per day, once per week and once every two weeks. A preferred route of administration is parenteral, e.g., intravenous infusion. In certain embodiments, a recombinant human sialidase or a fusion protein and/or antibody conjugate thereof is lyophilized, and then reconstituted in buffered saline, at the time of administration.

V. Therapeutic Uses

The compositions and methods disclosed herein can be used to treat various forms of cancer in a subject or inhibit cancer growth in a subject. The invention provides a method of treating a cancer in a subject. The method comprises administering to the subject an effective amount of a recombinant human sialidase or a fusion protein and/or antibody conjugate thereof, e.g., a recombinant human sialidase, fusion protein, or antibody conjugate disclosed herein, either alone or in a combination with another therapeutic agent to treat the cancer in the subject. The term "effective amount" as used herein refers to the amount of an active agent (e.g., recombinant human sialidase or fusion protein thereof according to the present invention) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments the cancer is an epithelial cancer, e.g., an epithelial cancer that upregulates the expression of sialylated glycans. Exemplary epithelial cancers include, but are not limited to, endometrial cancer, colon cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer and liver cancer. Epithelial cancers also include carcinomas, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, baso squamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In certain embodiments, the cancer is breast cancer. In certain embodiments, the cancer is an adenocarcinoma. In certain embodiments, the cancer is a metastatic cancer. In certain embodiments, the cancer is a refractory cancer.

In certain embodiments, the cancer is resistant to or non-responsive to treatment with an antibody, e.g., an antibody with ADCC activity, e.g., trastuzumab.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein, is administered in combination with one or more additional therapies, e.g., surgery, radiation therapy, or administration of another therapeutic preparation. In certain embodiments, the additional therapy may include chemotherapy, e.g., a cytotoxic agent. In certain embodiments the additional therapy may include a targeted therapy, e.g. a tyrosine kinase inhibitor, a proteasome inhibitor, or a protease inhibitor. In certain embodiments, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent (e.g. methotrexate), or an NSAID. In certain embodiments, the additional therapy may include a combination of therapeutics of different classes.

In certain embodiments, a method or composition described herein is administered in combination with a checkpoint inhibitor. The checkpoint inhibitor may, for example, be selected from a PD-1 antagonist, PD-L1 antagonist, CTLA-4 antagonist, adenosine A2A receptor antagonist, B7-H3 antagonist, B7-H4 antagonist, BTLA antagonist, KIR antagonist, LAG3 antagonist, TIM-3 antagonist, VISTA antagonist or TIGIT antagonist.

In certain embodiments, the checkpoint inhibitor is a PD-1 or PD-L1 inhibitor. PD-1 is a receptor present on the surface of T-cells that serves as an immune system checkpoint that inhibits or otherwise modulates T-cell activity at the appropriate time to prevent an overactive immune response. Cancer cells, however, can take advantage of this checkpoint by expressing ligands, for example, PD-L1, that interact with PD-1 on the surface of T-cells to shut down or modulate T-cell activity. Exemplary PD-1/PD-L1 based immune checkpoint inhibitors include antibody based therapeutics. Exemplary treatment methods that employ PD-1/PD-L1 based immune checkpoint inhibition are described in U.S. Pat. Nos. 8,728,474 and 9,073,994, and EP U.S. Pat. No. 1,537,878B1, and, for example, include the use of anti-PD-1 antibodies. Exemplary anti-PD-1 antibodies are described, for example, in U.S. Pat. Nos. 8,952,136, 8,779, 105, 8,008,449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273, 135, 7,943,743, 9,175,082, 8,741,295, 8,552,154, and 8,217, 149. Exemplary anti-PD-L1 antibodies include, for example, atezolizumab (Tecentriq®, Genentech), durvalumab (AstraZeneca), MEDI4736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T-cell with its ligands (e.g., CD80, also known as B7-1, and CD86) on the surface of an antigen presenting cells (rather than cancer cells) leads to T-cell inhibition. Exemplary CTLA-4 based immune checkpoint inhibition methods are described in U.S. Pat. Nos. 5,811, 097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO98/42752, WO00/37504, and WO01/14424, and European Patent No. EP 1212422 B1. Exemplary CTLA-4 antibodies include ipilimumab or tremelimumab.

In certain embodiments, a method or composition described herein is administered in combination with (i) a PD-1 or PD-L1 inhibitor, e.g., a PD-1 or PD-L1 inhibitor disclosed herein, and (ii) CTLA-4 inhibitor, e.g., a CTLA-4 inhibitor disclosed herein.

In certain embodiments, a method or composition described herein is administered in combination with an IDO inhibitor. Exemplary IDO inhibitors include 1-methyl-D-tryptophan (known as indoximod), epacadostat (INCB24360), navoximod (GDC-0919), and BMS-986205.

Exemplary cytotoxic agents that can be administered in combination with a method or composition described herein include, for example, antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, vinca alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with a method or composition described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

The invention also provides a method of increasing the expression of HLA-DR, CD86, CD83, IFNγ, IL-1b, IL-6, TNFα, IL-17A, IL-2, or IL-6 in a cell or tissue. The method comprises contacting the cell or tissue with an effective amount of a recombinant human sialidase or a fusion protein and/or antibody conjugate thereof, e.g., a recombinant human sialidase, fusion protein, or antibody conjugate dis-closed herein. In certain embodiments, the cell is selected from a dendritic cell and a peripheral blood mononuclear cell (PBMC).

In certain embodiments, expression of HLA-DR, CD86, CD83, IFNγ, IL-1b, IL-6, TNFα, IL-17A, IL-2, or IL-6 in the cell or tissue is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical cell or tissue that has not been contacted with the recombinant human sialidase, fusion protein, or antibody conjugate. Gene expression may be measured by any suitable method known in the art, for example, by ELISA, or by Luminex multiplex assays, as described in Example 13 herein.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1

This example describes the construction of recombinant human sialidases (Neu1, Neu2, and Neu3) with substitutions of cysteine residues to enhance expression and/or reduce aggregation.

The human sialidases Neu1, Neu2, Neu3 (isoform 1), and Neu4 (isoform 1) were expressed as secreted proteins with a 10×His tag (SEQ ID NO: 105). To express Neu1 as a secreted protein, the native N terminal signal peptide (MT-GERPSTALPDRRWGPRILGFWGGCRVWVFAAI-FLLLSLAASWSKA; SEQ ID NO: 27) was replaced by MDMRVPAQLLGLLLLWLPGARC (SEQ ID NO: 28), and the C terminal lysosomal signal motif (YGTL; SEQ ID NO: 29) was removed. To express Neu2, Neu3, and Neu4 as secreted proteins, the N terminal signal peptide MDMRVPAQLLGLLLLWLPGARC (SEQ ID NO: 28) was added to each.

Sialidases were expressed in a 200 mL transfection of HEK293F human cells in 24-well plates using the pCEP4 mammalian expression vector with an N-terminal 6×His tag (SEQ ID NO: 109). Sialidases were purified using Ni-NTA columns, quantified with a UV-Vis spectrophotometer (NanoDrop), and examined by SDS-PAGE as shown in FIG. 1. Neu1 expressed well, with a yield of ~3 μg/ml, and was present primarily in a monomeric form. Neu2 and Neu3 expression each gave yields of ~0.15 μg/mL and each were present primarily in a dimeric form. Neu4 had no detectable expression yield as measured by NanoDrop. Bacterial sialidase from *Salmonella typhimurium* (St-sialidase; SEQ ID NO: 30), which was used as a positive control for expression, gave a comparable yield to Neu1, and was present primarily in a monomeric form.

Figure 2:
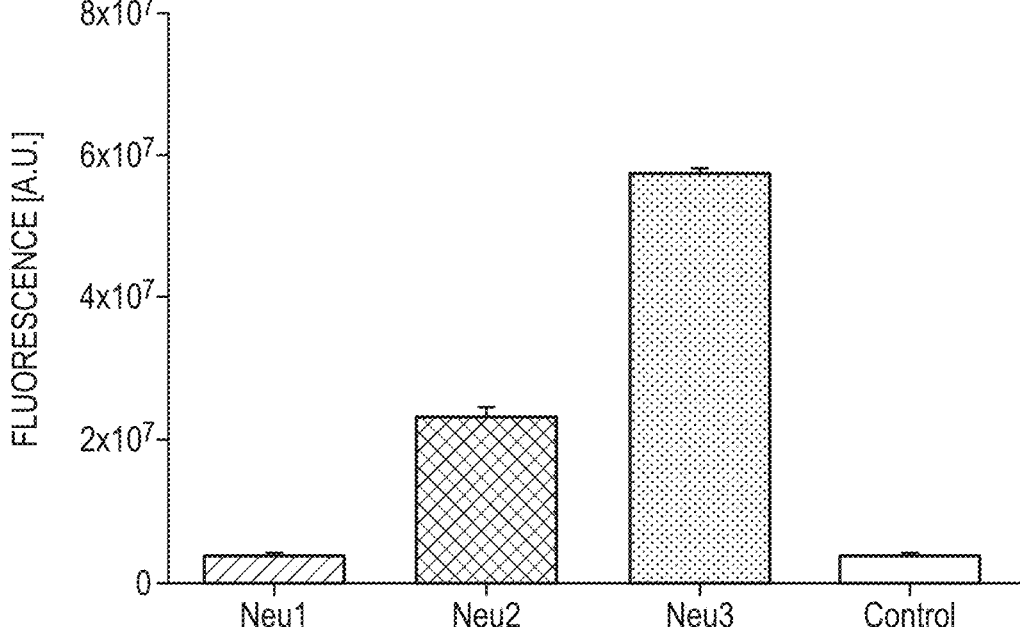
FIG. 2 is a bar graph showing the enzymatic activity of recombinant human Neu1, Neu2, and Neu3.
Figure 3:
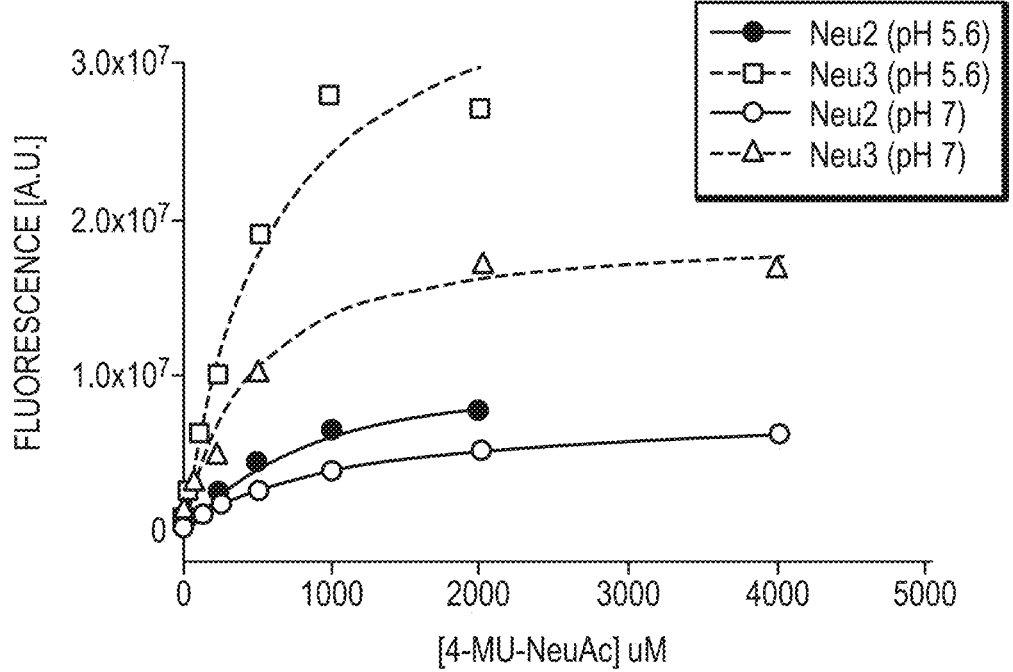
FIG. 3 is a line graph showing enzymatic activity as a function of substrate concentration for recombinant human Neu2 and Neu3 at the indicated pH.

The activity of the recombinantly expressed sialidases was assayed by measuring the release of sialic acid from the fluorogenic substrate 4-methylumbelliferyl-N-acetyl-neuraminic acid (4MU-NeuAc). As shown in FIG. 2, Neu1 has no detectable activity above a no-enzyme control, which is consistent with previous reports indicating that Neu1 is inactive unless it is in complex with beta-galactosidase and protective protein/cathepsin A (PPCA). Neu2 and Neu3 were active. An enzyme kinetics assay was performed with Neu2 and Neu3. A fixed concentration of enzyme at 1 nM was incubated with fluorogenic substrate 4MU-NeuAc at concentrations ranging from 4000 μM to 7.8 μM. Assays were conducted at both acidic (pH 5.6) and neutral (pH 7) conditions. As shown in FIG. 3, both Neu2 and Neu3 were active at acidic and neutral conditions and showed enzyme kinetics that were comparable to those previously reported.

Most of the recombinantly expressed sialidases ran as aggregates or dimers on a non-reducing SDS-PAGE gel. Subsequent treatment with the reducing agent dithiothreitol (DTT) resulted in a monomeric form of the enzyme that ran at 42 kDa on a reducing SDS-PAGE gel (FIG. 1). Thus, free cysteine residues in the sialidases may cause aggregation, dimerization, and/or low expression. Accordingly, each of the six free cysteine residues of Neu2 (125, 196, 219, 272, 332, 352) were substituted with the amino acids S, I, V, F, L, or A, using site-directed mutagenesis. The resulting mutant sialidases were expressed in 24-well plates as secreted proteins with an N-terminal human Fc tag in Expi293F cells using the pCEP4 mammalian expression vector. Expression was assayed using a ForteBio Octet with anti-human Fc sensors and Western blot and enzymatic activity was assayed using the fluorogenic substrate 4MU-NeuAc as described above. Expression and activity levels for the mutant sialidases are shown in TABLE 2.

In TABLE 2, enzymatic activity is indicated as "++," which denotes activity comparable to wild-type Neu2, "+," which denotes activity lower than wild-type Neu2, or "−," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "−," which denotes no detectable expression.

TABLE 2

| Identifier | Mutation(s) | Activity | Expression |
| --- | --- | --- | --- |
| Neu2 | Wild-type Neu2 | ++ | + |
| Neu2-M1 | C125A | ++ | + |
| Neu2-M2 | C125I | ++ | + |
| Neu2-M3 | C125S | ++ | + |
| Neu2-M4 | C125V | ++ | + |
| Neu2-M5 | C196A | ++ | + |
| Neu2-M6 | C196L | ++ | + |
| Neu2-M7 | C196F | − | − |
| Neu2-M8 | C196S | − | − |
| Neu2-M9 | C196V | ++ | + |
| Neu2-M10 | C219A | − | +++ |
| Neu2-M11 | C219N | − | +++ |
| Neu2-M12 | C219S | − | − |
| Neu2-M13 | C219V | − | − |
| Neu2-M14 | C219D | − | +++ |
| Neu2-M15 | C219I | − | + |
| Neu2-M16 | C219L | − | + |
| Neu2-M17 | C219Q | − | +++ |
| Neu2-M18 | C219M | − | +++ |
| Neu2-M19 | C219T | − | +++ |
| Neu2-M20 | C272S | + | + |
| Neu2-M21 | C272V | ++ | + |
| Neu2-M22 | C332A | ++ | + |
| Neu2-M23 | C332S | ++ | + |

TABLE 2-continued

| Identifier | Mutation(s) | Activity | Expression |
|---|---|---|---|
| Neu2-M24 | C332V | ++ | + |
| Neu2-M25 | C352L | ++ | + |
| Neu2-M26 | C352S | – | – |
| Neu2-M27 | C352V | ++ | + |
| Neu2-M28 | C196S + 219S + 332S | – | +++ |
| Neu2-M29 | C125S + C196S + C272S + C352S + C332S | – | – |
| Neu2-M30 | C125S + C196S + C219S + C272S + C352S + C332S | – | – |
| Neu2-M31 | C125S + C332S | ++ | + |
| Neu2-M32 | C196A + C219A | – | + |
| Neu2-M33 | C196V + C219V | – | – |
| Neu2-M34 | C196L + C219N | – | – |
| Neu2-M35 | C196L + C219A | – | + |
| Neu2-M36 | C272V + C332A | ++ | + |
| Neu2-M37 | C272V + C332S | ++ | + |
| Neu2-M38 | C332A + C352L | + | ++ |
| Neu2-M39 | C125S + C196L | ++ | + |
| Neu2-M40 | C196L + C219N + C332S | – | + |
| Neu2-M41 | C196L + C352L | ++ | + |
| Neu2-M42 | C196L + C219N + C332A | – | +++ |
| Neu2-M43 | C196L + C272V + C352L | – | + |
| Neu2-M44 | C272V + C332A + C352L | – | +++ |
| Neu2-M45 | C196L + C272V + C352L + C332A | – | + |
| Neu2-M46 | C196L + C272V + C352L + C332S | – | + |
| Neu2-M47 | C196L + C332S | + | – |
| Neu2-M48 | C196L + C332A | ++ | + |
| Neu2-M49 | C125S + C196L + C272V + C352L + C332A | – | + |
| Neu2-M50 | C125S + C196L + C272V + C352L + C332S | – | + |
| Neu2-M51 | C196L + C332A + C352L | + | + |
| Neu2-M52 | C125S + C272V + C332A + C352L | – | + |
| Neu2-M53 | C272V + C332A + C352L + K45A | – | + |
| Neu2-M54 | C196L + C219T + C332S | – | ++ |
| Neu2-M55 | C196L + C219T + C332A | – | +++ |
| Neu2-M56 | C125S + C196L + C219T + C272V + C352L + C332A | – | +++ |
| Neu2-M57 | C125S + C196L + C219T + C272V + C352L + C332S | – | +++ |
| Neu2-M58 | C196L + C219N + C332A | – | + |
| Neu2-M59 | C219N + C332A | – | +++ |
| Neu2-M60 | C219A + C332A | – | +++ |
| Neu2-M61 | C196L + C219A + C332A | – | +++ |

Figure 4A:
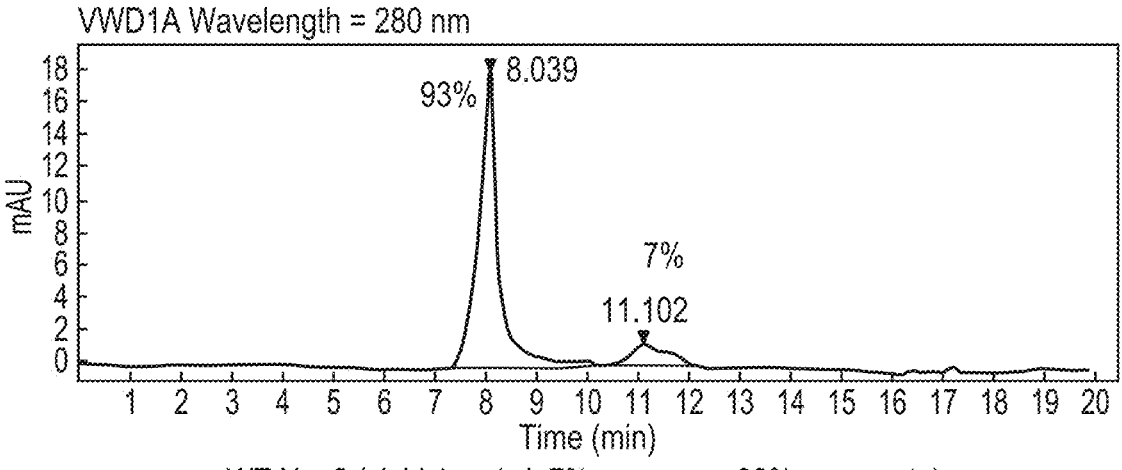
FIG. 4A is an SEC-HPLC trace of wild-type Neu2.
Figure 4B:
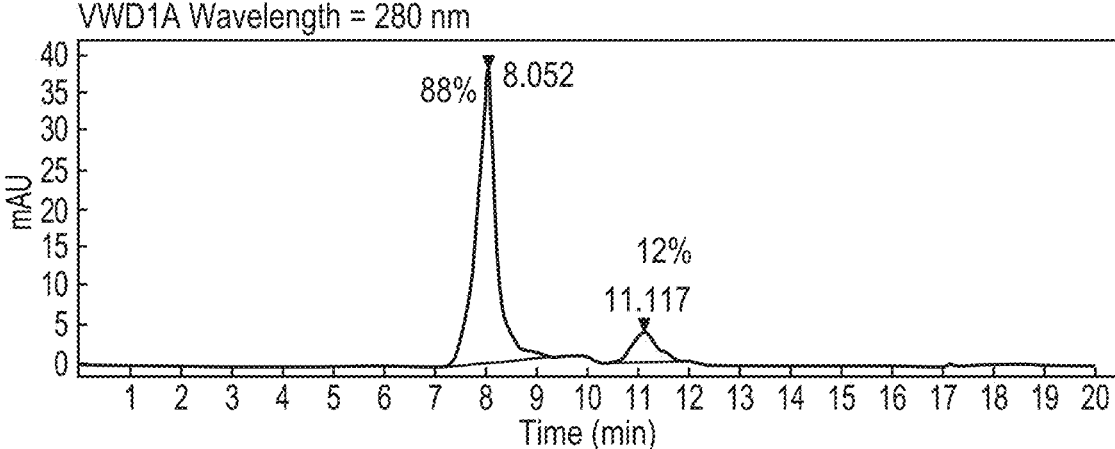
FIG. 4B is an SEC-HPLC trace of Neu2-M38 (containing C332A and C352L substitutions). Quantities of monomer and aggregate species are indicated.

As seen in TABLE 2, mutation of cysteine 219 greatly enhances expression, but negatively effects enzymatic activity. This may be due to the effects of the cysteine 219 mutation on the neighboring amino acid glutamate 218, which is believed to be a critical catalytic residue that acts a nucleophile for catalysis. Individual mutations of the other five cysteines (125, 196, 272, 332, and 352) had minimal impact on expression. However, through extensive combinatorial mutagenesis, a mutant sialidase with both the C332A and C352L substitutions (Neu2-M38) was identified that had improved expression and maintained enzymatic activity (although with reduced enzymatic activity relative to wild-type). To confirm these results, Neu2-M38 was expressed in a 100 mL transfection in shaking flasks and purified with a protein A column. Neu2-M38 had 2 fold higher expression than wild-type Neu2 under the same conditions and improved monomer content (12% vs 7%) as characterized by SEC-HPLC (FIGS. 4A and 4B). Together, these results show that mutating free cysteine residues in a human sialidase can be advantageous for producing secreted recombinant human sialidases and improving expression of recombinant human sialidases.

Example 2

This example demonstrates that engineering surface exposed residues of a human sialidase can increase the isoelectric point (pI) of the sialidase and/or reduce the hydrophobicity of a surface on the sialidase to improve solubility and/or decrease protein aggregation.

Human Neu2 has a predicted pI of 7.5, as compared to pI of 9.6 of the *Salmonella typhimurium* sialidase (St-sialidase). Additionally, an analysis of the surface hydrophobicity of Neu2 using the available crystal structure revealed a large exposed hydrophobic patch on the surface of Neu2, primarily including the N-terminal amino acids of Neu2, e.g., A2, as well as V325. These features may be suboptimal for protein stability and solubility in neutral aqueous conditions, possibly as a result of aggregation due to intermolecular hydrophobic interactions.

Surface residues of Neu2 were chosen as candidates for substitutions to increase solubility and/or expression, according to the following criteria: surface exposed D or E residues; hydrophobic residues contributing to surface hydrophobic patches; residues not involved in catalysis; residues not well conserved between human Neu 1, 3, 4, St-sialidase; and residues at positions that have a homologous K or R in other sialidases. Using these criteria, the acidic amino acids E72, D215, and E257 in Neu2 were mutated to lysine to increase pI, and the hydrophobic amino acids A2 and V325 in Neu2 were mutated to lysine or glutamate to reduce the hydrophobicity of the predicted Neu2 surface hydrophobic patch. The resulting mutant sialidases were expressed in 24-well plates as secreted proteins with a human Fc tag in Expi293F cells using the pCEP4 mammalian expression vector and assayed for expression and activity as described above in Example 1.

Expression and activity levels for the mutant sialidases are shown in TABLE 3. In TABLE 3, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 3

| Identifier | Mutation(s) | Activity | Expression |
|---|---|---|---|
| Neu2 | Wild-type Neu2 | ++ | + |
| Neu2-M62 | A2K | ++ | ++ |
| Neu2-M63 | E72K | + | – |
| Neu2-M64 | D215K | + | + |
| Neu2-M65 | E257K | + | ++ |
| Neu2-M66 | E319K | – | ++ |
| Neu2-M67 | V325K | + | ++ |
| Neu2-M68 | A2K + E257K | + | +++ |
| Neu2-M69 | A2K + V325E | + | + |
| Neu2-M70 | A2E + V325K | + | – |
| Neu2-M71 | A2K + V325K | + | +++ |
| Neu2-M72 | E257K + V325K | + | ++ |
| Neu2-M73 | E257K + A2K + V325K | – | +++ |

Figure 5A:
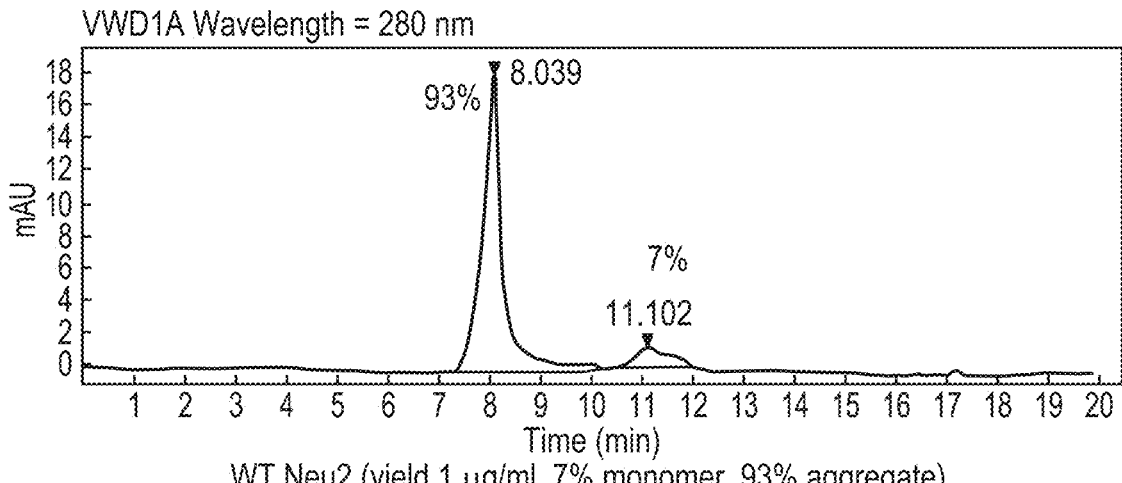
FIG. 5A is an SEC-HPLC trace of wild-type Neu2.
Figure 5B:
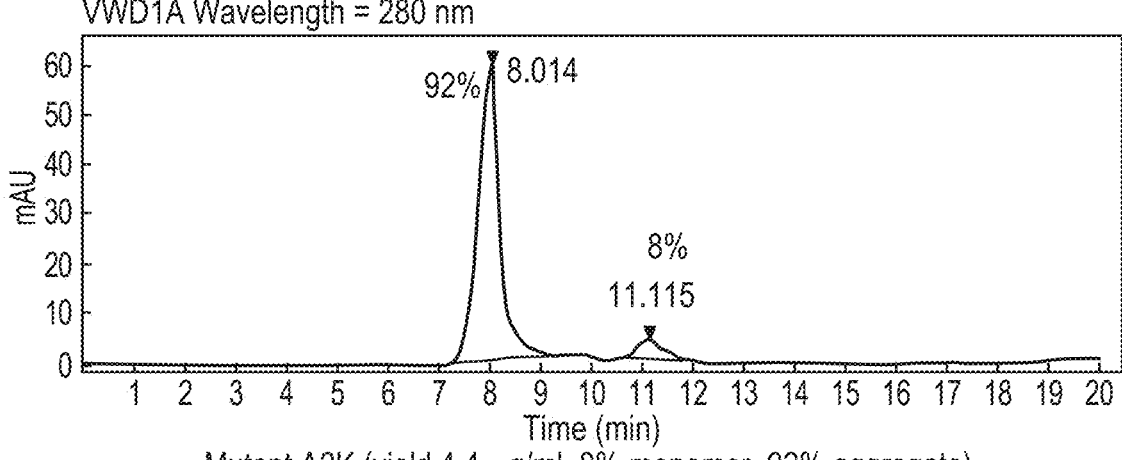
FIG. 5B is an SEC-HPLC trace of Neu2-M62 (containing the A2K substitution)
Figure 5C:
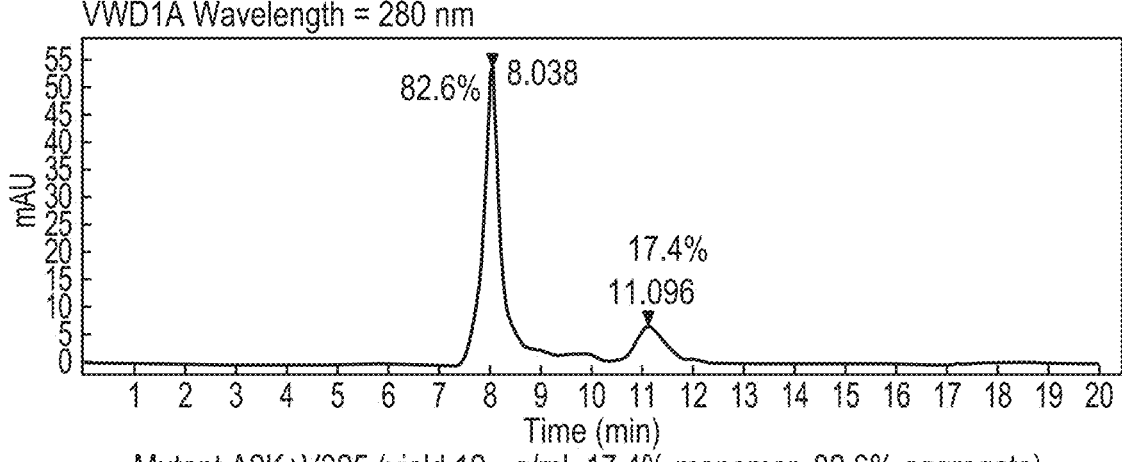
FIG. 5C is an SEC-HPLC trace of Neu2-M71 (containing A2K and V325 substitutions). Quantities of monomer and aggregate species are indicated.

As seen in TABLE 3, the Neu2-M62 (A2K), Neu2-M68 (A2K+E257K), and Neu2-M71 (A2K+V325K) mutant siali-dases showed improved expression and comparable or reduced enzymatic activity compared to wild-type Neu2. To confirm these results, the Neu2-M62 and Neu2-M71 mutant sialidases were expressed in a 100 mL transfection in shaking flasks and purified with a protein A column. Neu2-M62 had ~4.4 fold higher expression than wild-type Neu2 (4.4 µg/mL vs 1 µg/mL) and similar monomer content (8% vs 7%) as characterized by SEC-HPLC (FIGS. 5A and 5B). Neu2-M71 had ~12 fold higher expression than wild-type Neu2 (12 µg/mL vs 1 µg/mL) and improved monomer content (17% vs 7%) as characterized by SEC-HPLC (FIGS. 5A and 5C), but had no enzymatic activity.

Together, these results show that mutating surface exposed residues in a human sialidase can increase the isoelectric point (pI) of the sialidase and/or reduce the hydrophobicity of a surface on the sialidase to improve solubility, decrease protein aggregation, and/or improve expression of recombinant human sialidase.

Example 3

This Example demonstrates that the addition of a short peptide to the N-terminus of a human sialidase can increase expression and/or activity of the sialidase.

Using homology-based engineering, we grafted variants of an N-terminal sequence (MEDLRP; SEQ ID NO: 4) from mouse thymus Neu2 onto human Neu2 by overlapping PCR. The resulting mutant sialidases were expressed in 24-well plates as secreted proteins with a human Fc tag in Expi293F cells using the pCEP4 mammalian expression vector and assayed for expression and activity as described in Example 1.

Expression and activity levels for the mutant sialidases are shown in TABLE 4. In TABLE 4, enzymatic activity is indicated as "+++," which denotes activity greater than wild-type Neu2, "++," which denotes activity comparable to wild-type Neu2, "+," which denotes activity lower than wild-type Neu2, or "–," which denotes no activity, and expression is indicated as "+++," which denotes expression >6 fold higher than wild-type Neu2, "++," which denotes expression 2-5 fold higher than wild-type Neu2, or "+," which denotes expression comparable to wild-type Neu2.

TABLE 4

| Identifier | Mutation(s) | Activity | Expression |
|---|---|---|---|
| Neu2 | Wild-type Neu2 | ++ | + |
| Neu2-M74 | Substitute M at the N-terminus of Neu2 with EDLRP (SEQ ID NO: 3) | ++ | + |
| Neu2-M75 | Substitute M at the N-terminus of Neu2 with MEDLRP (SEQ ID NO: 4) | +++ | +++ |
| Neu2-M76 | Insert MEDLRP (SEQ ID NO: 4) at the N-terminus of Neu2 | +++ | +++ |
| Neu2-M77 | Substitute MASLP (SEQ ID NO: 12) at the N-terminus of Neu2 with MEDLRP (SEQ ID NO: 4) | +++ | +++ |

As shown in TABLE 4, all variants tested that included the MEDLRP (SEQ ID NO: 4) N-terminal sequence had both increased expression and activity relative to wild-type Neu2.

Figure 6A:
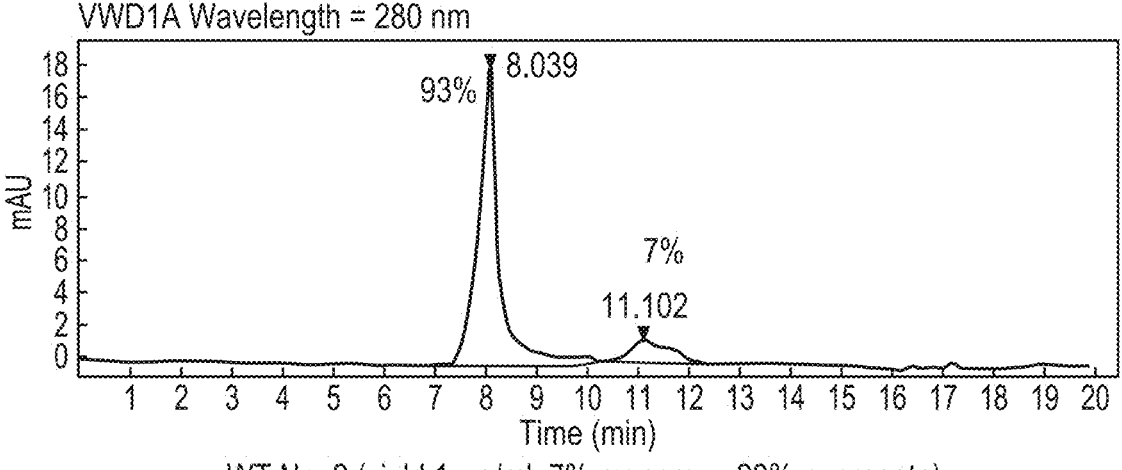
FIG. 6A is an SEC-HPLC trace of wild-type Neu2 and FIG. 6B is an SEC-HPLC trace of Neu2-M76 (which included MEDLRP (SEQ ID NO: 4) inserted at the N-terminus). Quantities of monomer and aggregate species are indicated.
Figure 6B:
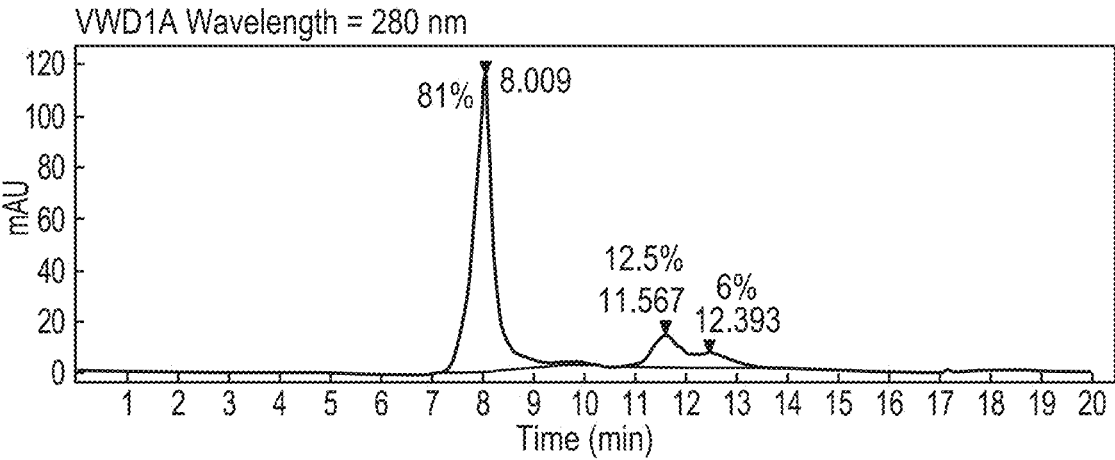

To confirm these results, the mutant Neu2-M76 (which included MEDLRP (SEQ ID NO: 4) inserted at the N-ter-minus) was expressed in a 100 mL transfection in shaking flasks and purified with a protein A column. Compared to the 24-well format, Neu2-M76 only showed a modest improve-ment in expression, ~1.5 fold higher than that of wild-type Neu2 (1.5 µg/mL vs 1 µg/mL) with improved monomer content (12.5% vs 7%) as characterized by SEC-HPLC (FIGS. 6A and 6B).

Figure 7A:
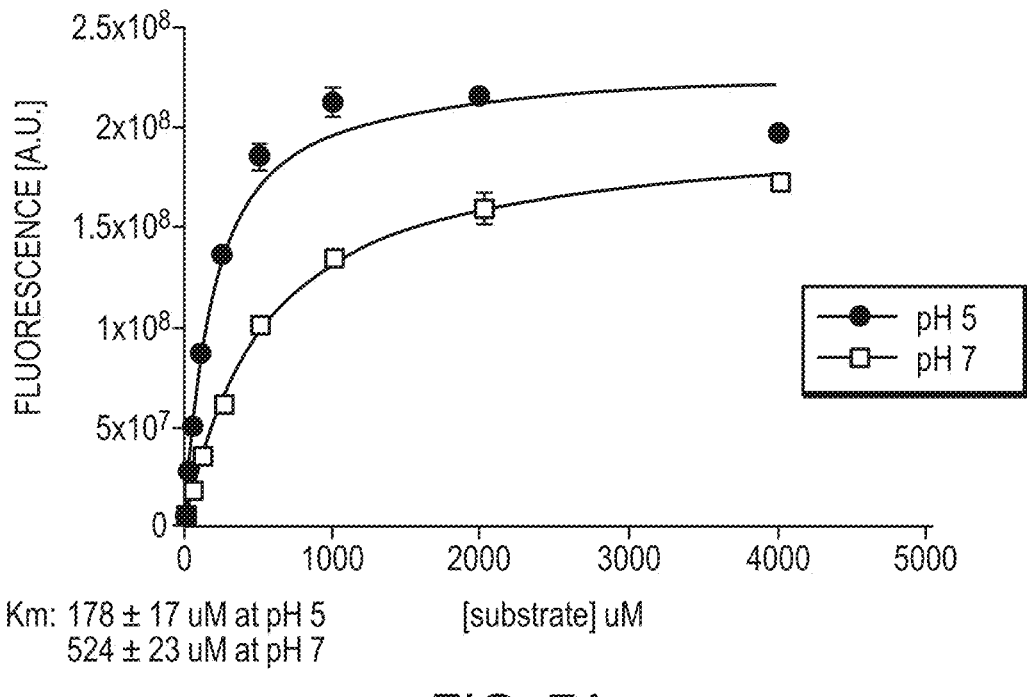
FIG. 7A is a line graph showing the enzymatic activity as a function of substrate concentration for Neu2-M76 at the indicated pH.
Figure 7B:
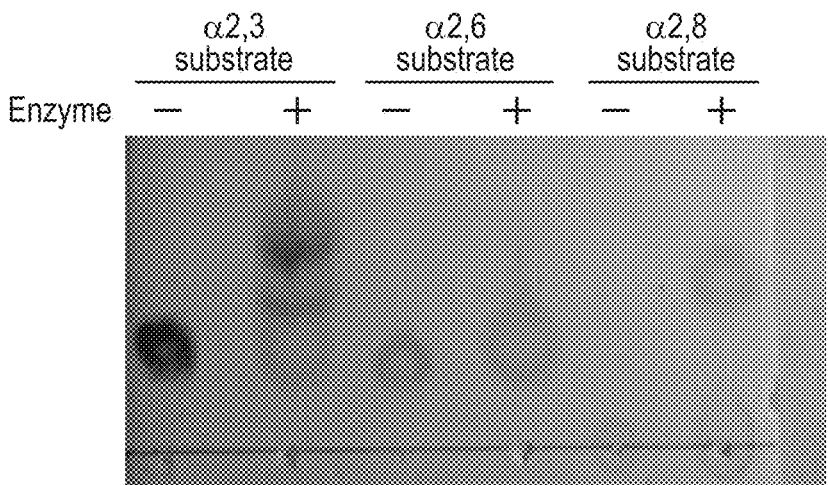
FIG. 7B depicts cleavage of α2-3, α2-6, or α2-8 substrate by Neu2-M76.

Enzyme kinetics measurements were carried out with purified Neu2-M76. A fixed concentration of Neu2-M76 at 100 nM was incubated with fluorogenic substrate 4MU-NeuAc at concentrations ranging from 4000 µM to 7.8 µM. As shown in FIG. 7A, this variant had a $K_M$ of ~175 µM, 5 fold more potent than that of wild-type Neu2 ($K_M$ of ~867 µM). Additionally, as shown in FIG. 7B, Neu2-M76 also had an altered substrate specificity relative to wild-type Neu2, as it cleaved sialic acid with α2,8 linkages (colominic acid) at pH 5, while wild-type Neu2 had no such activity.

Together, these results show that the addition of a short peptide to the N-terminus of a human sialidase can increase expression, increase activity, and/or modify the substrate specificity of the sialidase.

Example 4

This Example demonstrates that mutating residues in the N- or C-terminus of a human sialidase to increase hydro-phobic interactions and/or hydrogen bonding between the N- and C-termini can increase stability and/or expression of the sialidase.

Based on the crystal structure of Neu2, residues LA, V6, L7, and L12 were mutated to promote hydrophobic inter-actions or hydrogen bonding between the N- and C-termini of Neu2. The resulting mutant sialidases were expressed in 24-well plates as secreted proteins with a human Fc tag in Expi293F cells using the pCEP4 mammalian expression vector and assayed for expression and activity as described in Example 1.

Expression and activity levels for the mutant sialidases are shown in TABLE 5. In TABLE 5, enzymatic activity is indicated as "++," which denotes activity comparable to wild-type Neu2, "+," which denotes activity lower than wild-type Neu2, or "–," which denotes no detectable activ-ity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 5

| Identifier | Mutation(s) | Activity | Expression |
|---|---|---|---|
| Neu2 | Wild-type Neu2 | ++ | + |
| Neu2-M78 | L4N | ++ | + |
| Neu2-M79 | V6Y | ++ | +++ |
| Neu2-M80 | L7N | + | + |
| Neu2-M81 | L4N + L7N | – | – |
| Neu2-M82 | V12N | – | + |
| Neu2-M83 | V6F | + | +++ |
| Neu2-M84 | V6W | + | ++ |

As shown in TABLE 5, the V6Y substitution (Neu2-M79) resulted in improved expression and enzymatic activity compared to wild-type Neu2.

Figure 8A:
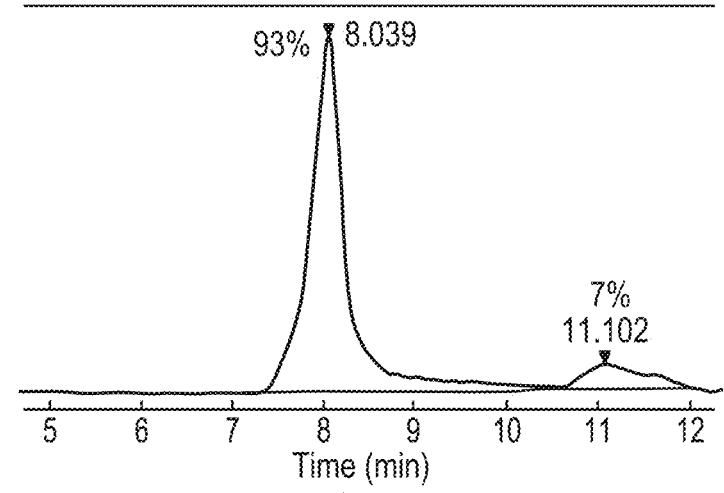
FIG. 8A is an SEC-HPLC trace of wild-type Neu2 and FIG. 8B is an SEC-HPLC trace of Neu2-M79 (containing the V6Y substitution). Quantities of monomer and aggregate species are indicated.
Figure 8B:
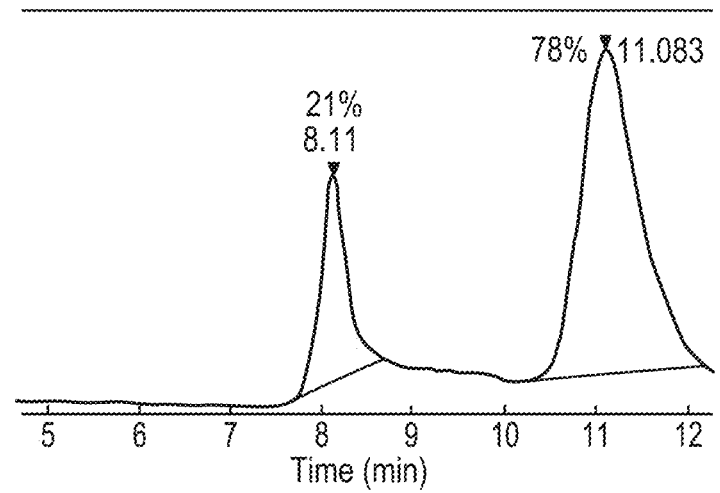

To confirm these results, Neu2-M79 was expressed in a 100 mL transfection in shaking flasks and purified with a protein A column. Neu2-M79 had ~10 fold higher expression than wild-type Neu2 (10 µg/mL vs 1 µg/mL), substantially improved monomer content (78% vs 7%) as characterized by SEC-HPLC (FIGS. 8A and 8B), and was as active as wild-type Neu2.

Together, these results show that mutating residues in the N- or C-termini of a human sialidase to increase hydrophobic interactions and/or hydrogen bonding between the N- and C-termini can increase stability and/or expression of the sialidase.

Example 5

This Example demonstrates that mutating the N-terminal methionine of a human sialidase can increase stability and/or expression of the sialidase.

The first residue (M1) of human Neu2 was deleted or mutated to R, H, K, D, E, S, T, N, Q, G, P, A, V, L, F, and Y. All mutations were tested in combination with V6Y and I187K substitutions. The resulting mutant sialidases were expressed in shaking flasks as secreted proteins with a human Fc tag in Expi293F cells using the pCEP4 mammalian expression vector. The proteins were purified with a protein A column, quantified by Nanodrop, and characterized for enzymatic activity as described in Example 1.

Expression and activity levels for the mutant sialidases are shown in TABLE 6. In TABLE 6, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "," which denotes no detectable expression.

TABLE 6

| Identifier | Mutation(s) | Activity | Expression |
|---|---|---|---|
| Neu2 | None-Wild-type Neu2 | ++ | + |
| Neu2-M85 | Deletion of M1, V6Y, I187K | + | +++ |
| Neu2-M86 | M1R, V6Y, I187K | + | +++ |
| Neu2-M87 | M1H, V6Y, I187K | +++ | ++ |
| Neu2-M88 | M1K, V6Y, I187K | + | +++ |
| Neu2-M89 | M1D, V6Y, I187K | +++ | +++ |
| Neu2-M90 | M1E, V6Y, I187K | – | +++ |
| Neu2-M91 | M1S, V6Y, I187K | – | – |
| Neu2-M92 | M1T, V6Y, I187K | ++ | ++ |
| Neu2-M93 | M1N, V6Y, I187K | ++ | +++ |
| Neu2-M94 | M1Q, V6Y, I187K | + | ++ |
| Neu2-M95 | M1G, V6Y, I187K | + | +++ |
| Neu2-M96 | M1P, V6Y, I187K | – | – |

TABLE 6-continued

| Identifier | Mutation(s) | Activity | Expression |
|---|---|---|---|
| Neu2-M97 | M1A, V6Y, I187K | ++ | +++ |
| Neu2-M98 | M1V, V6Y, I187K | + | +++ |
| Neu2-M99 | M1L, V6Y, I187K | +++ | +++ |
| Neu2-M100 | M1F, V6Y, I187K | +++ | ++ |
| Neu2-M101 | M1Y, V6Y, I187K | + | + |

As shown in TABLE 6, deletion of M1 or mutation of M1 to R, H, K, D, E, T, N, Q, G, A, V, L, or F in combination with V6Y and I187K substitutions increased expression of the sialidase, with the M1H, M1D, MIL, and MIF mutations resulting in increased expression and enzymatic activity. Together, these results show that mutating the N-terminal methionine of a human sialidase can increase stability and/or expression of the sialidase.

Example 6

This Example describes mutations and combinations of mutations that can increase stability and/or expression of the sialidase.

Human Neu2 was mutated as shown in TABLE 7. The resulting mutant sialidases were expressed in shaking flasks as secreted proteins with a human Fc tag in Expi293F cells using the pCEP4 mammalian expression vector. The proteins were purified with a protein A column, quantified by Nanodrop, and characterized for enzymatic activity as described in Example 1.

Expression and activity levels for the mutant sialidases are shown in TABLE 7. In TABLE 7, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 7

| Identifier | Mutation(s) | Activity | Expression |
|---|---|---|---|
| Neu2-M102 | M1D, V6Y, I187K, C332A | +++ | +++ |
| Neu2-M103 | V6Y, I187K, C332A | +++ | ++ |

Example 7

This Example describes the construction and expression of antibody-sialidase genetic fusion proteins, and antibody sialidase conjugates (ASCs) containing the fusion proteins, with bacterial and mutated human sialidases.

The architecture for three types of ASCs used in this Example is depicted in FIG. 10. The first type of ASC, referred to as "Raptor," includes an antibody (with two heavy chains and two light chains) with a sialidase fused at the C-terminus of each heavy chain of the antibody. The second type of ASC, referred to as "Janus," contains one antibody arm (with one heavy chain and one light chain), and one sialidase-Fc fusion with a sialidase fused at the N-terminus of the Fc. Each Fc domain polypeptide in the Janus ASC contains either the "knob" (T366Y) or "hole" (Y407T) mutation for heterodimerization (residue numbers according to EU numbering, Kabat, E. A., et al. (1991)

supra). The third type of ASC, referred to as "Lobster," contains two Fc domain polypeptides each with a sialidase fused at the N-terminus of the Fc and a scFv fused at the C-terminus of the Fc.

The following ASCs were expressed and characterized for purity using SDS-PAGE and SEC-HPLC, and assayed for enzymatic using 4MU-NeuAc as described in Example 1: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); and (iii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62).

Figure 11A:
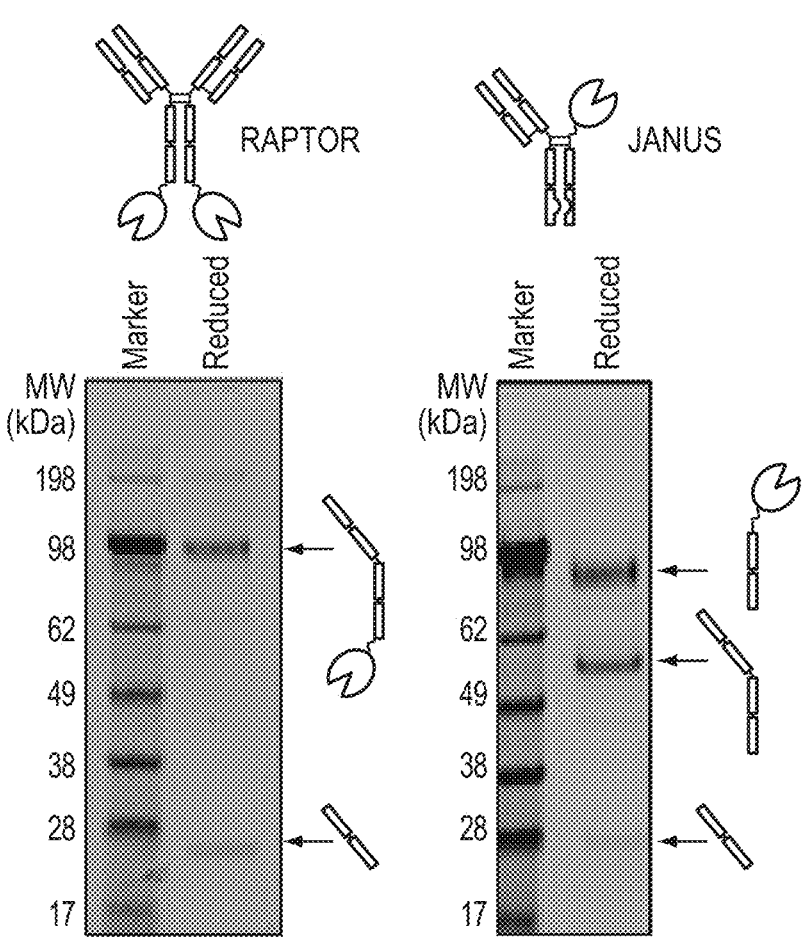
FIG. 11A is an SDS-PAGE gel showing antibody-sialidase conjugates (ASCs) made using *Salmonella typhimurium* sialidase (St-sialidase) and trastuzumab in the Raptor (left) and Janus (right) formats.
Figure 12B:
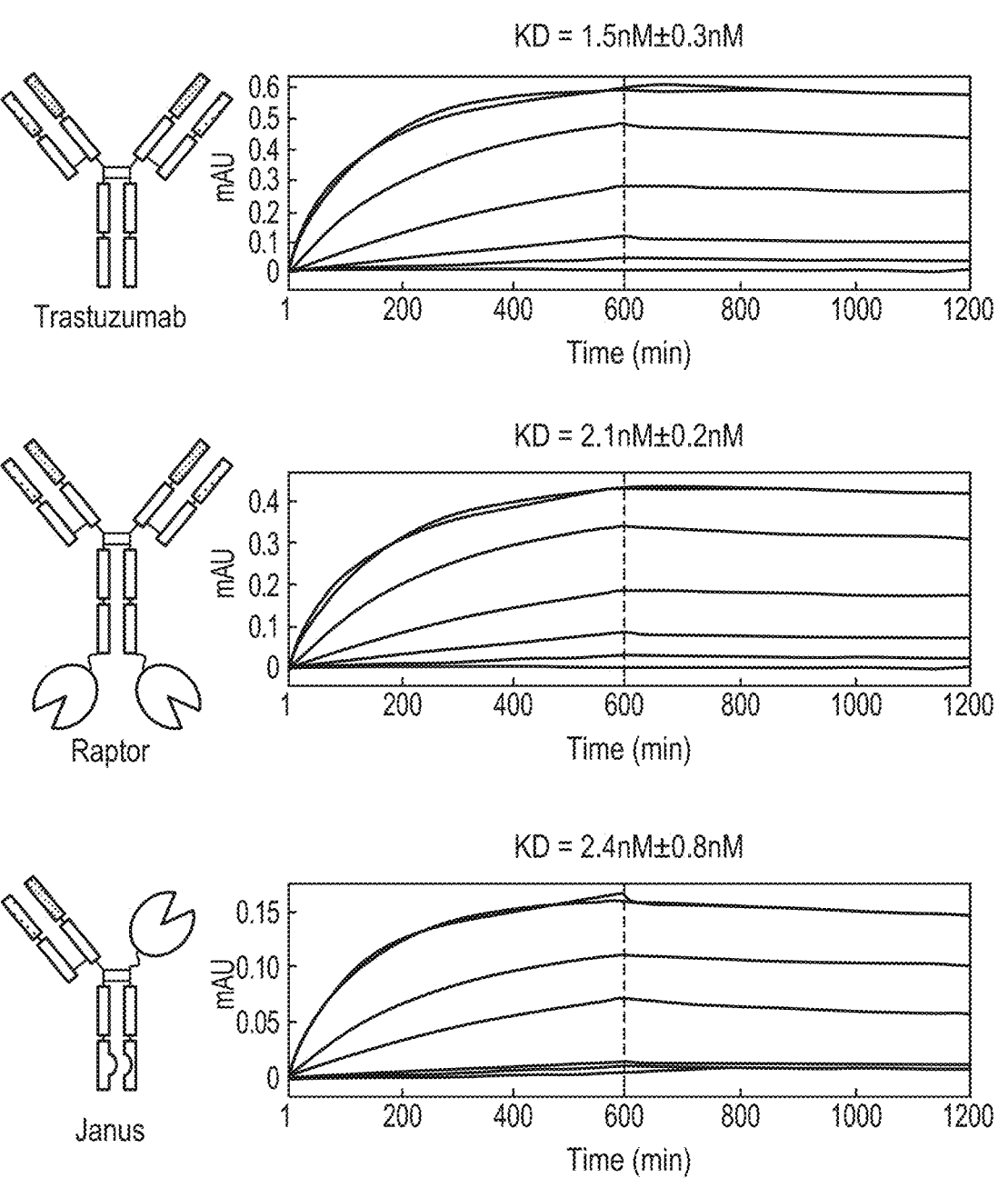
FIG. 12B depicts binding to Her2 as determined by ForteBio Octet for trastuzumab (top), and ASCs made using St-sialidase and trastuzumab in the Raptor (middle) and Janus (bottom) formats.

The ASCs were tested for antigen (Her2) binding by using ForteBio Octet with the ASC captured on anti-Fc sensors with dipping into serial dilutions of His-tagged Her2 (50 to 0.78 nM at 1:2 dilutions). The ASCs had good expression with a yield of 30 µg/mL and high purity, were as active as unconjugated St-sialidase, and bound to Her2 with comparable binding affinities to trastuzumab (FIGS. 11 and 12). Janus-LOF mutant abolished the sialidase activity as expected, and expressed well with similar biochemical characteristics as the parent Janus ASC.

Figure 13C:
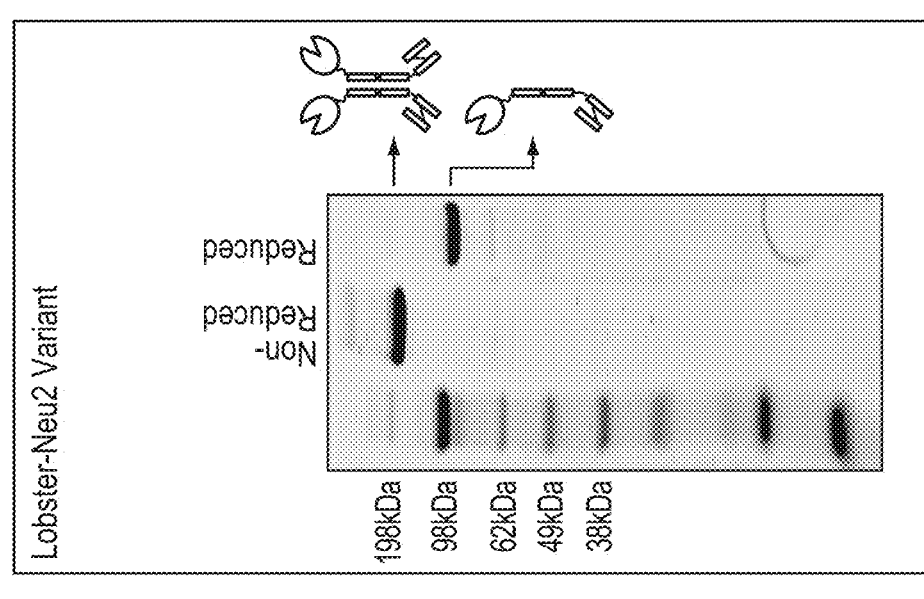
FIGS. 13A-C show an SDS-PAGE gel depicting an ASC made using St-sialidase and trastuzumab in the Janus format (FIG. 13A), an SDS-PAGE gel depicting an ASC made using Neu2-M76 (which included MEDLRP (SEQ ID NO: 4) inserted at the N-terminus) and trastuzumab in the Janus format (FIG. 13B), and an SDS-PAGE gel depicting an ASC made using a Neu2-M85 (which included a deletion of M1 and V6Y and I187K mutations) and a scFv derived from trastuzumab in the Lobster format (FIG. 13C).
Figure 13B:
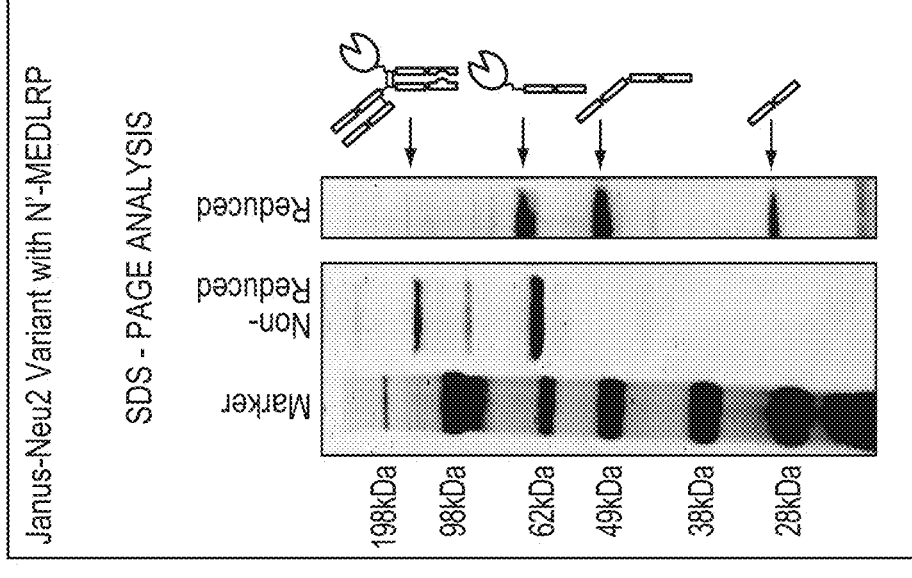
Figure 13A:
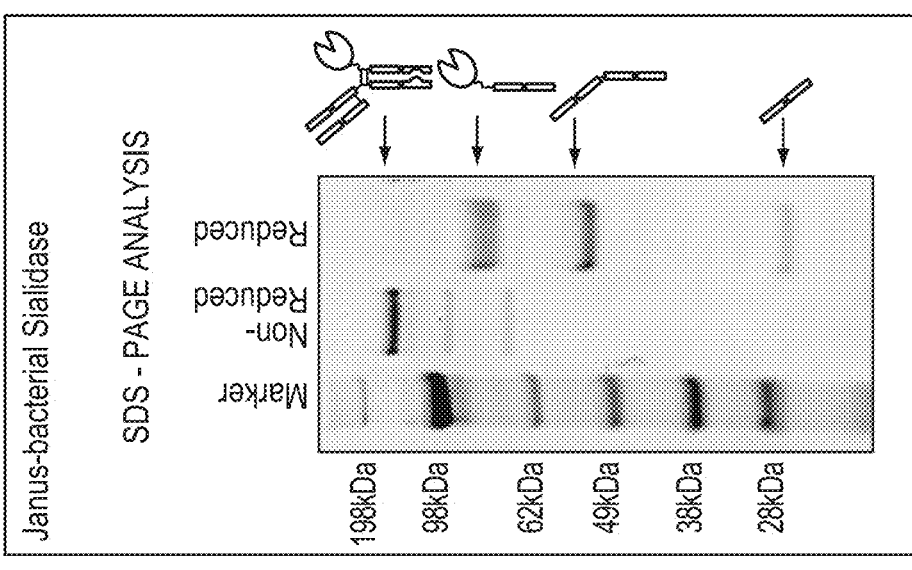
Figure 14A:
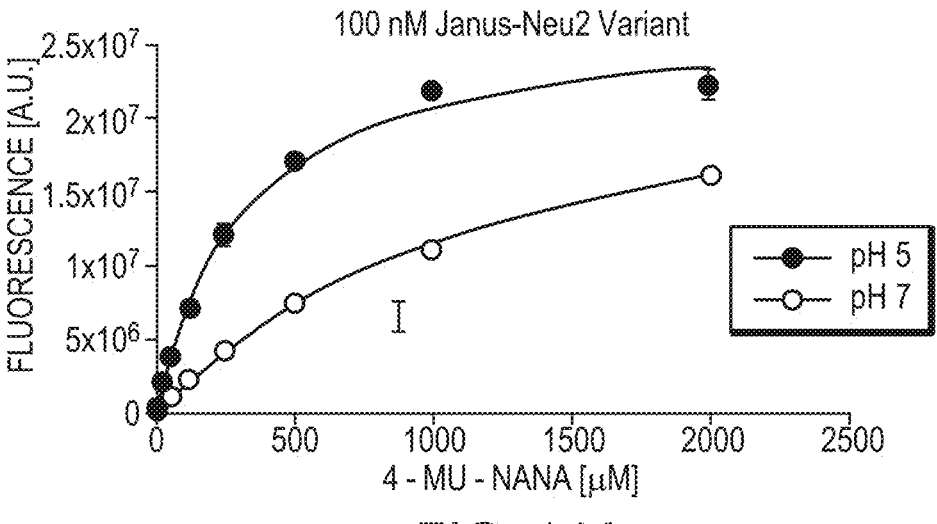
FIGS. 14A-C show line graphs depicting enzymatic activity as a function of substrate concentration for an ASC made using Neu2-M76 (which included MEDLRP (SEQ ID NO: 4) inserted at the N-terminus) and trastuzumab in the Janus format (FIG. 14A), wild-type Neu2 (FIG. 14B), and an ASC made using a Neu2-M85 (which included a deletion of M1 and V6Y and I187K mutations) and a scFv derived from trastuzumab in the Lobster format (FIG. 14C).
Figure 14B:
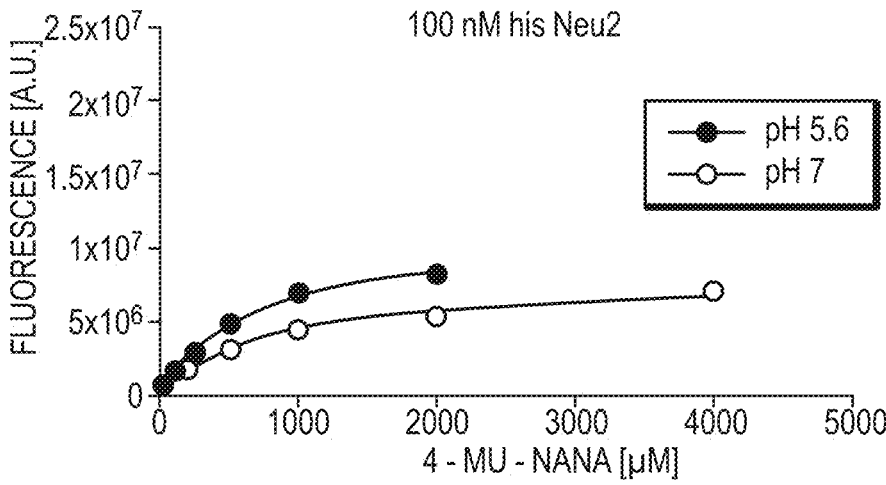
Figure 14C:
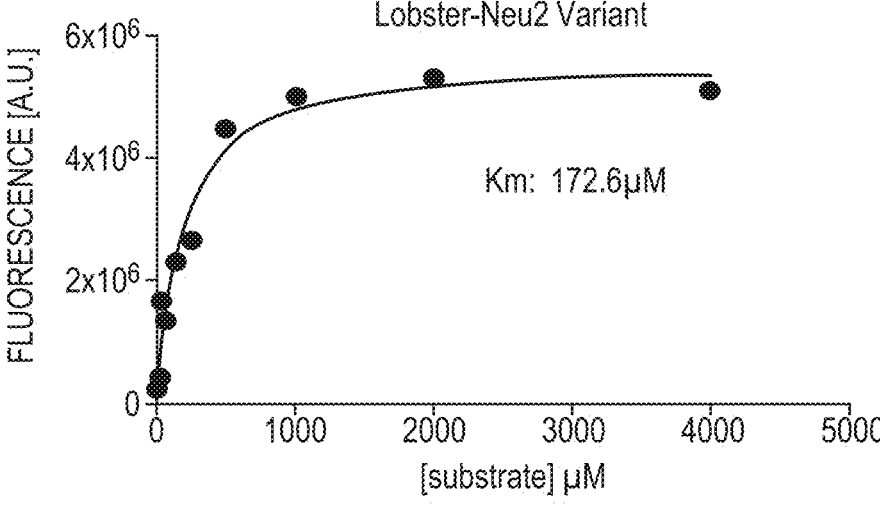

A Janus ASC was made using Neu2-M76 (which included MEDLRP (SEQ ID NO: 4) inserted at the N-terminus) and trastuzumab. This Janus ASC (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 63, encoded by nucleotide sequence SEQ ID NO: 64) was expressed and characterized for purity using SDS-PAGE and enzymatic activity using 4MU-NeuAc as described in Example 1. The Janus ASC had an expression yield of ~5

µg/mL with good purity after purification (FIG. 13), and showed improved activity compared to a Janus ASC wild-type conjugated Neu2 (FIG. 14).

Additionally a Lobster ASC was made using Neu2-M85 (which included a deletion of M1 and mutations V6Y and I187K) and a scFv derived from trastuzumab. This Lobster ASC (including first and second polypeptide chains with amino acid sequence SEQ ID NO: 65, encoded by nucleotide sequence SEQ ID NO: 66) was expressed and characterized for purity using SDS-PAGE and enzymatic activity using 4MU-NeuAc as described in Example 1. The Lobster ASC had an expression yield of ~5 µg/mL with good purity after purification (FIG. 13), and a Km of 172.6 µM (FIG. 14).

Example 8

This Example describes the in vivo administration of antibody sialidase conjugates (ASCs) containing bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); and (iii) a Lobster ASC including St-sialidase and an scFv derived from trastuzumab (including first and second polypeptide chains with amino acid sequence SEQ ID NO: 103, encoded by nucleotide sequence SEQ ID NO: 104). ASCs were made as described in Example 7.

These ASCs were compared to trastuzumab in a mouse syngeneic tumor model injected with a murine breast cancer cell line expressing human Her2 (EMT6-hHer2 cells). Female BALB/c mice, 6-8 weeks of age, were inoculated subcutaneously in the right lower flank region with EMT6-Her2 tumor cells ($5 \times 10^5$) in 0.1 ml of PBS for tumor development. Mice were randomly allocated to 8 groups when tumors reached 50-100 mm³, mean ~75-100 mm³. Treatment groups are described in TABLE 8 with dosing schedule indicated post randomization. Anti-mouse NK1.1 (Clone: PK136; BioXcell, 621717N1), anti-mouse CD8a (Clone: 53-6.7; BioXcell, BE0004-1) and liposomal clodronate (FormuMax Scientific, Inc.) were included in treatment groups as indicated.

TABLE 8

| Group | Animal No. | Treatment | Dose (mg/kg) | Dose volume (µL/g) | Route | Schedule (Days) |
|---|---|---|---|---|---|---|
| 1 | 8 | Vehicle (PBS) | NA | 10 | i.p. | 0, 3, 7, 10, 14, 17 |
| 2 | 8 | Trastuzumab | 10 | 10 | i.p. | 0, 3, 7, 10, 14, 17 |
| 3 | 8 | Raptor | 10 | 10 | i.p. | 0, 3, 7, 10, 14, 17 |
| 4 | 8 | Janus | 10 | 10 | i.p. | 0, 3, 7, 10, 14, 17 |
| 5 | 8 | Lobster | 10 | 10 | i.p. | 0, 3, 7, 10, 14, 17 |
| 6 | 8 | Janus | 10 | 10 | i.p. | 0, 3, 7, 10, 14, 17 |
| | | anti-mouse NK1.1 (Clone: PK136) | 10 | 10 | i.p. | 0, 3, 7, 10, 14, 17 |

TABLE 8-continued

| Group | Animal No. | Treatment | Dose (mg/kg) | Dose volume (μL/g) | Route | Schedule (Days) |
|---|---|---|---|---|---|---|
| 7 | 8 | Janus | 10 | 10 | i.p. | 0, 3, 7, 10, 14, 17 |
| | | anti-mouse CD8α (Clone: 53-6.7) | 10 | 10 | i.p. | 0, 3, 7, 10, 14, 17 |
| 8 | 8 | Janus | 10 | 10 | i.p. | 0, 3, 7, 10, 14, 17 |
| | | liposomal clodronate | 0.5 mg/ mouse | 100 μL/ mouse | i.p. | TIW × 2 wks |

Figures 15A, 15B:
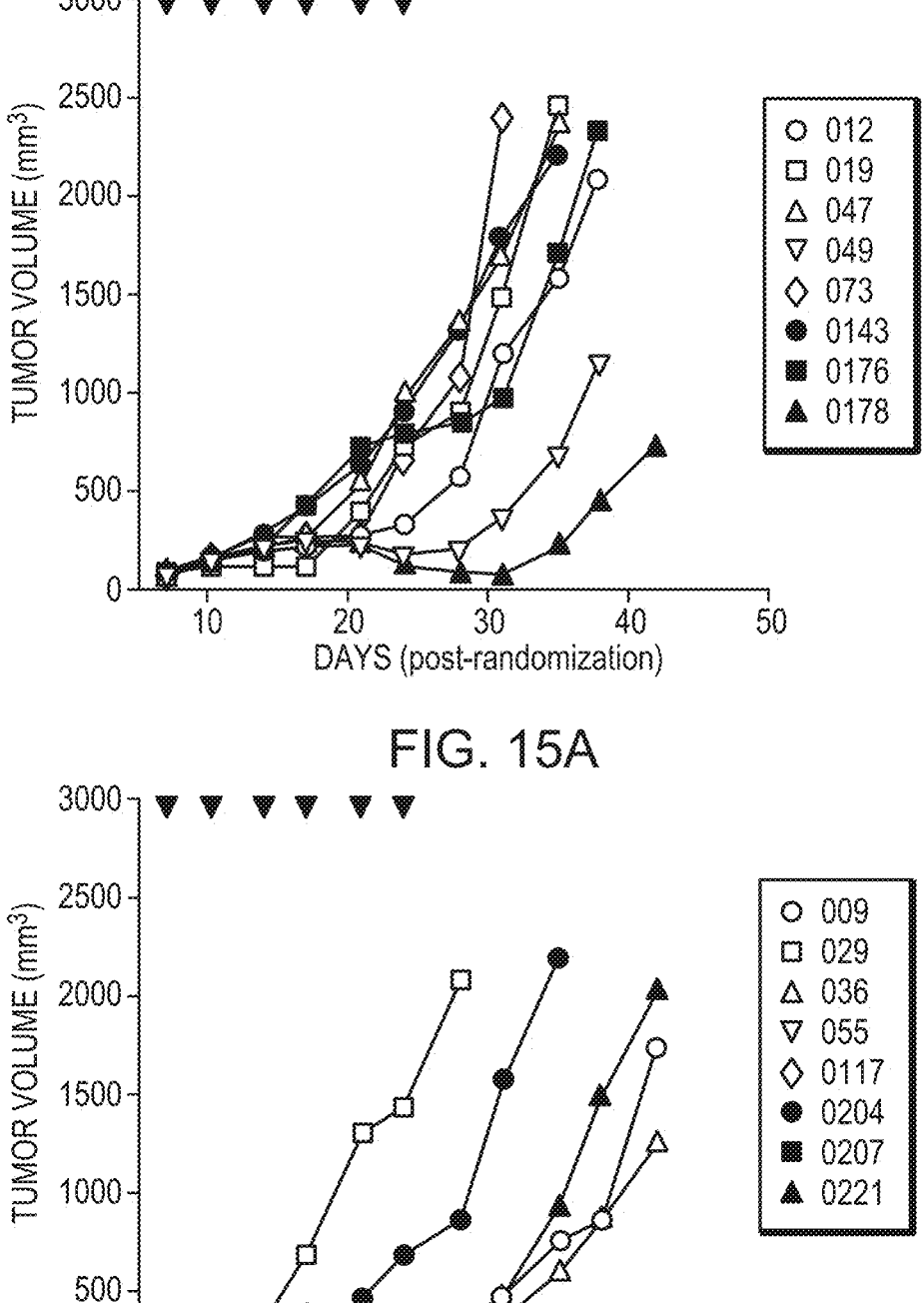
FIGS. 15A-D depict the testing of various configurations of antibody sialidase conjugates in a mouse syngeneic tumor model utilizing EMT6 mouse breast cancer cells engineered to express human Her2. Mice are treated via intraperitoneal injection of 10 mg/kg of each test article on the days marked with black triangles and tumor volume (mm$^3$) recorded. Each line represents an individual mouse. Mice are treated with either trastuzumab (FIG. 15A), Raptor (FIG. 15B), Janus (FIG. 15C) or Lobster (FIG. 15D).
Figures 15C, 15D:
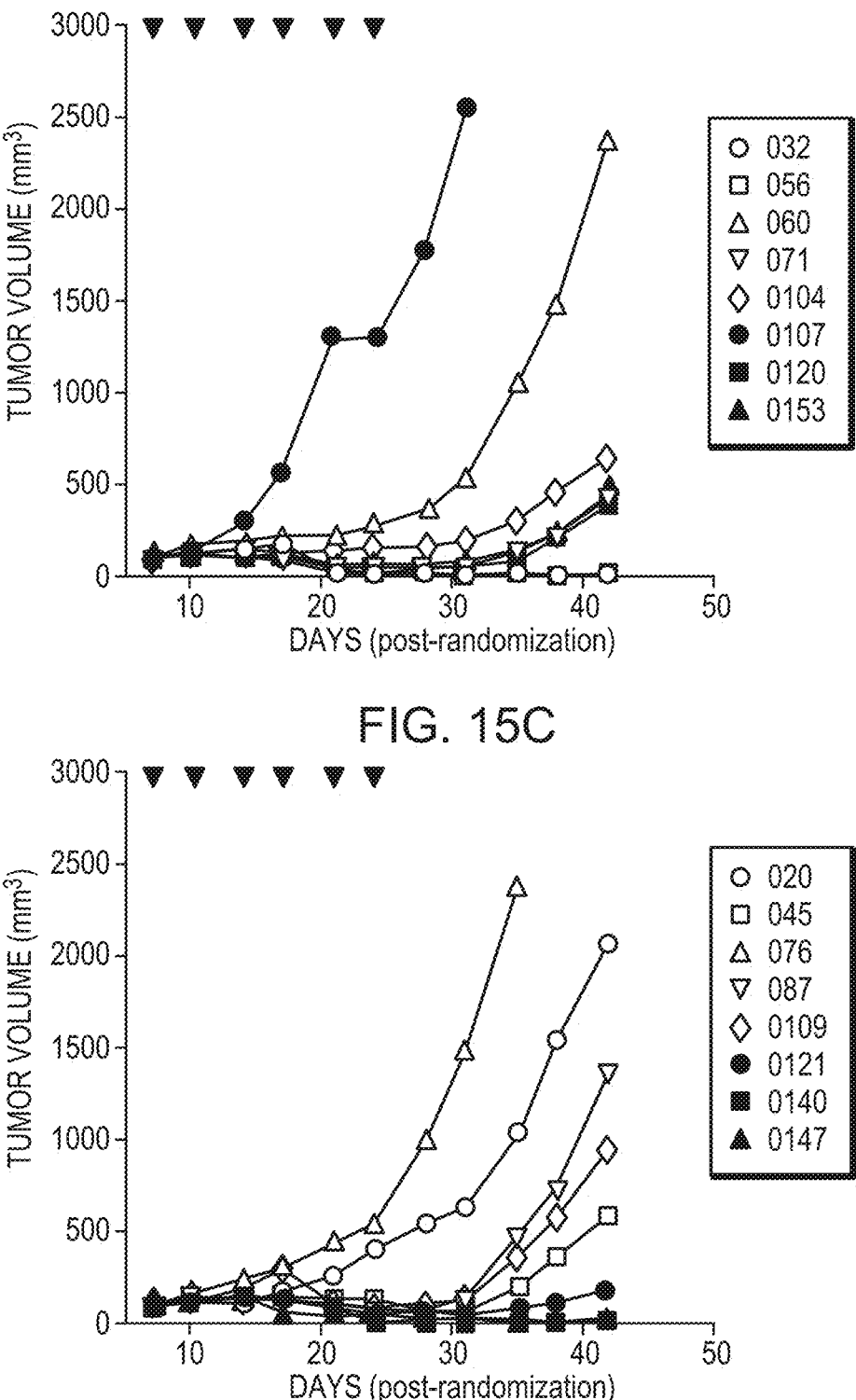

The results from for treatment with trastuzumab, and Raptor, Janus and Lobster ASCs are shown in FIGS. 15A, 15B, 15C and 15D respectively. As can be seen, trastuzumab resulted in no complete responses in eight individual mice as treated (defined as regression below the limit of palpation at any point for the duration of the study, FIG. 15A). This is in contrast to Raptor which demonstrated 2 out of 8 animals with a complete response (FIG. 15B), Janus which demonstrated 3 out of 8 animals with a complete response (FIG. 15C) and Lobster which demonstrated 2 out of 8 animals with a complete response (FIG. 15D).

Figures 16A, 16B:
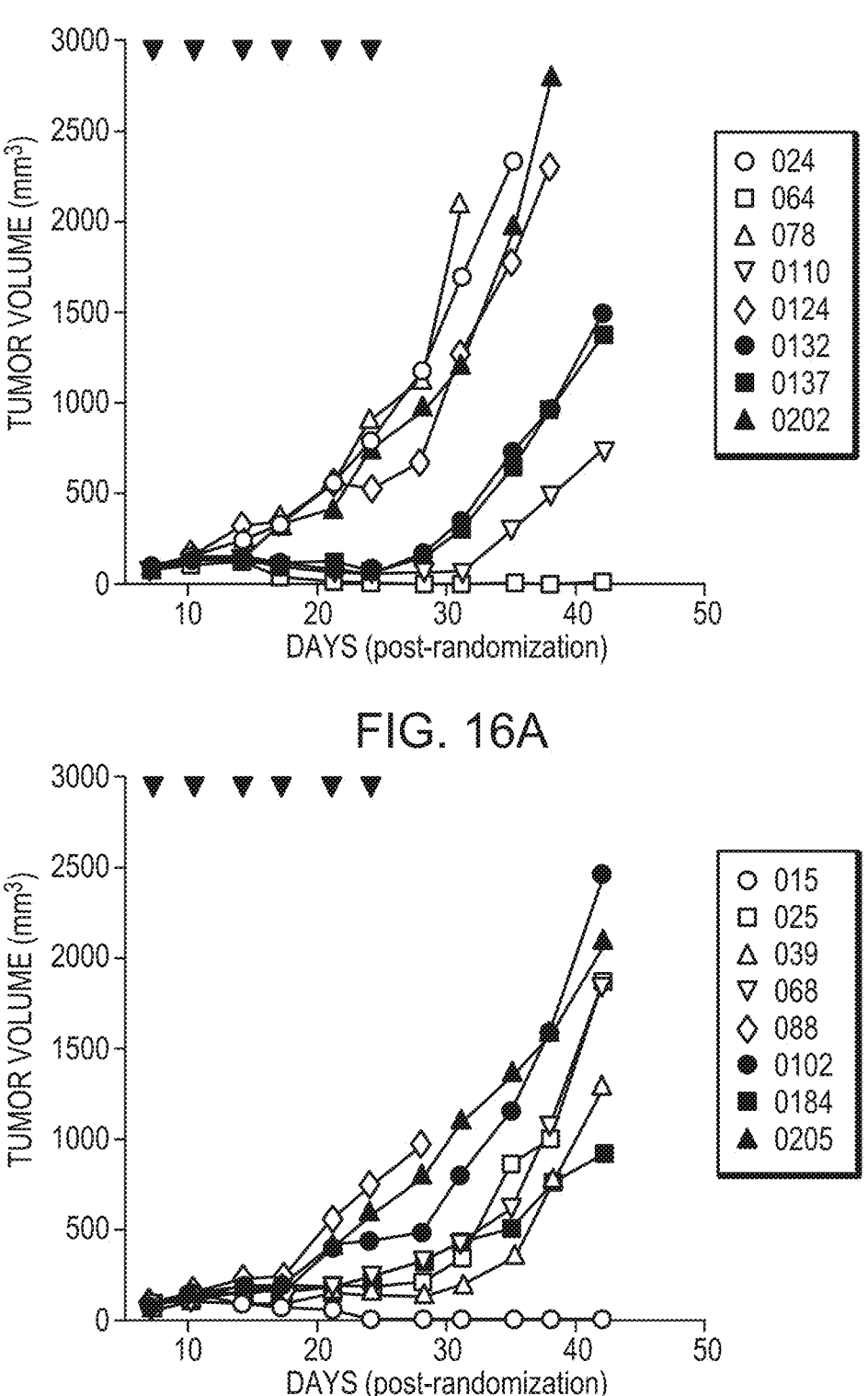
FIGS. 16A-D depict the testing of the Janus antibody sialidase conjugate in a mouse syngeneic tumor model utilizing EMT6 mouse breast cancer cells engineered to express human Her2. Mice were treated via intraperitoneal injection of 10 mg/kg of Janus on the days marked with black triangles and tumor volume (mm$^3$) recorded. Mice were also treated on the same days as Janus with either anti-mouse NK1.1 (10 mg/kg) to deplete natural killer cells (FIG. 16A), liposomal clodronate (0.5 mg/mouse, three times a week for two weeks) to deplete macrophages (FIG. 16B), or anti-mouse CD8α (10 mg/kg) to deplete CD8+ T cells (FIG. 16C). Each line represents an individual mouse.
Figure 16C:
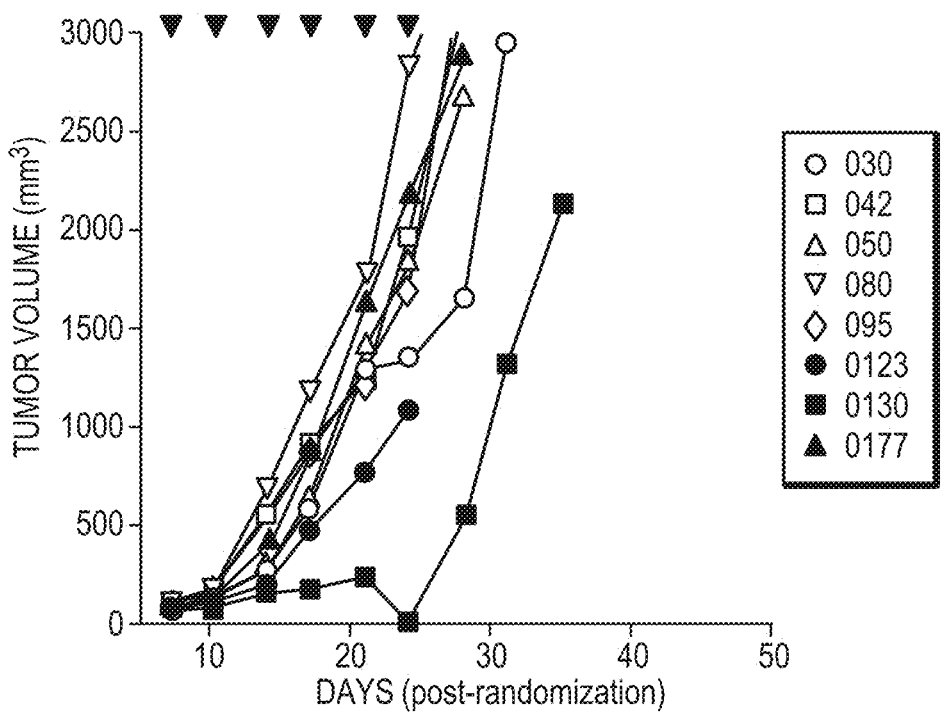
Figure 16D:
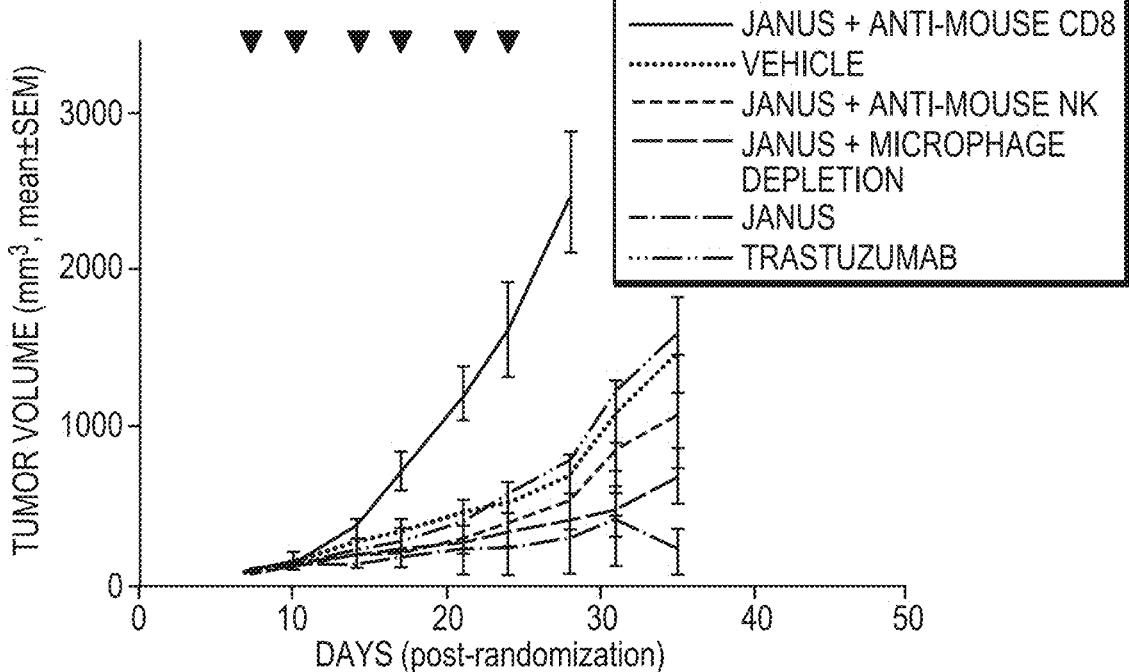

The results of administration of Janus with NK depletion (anti-mouse NK1.1), macrophage depletion (liposomal clodronate) and CD8 T cell depletion (anti-mouse CD8a) are shown in FIG. 16. As can be seen, compared to Janus treatment alone (FIG. 15C), where there was a complete response in 3 out of 8 animals, NK depletion reduced the number of complete responses to 1 out of 8 animals (FIG. 16A). Macrophage depletion also reduced the number of complete responses to 1 out of 8 animals (FIG. 16B). CD8 T cell depletion completely reversed the effects of Janus, with no animals showing a complete response (FIG. 16C). FIG. 16D shows the mean tumor volume for vehicle, Janus alone, trastuzumab alone and Janus with NK, macrophage and CD8 T cell depletions. These results demonstrate that innate immunity (NK and macrophage dependent) as well as adaptive immunity (CD8 T cells) contribute to in vivo ASC activity.

Example 9

This Example describes the in vivo administration of antibody sialidase conjugates (ASCs) with bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); and (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62). ASCs were made as described in Example 7.

These ASCs were tested in a mouse syngeneic orthotopic tumor model injected with an independent EMT6 cell line expressing human Her2 (EMT6-hHer2 cells as described in D'Amico et al. (2016) ANNALS OF ONCOLOGY, Volume 27, Issue suppl_8, 41P. Female BALB/c mice, 6-8 weeks of age, were inoculated via intra mammary implantation with EMT6-Her2 tumor cells ($5\times10^6$). Mice were randomly allocated to 6 groups when tumors reached approximately 250 mm$^3$. The treatment groups are described in TABLE 9 with dosing schedule indicated post randomization. Anti-mouse PD1 was obtained from BioXcell (RMP1-14, Cat. #665418F1). Janus and Janus Loss of Function (Janus LOF) are described above in Example 7.

TABLE 9

| Group | Animal No. | Treatment | Dose (mg/kg) | Dose volume (μL/g) | Route | Schedule (Days) |
|---|---|---|---|---|---|---|
| 1 | 6 | Vehicle (PBS) | NA | 10 | i.p. | 0, 3, 7, 10 |
| 2 | 6 | Trastuzumab | 10 | 10 | i.p. | 0, 3, 7, 10 |
| 3 | 6 | Janus | 10 | 10 | i.p. | 0, 3, 7, 10 |
| 4 | 6 | Janus Loss of Function (LOF) | 10 | 10 | i.p. | 0, 3, 7, 10 |
| 5 | 6 | anti-mouse PD1 | 10 | 10 | i.p. | 0, 3, 7, 10 |
| 6 | 6 | Janus | 10 | 10 | i.p. | 0, 3, 7, 10 |
| | | anti-mouse PD1 | 10 | 10 | i.p. | 0, 3, 7, 10 |

59                                                                                                60

Figure 17A:
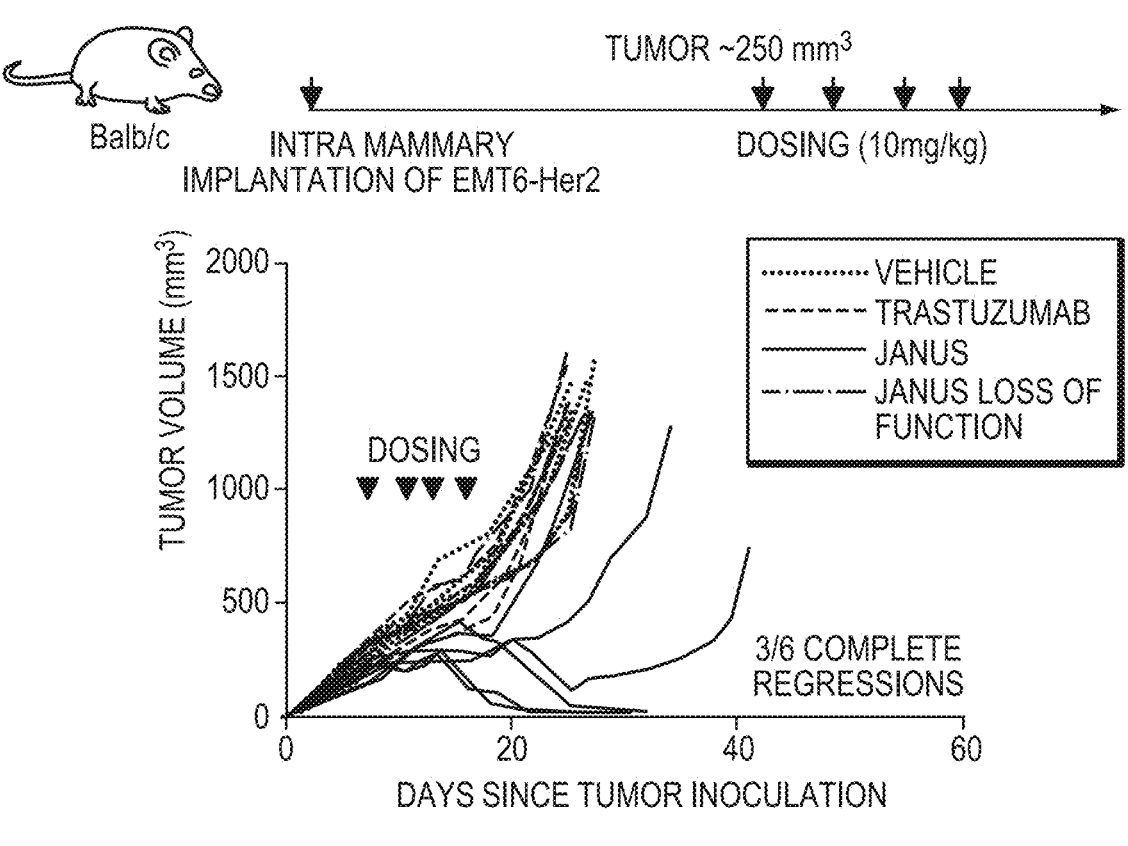
FIGS. 17A-B depict the testing of the Janus antibody sialidase conjugate in a mouse syngeneic orthotopic tumor model utilizing a second source of EMT6 mouse breast cancer cells engineered to express human Her2. Mice are treated via intraperitoneal injection of 10 mg/kg of each test article on the days marked with black triangles and tumor volume (mm$^3$) recorded. Each line represents an individual mouse. Mice are treated (▼) with either vehicle, trastuzumab, Janus or Janus Loss of Function (FIG. 17A).

The results for Groups 1 through 4 (vehicle, trastuzumab, Janus and Janus LOF) are shown in FIG. 17A. As can be seen, 3 out of 6 animals treated with Janus had a complete regression of tumor growth. Notably, Janus LOF and trastuzumab were both comparable to vehicle treated animals.

approximately 50 to 100 mm³. Treatment groups are described in TABLE 10 with dosing schedule indicated post randomization. Anti-mouse PD1, obtained from BioXcell (RMP1-14, Cat. No. 665418F1) and anti-mouse CTLA4, obtained from BioXcell (9D9, Cat. #BE0164), and were used in combination.

TABLE 10

| Group | No. of Animal | Treatment | Dose (mg/kg) | Dose volume (uL/g) | Route | Schedule (Days) |
|---|---|---|---|---|---|---|
| 1 | 6 | Janus | NA | 10 | i.p. | 0, 3, 7, 10 |
| 2 | 6 | Trastuzumab | 10 | 10 | i.p. | 0, 3, 7, 10 |
| 3 | 6 | anti-mouse CTLA4 | 10 | 10 | i.p. | 0, 3, 7, 10 |
|   |   | anti-mouse PD1 | 10 | 10 | i.p. | 0, 3, 7, 10 |

Figure 17B:
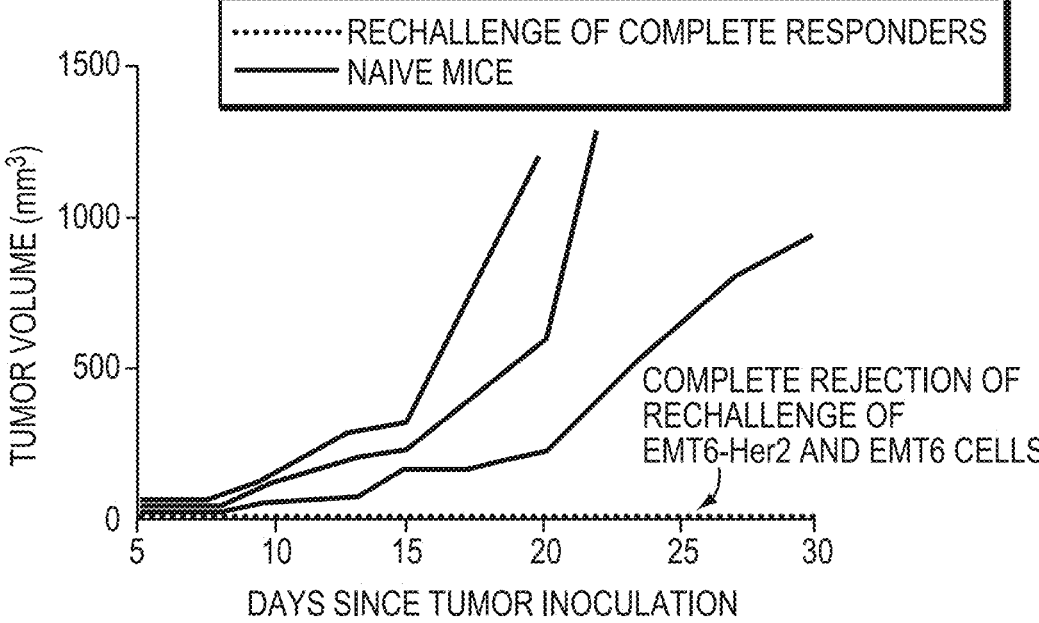

The 3 mice with a complete regression ("cured mice") were rechallenged with either the same EMT6-Her2 cells used originally or parental EMT6 cells (lacking engineered human Her2 expression). EMT6 cells and EMT6-Her2 cells were inoculated subcutaneously in the right or left lower flank region respectively (5×10⁵) in 0.1 ml of PBS for tumor development of all three cured mice. EMT6-Her2 cells were also inoculated subcutaneously into naïve mice as a control. As can be seen in FIG. 17B, neither EMT6-Her2 cells nor parental EMT6 cells resulted in tumor growth in the cured mice while EMT6-Her2 cells developed into tumors as expected in the naïve mice. These results suggest that the antibody sialidase conjugates of the present invention are capable of inducing long term memory against tumors. In addition, the long term memory is towards the tumor cell and is independent of the originally targeted cancer antigen (Her2 in this case).

Figures 18A, 18B:
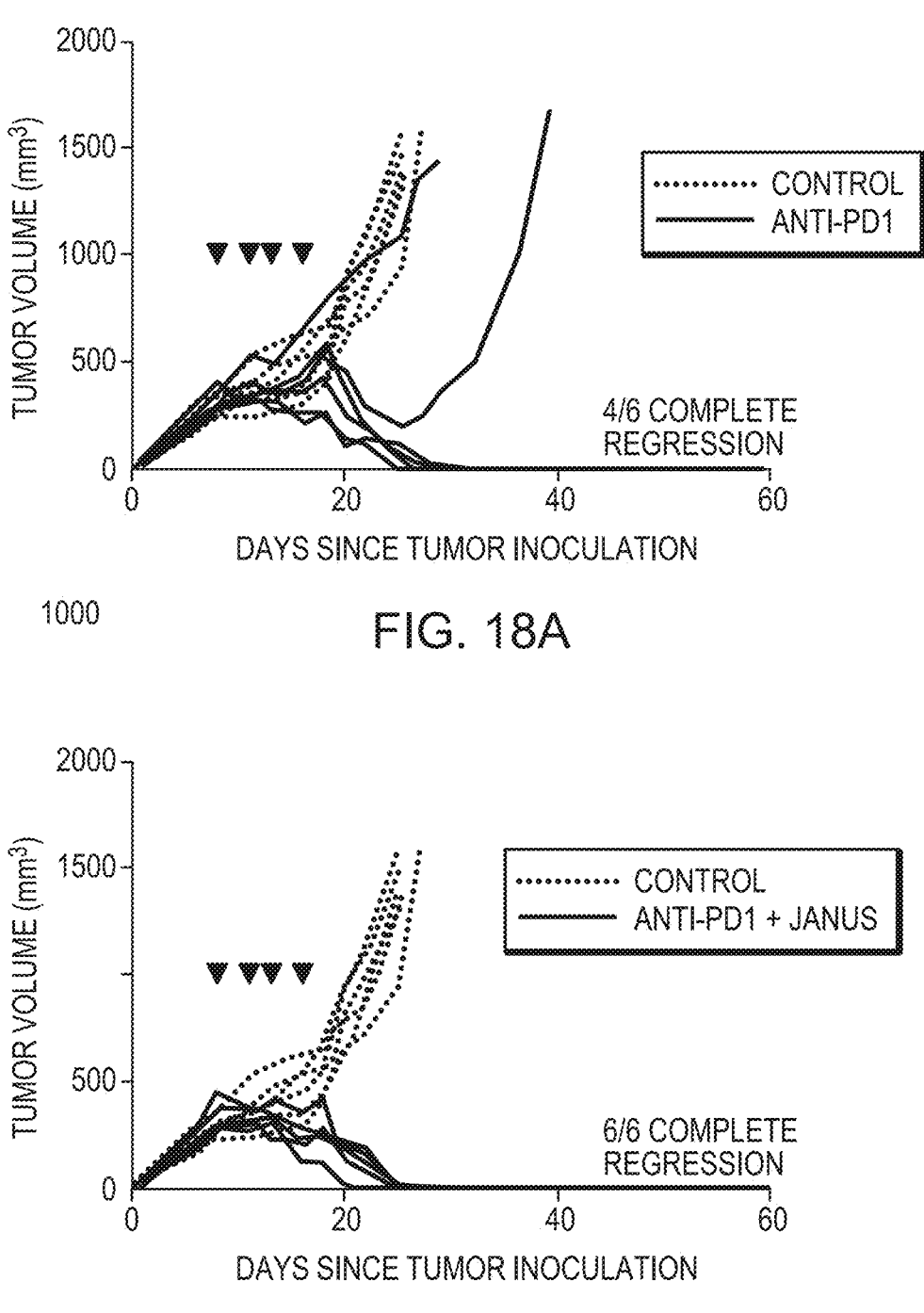
FIGS. 18A-B depict the testing of the Janus antibody sialidase conjugate in a mouse syngeneic orthotopic tumor model in combination with anti-mouse PD1. Mice are treated via intraperitoneal injection of 10 mg/kg of either anti-mouse PD1 alone (FIG. 18A) or Janus and anti-mouse PD1 (10 mg/kg of each, FIG. 18B) on the days marked with black triangles (▼) and tumor volume (mm$^3$) recorded. Each line represents an individual mouse.

The results for Groups 1, 5 and 6 (vehicle, anti-mouse PD1 and anti-mouse PD1 combined with Janus) are shown in FIG. 18A and FIG. 18B. While anti-mouse PD1 had good activity with 4 out of 6 mice demonstrating complete regressions (similar to Janus alone with 3 out of 6 mice demonstrating complete regression, see FIG. 17A), the combination of anti-mouse PD1 with Janus demonstrated complete regression of tumor growth in all 6 mice (FIG. 18B). There was no body weight loss in any of the animals given this combination.

Example 10

This Example describes the in vivo administration of antibody sialidase conjugates (ASCs) with bacterial sialidases.

A Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56) was made as described in Example 7.

Figure 19:
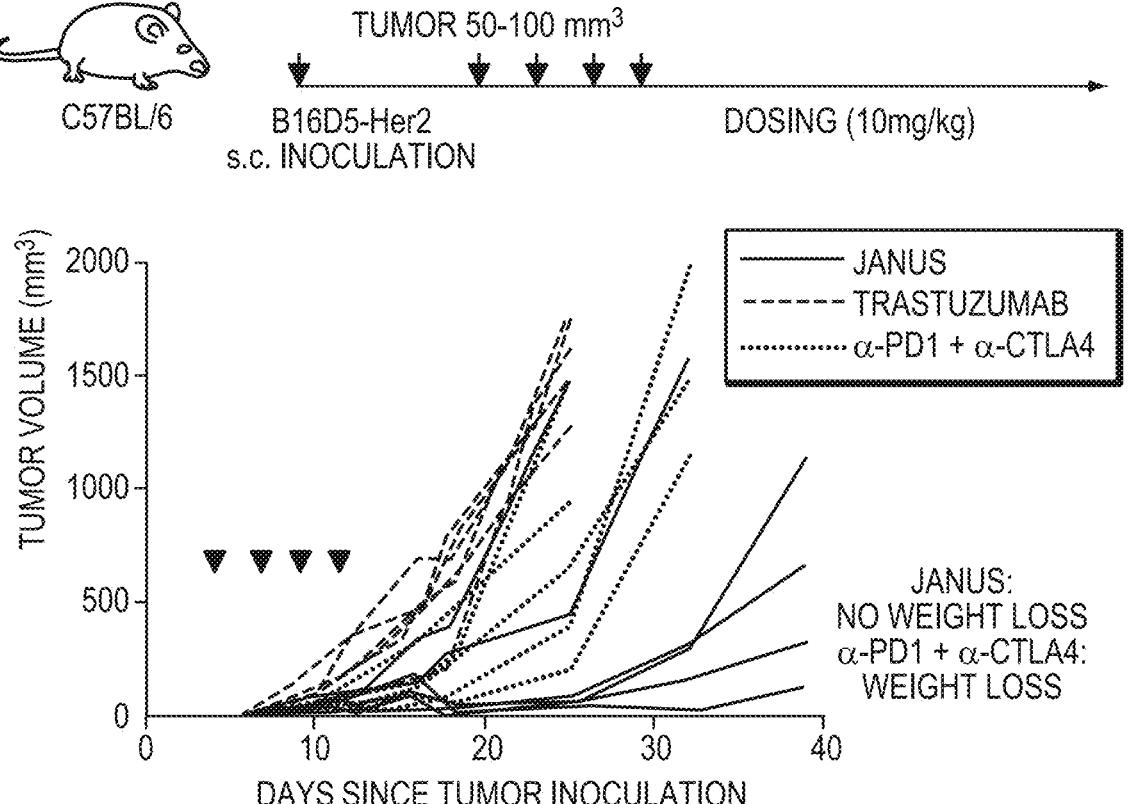
FIG. 19 depicts the testing of various test articles in a mouse syngeneic tumor model injected with a B16 melanoma cell line expressing human Her2. Mice are treated via intraperitoneal injection of 10 mg/kg of either Janus, trastuzumab or a combination of anti-mouse PD1 and anti-mouse CTLA4 (10 mg/kg of each) on the days marked with black triangles (▼) and tumor volume (mm$^3$) recorded. Each line represents an individual mouse.

The ASC was tested in a mouse syngeneic tumor model injected with a B16 melanoma cell line expressing human Her2 (B16D5-Her2, Surana et al. CANCER IMMUNOL RES, 2 (11): 1103-1112). Female C57BL/6 mice, 6-8 weeks of age, were inoculated subcutaneously in the right lower flank region with B16D5-Her2 tumor cells (5×10⁵). Mice were randomly allocated to 3 groups when tumors reached The B16 melanoma mouse model is considered a difficult tumor model to treat with immuno-oncology approaches. A comparison of Janus to a combination of anti-mouse PD1 and anti-mouse CTLA4 was carried out. The results are shown in FIG. 19. Anti-mouse PD1 combined with anti-mouse CTLA4 had an impact on B16D5-Her2 tumor growth, but this combination also demonstrated significant weight loss in the treated animals. By comparison, Janus demonstrated a more robust anti-tumor activity with no significant weight loss. Trastuzumab alone demonstrated marginal activity in this model.

Example 11

This example describes targeted cleavage of terminal sialic acids from tumor cells by antibody sialidase conjugates (ASCs).

The following ASCs were made and tested in this Example: (i) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); (ii) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (iii) a Lobster ASC including St-sialidase and an scFv derived from trastuzumab (including first and second polypeptide chains with amino acid sequence SEQ ID NO: 103, encoded by nucleotide sequence SEQ ID NO: 104); (iv) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); and (v) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7.

Figure 20:
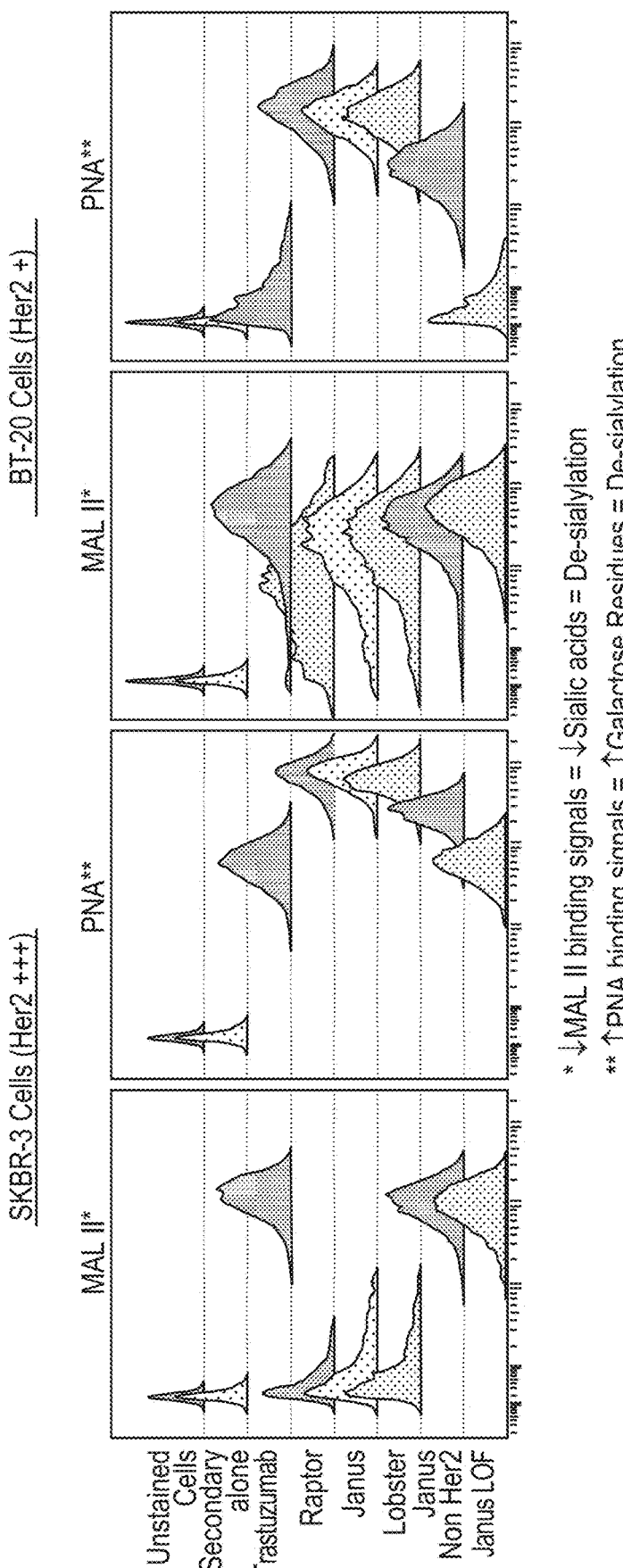
FIG. 20 depicts binding of MAL II and PNA lectins to tumor cells, as assayed by FACS staining, following the indicated treatment. MAL II and PNA staining are indicative of cleavage of terminal sialic acids from the tumor cells, MAL II staining is expected to decrease upon loss of cell surface sialic acid and PNA staining is expected to increase with loss of cell surface sialic acid.

SKBR-3 cells (Her2+++) or BT-20 cells (Her2+) were incubated with trastuzumab or the indicated ASCs, and FACS staining with MAL II and PNA was used to measure the degree of sialic acid removal (see, FIG. 20). MAL II is a lectin with high affinity for sialic acid, and therefore MAL II staining was expected to decrease upon loss of cell surface sialic acid following cleavage by an ASC. PNA is a lectin with high affinity for terminal galactose residues and therefore PNA staining was expected to increase with loss of cell surface galactose coupled sialic acid following cleavage by an ASC. Compared to trastuzumab, treatment with Janus, Raptor and Lobster ASCs decreased sialic acid levels on cancer cells with high or low levels of Her2 (SKBR-3 and BT-20 cells, respectively). No sialic acid cleavage was observed for the Janus LOF construct and substantially reduced sialic acid cleavage was observed for the Janus non-Her2 binding construct.

Example 12

This example describes a reduction in cancer-cell mediated inhibition of dendritic cell (DC) activation by antibody sialidase conjugates (ASCs).

DCs play a major role in initiating and sustaining an immune response. They seek antigens in tissues (including tumor sites). Once DCs encounter antigens, they mature, activate, and move to draining lymph nodes for presentation of the processed antigen to T cells. This process of DC activation can be inhibited by the interaction of hypersialylated proteins on cancer cells with Siglecs on the surface of DCs. Desialylation of hypersialylated proteins on cancer cells by an ASC can potentially reduce this inhibition and result in increased activation of DCs.

To test this, SKBR-3 cells (which express high levels of Her2) were initially incubated with either: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); or (iii) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7. Cells were then washed and co-cultured with DCs for 16 hours in presence or absence of lipopolysaccharide (LPS; a DC activation signal). DC surface activation markers were assessed by flow cytometry.

Figure 21:
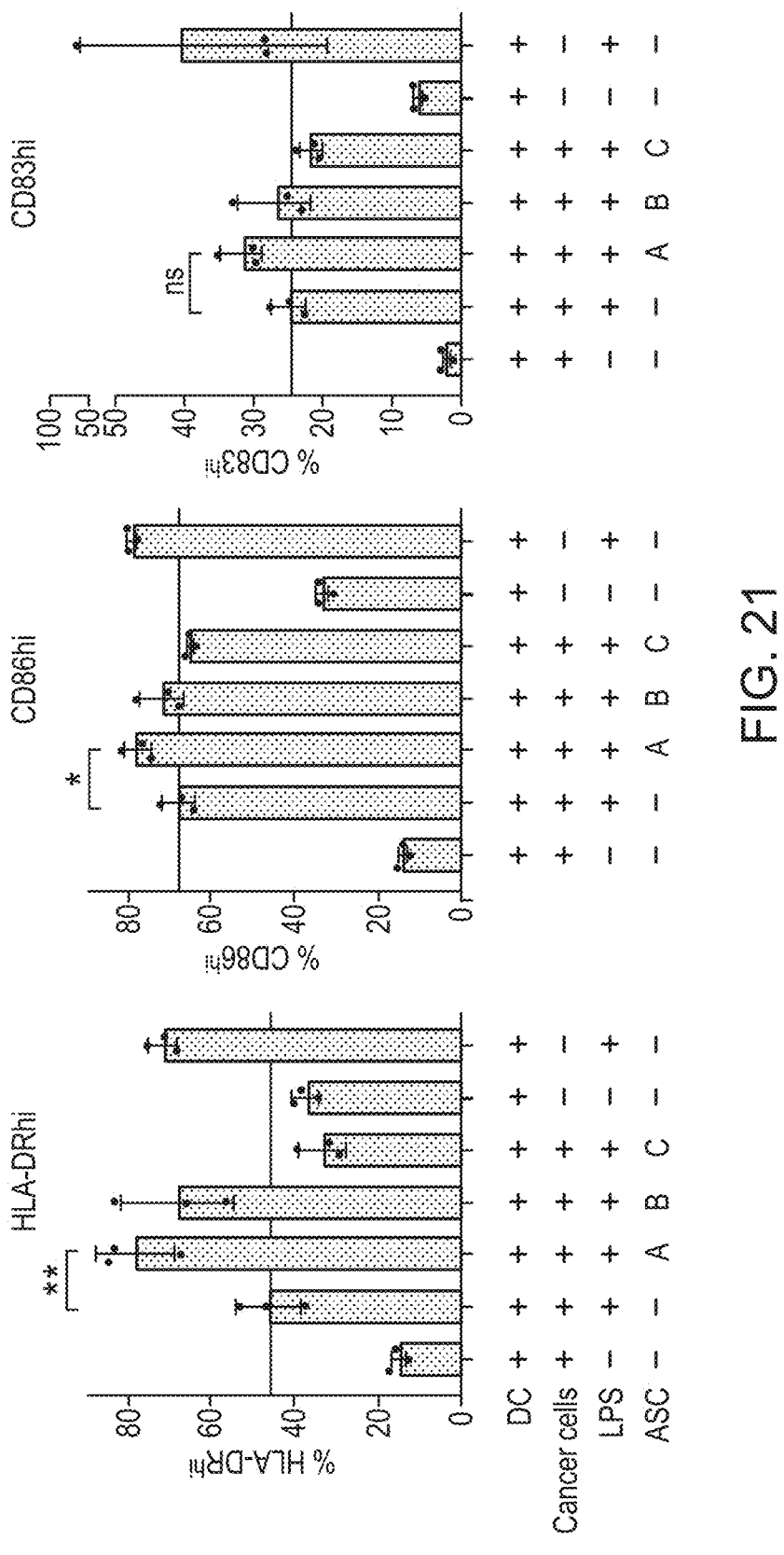
FIG. 21 depicts cell surface expression of dendritic cell (DC) activation markers HLA-DR, CD86 and CD83, as assayed by flow cytometry, following the indicated treatment. A indicates a Janus ASC made with St-sialidase and trastuzumab, B indicates a non-Her2 binding Janus ASC made with St-sialidase, and C indicates a Janus ASC made with a loss of function St-sialidase mutant and trastuzumab. *P≤0.05, P≤0.01, *P≤0.001, and **** P≤0.0001.

As can be seen in FIG. 21, co-culture of DCs with LPS increased levels of the surface activation markers HLA-DR, CD86 and CD83. However, this increase was reduced in the presence of SKBR-3 cancer cells, reflecting inhibition of DC activation by the cancer cells. Treatment of the SKBR-3 cell line with Janus blocked SKBR-3-mediated inhibition of DCs, as evidenced by increased cell surface expression of HLA-DR, CD86 and CD83 on the DCs. The effect was reduced for Janus non-Her2 and completely absent for Janus LOF versions of the ASC, indicating that both active and targeted sialidase activity in the ASC is required for an optimal effect.

These results demonstrate that targeted desialylation of cancer cells by ASCs can reduce cancer-cell mediated inhibition of dendritic cell (DC) activation. Accordingly, treatment with ASCs may be an effective strategy for enhancing immunogenicity of tumor antigens by enhancing their presentation by DCs.

Example 13

This Example describes induction of proinflammatory cytokines in peripheral blood mononuclear cells (PBMCs) by an antibody sialidase conjugate (ASC) with a human sialidase.

A Janus ASC was constructed that includes Neu2 with M1D, V6Y, I187K, and C332A mutations and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 54, encoded by nucleotide sequence SEQ ID NO: 98)

Human PBMCs were freshly isolated, washed two times, and plated in culture medium (RPMI 1640+L-glut, 10% FBS, 1% P/S) at 250,000 PBMCs per well. PBMCs were incubated in quadruplicate with the Janus ASC at 2.5× serial dilutions, with a maximum concentration of 100 µg/ml. After 24 hours at 37° C., cells were removed by centrifugation and supernatants collected for cytokine measurement using Luminex multiplex assays according to manufacturer's instruction.

Figures 22A, 22B, 22C, 22D:
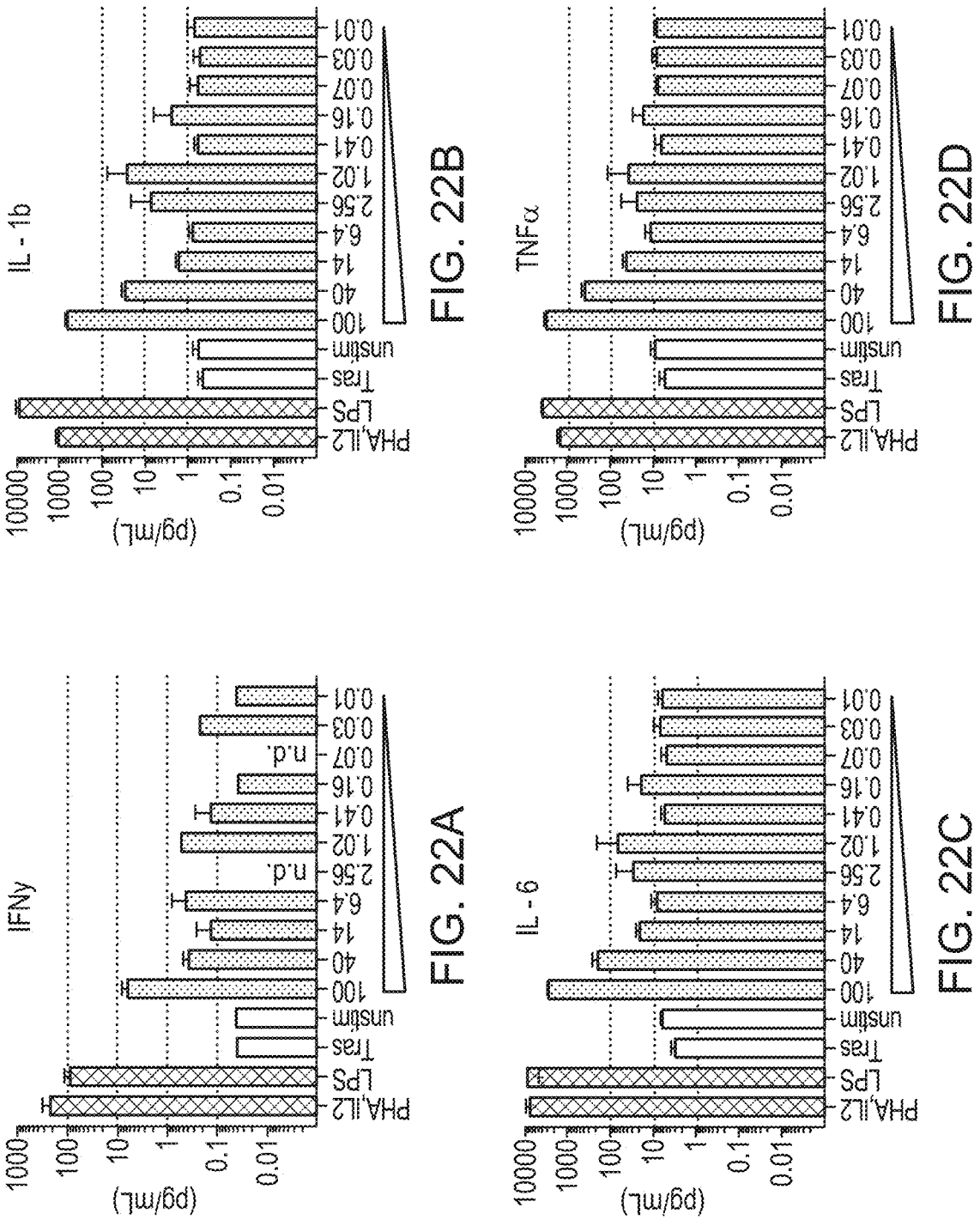
FIGS. 22A-D depict IFNγ (FIG. 22A), IL-1b (FIG. 22B), IL-6 (FIG. 22C), and TNFα (FIG. 22D) release following treatment with a Janus ASC including human Neu2 with ΔM1, V6Y, I187K, and C332A mutations and trastuzumab. Freshly isolated human peripheral blood mononuclear cells (PBMCs) were incubated with Janus at the indicated concentrations (shown in μg/ml) for 24 hours. PHA-L with IL-2 or LPS were used as positive controls to stimulate cytokine release. Trastuzumab (Tras) was used as a negative control.

As positive controls, phytohemagglutinin-L (PHA-L; 5 µg/mL) with IL-2 (10 U/mL) or LPS (10 ng/mL) were used to stimulate cytokine release. As a negative control, trastuzumab (10 µg/mL) was used. As seen FIG. 22, the human Janus ASC induced proinflammatory cytokine secretion in PBMCs (e.g., INFγ, IL-1b, IL-6 and TNFα). FIG. 23 depicts the effects of the human Janus ASC on PBMC secretion of proinflammatory cytokine IL-2, antiinflammatory cytokines IL-4 and IL-10, and pro- and antiinflammatory cytokine IL-13.

These results demonstrate that ASCs can induce secretion of proinflammatory cytokines in PBMCs.

Example 14

This example describes increased immune-related activities following addition of antibody sialidase conjugates (ASCs) to a host-tumor microenvironment model system.

BioMAP Oncology Panels (Eurofins, Fremont, CA) are a complex co-culture of tumor cell lines and early passage primary human cells (endothelial cells/fibroblasts and PBMCs) that mimic cancer-induced immune suppression. In certain circumstances, BioMAP results have correlated with clinical outcomes. For example, pembrolizumab has been shown to increase immune response in the model, while IDO inhibitors had no effect.

The following constructs were tested in a blinded study using the BioMAP VascHT29 co-culture system: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); (iii) isotype control; (iv) trastuzumab; or (v) pembrolizumab. All ASCs were made as described in Example 7.

Figure 24:
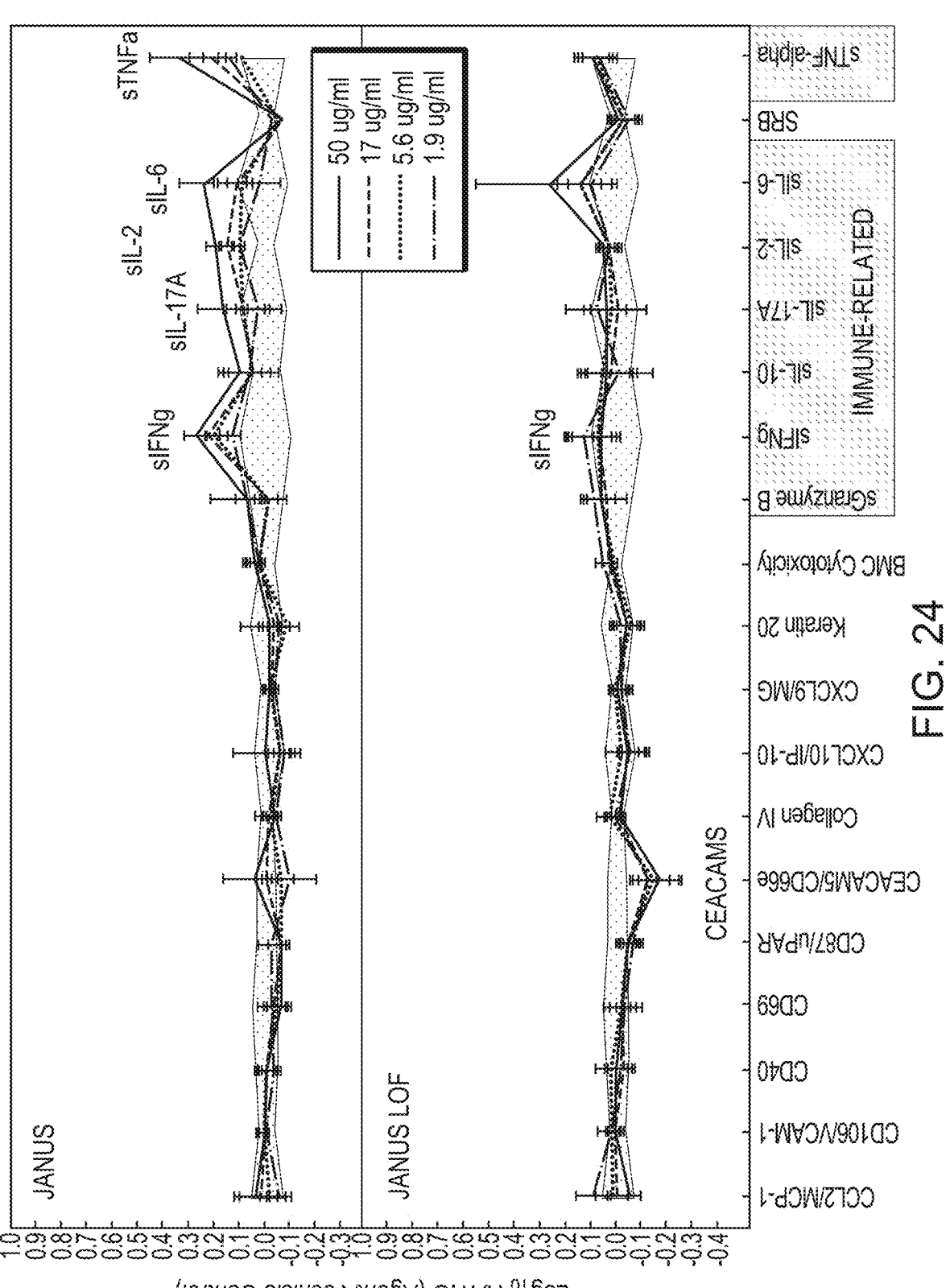
FIG. 24 depicts relative expression of the indicated markers following addition of Janus and Janus LOF to the BioMAP VascHT29 co-culture tumor microenvironment model. The historical range of vehicle response is represented by the shaded area along the zero baseline. Values for each measurement are represented by the log of the ratio of test article to vehicle control. Analytes with a statistically meaningful value above historical ranges are annotated.
Figure 25:
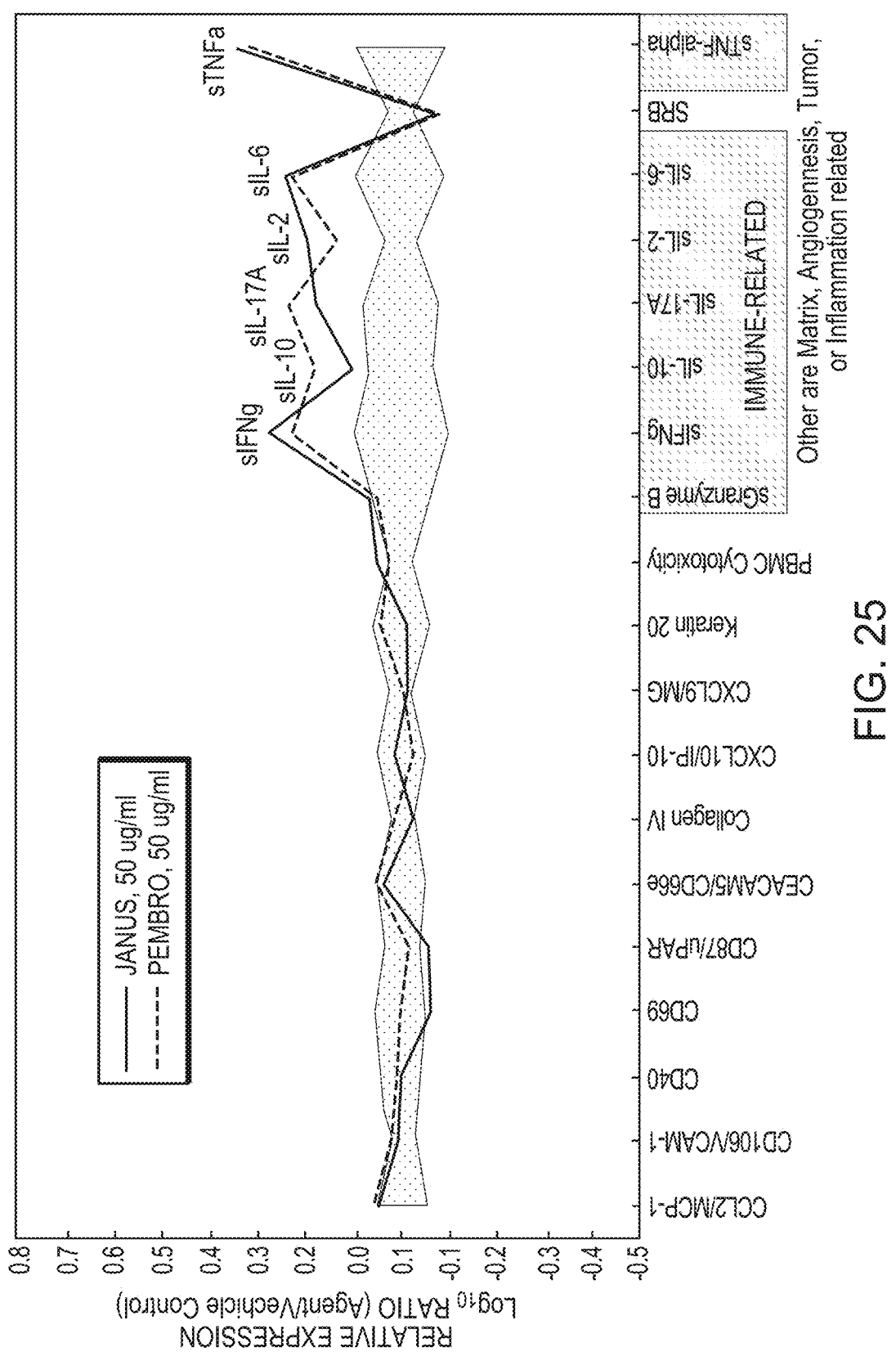
FIG. 25 depicts relative expression of the indicated markers following addition of Janus and pembrolizumab to the BioMAP VascHT29 co-culture tumor microenvironment model. The historical range of vehicle response is represented by the shaded area along the zero baseline. Values for each measurement are represented by the log of the ratio of test article to vehicle control. Analytes with a statistically meaningful value above historical ranges are annotated.

Test reagents were tested at a range of concentrations (50, 17, 5.6 and 1.9 μg/ml) for 48 hours. Following exposure, a number of parameters were analyzed as depicted in FIG. 24 and FIG. 25. In both figures, the historical range of vehicle response is represented by the shaded area along the zero baseline. Values for each measurement are represented by the log of the ratio of test article to vehicle control. Analytes with a statistically meaningful value above historical ranges are annotated.

FIG. 24 demonstrates that Janus is not cytotoxic at the concentrations tested in this study. Janus demonstrated a dose dependent increase in a number of immune-related activities, including increased soluble IL-17A, IL-6, IL-2, and IFNγ as well as inflammation-related activities as seen by increased TNFα. Janus LOF is not cytotoxic at the concentrations tested in this study and demonstrated modest immune-related activities with increased IFNγ and tumor-related activities with decreased CEACAM5. FIG. 25 is a comparison of Janus to pembrolizumab. As can be seen in FIG. 25, Janus has a similar activity to pembrolizumab in this tumor microenvironment model.

Example 15

This Example describes the in vivo administration of antibody sialidase conjugates (ASCs) containing bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); and (ii) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7.

The ASCs were compared to trastuzumab in a mouse syngeneic tumor model. Female BALB/c mice, 6-8 weeks of age, were inoculated subcutaneously in the right lower flank region with a murine breast cancer cell line expressing human Her2 (EMT6-hHer2 cells; $5 \times 10^5$ cells) in 0.1 ml of PBS for tumor development. Mice were randomly allocated to 4 groups of 8 animals each when tumors reached 50-100 mm³, mean ~75-100 mm³.

Figure 26:
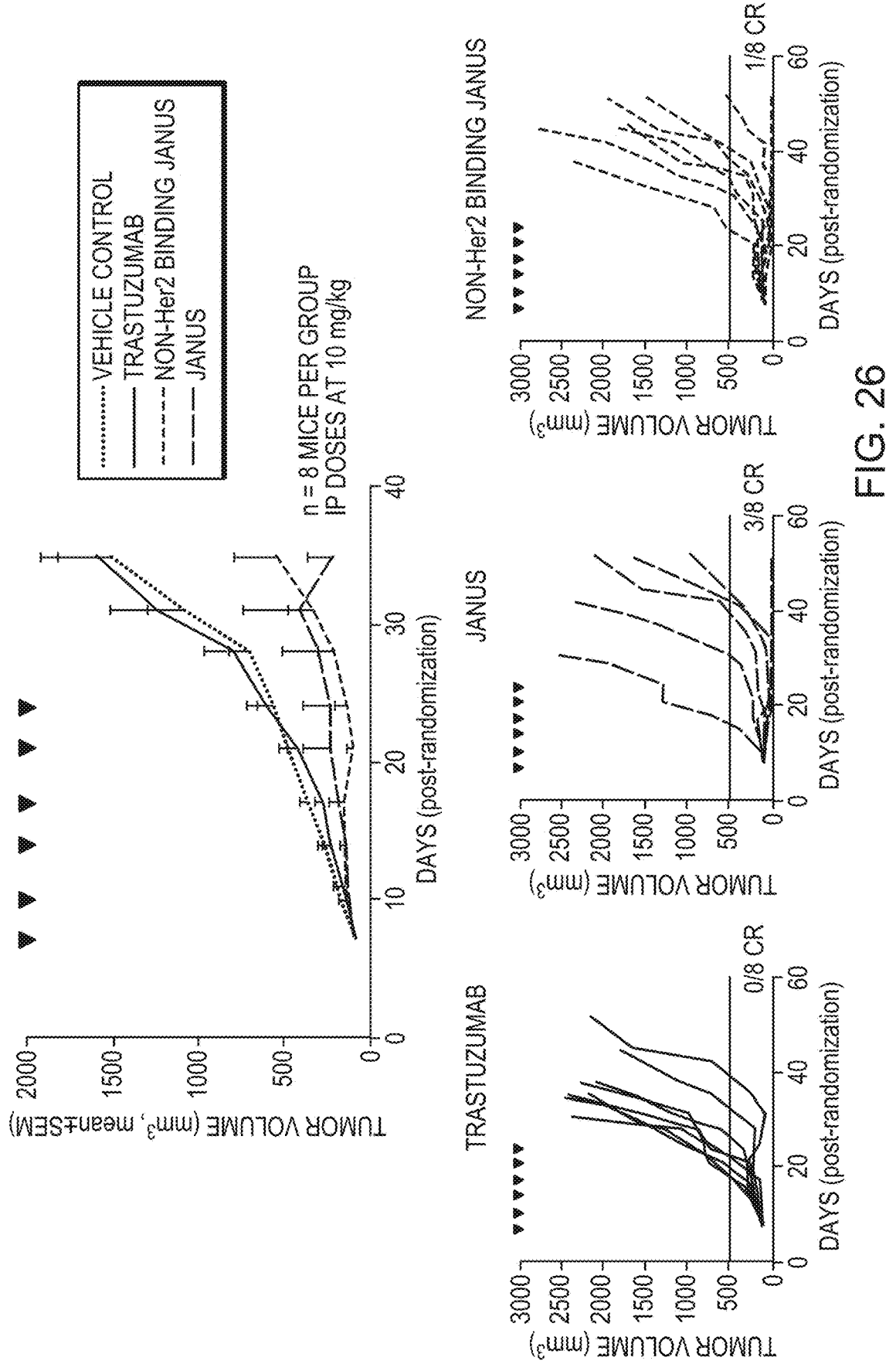
FIG. 26 depicts the testing of the Janus antibody sialidase conjugate in a mouse syngeneic tumor model utilizing EMT6 mouse breast cancer cells engineered to express human Her2. Mice were treated via intraperitoneal injection of 10 mg/kg of Janus, trastuzumab or a non-Her2 binding Janus versus vehicle on the days marked with black triangles (▼) and tumor volume (mm$^3$) was recorded. Mean tumor volumes for each treatment group are shown. Tumor volumes for individual mice in each treatment group are shown.

Mice were treated via intraperitoneal injection of 10 mg/kg of Janus, trastuzumab or non-Her2 binding Janus and tumor volume (mm³) was recorded. FIG. 26 shows mean tumor volumes for each treatment group. FIG. 26 shows tumor volumes for individual mice in each treatment group. Complete Responses (CR, defined as regression below the limit of palpation at any point during the study) are shown as well. Trastuzumab and vehicle control demonstrated similar tumor growth curves and no CRs. In contrast, Janus demonstrated reduced tumor growth compared to vehicle with 3 out of 8 mice demonstrating CR. Non-Her2 binding Janus demonstrated a reduced tumor growth compared to vehicle with 1 out of 8 mice demonstrating CR. These results show that ASCs may be active towards a tumor with low expression levels of the tumor antigen targeted by the ASC. Additionally, these results suggest that a non-targeted ASC, e.g., a sialidase-Fc fusion protein, may be active towards a tumor lacking a specific tumor-associated antigen.

Example 16

This Example describes the in vivo administration of antibody sialidase conjugates (ASCs) containing human sialidases.

The following ASCs were made and tested in this Example: (i) a Lobster ASC including Neu2 with ΔM1, V6Y and I187K mutations and an scFv derived from trastuzumab (including first and second polypeptide chains with amino acid sequence SEQ ID NO: 65, encoded by nucleotide sequence SEQ ID NO: 66, and referred to as "Lobster 1" in this example); and (ii) a Lobster ASC including Neu2 with V6Y and I187K mutations and an scFv derived from trastuzumab (including first and second polypeptide chains with amino acid sequence SEQ ID NO: 74, encoded by nucleotide sequence SEQ ID NO: 99, and referred to as "Lobster 2" in this example). ASCs were made as described in Example 7.

These ASCs were compared to trastuzumab in a mouse syngeneic tumor model injected with a murine breast cancer cell line expressing human Her2 (EMT6-hHer2 cells). Female BALB/c mice, 6-8 weeks of age, were inoculated subcutaneously in the right lower flank region with EMT6-Her2 tumor cells ($5 \times 10^5$) in 0.1 ml of PBS for tumor development. Mice were randomly allocated to 4 groups of 5 animals each when tumors reached 50-100 mm³, mean ~75-100 mm³.

Mice were treated via intraperitoneal injection of 10 mg/kg of either human Lobster 1, human Lobster 2, or trastuzumab and tumor volume (mm³) was recorded. FIG. 27 shows mean tumor volumes for the individual mice for the indicated treatments. Complete Responses (CR, defined as regression below the limit of palpation at any point during the study) are shown. Trastuzumab and vehicle control demonstrated no CRs. In contrast, both human Lobster 1 and human Lobster 2 demonstrated a reduced tumor growth compared to vehicle with 1 out of 5 mice in both groups demonstrating CR. This example demonstrates that human sialidase based ASCs demonstrate efficacy in an in vivo tumor model.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

SEQ ID NO: 1:
MASLPVLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPIQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQ

SEQ ID NO: 2:
MEDLRPMATCPVLQKETLFRTGVHAYRIPALLYLKKQKTLLAFAEKRASKTDEHAELIVLRRGSYNEATNRVKWQPEEVVTQAQL

EGHRSMNPCPLYDKQTKTLFLFFIAVPGRVSEHHQLHTKVNVTRLCCVSSTDHGRTWSPIQDLTETTIGSTHQEWATFAVGPGHC

LQLRNPAGSLLVPAYAYRKLHPAQKPTPFAFCFISLDHGHTWKLGNFVAENSLECQVAEVGTGAQRMVYLNARSFLGARVQAQSP

NDGLDFQDNRVVSKLVEPPHGCHGSVVAFHNPISKPHALDTWLLYTHPTDSRNRTNLGVYLNQMPLDPTAWSEPTLLAMGICAYS

DLQNMGQGPDGSPQFGCLYESGNYEEIIFLIFTLKQAFPTVFDAQ

SEQ ID NO: 3:
EDLRP

SEQ ID NO: 4:
MEDLRP

SEQ ID NO: 5:
MASLPVLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPIQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGLLYEANDYEEIVFLMFTLKQAFPAEYLPQ

SEQ ID NO: 6:
MEDLRPMASLPVLQKESVFQSGAHAYRIPALLYLPGQQSLLAFAEQRASKKDEHAELIVLRRGDYDAPTHQVQWQAQEVVAQARL

DGHRSMNPCPLYDAQTGTLFLFFIAIPGQVTEQQQLQTRANVTRLCQVTSTDHGRTWSSPRDLTDAAIGPAYREWSTFAVGPGHC

LQLHDRARSLVVPAYAYRKLHPIQRPIPSAFCFLSHDHGRTWARGHFVAQDTLECQVAEVETGEQRVVTLNARSHLRARVQAQST

NDGLDFQESQLVKKLVEPPPQGCQGSVISFPSPRSGPGSPAQWLLYTHPTHSWQRADLGAYLNPRPPAPEAWSEPVLLAKGSCAY

SDLQSMGTGPDGSPLFGCLYEANDYEEIVFLMFTLKQAFPAEYLPQ

SEQ ID NO: 7:
ENDFGLVQPLVTMEQLLWVSGRQIGSVDTFRIPLITATPRGTLLAFAEARKVISSSDEGAKFIALRRSMDQGSTWSPTAFIVNDG

DVPDGLNLGAVVSDVETGVVFLFYSLCAHKAGCQVASTMLVWSKDDGVSWSTPRNLSLDIGTEVFAPGPGSGIQKQREPRKGRLI

VCGHGTLERDGVFCLLSDDHGASWRYGSGVSGIPYGQPKQENDFNPDECQPYELPDGSVVINARNQNNYHCHCRIVLRSYDACDT

LRPRDVTFDPELVDPVVAAGAVVTSSGIVFFSNPAHPEFRVNLTLRWSFSNGTSWRKETVQLWPGPSGYSSLATLEGSMDGEEQA

PQLYVLYEKGRNHYTESISVAKISV

SEQUENCE LISTING

SEQ ID NO: 8:
MEEVTTCSFNSPLFRQEDDRGITYRIPALLYIPPTHTFLAFAEKRSTRRDEDALHLVLRRGLRIGQLVQWGPLKPLMEATLPGHR

TMNPCPVWEQKSGCVFLFFICVRGHVTERQQIVSGRNAARLCFIYSQDAGCSWSEVRDLTEEVIGSELKHWATFAVGPGHGIQLQ

SGRLVIPAYTYYIPSWFFCFQLPCKTRPHSLMIYSDDLGVTWHHGRLIRPMVTVECEVAEVTGRAGHPVLYCSARTPNRCRAEAL

STDHGEGFQRLALSRQLCEPPHGCQGSVVSFRPLEIPHRCQDSSSKDAPTIQQSSPGSSLRLEEEAGTPSESWLLYSHPTSRKQR

VDLGIYLNQTPLEAACWSRPWILHCGPCGYSDLAALEEEGLFGCLFECGTKQECEQIAFRLFTHREILSHLQGDCTSPGRNPSQF

KSN

SEQ ID NO: 9:
MRPADLPPRPMEESPASSSAPTETEEPGSSAEVMEEVTTCSFNSPLFRQEDDRGITYRIPALLYIPPTHTFLAFAEKRSTRRDED

ALHLVLRRGLRIGQLVQWGPLKPLMEATLPGHRTMNPCPVWEQKSGCVFLFFICVRGHVTERQQIVSGRNAARLCFIYSQDAGCS

WSEVRDLTEEVIGSELKHWATFAVGPGHGIQLQSGRLVIPAYTYYIPSWFFCFQLPCKTRPHSLMIYSDDLGVTWHHGRLIRPMV

TVECEVAEVTGRAGHPVLYCSARTPNRCRAEALSTDHGEGFQRLALSRQLCEPPHGCQGSVVSFRPLEIPHRCQDSSSKDAPTIQ

QSSPGSSLRLEEEAGTPSESWLLYSHPTSRKQRVDLGIYLNQTPLEAACWSRPWILHCGPCGYSDLAALEEEGLFGCLFECGTKQ

ECEQIAFRLFTHREILSHLQGDCTSPGRNPSQFKSN

SEQ ID NO: 10:
MGVPRTPSRTVLFERERTGLTYRVPSLLPVPPGPTLLAFVEQRLSPDDSHAHRLVLRRGTLAGGSVRWGALHVLGTAALAEHRSM

NPCPVHDAGTGTVFLFFIAVLGHTPEAVQIATGRNAARLCCVASRDAGLSWGSARDLTEEAIGGAVQDWATFAVGPGHGVQLPSG

RLLVPAYTYRVDRRECFGKICRTSPHSFAFYSDDHGRTWRCGGLVPNLRSGECQLAAVDGGQAGSFLYCNARSPLGSRVQALSTD

EGTSFLPAERVASLPETAWGCQGSIVGFPAPAPNRPRDDSWSVGPGSPLQPPLLGPGVHEPPEEAAVDPRGGQVPGGPFSRLQPR

GDGPRQPGPRPGVSGDVGSWTLALPMPFAAPPQSPTWLLYSHPVGRRARLHMGIRLSQSPLDPRSWTEPWVIYEGPSGYSDLASI

GPAPEGGLVFACLYESGARTSYDEISFCTFSLREVLENVPASPKPPNLGDKPRGCCWPS

SEQ ID NO: 11:
MMSSAAFPRWLSMGVPRTPSRTVLFERERTGLTYRVPSLLPVPPGPTLLAFVEQRLSPDDSHAHRLVLRRGTLAGGSVRWGALHV

LGTAALAEHRSMNPCPVHDAGTGTVFLFFIAVLGHTPEAVQIATGRNAARLCCVASRDAGLSWGSARDLTEEAIGGAVQDWATFA

VGPGHGVQLPSGRLLVPAYTYRVDRRECFGKICRTSPHSFAFYSDDHGRTWRCGGLVPNLRSGECQLAAVDGGQAGSFLYCNARS

PLGSRVQALSTDEGTSFLPAERVASLPETAWGCQGSIVGFPAPAPNRPRDDSWSVGPGSPLQPPLLGPGVHEPPEEAAVDPRGGQ

VPGGPFSRLQPRGDGPRQPGPRPGVSGDVGSWTLALPMPFAAPPQSPTWLLYSHPVGRRARLHMGIRLSQSPLDPRSWTEPWVIY

EGPSGYSDLASIGPAPEGGLVFACLYESGARTSYDEISFCTFSLREVLENVPASPKPPNLGDKPRGCCWPS

SEQ ID NO: 12:
MASLP

SEQ ID NO: 13:
ASLP

SEQ ID NO: 14:
TVEKSVVF

SEQ ID NO: 15:
GDYDAPTHQVQW

SEQ ID NO: 16:
SMDQGSTW

SEQ ID NO: 17:
STDGGKTW

SEQ ID NO: 18:
PRPPAPEA

SEQ ID NO: 19:
QTPLEAAC

SEQUENCE LISTING

SEQ ID NO: 20:
NPRPPAPEA

SEQ ID NO: 21:
SQNDGES

SEQ ID NO: 22:
LSHSLST

SEQ ID NO: 23:
GAGAACGACTTTGGACTGGTGCAGCCTCTGGTCACCATGGAACAGCTGCTGTGGGTTTCCGGCAGACAGATCGGCAGCGTGGACA

CCTTCAGAATCCCTCTGATCACCGCCACACCTAGAGGCACCCTGCTGGCCTTTGCCGAGGCCAGAAAGATGAGCAGCTCTGACGA

GGGCGCCAAGTTTATTGCCCTGAGGCGGTCTATGGACCAGGGCTCTACATGGTCCCCTACCGCCTTCATCGTGAACGATGGCGAC

GTGCCCGATGGCCTGAATCTGGGAGCTGTGGTGTCCGATGTGGAAACCGGCGTGGTGTTCCTGTTCTACAGCCTGTGTGCCCACA

AGGCCGGTTGTCAGGTGGCCAGCACAATGCTCGTGTGGTCCAAGGACGACGGCGTGTCCTGGTCTACCCCTAGAAACCTGAGCCT

GGACATCGGCACCGAAGTGTTTGCTCCAGGACCTGGCTCTGGCATCCAGAAGCAGAGAGAGCCCAGAAAGGGCAGACTGATCGTG

TGTGGCCACGGCACCCTTGAGAGAGATGGCGTTTTCTGCCTGCTGAGCGACGATCATGGCGCCTCTTGGAGATACGGCAGCGGAG

TGTCTGGAATCCCTTACGGCCAGCCTAAGCAAGAGAACGATTTCAACCCCGACGAGTGCCAGCCTTACGAGCTGCCTGATGGCAG

CGTCGTGATCAACGCCCGGAACCAGAACAACTACCACTGCCACTGCCGGATCGTGCTGAGAAGCTACGACGCCTGCGATACCCTG

CGGCCTAGAGATGTGACCTTCGATCCTGAGCTGGTGGACCCTGTTGTTGCCGCTGGTGCCGTCGTGACATCTAGCGGCATCGTGT

TCTTCAGCAACCCTGCTCACCCCGAGTTCAGAGTGAATCTGACCCTGCGGTGGTCCTTCAGCAATGGCACAAGCTGGCGGAAAGA

AACCGTGCAGCTTTGGCCTGGACCTAGCGGCTACTCTTCTCTGGCTACACTGGAAGGCAGCATGGACGGCGAAGAACAGGCCCCT

CAGCTGTACGTGCTGTACGAGAAGGGCAGAAACCACTACACCGAGAGCATCAGCGTGGCCAAGATCAGCGTT

SEQ ID NO: 24:
ATGGCCAGCCTGCCTGTGCTGCAGAAAGAAAGCGTGTTCCAGTCTGGCGCCCACGCCTACAGAATTCCCGCTCTGCTGTATCTGC

CAGGCCAGCAGTCTCTGCTGGCTTTCGCTGAACAGCGGGCCAGCAAGAAGGATGAGCACGCCGAACTGATCGTGCTGCGGGAGAGG

CGATTACGACGCCCCTACACATCAGGTGCAGTGGCAGGCTCAAGAGGTGGTGGCTCAGGCTAGACTGGACGGCCACAGATCTATG

AACCCCTGTCCTCTGTACGATGCCCAGACCGGCACACTGTTTCTGTTCTTTATCGCTATCCCCGGCCAAGTGACCGAGCAGCAGC

AGCTGCAGACAAGAGCCAACGTGACCAGACTGTGTCAAGTGACCTCCACCGACCACGGCAGAACCTGGTCTAGCCCTAGAGATCT

GACCGACGCCGCCATCGGACCTGCCTATAGAGAGTGGTCCACCTTCGCCGTTGGACCTGGACACTGTCTCCAGCTGCACGACAGG

GCTAGATCTCTGGTGGTGCCTGCCTACGCCTATAGAAAGCTGCACCCCATCCAGCGGCCTATTCCTAGCGCCTTCTGCTTTCTGA

GCCACGATCACGGCAGGACATGGGCCAGAGGACATTTCGTGGCCCAGGACACACTGGAATGCCAGGTGGCCGAAGTGGAAACCGG

CGAGCAGAGAGTCGTGACCCTGAACGCCAGATCTCACCTGAGAGCCAGAGTGCAGGCCCAGAGCACAAACGACGGCCTGGATTTC

CAAGAGAGCCAGCTGGTCAAGAAACTGGTGGAACCTCCTCCACAGGGCTGTCAGGGAAGCGTGATCAGCTTTCCATCTCCTAGAA

GCGGCCCTGGCTCTCCTGCTCAGTGGCTGCTGTATACACACCCCACACACAGCTGGCAGAGAGCCGATCTGGGCGCCTACCTGAA

TCCTAGACCTCCTGCTCCTGAGGCTTGGAGCGAACCTGTTCTGCTGGCCAAGGGCAGCTGTGCCTACAGCGATCTGCAGTCTATG

GGCACAGGCCCTGATGGCAGCCCTCTGTTTGGCTGTCTGTACGAGGCCAACGACTACGAAGAGATCGTGTTCCTGATGTTCACCC

TGAAGCAGGCCTTTCCAGCCGAGTACCTGCCTCAA

SEQ ID NO: 25:
ATGGAGGAAGTGACCACCTGTAGCTTCAACAGCCCTCTGTTCCGGCAAGAGGACGACCGGGGCATCACCTACAGAATCCCTGCTC

TGCTGTACATCCCTCCTACACACACCTTTCTGGCCTTCGCCGAGAAGCGGAGCACCAGACGAGATGAAGATGCCCTGCACCTGGT

GCTGAGAAGAGGCCTGAGAATCGGACAGCTGGTGCAGTGGGGACCTCTGAAGCCTCTGATGGAAGCCACACTGCCCGGCCACAGA

ACCATGAATCCTTGTCCTGTGTGGGAGCAGAAAAGCGGCTGCGTGTTCCTGTTCTTCATCTGCGTGCGGGGCCACGTGACCGAGA

GACAGCAAATCGTGTCCGGCAGAAACGCCGCCAGACTGTGCTTCATCTACAGCCAGGATGCCGGCTGCTCTTGGAGCGAAGTTCG

GGATCTGACCGAAGAAGTGATCGGCAGCGAGCTGAAGCACTGGGCCACATTTGCTGTTGGCCCTGGCCACGGAATCCAGCTGCAA

SEQUENCE LISTING

TCTGGCAGACTGGTCATCCCCGCCTACACCTACTATATCCCCAGCTGGTTCTTCTGCTTCCAACTGCCTTGCAAGACCCGGCCTC

ACAGCCTGATGATCTACAGCGACGATCTGGGCGTGACATGGCACCACGGCAGACTGATCAGACCCATGGTCACCGTGGAATGCGA

GGTGGCCGAAGTGACAGGCAGAGCTGGACACCCTGTGCTGTACTGCTCTGCCAGAACACCCAACCGGTGTAGAGCCGAGGCTCTG

TCTACAGATCACGGCGAGGGCTTTCAGAGACTGGCCCTCTCTAGACAGCTGTGCGAACCTCCTCATGGCTGTCAGGGCAGCGTGG

TGTCCTTCAGACCTCTGGAAATCCCTCACCGGTGCCAGGACAGCAGCTCTAAGGATGCCCCTACCATCCAGCAGTCTAGCCCTGG

CAGCAGCCTGAGACTGGAAGAGGAAGCCGGAACACCTAGCGAGAGCTGGCTGCTGTACTCTCACCCCACCAGCAGAAAGCAGAGA

GTGGACCTGGGCATCTACCTGAATCAGACCCCTCTGGAAGCCGCCTGTTGGAGCAGACCTTGGATTCTGCACTGTGGCCCTTGCG

GCTACTCTGATCTGGCCGCTCTGGAAGAAGAGGGCCTGTTCGGCTGCCTGTTTGAGTGCGGCACAAAGCAAGAGTGCGAGCAGAT

CGCCTTCCGGCTGTTCACCCACAGAGAGATCCTGAGCCATCTGCAGGGCGACTGCACAAGCCCAGGCAGAAATCCCAGCCAGTTC

AAGAGCAAC

SEQ ID NO: 26:
ATGGGCGTGCCCAGAACACCCAGCAGAACCGTGCTGTTCGAGAGAGAGAGGACCGGCCTGACCTACAGAGTGCCTTCTCTGCTGC

CTGTGCCTCCTGGACCTACACTGCTGGCCTTCGTGGAACAGAGACTGAGCCCCGATGATTCTCACGCCCACAGACTGGTGCTGAG

AAGAGGAACACTGGCTGGCGGCTCTGTTAGATGGGGGAGCACTGCATGTGCTGGGCACAGCTGCTCTTGCCGAGCACAGATCCATG

AATCCCTGTCCTGTGCACGACGCCGGAACCGGCACAGTGTTTCTGTTCTTTATCGCCGTGCTGGGCCACACACCTGAGGCCGTTC

AAATTGCCACCGGCAGAAATGCCGCCAGACTGTGTTGTGTGGCCTCCAGAGATGCCGGCCTGTCTTGGGGATCTGCCAGAGATCT

GACCGAGGAAGCCATTGGCGGAGCCGTTCAGGATTGGGCCACATTTGCTGTTGGACCTGGACACGGCGTGCAGCTGCCAAGTGGT

AGACTGCTGGTGCCTGCCTACACATACAGAGTGGATCGGAGAGAGTGCTTCGGAAAGATCTGCCGGACAAGCCCTCACAGCTTCG

CCTTCTACTCCGACGATCACGGCCGGACTTGGAGATGTGGTGGCCTGGTGCCTAATCTGAGAAGCGGCGAATGTCAACTGGCCGC

CGTTGATGGTGGACAGGCTGGCAGCTTCCTGTACTGCAACGCCGATCTCCTCTGGGCTCTAGAGTGCAGGCCCGTGTCTACCGAT

GAGGGCACCAGTTTTCTGCCCGCCGAAAGAGTTGCCTCTCTGCCTGAAACAGCCTGGGGCTGTCAGGGCTCTATCGTGGGATTTC

CTGCTCCTGCTCCAAACAGACCCCGGGACGATTCTTGGAGTGTCGGCCCTGGATCTCCACTGCAGCCTCCATTGCTTGGACCAGG

CGTTCACGAGCCACCTGAAGAGGCTGCCGTTGATCCTAGAGGCGGACAAGTTCCTGGCGGCCCTTTTAGCAGACTGCAGCCAAGA

GGCGACGGCCCTAGACAACCTGGACCAAGACCTGGCGTCAGCGGAGATGTTGGCTCTTGGACACTGGCCCTGCCTATGCCTTTTG

CCGCTCCTCCTCAGTCTCCTACCTGGCTGCTGTACTCTCACCCTGTTGGCAGACGGGCCAGACTGCACATGGGCATCAGACTGTC

TCAGAGCCCTCTGGACCCCAGAAGCTGGACAGAGCCTTGGGTCATCTATGAGGGCCCTAGCGGCTACAGCGATCTGGCCTCTATT

GGCCCAGCTCCTGAAGGCGGACTGGTGTTCGCTTGTCTGTATGAGAGCGGCGCCAGAACCAGCTACGACGAGATCAGCTTCTGCA

CCTTCAGCCTGCGCGAGGTGCTGGAAAATGTGCCCGCCTCTCCTAAGCCTCCTAACCTGGGCGATAAGCCTAGAGGCTGTTGCTG

GCCATCT

SEQ ID NO: 27:
MTGERPSTALPDRRWGPRILGFWGGCRVWVFAAIFLLLSLAASWSKA

SEQ ID NO: 28:
MDMRVPAQLLGLLLLWLPGARC

SEQ ID NO: 29:
YGTL

SEQ ID NO: 30:
MTVEKSVVFKAEGEHFTDQKGNTIVGSGSGGTTKYFRIPAMCTTSKGTIVVFADARHNTASDQSFIDTAAARSTDGGKTWNKKIA

IYNDRVNSKLSRVMDPTCIVANIQGRETILVMVGKWNNNDKTWGAYRDKAPDTDWDLVLYKSTDDGVTFSKVETNIHDIVTKNGT

ISAMLGGVGSGLQLNDGKLVFPVQMVRTKNITTVLNTSFIYSTDGITWSLPSGYCEGFGSENNIIEFNASLVNNIRNSGLRRSFE

TKDFGKTWTEFPPMDKKVDNRNHGVQGSTITIPSGNKLVAAHSSAQNKNNDYTRSDISLYAHNLYSGEVKLIDDFYPKVGNASGA

GYSCLSYRKNVDKETLYVVYEANGSIEFQDLSRHLPVIKSYN

SEQUENCE LISTING

SEQ ID NO: 31:
EPKSCDKTHTCPPCPAPELLGGPSVFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 32:
DKTHTCPPCPAPELLGGPSVFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSREEMTKNQVSLTCLVKGFYPSDIAVEWESNGQPENN

YKTTPPVLDSDGSFELTSKLTVDKSRWQQGNVFSCSVMHEALHNHYTQKSLSLSPGK

SEQ ID NO: 33:
EPKSCDKTHTCPPCPAPELLGGPSVFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSREEMTKNQVSLYCLVKGFYPSDIAVEWESNG

QPENNYKTTPPVLDSDGSFFLYSKLTVDKSRWQQGNVFSCSVMHEALHNHYTQKSLSLSPGK

SEQ ID NO: 34:
ATGAGACCTGCGGACCTGCCCCCGCGCCCCATGGAAGAATCCCCGGCGTCCAGCTCTGCCCCGACAGAGACGGAGGAGCCGGGGT

CCAGTGCAGAGGTCATGGAAGAAGTGACAACATGCTCCTTCAACAGCCCTCTGTTCCGGCAGGAAGATGACAGAGGGATTACCTA

CCGGATCCCAGCCCTGCTCTACATACCCCCCACCCACACCTTCCTGGCCTTTGCAGAGAAGCGTTCTACGAGGAGAGATGAGGAT

GCTCTCCACCTGGTGCTGAGGCGAGGGTTGAGGATTGGGCAGTTGGTACAGTGGGGGCCCCTGAAGCCACTGATGGAAGCCACAC

TACCGGGGCATCGGACCATGAACCCCTGTCCTGTATGGGAGCAGAAGAGTGGTTGTGTGTTCCTGTTCTTCATCTGTGTGCGGGG

CCATGTCACAGAGCGTCAACAGATTGTGTCAGGCAGGAATGCTGCCCGCCTTTGCTTCATCTACAGTCAGGATGCTGGATGTTCA

TGGAGTGAGGTGAGGGACTTGACTGAGGAGGTCATTGGCTCAGAGCTGAAGCACTGGGCCACATTTGCTGTGGGCCCAGGTCATG

GCATCCAGCTGCAGTCAGGGAGACTGGTCATCCCTGCGTATACCTACTACATCCCTTCCTGGTTCTTTTGCTTCCAGCTACCATG

TAAAACCAGGCCTCATTCTCTGATGATCTACAGTGATGACCTAGGGGTCACATGGCACCATGGTAGACTCATTAGGCCCATGGTT

ACAGTAGAATGTGAAGTGGCAGAGGTGACTGGGAGGGCTGGCCACCCTGTGCTATATTGCAGTGCCCGGACACCAAACAGGTGCC

GGGCAGAGGCGCTCAGCACTGACCATGGTGAAGGCTTTCAGAGACTGGCCCTGAGTCGACAGCTCTGTGAGCCCCCACATGGTTG

CCAAGGGAGTGTGGTAAGTTTCCGGCCCCTGGAGATCCCACATAGGTGCCAGGACTCTAGCAGCAAAGATGCACCCACCATTCAG

CAGAGCTCTCCAGGCAGTTCACTGAGGCTGGAGGAGGAAGCTGGAACACCGTCAGAATCATGGCTCTTGTACTCACACCCAACCA

GTAGGAAACAGAGGGTTGACCTAGGTATCTATCTCAACCAGACCCCCTTGGAGGCTGCCTGCTGGTCCCGCCCCTGGATCTTGCA

CTGTGGGCCCTGTGGCTACTCTGATCTGGCTGCTCTGGAGGAGGAGGGCTTGTTTGGGTGTTTGTTTGAATGTGGGACCAAGCAA

GAGTGTGAGCAGATTGCCTTCCGCCTGTTTACACACCGGGAGATCCTGAGTCACCTGCAGGGGGACTGCACCAGCCCTGGTAGGA

ACCCAAGCCAATTCAAAAGCAAT

SEQ ID NO: 35:
ATGATGAGCTCTGCAGCCTTCCCAAGGTGGCTGAGCATGGGGGTCCCTCGTACCCCTTCACGGACAGTGCTCTTCGAGCGGGAGA

GGACGGGCCTGACCTACCGCGTGCCCTCGCTGCTCCCCGTGCCCCCCGGGCCCACCCTGCTGGCCTTTGTGGAGCAGCGGCTCAG

CCCTGACGACTCCCACGCCCACCGCCTGGTGCTGAGGAGGGGCACGCTGGCCGGGGGCTCCGTGCGGTGGGGTGCCCTGCACGTG

CTGGGGACAGCAGCCCTGGCGGAGCACCGGTCCATGAACCCCTGCCCTGTGCACGATGCTGGCACGGGCACCGTCTTCCTCTTCT

TCATCGCGGTGCTGGGCCACACGCCTGAGGCCGTGCAGATCGCCACGGGAAGGAACGCCGCGCGCCTCTGCTGTGTGGCCAGCCG

TGACGCCGGCCTCTCGTGGGGCAGCGCCCGGGACCTCACCGAGGAGGCCATCGGTGGTGCCGTGCAGGACTGGGCCACATTCGCT

GTGGGTCCCGGCCACGGTGTGCAGCTGCCCTCAGGCCGCCTGCTGGTACCCGCCTACACCTACCGCGTGGACCGCCGAGAGTGTT

TTGGCAAGATCTGCCGGACCAGCCCTCACTCCTTCGCCTTCTACAGCGATGACCACGGCCGCACCTGGCGCTGTGGAGGCCTCGT

GCCCAACCTGCGCTCAGGCGAGTGCCAGCTGGCAGCGGTGGACGGTGGGCAGGCCGGCAGCTTCCTCTACTGCAATGCCCGGAGC

CCACTGGGCAGCCGTGTGCAGGCGCTCAGCACTGACGAGGGCACCTCCTTCCTGCCCCGCAGAGCGCGTGGCTTCCCTGCCCGAGA

SEQUENCE LISTING

CTGCCTGGGGCTGCCAGGGCAGCATCGTGGGCTTCCCAGCCCCCGCCCCCAACAGGCCACGGGATGACAGTTGGTCAGTGGGCCC

CGGGAGTCCCCTCCAGCCTCCACTCCTCGGTCCTGGAGTCCACGAACCCCCAGAGGAGGCTGCTGTAGACCCCCGTGGAGGCCAG

GTGCCTGGTGGGCCCTTCAGCCGTCTGCAGCCTCGGGGGGATGGCCCCAGGCAGCCTGGCCCCAGGCCTGGGGTCAGTGGGGATG

TGGGGTCCTGGACCCTGGCACTCCCCATGCCCTTTGCTGCCCCGCCCCAGAGCCCCACGTGGCTGCTGTACTCCCACCCAGTGGG

GCGCAGGGCTCGGCTACACATGGGTATCCGCCTGAGCCAGTCCCCGCTGGACCCGCGCAGCTGGACAGAGCCCTGGGTGATCTAC

GAGGGCCCCAGCGGCTACTCCGACCTGGCGTCCATCGGGCCGGCCCCTGAGGGGGGCCTGGTTTTTGCCTGCCTGTACGAGAGCG

GGGCCAGGACCTCCTATGATGAGATTTCCTTTTGTACATTCTCCCTGCGTGAGGTCCTGGAGAACGTGCCCGCCAGCCCCAAACC

GCCCAACCTTGGGGACAAGCCTCGGGGGTGCTGCTGGCCCTCC

SEQ ID NO: 36:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSCAYSDLQSMG

TGPDGSPLFGCLYEANDYEEIVFLMFTLKQAFPAEYLPQ

SEQ ID NO: 37:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSAAYSDLQSMG

TGPDGSPLFGCLYEANDYEEIVFLMFTLKQAFPAEYLPQ

SEQ ID NO: 38:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQ

SEQ ID NO: 39:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQ

SEQ ID NO: 40:
EVQLVESGGGLVQPGGSLRLSCAASGFNIKDTYIHWVRQAPGKGLEWVARIYPTNGYTRYADSVKGRFTISADTSKNTAYLQMNS

LRAEDTAVYYCSRWGGDGFYAMDYWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSREEMTKNQVSLYCLVKGFYPSDIAVEWESNGQPENNYKTTPPVLDSDGSFFLYSKLTVDKSRWQQGNV

FSCSVMHEALHNHYTQKSLSLSPGK

SEQUENCE LISTING

SEQ ID NO: 41:
DIQMTQSPSSLSASVGDRVTITCRASQDVNTAVAWYQQKPGKAPKLLIYSASFLYSGVPSRFSGSRSGTDFTLTISSLQPEDFAT

YYCQQHYTTPPTFGQGTKVEIKRTVAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

SEQ ID NO: 42:
EVQLVESGGGLVQPGGSLRLSCAASGFNIKDTYIHWVRQAPGKGLEWVARIYPTNGYTRYADSVKGRFTISADTSKNTAYLQMNS

LRAEDTAVYYCSRWGGDGFYAMDYWGQGTLVTVSSGGGGSGGGGSGGGGSDIQMTQSPSSLSASVGDRVTITCRASQDVNTAVAW

YQQKPGKAPKLLIYSASFLYSGVPSRFSGSRSGTDFTLTISSLQPEDFATYYCQQHYTTPPTFGQGTKVEIK

SEQ ID NO: 43:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSCAYSDLQSMG

TGPDGSPLFGCLYEANDYEEIVFLMFTLKQAFPAEYLPQGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLDSDGSFFLYSKLTVDKSRWQQGNVFSCS

VMHEALHNHYTQKSLSLSPGKGGGGSGGGGSGGGGSEVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSRWGGDGFYAMDYWGQGTLVTVSSGGGGSGGGGSGGGG

SDIQMTQSPSSLSASVGDRVTITCRASQDVNTAVAWYQQKPGKAPKLLIYSASFLYSGVPSRFSGSRSGTDFTLTISSLQPEDFA

TYYCQQHYTTPPTFGQGTKVEIK

SEQ ID NO: 44:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSAAYSDLQSMG

TGPDGSPLFGCLYEANDYEEIVFLMFTLKQAFPAEYLPQGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLDSDGSFFLYSKLTVDKSRWQQGNVFSCS

VMHEALHNHYTQKSLSLSPGKGGGGSGGGGSGGGGSEVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSRWGGDGFYAMDYWGQGTLVTVSSGGGGSGGGGSGGGG

SDIQMTQSPSSLSASVGDRVTITCRASQDVNTAVAWYQQKPGKAPKLLIYSASFLYSGVPSRFSGSRSGTDFTLTISSLQPEDFA

TYYCQQHYTTPPTFGQGTKVEIK

SEQ ID NO: 45:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSGAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCAASGFNIKDTYIHWVRQAPGKGLEWV

SEQUENCE LISTING

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

SEQ ID NO: 46:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

SEQ ID NO: 47:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

SEQ ID NO: 48:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

-continued

---
SEQUENCE LISTING
---

SEQ ID NO: 49:
DIQMTQSPSSLSASVGDRVTITCRASQDVNTAVAWYQQKPGKAPKLLIYSASFLYSGVPSRFSGSRSGTDFTLTISSLQPEDFAT

YYCQQHYTTPPTFGQGTKVEIKRTVAPSVFIFPPSDEQLKSGTASVVCLLNNFYPREAKVQWKVDNALQSGNSQESVTEQDSKDS

TYSLSSTLTLSKADYEKHKVYACEVTHQGLSSPVTKSFNRGEC

SEQ ID NO: 50:
EVQLVESGGGLVQPGGSLRLSCAASGFNIKDTYIHWVRQAPGKGLEWVARIYPTNGYTRYADSVKGRFTISADTSKNTAYLQMNS

LRAEDTAVYYCSRWGGDGFYAMDYWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSREEMTKNQVSLYCLVKGFYPSDIAVEWESNGQPENNYKTTPPVLDSDGSFFLYSKLTVDKSRWQQGNV

FSCSVMHEALHNHYTQKSLSLSPGK

SEQ ID NO: 51:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSCAYSDLQSMG

TGPDGSPLFGCLYEANDYEEIVFLMFTLKQAFPAEYLPQGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLDSDGSFFLTSKLTVDKSRWQQGNVFSCS

VMHEALHNHYTQKSLSLSPGK

SEQ ID NO: 52:
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSAAYSDLQSMG

TGPDGSPLFGCLYEANDYEEIVFLMFTLKQAFPAEYLPQGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLDSDGSFFLTSKLTVDKSRWQQGNVFSCS

VMHEALHNHYTQKSLSLSPGK

SEQ ID NO: 53:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 54:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

-continued

SEQUENCE LISTING

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 55
TVEKSVVFKAEGEHFTDQKGNTIVGSGSGGTTKYFRIPAMCTTSKGTIVVFADARHNTASDQSFIDTAAARSTDGGKTWNKKIAI

YNDRVNSKLSRVMDPTCIVANIQGRETILVMVGKWNNNDKTWGAYRDKAPDTDWDLVLYKSTDDGVTFSKVETNIHDIVTKNGTI

SAMLGGVGSGLQLNDGKLVFPVQMVRTKNITTVLNTSFIYSTDGITWSLPSGYCEGFGSENNIIEFNASLVNNIRNSGLRRSFET

KDFGKTWTEFPPMDKKVDNRNHGVQGSTITIPSGNKLVAAHSSAQNKNNDYTRSDISLYAHNLYSGEVKLIDDFYPKVGNASGAG

YSCLSYRKNVDKETLYVVYEANGSIEFQDLSRHLPVIKSYNGGGGSGGGGSDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSDGSFFLTSKLTVDKSRWQQGNVFS

CSVMHEALHNHYTQKSLSLSPGK

SEQ ID NO: 56
ACAGTGGAAAAGTCCGTGGTGTTCAAGGCCGAGGGCGAGCACTTCACCGACCAGAAAGGCAATACCATCGTCGGCTCTGGCAGCG

GCGGCACCACCAAGTACTTTAGAATCCCCGCCATGTGCACCACCAGCAAGGGCACCATTGTGGTGTTCGCCGACGCCAGACACAA

CACCGCCAGCGATCAGAGCTTCATCGATACCGCTGCCGCCAGATCTACCGATGGCGGCAAGACCTGGAACAAGAAGATCGCCATC

TACAACGACCGCGTGAACAGCAAGCTGAGCAGAGTGATGGACCCTACCTGCATCGTGGCCAACATCCAGGGCAGAGAAACCATCC

TGGTCATGGTCGGAAAGTGGAACAACAACGATAAGACCTGGGGCGCCTACAGAGACAAGGCCCCTGATACCGATTGGGACCTCGT

GCTGTACAAGAGCACCGATGACGGCGTGACCTTCAGCAAGGTGGAAACAAACATCCACGACATCGTGACCAAGAACGGCACCATC

TCTGCCATGCTCGGCGGCGTTGGATCTGGCCTGCAACTGAATGATGGCAAGCTGGTGTTCCCCGTGCAGATGGTCCGAACAAAGA

ATATCACCACCGTGCTGAATACCAGCTTCATCTACAGCACCGACGGCATCACATGGTCCCTGCCTAGCGGCTACTGTGAAGGCTT

TGGCAGCGAGAACAACATCATCGAGTTCAACGCCAGCCTGGTCAACAACATCCGGAACAGCGGCCTGCGGAGAAGCTTCGAGACA

AAGGACTTCGGAAAGACGTGGACCGAGTTTCCTCCAATGGACAAGAAGGTGGACAACCGGAACCACGGCGTGCAGGGCAGCACAA

TCACAATCCCTAGCGGCAACAAACTGGTGGCCGCTCACTCTAGCGCCCAGAACAAGAACAACGACTACACCAGAAGCGACATCAG

CCTGTACGCCCACAACCTGTACAGCGGCGAAGTGAAGCTGATCGACGACTTCTACCCCAAAGTGGGCAATGCCAGCGGAGCCGGC

TACAGCTGTCTGAGCTACCGGAAAAATGTGGACAAGAAACCCTGTACGTGGTGTACGAGGCCAACGGCAGCATCGAGTTTCAGG

ACCTGAGCAGACATCTGCCCGTGATCAAGAGCTACAACggcggaggtggaagtggcggaggcggatccgacaaaactcacacatg cccaccgtgcccagcacctgaactcctggggggaccgtcagtcttcctcttccccccaaaacccaaggacaccctcatgatctcc cggacccctgaggtcacatgcgtggtggtggacgtgagccacgaagaccctgaggtcaagttcaactggtacgtggacggcgtgg aggtgcataatgccaagacaaagccgcgggaggagcagtacaacagcacgtaccgtgtggtcagcgtcctcaccgtcctgcacca ggactggctgaatggcaaggagtacaagtgcaaggtctccaacaaagccctcccagcccccatcgagaaaaccatctccaaagcc aaagggcagccccgagaaccacaggtctacaccctgcccccatcccgggaggagatgaccaagaaccaggtcagcctgacctgcc tggtcaaaggcttctatcccagcgacatcgccgtggagtgggagagcaatgggcagccggagaacaactacaagaccacgcctcc cgtgctggactccgacggctccttcttcctctacagcaagctcaccgtggacaagagcaggtggcagcaggggaacgtcttctca tgctccgtgatgcatgaggctctgcacaaccactacacgcagaagagcctctccctgtctccgggtaaa

SEQUENCE LISTING

SEQ ID NO: 57
EVQLVESGGGLVQPGGSLRLSCAASGFNIKDTYIHWVRQAPGKGLEWVARIYPTNGYTRYADSVKGRFTISADTSKNTAYLQMNS

LRAEDTAVYYCSRWGGDGFYAMDYWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSREEMTKNQVSLYCLVKGFYPSDIAVEWESNGQPENNYKTTPPVLDSDGSFFLYSKLTVDKSRWQQGNV

FSCSVMHEALHNHYTQKSLSLSPGK

SEQ ID NO: 58
GAGGTGCAGCTGGTTGAATCTGGCGGAGGACTGGTTCAGCCTGGCGGATCTCTGAGACTGTCTTGTGCCGCCAGCGGCTTCAACA

TCAAGGACACCTACATCCACTGGGTCCGACAGGCCCCTGGCAAAGGACTTGAATGGGTCGCCAGAATCTACCCCACCAACGGCTA

CACCAGATACGCCGACTCTGTGAAGGGCAGATTCACCATCAGCGCCGACACCAGCAAGAACACCGCCTACCTGCAGATGAACAGC

CTGAGAGCCGAGGACACCGCCGTGTACTACTGTTCTAGATGGGGAGGCGACGGCTTCTACGCCATGGATTATTGGGGCCAGGGCA

CCCTGGTCACCGTTTCTTCTGCtagcACCAAGGGCCCATCcGTCTTCCCCCTGGCACCCTCCTCCAAGAGCACCTCTGGGGGCAC AGCGGCCCTGGGCTGCCTGGTCAAGGACTACTTCCCCGAACCGGTGACGGTGTCcTGGAACTCAGGCGCtCTGACCAGCGGCGTG CACACCTTCCCGGCTGTCCTACAGTCCTCAGGACTCTACTCCCTCAGCAGCGTGGTGACCGTGCCCTCCAGCAGCTTGGGCACCC AGACCTACATCTGCAACGTGAATCACAAGCCCAGCAACACCAAGGTGGACAAGAAAGTTGAGCCCAAATCTTGTGACAAAACTCA CACATGCCCACCGTGCCCAGCACCTGAACTCCTGGGGGGACCGTCAGTCTTCCTCTTCCCCCCAAAACCCAAGGACACCCTCATG ATCTCCCGGACCCCTGAGGTCACATGCGTGGTGGTGGACGTGAGCCACGAAGACCCTGAGGTCAAGTTCAACTGGTACGTGGACG GCGTGGAGGTGCATAATGCCAAGACAAAGCCGCGGGAGGAGCAGTACAACAGCACGTACCGTGTGGTCAGCGTCCTCACCGTCCT GCACCAGGACTGGCTGAATGGCAAGGAGTACAAGTGCAAGGTCTCCAACAAAGCCCTCCCAGCCCCCATCGAGAAAACCATCTCC AAAGCCAAAGGGCAGCCCCGAGAACCACAGGTcTACACCCTGCCCCCATCCCGGGAGGAGATGACCAAGAACCAGGTCAGCCTGt acTGCCTGGTCAAAGGCTTCTATCCCAGCGACATCGCCGTGGAGTGGGAGAGCAATGGGCAGCCGGAGAACAACTACAAGACCAC GCCTCCCGTGCTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGTAAA

SEQ ID NO: 59
EVQLVESGGGLVQPGGSLRLSCAASGFNIKDTYIHWVRQAPGKGLEWVARIYPTNGYTRYADSVKGRFTISADTSKNTAYLQMNS

LRAEDTAVYYCSRWGGDGFYAMDYWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSREEMTKNQVSLTCLVKGFYPSDIAVEWESNGQPENNYKTTPPVLDSDGSFFLYSKLTVDKSRWQQGNV

FSCSVMHEALHNHYTQKSLSLSPGKGGGGSGGGGSGGGGSTVEKSVVFKAEGEHFTDQKGNTIVGSGSGGTTKYFRIPAMCTTSK

GTIVVFADARHNTASDQSFIDTAAARSTDGGKTWNKKIAIYNDRVNSKLSRVMDPTCIVANIQGRETILVMVGKWNNNDKTWGAY

RDKAPDTDWDLVLYKSTDDGVTFSKVETNIHDIVTKNGTISAMLGGVGSGLQLNDGKLVFPVQMVRTKNITTVLNTSFIYSTDGI

TWSLPSGYCEGFGSENNIIEFNASLVNNIRNSGLRRSFETKDFGKTWTEFPPMDKKVDNRNHGVQGSTITIPSGNKLVAAHSSAQ

NKNNDYTRSDISLYAHNLYSGEVKLIDDFYPKVGNASGAGYSCLSYRKNVDKETLYVVYEANGSIEFQDLSRHLPVIKSYN

SEQ ID NO: 60
gaggtgcagctggttgaatctggcggaggactggttcagcctggcggatctctgagactgtcttgtgccgccagcggcttcaaca tcaaggacacctacatccactgggtccgacaggcccctggcaaaggacttgaatgggtcgccagaatctaccccaccaacggcta caccagatacgccgactctgtgaagggcagattcaccatcagcgccgacaccagcaagaacaccgcctacctgcagatgaacagc ctgagagccgaggacaccgccgtgtactactgttctagatgggggaggcgacggcttctacgccatggattattggggccagggca

SEQUENCE LISTING ccctggtcaccgtttcttctgctagcaccaagggcccatccgtcttccccctggcaccctcctccaagagcacctctggggcac agcggccctgggctgcctggtcaaggactacttccccgaaccggtgacggtgtcctggaactcaggcgctctgaccagcggcgtg cacaccttcccggctgtcctacagtcctcaggactctactccctcagcagcgtggtgaccgtgccctccagcagcttgggcaccc agacctacatctgcaacgtgaatcacaagcccagcaacaccaaggtggacaagaaagttgagcccaaatcttgtgacaaaactca cacatgcccaccgtgcccagcacctgaactcctggggggaccgtcagtcttcctcttccccccaaaacccaaggacaccctcatg atctcccggacccctgaggtcacatgcgtggtggtggacgtgagccacgaagaccctgaggtcaagttcaactggtacgtggacg gcgtggaggtgcataatgccaagacaaagccgcgggaggagcagtacaacagcacgtaccgtgtggtcagcgtcctcaccgtcct gcaccaggactggctgaatggcaaggagtacaagtgcaaggtctccaacaaagccctcccagcccccatcgagaaaaccatctcc aaagccaaagggcagccccgagaaccacaggtctacaccctgcccccatcccgggaggagatgaccaagaaccaggtcagcctga cctgcctggtcaaaggcttctatcccagcgacatcgccgtggagtgggagagcaatgggcagccggagaacaactacaagaccac gcctcccgtgctggactccgacggctccttcttcctctatagcaagctcaccgtggacaagagcaggtggcagcaggggaacgtc ttctcatgctccgtgatgcatgaggctctgcacaaccactacacgcagaagagcctctccctgtctccgggtaaaggtggcggag gatctggcggaggtggaagcggcggaggcggatctacagtggaaaagtccgtggtgttcaaggccgagggcgagcacttcaccga ccagaaaggcaataccatcgtcggctctggcagcggcggcaccaccaagtactttagaatccccgccatgtgcaccaccagcaag ggcaccattgtggtgttcgccgacgccagacacaacaccgccagcgatcagagcttcatcgataccgctgccgccagaagtacag acggcggcaagacctggaacaagaagatcgccatctacaacgaccgcgtgaacagcaagctgagcagagtgatggaccctacctg catcgtggccaacatccagggcagagaaaccatcctggtcatggtcggaaagtggaacaacaacgataagacctggggcgcctac agagacaaggcccctgataccgattgggacctcgtgctgtataagagcaccgacgacggcgtgaccttcagcaaggtggaaacaa acatccacgacatcgtgaccaagaacggcaccatctctgccatgctcggcggcgttggatctggcctgcaactgaatgatggcaa gctggtgttccccgtgcagatggtccgaacaaagaacatcaccaccgtgctgaataccagcttcatctactccaccgacggcatc acatggtccctgcctagcggctactgtgaaggctttggcagcgagaacaacatcatcgagttcaacgccagcctggtcaacaaca tccggaacagcggcctgcgcgagaagcttcgagacaaaggacttcggaaagacgtggaccgagtttcctccaatggacaagaaggt ggacaaccggaaccacggcgtgcagggcagcacaatcacaatccctagcggcaacaaactggtggccgctcactctagcgcccag aacaagaacaacgattacaccagaagcgacatcagcctgtacgcccacaacctgtactccggcgaagtgaagctgatcgacgact tctaccccaaagtgggcaatgccagcggagccggctacagctgtctgagctaccggaaaaatgtggacaaagaaaccctgtacgt ggtgtacgaggccaacggcagcatcgagtttcaggacctgagcagacatctgcccgtgatcaagagctacaat SEQ ID NO: 61
TVEKSVVFKAEGEHFTDQKGNTIVGSGSGGTTKYFRIPAMCTTSKGTIVVFADARHNTASDQSFIDTAAARSTDGGKTWNKKIAI YNDRVNSKLSRVMVPTCIVANIQGRETILVMVGKWNNNDKTWGAYRDKAPDTDWDLVLYKSTDDGVTFSKVETNIHDIVTKNGTI SAMLGGVGSGLQLNDGKLVFPVQMVRTKNITTVLNTSFIYSTDGITWSLPSGYCEGFGSVNNIIEFNASLVNNIRNSGLRRSFET KDFGKTWTEFPPMDKKVDNRNHGVQGSTITIPSGNKLVAAHSSAQNKNNDYTRSDISLYAHNLYSGEVKLIDDFYPKVGNASGAG YSCLSYRKNVDKETLYVVYEANGSIEFQDLSRHLPVIKSYNGGGGSGGGGSDKTHTCPPCPAPELLGGPSVFLFPPKPKDTLMIS RTPEVTCVVVDVSHEDPEVKFNWYVDGVEVHNAKTKPREEQYNSTYRVVSVLTVLHQDWLNGKEYKCKVSNKALPAPIEKTISKA KGQPREPQVYTLPPSREEMTKNQVSLTCLVKGFYPSDIAVEWESNGQPENNYKTTPPVLDSDGSFFLTSKLTVDKSRWQQGNVFS

CSVMHEALHNHYTQKSLSLSPGK

SEQ ID NO: 62
acagtggaaaagtccgtggtgttcaaggccgagggcgagcacttcaccgaccagaaaggcaataccatcgtcggctctggcagcg gcggcaccaccaagtactttagaatccccgccatgtgcaccaccagcaagggcaccattgtggtgttcgccgacgccagacacaa caccgccagcgatcagagcttcatcgataccgctgccgccagaagtacagacggcggcaagacctggaacaagaagatcgccatc tacaacgaccgcgtgaacagcaagctgagcagagtgatggtccctacctgcatcgtggccaacatccagggcagagaaaccatcc tggtcatggtcggaaagtggaacaacaacgataagacctggggcgcctacagagacaaggcccctgataccgattgggacctcgt gctgtataagagcaccgacgacggcgtgaccttcagcaaggtggaaacaaacatccacgacatcgtgaccaagaacggcaccatc tctgccatgctcggcggcgttggatctggcctgcaactgaatgatggcaagctggtgttccccgtgcagatggtccgaacaaaga acatcaccaccgtgctgaataccagcttcatctactccaccgacggcatcacatggtccctgcctagcggctactgtgaaggctt tggcagcgtgaacaacatcatcgagttcaacgccagcctggtcaacaacatccggaacagcggcctgcgggagaagcttcgagaca aaggacttcggaaagacgtggaccgagtttcctccaatggacaagaaggtggacaaccggaaccacggcgtgcagggcagcacaa tcacaatccctagcggcaacaaactggtggccgctcactctagcgcccagaacaagaacaacgattacaccagaagcgacatcag cctgtacgcccacaacctgtactccggcgaagtgaagctgatcgacgacttctaccccaaagtgggcaatgccagcggagccggc tacagctgtctgagctaccggaaaaatgtggacaaagaaaccctgtacgtggtgtacgaggccaacggcagcatcgagtttcagg acctgagcagacatctgcccgtgatcaagagctacaatggcggaggtggaagtggcggaggcggatccgacaaaactcacacatg cccaccgtgcccagcacctgaactcctggggggaccgtcagtcttcctcttccccccaaaacccaaggacaccctcatgatctcc cggacccctgaggtcacatgcgtggtggtggacgtgagccacgaagaccctgaggtcaagttcaactggtacgtggacggcgtgg aggtgcataatgccaagacaaagccgcgggaggagcagtacaacagcacgtaccgtgtggtcagcgtcctcaccgtcctgcacca ggactggctgaatggcaaggagtacaagtgcaaggtctccaacaaagccctcccagcccccatcgagaaaaccatctccaaagcc aaagggcagccccgagaaccacaggtctacaccctgcccccatcccgggaggagatgaccaagaaccaggtcagcctgacctgcc tggtcaaaggcttctatcccagcgacatcgccgtggagtgggagagcaatgggcagccggagaacaactacaagaccacgcctcc cgtgctggactccgacggctccttcttcctctactagcaagctcaccgtggacaagagcaggtggcagcaggggaacgtcttctca tgctccgtgatgcatgaggctctgcacaaccactacacgcagaagagcctctccctgtctccgggtaaa SEQ ID NO: 63
MEDLRPMASLPVLQKESVFQSGAHAYRIPALLYLPGQQSLLAFAEQRASKKDEHAELIVLRRGDYDAPTHQVQWQAQEVVAQARL DGHRSMNPCPLYDAQTGTLFLFFIAIPGQVTEQQQLQTRANVTRLCQVTSTDHGRTWSSPRDLTDAAIGPAYREWSTFAVGPGHC LQLHDRARSLVVPAYAYRKLHPIQRPIPSAFCFLSHDHGRTWARGHFVAQDTLECQVAEVETGEQRVVTLNARSHLRARVQAQST NDGLDFQESQLVKKLVEPPPQGCQGSVISFPSPRSGPGSPAQWLLYTHPTHSWQRADLGAYLNPRPPAPEAWSEPVLLAKGSCAY

SDLQSMGTGPDGSPLFGCLYEANDYEEIVFLMFTLKQAFPAEYLPQ

SEQ ID NO: 64
ATGGAAGATCTCAGGCCCATGGCATCTCTGCCTGTGCTGCAGAAAGAAAGCGTGTTCCAGTCTGGCGCCCACGCCTACAGAATTC

CCGCTCTGCTGTATCTGCCAGGCCAGCAGTCTCTGCTGGCTTTCGCTGAACAGCGGGCCAGCAAGAAGGATGAGCACGCCGAACT

GATCGTGCTGCGGAGAGGCGATTACGACGCCCCTACACATCAGGTGCAGTGGCAGGCTCAAGAGGTGGTGGCTCAGGCTAGACTG

GACGGCCACAGATCTATGAACCCCTGTCCTCTGTACGATGCCCAGACCGGCACACTGTTTCTGTTCTTTATCGCTATCCCCGGCC

AAGTGACCGAGCAGCAGCAGCTGCAGACAAGAGCCAACGTGACCAGACTGTGTCAAGTGACCTCCACCGACCACGGCAGAACCTG

GTCTAGCCCTAGAGATCTGACCGACGCCGCCATCGGACCTGCCTATAGAGAGTGGTCCACCTTCGCCGTTGGACCTGGACACTGT

CTCCAGCTGCACGACAGGGCTAGATCTCTGGTGGTGCCTGCCTACGCCTATAGAAAGCTGCACCCCATCCAGCGGCCTATTCCTA

GCGCCTTCTGCTTTCTGAGCCACGATCACGGCAGGACATGGGCCAGAGGACATTTCGTGGCCCAGGACACACTGGAATGCCAGGT

GGCCGAAGTGGAAACCGGCGAGCAGAGAGTCGTGACCCTGAACGCCAGATCTCACCTGAGAGCCAGAGTGCAGGCCCAGAGCACA

AACGACGGCCTGGATTTCCAAGAGAGCCAGCTGGTCAAGAAACTGGTGGAACCTCCTCCACAGGGCTGTCAGGGAAGCGTGATCA

GCTTTCCATCTCCTAGAAGCGGCCCTGGCTCTCCTGCTCAGTGGCTGCTGTATACACACCCCACACACAGCTGGCACACAGCCGA

TCTGGGCGCCTACCTGAATCCTAGACCTCCTGCTCCTGAGGCTTGGAGCGAACCTGTTCTGCTGGCCAAGGGCAGCTGTGCCTAC

AGCGATCTGCAGTCTATGGGCACAGGCCCTGATGGCAGCCCTCTGTTTGGCTGTCTGTACGAGGCCAACGACTACGAAGAGATCG

TGTTCCTGATGTTCACCCTGAAGCAGGCCTTTCCAGCCGAGTACCTGCCTCAA

SEQUENCE LISTING

SEQ ID NO: 65
ASLPYLQKESVFQSGAHAYRIPALLYLPGQQSLLAFAEQRASKKDEHAELIVLRRGDYDAPTHQVQWQAQEVVAQARLDGHRSMN

PCPLYDAQTGTLFLFFIAIPGQVTEQQQLQTRANVTRLCQVTSTDHGRTWSSPRDLTDAAIGPAYREWSTFAVGPGHCLQLHDRA

RSLVVPAYAYRKLHPKQRPIPSAFCFLSHDHGRTWARGHFVAQDTLECQVAEVETGEQRVVTLNARSHLRARVQAQSTNDGLDFQ

ESQLVKKLVEPPPQGCQGSVISFPSPRSGPGSPAQWLLYTHPTHSWQRADLGAYLNPRPPAPEAWSEPVLLAKGSCAYSDLQSMG

TGPDGSPLFGCLYEANDYEEIVFLMFTLKQAFPAEYLPQGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNYKTTPPVLDSDGSFFLYSKLTVDKSRWQQGNVFSCS

VMHEALHNHYTQKSLSLSPGKGGGGSGGGGSGGGGSEVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSRWGGDGFYAMDYWGQGTLVTVSSGGGGSGGGGSGGGG

SDIQMTQSPSSLSASVGDRVTITCRASQDVNTAVAWYQQKPGKAPKLLIYSASFLYSGVPSRFSGSRSGTDFTLTISSLQPEDFA

TYYCQQHYTTPPTFGQGTKVEIK

SEQ ID NO: 66
GCATCTCTGCCTTACCTGCAGAAAGAAAGCGTGTTCCAGTCTGGCGCCCACGCCTACAGAATTCCCGCTCTGCTGTATCTGCCAG

GCCAGCAGTCTCTGCTGGCTTTCGCTGAACAGCGGGCCAGCAAGAAGGATGAGCACGCCGAACTGATCGTGCTGCGGAGAGGCGA

TTACGACGCCCCTACACATCAGGTGCAGTGGCAGGCTCAAGAGGTGGTGGCTCAGGCTAGACTGGACGGCCACAGATCTATGAAC

CCCTGTCCTCTGTACGATGCCCAGACCGGCACACTGTTTCTGTTCTTTATCGCTATCCCCGGCCAAGTGACCGAGCAGCAGCAGC

TGCAGACAAGAGCCAACGTGACCAGACTGTGTCAAGTGACCTCCACCGACCACGGCAGAACCTGGTCTAGCCCTAGAGATCTGAC

CGACGCCGCCATCGGACCTGCCTATAGAGAGTGGTCCACCTTCGCCGTTGGACCTGGACACTGTCTCCAGCTGCACGACAGGGCT

AGATCTCTGGTGGTGCCTGCCTACGCCTATAGAAAGCTGCACCCCAAACAGCGGCCTATTCCTAGCGCCTTCTGCTTTCTGAGCC

ACGATCACGGCAGGACATGGGCCAGAGGACATTTCGTGGCCCAGGACACACTGGAATGCCAGGTGGCCGAAGTGGAAACCGGCGA

GCAGAGAGTCGTGACCCTGAACGCCAGATCTCACCTGAGAGCCAGAGTGCAGGCCCAGAGCACAAACGACGGCCTGGATTTCCAA

GAGAGCCAGCTGGTCAAGAAACTGGTGGAACCTCCTCCACAGGGCTGTCAGGGAAGCGTGATCAGCTTTCCATCTCCTAGAAGCG

GCCCTGGCTCTCCTGCTCAGTGGCTGCTGTATACACACCCCACACAGCTGGCAGAGAGCCGATCTGGGCGCCTACCTGAATCC

TAGACCTCCTGCTCCTGAGGCTTGGAGCGAACCTGTTCTGCTGGCCAAGGGCAGCTGTGCCTACAGCGATCTGCAGTCTATGGGC

ACAGGCCCTGATGGCAGCCCTCTGTTTGGCTGTCTGTACGAGGCCAACGACTACGAAGAGATCGTGTTCCTGATGTTCACCCTGA

AGCAGGCCTTTCCAGCCGAGTACCTGCCTCAAGGCGGAGGTGGAAGTGGCGGAGGCGGATCcGACAAAACTCACACATGCCCACC

GTGCCCAGCACCTGAACTCCTGGGGGGACCGTCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAAGTTCAACTGGTACGTGGACGGCGTGGAGGTGC

ATAATGCCAAGACAAAGCCGCGGGAGGAGCAGTACAACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAGCCCCCATCGAGAAAACCATCTCCAAAGCCAAAGGG

CAGCCCCGAGAACCACAGGTcTACACCCTGCCCCCATCCCGGGAGGAGATGACCAAGAACCAGGTCAGCCTGACCTGCCTGGTCA

AAGGCTTCTATCCCAGCGACATCGCCGTGGAGTGGGAGAGCAATGGGCAGCCGGAGAACAACTACAAGACCACGCCTCCCGTGCT

GGACTCCGACGGCTCCTTCTTCCTCTATAGCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCTCCGGGTAAAGGAGGCGGAGGATCTGGCGGAG

GTGGAAGTGGCGGAGGCGGATCTGAGGTGCAGCTGGTTGAATCTGGCGGAGGACTGGTTCAGCCTGGCGGATCTCTGAGACTGTC

TTGTGCCGCCAGCGGCTTCAACATCAAGGACACCTACATCCACTGGGTCCGACAGGCCCCTGGCAAAGGACTTGAATGGGTCGCC

AGAATCTACCCCACCAACGGCTACACCAGATACGCCGACTCTGTGAAGGGCAGATTCACCATCAGCGCCGACACCAGCAAGAACA

CCGCCTACCTGCAGATGAACAGCCTGAGAGCCGAGGACACCGCCGTGTACTACTGTTCTAGATGGGGGAGGCGACGGCTTCTACGC

CATGGATTATTGGGGCCAGGGCACCCTGGTCACCGTTTCTTCTGGCGGAGGAGGATCTGGCGGAGGCGGAAGTGGCGGAGGCGGA

TCTGACATCCAGATGACACAGAGCCCTAGCAGCCTGTCTGCCAGCGTGGGAGACAGAGTGACCATCACCTGTAGAGCCAGCCAGG

ACGTGAACACAGCCGTGGCTTGGTATCAGCAGAAGCCTGGCAAGGCCCCTAAGCTGCTGATCTACAGCGCCAGCTTTCTGTACTC

CGGCGTGCCCAGCAGATTCAGCGGCTCTAGAAGCGGCACCGACTTCACCCTGACCATAAGCAGTCTGCAGCCCGAGGACTTCGCC

ACCTACTACTGTCAGCAGCACTACACCACACCTCCAACCTTTGGCCAGGGCACCAAGGTGGAAATCAG

SEQ ID NO: 67
DIQMTQSPSSLSASVGDRVTITCRASQDVNTAVAWYQQKPGKAPKLLIYSASFLYSGVPSRFSGSRSGTDFTLTISSLQPEDFAT

YYCQQHYTTPPTFGQGTKVEIKRTVAAPSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

SEQ ID NO: 68
GACATCCAGATGACACAGAGCCCTAGCAGCCTGTCTGCCAGCGTGGGAGACAGAGTGACCATCACCTGTAGAGCCAGCCAGGACG

TGAACACAGCCGTGGCTTGGTATCAGCAGAAGCCTGGCAAGGCCCCTAAGCTGCTGATCTACAGCGCCAGCTTTCTGTACTCCGG

CGTGCCCAGCAGATTCAGCGGCTCTAGAAGCGGCACCGACTTCACCCTGACCATAAGCAGTCTGCAGCCCGAGGACTTCGCCACC

TACTACTGTCAGCAGCACTACACCACACCTCCAACCTTTGGCCAGGGCACCAAGGTGGAAATCAAGCGTACGGTGGCTGCACCAT

CTGTCTTCATCTTCCCGCCATCTGATGAGCAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAGGAGAGTGTCACAGAGCAGGACAGCAAGGAC

AGCACCTACAGCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

SEQ ID NO: 69
DKTHTCPPCPAPELLGGPSVFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPGK

SEQ ID NO: 70:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQ

SEQ ID NO: 71:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQ

SEQ ID NO: 72:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQ

SEQ ID NO: 73:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

-continued

---

SEQUENCE LISTING

---

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQ

SEQ ID NO: 74:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCARSGFNIKDTYIHWVRQAPGKGLEWV

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

SEQ ID NO: 75:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLYSKLTVDKSRWQQGNVFSC

SVMHEALHNHYTQKSLSLSPGKGGGGSGGGGSGGGGSEVQLVESGGGLVQPGGSLRLSCAASGFNIKDTYIHWVRQAPGKGLEWV

ARIYPTNGYTRYADSVKGRFTISADTSKNTAYLQMNSLRAEDTAVYYCSRWGGDGFYAMDYWGQGTLVTVSSGGGGSGGGGSGGG

GSDIQMTQSPSSLSASVGDRVTITCRASQDVNTAVAWYQQKPGKAPKLLIYSASFLYSGVPSRFSGSRSGTDFTLTISSLQPEDF

ATYYCQQHYTTPPTFGQGTKVEIK

SEQ ID NO: 76:
AASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 77:
DASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

SEQUENCE LISTING

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 78:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSCAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 79:
MASLPYLQKESVFQSGAHAYRIPALLYLPGQQSLLAFAEQRASKKDEHAELIVLRRGDYDAPTHQVQWQAQEVVAQARLDGHRSM

NPCPLYDAQTGTLFLFFIAIPGQVTEQQQLQTRANVTRLCQVTSTDHGRTWSSPRDLTDAAIGPAYREWSTFAVGPGHCLQLHDR

ARSLVVPAYAYRKLHPKQRPIPSAFCFLSHDHGRTWARGHFVAQDTLECQVAEVETGEQRVVTLNARSHLRARVQAQSTNDGLDF

QESQLVKKLVEPPPQGCQGSVISFPSPRSGPGSPAQWLLYTHPTHSWQRADLGAYLNPRPPAPEAWSEPVLLAKGSAAYSDLQSM

GTGPDGSPLFGCLYEANDYEEIVFLMFTLKQAFPAEYLPQGGGGSGGGGSDKTHTCPPCPAPELLGGPSVFLFPPKPKDTLMISR

TPEVTCVVVDVSHEDPEVKFNWYVDGVEVHNAKTKPREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPVLDSDGSFFLTSKLTVDKSRWQQGNVFSC

SVMHEALHNHYTQKSLSLSPGK

SEQ ID NO: 80:
ACAGTGGAAAAGTCCGTGGTGTTCAAGGCCGAGGGCGAGCACTTCACCGACCAGAAAGGCAATACCATCGTCGGCTCTGGCAGCG

GCGGCACCACCAAGTACTTTAGAATCCCCGCCATGTGCACCACCAGCAAGGGCACCATTGTGGTGTTCGCCGACGCCAGACACAA

CACCGCCAGCGATCAGAGCTTCATCGATACCGCTGCCGCCAGATCTACCGATGGCGGCAAGACCTGGAACAAGAAGATCGCCATC

TACAACGACCGCGTGAACAGCAAGCTGAGCAGAGTGATGGACCCTACCTGCATCGTGGCCAACATCCAGGGCAGAGAAACCATCC

TGGTCATGGTCGGAAAGTGGAACAACAACGATAAGACCTGGGGCGCCTACAGAGACAAGGCCCCTGATACCGATTGGGACCTCGT

GCTGTACAAGAGCACCGATGACGGCGTGACCTTCAGCAAGGTGGAAACAAACATCCACGACATCGTGACCAAGAACGGCACCATC

TCTGCCATGCTCGGCGGCGTTGGATCTGGCCTGCAACTGAATGATGGCAAGCTGGTGTTCCCCGTGCAGATGGTCCGAACAAAGA

ATATCACCACCGTGCTGAATACCAGCTTCATCTACAGCACCGACGGCATCACATGGTCCCTGCCTAGCGGCTACTGTGAAGGCTT

TGGCAGCGAGAACAACATCATCGAGTTCAACGCCAGCCTGGTCAACAACATCCGGAACAGCGGCCTGCGGGAGAAGCTTCGAGACA

AAGGACTTCGGAAAGACGTGGACCGAGTTTCCTCCAATGGACAAGAAGGTGGACAACCGGAACCACGGCGTGCAGGGCAGCACAA

TCACAATCCCTAGCGGCAACAAACTGGTGGCCGCTCACTCTAGCGCCCAGAACAAGAACAACGACTACACCAGAAGCGACATCAG

CCTGTACGCCCACAACCTGTACAGCGGCGAAGTGAAGCTGATCGACGACTTCTACCCCAAAGTGGGCAATGCCAGCGGAGCCGGC

TACAGCTGTCTGAGCTACCGGAAAAATGTGGACAAAGAAACCCTGTACGTGGTGTACGAGGCCAACGGCAGCATCGAGTTTCAGG

ACCTGAGCAGACATCTGCCCGTGATCAAGAGCTACAAC

SEQ ID NO: 81:
MRFKNVKKTALMLAMFGMATSSNAALFDYNATGDTEFDSPAKQGWMQDNTNNGSGVLTNADGMPAWLVQGIGGRAQWTYSLSTNQ

HAQASSFGWRMTTEMKVLSGGMITNYYANGTQRVLPIISLDSSGNLVVEFEGQTGRTVLATGTAATEYHKFELVFLPGSNPSASF

SEQUENCE LISTING

YFDGKLIRDNIQPTASKQNMIVWGNGSSNTDGVAAYRDIKFEIQGDVIFRGPDRIPSIVASSVTPGVVTAFAEKRVGGGDPGALS

NTNDIITRTSRDGGITWDTELNLTEQINVSDEFDFSDPRPIYDPSSNTVLVSYARWPTDAAQNGDRIKPWMPNGIFYSVYDVASG

NWQAPIDVTDQVKERSFQIAGWGGSELYRRNTSLNSQQDWQSNAKIRIVDGAANQIQVADGSRKYVVTLSIDESGGLVANLNGVS

APIILQSEHAKVHSFHDYELQYSALNHTTTLFVDGQQITTWAGEVSQENNIQFGNADAQIDGRLHVQKIVLTQQGHNLVEFDAFY

LAQQTPEVEKDLEKLGWTKIKTGNTMSLYGNASVNPGPGHGITLTRQQNISGSQNGRLIYPAIVLDRFFLNVMSIYSDDGGSNWQ

TGSTLPIPFRWKSSSILETLEPSEADMVELQNGDLLLTARLDFNQIVNGVNYSPRQQFLSKDGGITWSLLEANNANVFSNISTGT

VDASITRFEQSDGSHFLLFTNPQGNPAGTNGRQNLGLWFSFDEGVTWKGPIQLVNGASAYSDIYQLDSENAIVIVETDNSNMRIL

RMPITLLKQKLTLSQN

SEQ ID NO: 82:
TTGTCAATCAAGATGACTTCACAACGAAGAAGAGCATCGATTCACAAGGAAACAGATTCTAATATAAAGGGAGTAGATATGCGTT

TCAAAAACGTAAAGAAAACCGCTTTAATGCTTGCAATGTTCGGTATGGCGACAAGCTCAAACGCCGCACTTTTTGACTATAACGC

AACGGGTGACACTGAGTTTGACAGTCCAGCCAAACAGGGATGGATGCAAGACAACACGAATAATGGCAGCGGCGTTTTAACCAAT

GCAGATGGAATGCCCGCTTGGTTGGTGCAAGGTATTGGAGGGAGAGCTCAATGGACATATTCTCTCTCTACTAATCAACATGCCC

AAGCATCAAGTTTCGGTTGGCGAATGACGACAGAAATGAAAGTGCTCAGTGGTGGAATGATCACAAACTACTACGCCAACGGCAC

TCAGCGTGTCTTACCCATCATTTCATTAGATAGCAGTGGTAACTTAGTTGTTGAGTTTGAAGGGCAAACTGGACGCACCGTTTTG

GCAACCGGCACAGCAGCAACGGAATATCATAAATTTGAATTGGTATTCCTTCCTGGAAGTAACCCATCCGCTAGCTTTTACTTCG

ATGGCAAACTCATTCGTGACAACATCCAGCCGACTGCATCAAAACAAAATATGATCGTATGGGGGAATGGCTCATCAAATACGGA

TGGTGTCGCCGCTTATCGTGATATTAAGTTTGAAATTCAAGGCGACGTCATCTTCAGAGGCCCAGACCGTATACCGTCCATTGTA

GCAAGTAGCGTAACACCAGGGGTGGTAACCGCATTTGCAGAGAAACGTGTGGGGGGAGGAGATCCCGGTGCTCTGAGTAATACCA

ATGACATAATCACTCGTACCTCACGAGATGGCGGTATAACTTGGGATACCGAGCTCAACCTCACTGAGCAAATCAATGTCAGTGA

TGAGTTTGATTTCTCCGATCCTCGGCCTATCTATGATCCTTCCTCCAATACGGTTCTTGTCTCTTATGCTCGATGGCCGACCGAT

GCCGCTCAAAACGGAGATCGAATAAAACCATGGATGCCAAACGGTATTTTTTACAGCGTCTATGATGTTGCATCAGGGAACTGGC

AAGCGCCTATCGATGTTACCGATCAGGTGAAAGAACGCAGTTTCCAAATCGCTGGTTGGGGTGGTTCAGAGCTGTATCGCCGAAA

TACCAGCCTAAATAGCCAGCAAGACTGGCAATCAAACGCTAAGATCCGAATTGTTGATGGTGCAGCGAACCAGATACAAGTTGCC

GATGGTAGCCGAAAATATGTTGTCACACTGAGTATTGATGAATCAGGTGGTCTAGTCGCTAATCTAAACGGTGTTAGTGCTCCGA

TTATCCTGCAATCTGAACACGCAAAGGTACACTCTTTCCATGACTACGAACTTCAATATTCGGCGTTAAACCACACCACAACGTT

ATTCGTGGATGGTCAGCAAATCACAACTTGGGCTGGCGAAGTATCGCAGGAGAACAACATTCAGTTTGGTAATGCGGATGCCCAA

ATTGACGGCAGACTGCATGTGCAAAAAATTGTTCTCACACAGCAAGGCCATAACCTCGTGGAGTTTGATGCTTTCTATTTAGCAC

AGCAAACCCCTGAAGTAGAGAAAGACCTTGAAAAGCTTGGTTGGACAAAAATTAAAACGGGCAACACCATGAGTTTGTATGGAAA

TGCCAGTGTCAACCCAGGACCGGGTCATGGCATCACCCTTACTCGACAACAAAATATCAGTGGCAGCCAAAACGGCCGCTTGATC

TACCCAGCGATTGTGCTTGATCGTTTCTTCTTGAACGTCATGTCTATTTACAGTGATGATGGCGGTTCAAACTGGCAAACCGGTT

CAACACTCCCTATCCCCTTTCGCTGGAAGAGTTCGAGTATCCTAGAAACTCTCGAACCTAGTGAAGCTGATATGGTTGAACTCCA

AAACGGTGATCTACTCCTTACTGCACGCCTTGATTTTAACCAAATCGTTAATGGTGTGAACTATAGCCCACGCCAGCAATTTTTG

AGTAAAGATGGTGGAATCACGTGGAGCCTACTTGAGGCTAACAACGCTAACGTCTTTAGCAATATCAGTACTGGTACCGTTGATG

CTTCTATTACTCGGTTCGAGCAAAGTGACGGTAGCCATTTCTTACTCTTTACTAACCCACAAGGAAACCCTGCGGGGACAAATGG

CAGGCAAAATCTAGGCTTATGGTTTAGCTTCGATGAAGGGGTGACATGGAAAGGACCAATTCAACTTGTTAATGGTGCATCGGCA

TATTCTGATATTTATCAATTGGATTCGGAAAATGCGATTGTCATTGTTGAAACGGATAATTCAAATATGCGAATTCTTCGTATGC

CTATCACATTGCTAAAACAGAAGCTGACCTTATCGCAAAACTAA

SEQUENCE LISTING

SEQ ID NO: 83:
MVGADPTRPRGPLSYWAGRRGQGLAAIFLLLVSAAESEARAEDDFSLVQPLVTMEQLLWVSGKQIGSVDTFRIPLITATPRGTLL

AFAEARKKSASDEGAKFIAMRRSTDQGSTWSSTAFIVDDGEASDGLNLGAVVNDVDTGIVFLIYTLCAHKVNCQVASTMLVWSKD

DGISWSPPRNLSVDIGTEMFAPGPGSGIQKQREPGKGRLIVCGHGTLERDGVFCLLSDDHGASWHYGTGVSGIPFGQPKHDHDFN

PDECQPYELPDGSVIINARNQNNYHCRCRIVLRSYDACDTLRPRDVTFDPELVDPVVAAGALATSSGIVFFSNPAHPEFRVNLTL

RWSFSNGTSWLKERVQVWPGPSGYSSLTALENSTDGKKQPPQLFVLYEKGLNRYTESISMVKISVYGTL

SEQ ID NO: 84:
MTVQPSPWFSDLRPMATCPVLQKETLFRTGVHAYRIPALLYLKKQKTLLAFAEKRASKTDEHAELIVLRRGSYNEATNRVKWQPE

EVVTQAQLEGHRSMNPCPLYDKQTKTLFLFFIAVPGRVSEHHQLHTKVNVTRLCCVSSTDHGRTWSP1QDLTETTIGSTHQEWAT

FAVGPGHCLQLRNPAGSLLVPAYAYRKLHPAQKPTPFAFCFISLDHGHTWKLGNFVAENSLECQVAEVGTGAQRMVYLNARSFLG

ARVQAQSPNDGLDFQDNRVVSKLVEPPHGCHGSVVAFHNPISKPHALDTWLLYTHPTDSRNRTNLGVYLNQMPLDPTAWSEPTLL

AMGICAYSDLQNMGQGPDGSPQFGCLYESGNYEEIIFLIFTLKQAFPTVFDAQ

SEQ ID NO: 85:
MEEVPPYSLSSTLFQQEEQSGVTYRIPALLYLPPTHTFLAFAEKRTSVRDEDAACLVLRRGLMKGRSVQWGPQRLLMEATLPGHR

TMNPCPVWEKNTGRVYLFFICVRGHVTERCQIVWGKNAARLCFLCSEDAGCSWGEVKDLTEEVIGSEVKRWATFAVGPGHGIQLH

SGRLIIPAYAYYVSRWFLCFACSVKPHSLMIYSDDFGVTWHHGKFIEPQVTGECQVAEVAGTAGNPVLYCSARTPSRFRAEAFST

DSGGCFQKPTLNPQLHEPRTGCQGSVVSFRPLKMPNTYQDSIGKGAPATQKCPLLDSPLEVEKGAETPSATWLLYSHPTSKRKRI

NLGIYYNRNPLEVNCWSRPWILNRGPSGYSDLAVVEEQDLVACLFECGEKNEYERIDFCLFSDHEVLSCEDCTSPSSD

SEQ ID NO: 86:
METAGAPFCFHVDSLVPCSYWKVMGPTRVPRRTVLFQRERTGLTYRVPALLCVPPRPTLLAFAEQRLSPDDSHAHRLVLRRGTLT

RGSVRWGTLSVLETAVLEEHRSMNPCPVLDEHSGTIFLFFIAVLGHTPEAVQIATGKNAARLCCVTSCDAGLTWGSVRDLTEEAI

GAALQDWATFAVGPGHGVQLRSGRLLVPAYTYHVDRRECFGKICWTSPHSLAFYSDDHGISWHCGGLVPNLRSGECQLAAVDGDF

LYCNARSPLGNRVQALSADEGTSFLPGELVPTLAETARGCQGSIVGFLAPPSIEPQDDRWTGSPRNTPHSPCFNLRVQESSGEGA

RGLLERWMPRLPLCYPQSRSPENHGLEPGSDGDKTSWTPECPMSSDSMLQSPTWLLYSHPAGRRARLHMGIYLSRSPLDPHSWTE

PWVIYEGPSGYSDLAFLGPMPGASLVFACLFESGTRTSYEDISFCLFSLADVLENVPTGLEMLSLRDKAQGHCWPS

SEQ ID NO: 87:
GGGTCACATGCTGATGGACTAATTGGAGTCGCGGCAGCGCGGGCTGCGGCCCCCAAGGGGAGGGGTCGGAGTGACGTGCGCGCTT

TTAAAGGGCCGAGGTCAGCTGACGGCTTGCCACCGGTGACCAGTTCCTGGACAGGGATCGCCGGGAGCTATGGTGGGGGCAGACC

CGACCAGACCCCGGGGACCGCTGAGCTATTGGGCGGGCCGTCGGGGTCAGGGGCTCGCAGCGATCTTCCTGCTCCTGGTGTCCGC

GGCGGAATCCGAGGCCAGGGCAGAGGATGACTTCAGCCTGGTGCAGCCGCTGGTGACCATGGAGCAGCTGCTGTGGGTGAGCGGG

AAGCAGATCGGCTCTGTAGACACTTTCCGCATCCCGCTCATCACAGCCACCCCTCGGGGCACGCTCCTGGCCTTCGCTGAGGCCA

GGAAAAAATCTGCATCCGATGAGGGGGCCAAGTTCATCGCCATGAGGAGGTCCACGGACCAGGGTAGCACGTGGTCCTCTACAGC

CTTCATCGTAGACGATGGGGAGGCCTCCGATGGCCTGAACCTGGGCGCTGTGGTGAACGATGTAGACACAGGGATAGTGTTCCTT

ATCTATACCCTCTGTGCTCACAAGGTCAACTGCCAGGTGGCCTCTACCATGTTGGTTTGGAGTAAGGACGACGGCATTTCCTGGA

GCCCACCCCGGAATCTCTCTGTGGATATTGGCACAGAGATGTTTGCCCCTGGACCTGGCTCAGGCATTCAGAAACAGCGGGAGCC

TGGGAAGGGCCGGCTCATTGTGTGTGGACACGGGACGCTGGAGCGAGATGGGGTCTTCTGTCTCCTCAGTGATGACCACGGTGCC

TCCTGGCACTACGGCACTGGAGTGAGCGGCATTCCCTTTGGCCAGCCCAAACACGATCACGATTTCAACCCCGACGAGTGCCAGC

CCTACGAGCTTCCAGATGGCTCGGTCATCATCAACGCCCGGAACCAGAATAACTACCATTGCCGCTGCAGGATCGTCCTCCGCAG

CTATGACGCCTGTGACACCCTCAGGCCCCGGGATGTGACCTTCGACCCTGAGCTCGTGGACCCTGTGGTAGCTGCAGGAGCACTA

GCCACCAGCTCCGGCATTGTCTTCTTCTCCAATCCAGCCCACCCTGAGTTCCGAGTGAACCTGACCCTGCGCTGGAGTTTCAGCA

ATGGTACATCCTGGCAGAAGGAGAGGGTCCAGGTGTGGCCGGGACCCAGCGGCTACTCGTCCCTGACAGCCCTGGAAAACAGCAC

-continued

SEQUENCE LISTING

GGATGGAAAGAAGCAGCCCCCGCAGCTGTTCGTTCTGTACGAGAAAGGCCTGAACCGGTACACCGAGAGCATCTCCATGGTCAAA

ATCAGCGTCTACGGCACGCTCTGAGCCCCGTGCCCAAAGGACACCAAGTCCTGGTCGCTGACTTCACAGCTCTCTGGACCATCTG

CAGAGGGTGCCTGAAACACAGCTCTTCCTCTGAACTCTGACCTTTTGCAACTTCTCATCAACAGGGAGTCTCTTCGTTATGACT

TAACACCCAGCTTCCTCTCGGGGCAGGAAGTCCCTCCGTCACCAAGAGCACTTTTTTCCAGTATGCTGGGGATGGCCCCTGTCCA

TTCTCTTCCAGGACAACGGAGCTGTGCCTTTCTGGGACAGGATGGGGGAGGGGCTCCCCCTGGAGAGATGAACAGATACGAACTC

AGGGAACTGAGAAGGCCCGGTGTCCTAGGGTACAAAGGCAGGTACTAGATGTGATTGCTGAAAGTCCCCAGGGCAGAGTGTCCTT

TCAGAGCAAGGATAAGCACACCTACGTGTGCACCTTTGATTATTTATGAATCGAAATATTTGTAACTTAAAATTTTTGATGCAGA

AAAAGCGTTTGTGGAGTCTGTGGTTCTGTCTGCTCACGCCTTCCCAATTGCCTCCTGGAGAGACAGGAAGGCAGCTGGAAGAGGA

GCCGATGTACTTACTGGGAAGCAGAAACCCCTAGATTCCATCCTGGCTGCTGCTGTTTGCAAGTGTCAAAGATGGGGGGGCGTGT

TTATATTTTATATTTCTAAGATGGGGTGGCATAGGAAATAGGGAACAGATGTGTAAAACCAGATGGGAAGGACAGTCTGTGAGAA

AGGAGCAAGCAGTTGCTGCAGGTGTGGGAGAGCAAAGCCCTTCTCCACGTGGAAAGAGCCCAGATGGACGCTAAGCATGTTGGGC

ACCTGTAACCCCGCACTCGCTGGACTGACGGTGTAGCTCAGTGGTGGAGCTAGTACTTGGAACGCCTAAGACTCTGGGTTCAGTC

CTTGGGGGGGGGGGTATGTGTTTATTGAGAGGAAGGTGTACGTACTGTAGGTCAGAGGACAGCTTACTGGAGTTGTCTCTCTCCT

TCACGCTGTGAGTCCTGTGGAATGACCTCAGGTGTCAGAGTTGGGGGCAGGTGCCTTTGCCAGCTGAGCCATCTTGCTGTCTCTG

CTTTAATTTAAAAAAAAAAAAAAAAAAAGAATATTAAGGTCTGAGGGATTCGGGCTGCGTTCATTTCAATTAGAGGGTCATATTTC

TTTTGACATTTCTTCTCTAAGAAATGTTAAGATCATTTGTTCTGTGTGATAGAGGTATAGCTCCATTGTATGTCAGCAGTGAGGG

ATCCTGTGCATTTTATCCAGAGTTTGTACGGTGTTCTAGGGGCTGCTAGTGCAGCCCAGTGCTAAACACTTCAGCATGCACAAGG

CCTCAATCAGTGCATGCATGTGCACACACACAGACACACACGTACACACTGACACAGGTACACAAATACACACTGGCCCACAT

GTACACATCGACTCACAGGTACACAGACCCACTTTGACACACATATACACAGACACAAACGCACTGGCACACACATATACACAGG

CACACATGGATAGATGGACACACGTGTACACATACACACACACACAGAAATACAAATGTTCAGGTTTTCTAAAAAAAAAAAAAATT

AGAGACGTGTTGACTTCATTTTTAGCAAAAATCCTGTCATGTATCTTAAAGTGGATTGAACCCACTATGTAGCCCAGGCTGGCCT

CCAAATGGGCATCCTTCTGCCTCAGTCTCCCGAGGGCTAGGATAACAGGAGTATGCCATCACACCTGGCTAATAGAAATTTTCAA

AATTGTTTGTTTGAAGGTGACTCTTACTATATTGCCTAACTGATCTCCAGTTCGTGAAATCCTCCTGCCTCAGAACCAGGACTGT

CAATATAACCCACCAAGACAGGCCAACATTCACAATTGATTGTTAGTTTGTGGTCTGAATCAAGGTCTTATACTGTAGCCCAGGC

TAGCCCGGAATACACGATATCTCCAGTGCTTCAGATCCTCAGTTCTAACTAAGCATGGCCACATCCATGTTTAACTGCAAATTTG

ATGTTACCATGGTTTGGTTTGGTTTGGTTTGGTTTGGTTTGGTTTGGTTTTTTGGCCATTTTTTTTTTCTCATGCTGAGG

CCTTGTGCTCTCAAGTTGGGGAGACAGCATGGAGGGTAGCTGCAACTGTAACCCCAGTTCCAGGGGACCTGACACCCTCTGGCCT

CCACAAGTATTAGGCACATCTGTGGTGCACAGACATACAATCAGGCAAAATATTCATACACATAAAATAAAATAATTTAAAACAA

AAGCAAAAATCAGGACCTAAGAAAAAAATCTATTCCTGATTCTTTTATGTTTTGTTTGTATTTTATCAAGACAGGGTTGTTTCTC

TGTATAGCCCTGGCTGTCTTGGAATTCACTCTGTAGACCAGGCTGGCCTCAAACTCAGAAATCCTCCTGCCTTTGCCTTCCAAGT

GCTGGAATTAAAGGCATGCGCCACC

SEQ ID NO: 88:
GACATGACCCAAACGGCCCCTGGCTGCAAGGTAATATCGGAAGTTGACTAAGAATGGACGCCCCACCACTGACTGACCCGCCCCC

TGAGTCTGAGATTGGACTTGTCTCTGGATACAGTCATACTTTGAGGTACTACAAGTTAGAAACTGTTAGGTTACTCAGTTCAGTC

CATGACAGTCCAACCTTCTCCATGGTTTTCCGATCTCAGGCCCATGGCGACCTGCCCTGTCCTGCAGAAGGAGACACTGTTCCGC

ACAGGCGTCCATGCTTACAGAATCCCTGCTCTGCTCTACCTGAAGAAGCAGAAGACCCTGCTGGCCTTTGCGGAAAAGCGAGCCA

GCAAGACGGATGAGCACGCAGAGTTGATTGTCCTGAGAAGAGGAAGCTACAACGAAGCCACCAACCGTGTCAAGTGGCAGCCTGA

GGAAGTGGTGACCCAAGCCCAGCTGGAAGGCCACCGCTCCATGAATCCATGTCCCTTGTATGACAAGCAAACAAAGACCCTCTTC

CTTTTCTTCATCGCTGTCCCTGGGCGTGTATCAGAACATCATCAGCTCCACACTAAGGTTAATGTCACACGGCTGTGCTGTGTCA

SEQUENCE LISTING

GCAGCACTGACCATGGGAGGACCTGGAGCCCCATCCAGGACCTCACAGAGACCACCATTGGCAGCACTCATCAGGAATGGGCCAC

ATTTGCTGTGGGTCCTGGGCATTGTCTGCAGCTGCGGAACCCAGCTGGGAGCCTGCTGGTACCTGCTTATGCCTACCGGAAACTG

CACCCTGCTCAGAAGCCTACCCCCTTTGCCTTCTGCTTCATCAGCCTTGACCATGGGCACACATGGAAACTAGGCAACTTTGTGG

CTGAAAACTCACTGGAGTGCCAGGTGGCTGAGGTTGGCACTGGAGCTCAGAGGATGGTATATCTCAATGCTAGGAGCTTCCTGGG

AGCCAGGGTCCAGGCACAAAGTCCTAATGATGGTCTGGATTTCCAGGACAACCGGGTAGTGAGTAAGCTTGTAGAGCCCCCCCAC

GGGTGTCATGGAAGTGTGGTTGCCTTCCACAACCCCATCTCTAAGCCACATGCCTTAGACACATGGCTTCTTTATACACACCCTA

CAGACTCCAGGAATAGAACCAACCTGGGTGTGTACCTAAACCAGATGCCACTAGATCCCACAGCCTGGTCAGAGCCCACCCTGCT

GGCCATGGGCATCTGTGCCTACTCAGACTTACAGAACATGGGGCAAGGCCCTGATGGCTCCCCACAGTTTGGGTGTCTGTATGAA

TCAGGTAACTATGAAGAGATCATTTTCCTCATATTCACCCTGAAGCAAGCTTTCCCCACTGTATTTGATGCCCAGTGATCTCAGT

GCACGTGGCCCAAAGGGCTTCCTTGTGCTTCAAAACACCCATCTCTCTTTGCTTCCAGCATCCTCTGGACTCTTGAGTCCAGCTC

TTGGGTAACTTCCTCAGGAGGATGCAGAGAATTTGGTCTCTTGACTCTCTGCAGGCCTTATTGTTTCAGCCTCTGGTTCTCTTTT

CAGCCCAGAAATCAAAGGAG1CCTGGCTTTCCTCAGCCTGTTGGCAGGGCAGGTGGGGACAGTATATATAGAGGCTGCCATTCTG

CATGTCGGTTGTCACTATGCTAGTTTAACCTGCCTGTTTCCCCATGCCTAGTGTTTGAATGAGTATTAATAAAATATCCAACCCA

GCCCATTTCTTCCTGGAAAAAAA

SEQ ID NO: 89:
ACTGCGCGGTGAAGGGGCGTGGCCTGGCCGGGGAGGTTGACACCCAGACGCTGCTCTCAGTCCTCTGGCGCCTGCTCCCCAGCGC

ATTCCTTCTGCTCCTGGGATATTTGTCTCATTACTGCCAGTTCTTGCGCAGCGGTCACTGGGTTCGTTTCAGCGTCTGTGGTTTC

TGTCGCTGTTATCCAGTCTCCATCGCCCCAGCTCAGCTTCAGGCCTTCTTCCGAGACTCCACGGGAGAGCCCAGAGAGCCTCCGG

AGCCGAAGCCATGGAGGAAGTCCCACCCTACTCCCTCAGCAGCACCCTGTTCCAGCAGGAAGAACAGAGTGGGGTGACCTACCGG

ATCCCAGCCCTGCTGTACCTTCCTCCCACCCACACCTTCCTGGCCTTTGCAGAGAAGCGGACCTCAGTCAGAGATGAGGATGCTG

CCTGCCTGGTGCTCAGACGAGGGCTGATGAAGGGGCGCTCTGTACAGTGGGGCCCCCAACGGCTACTGATGGAGGCCACATTACC

TGGGCATCGCACCATGAACCCCTGCCCTGTGTGGGAGAAAAATACTGGCCGTGTGTACCTGTTTTTCATCTGTGTGCGGGGCCAT

GTTACTGAGAGGTGCCAGATTGTGTGGGGCAAAAATGCCGCCCGTCTCTGCTTCCTTTGCAGTGAAGATGCCGGCTGCTCTTGGG

GTGAAGTGAAAGACTTGACCGAGGAGGTCATTGGCTCAGAGGTGAAGCGCTGGGCCACATTTGCTGTGGGCCCAGGTCATGGCAT

CCAGCTACACTCGGGAAGGCTGATCATCCCCGCCTATGCCTACTATGTCTCACGTTGGTTTCTCTGCTTTGCGTGTTCAGTCAAG

CCCCATTCCCTGATGATCTACAGTGATGACTTTGGAGTCACATGGCACCATGGCAAGTTCATTGAGCCCCAGGTGACAGGGGAGT

GCCAAGTGGCCGAAGTGGCTGGGACGGCTGGTAACCCTGTGCTCACTGCAGTGCCCGAACACCAAGCCGATTTCGAGCAGAGGCT

TTTAGTACTGATAGTGGTGGCTGCTTTCAGAAGCCAACCCTGAACCCACAACTCCATGAGCCTCGAACCGGCTGCCAAGGTAGTG

TAGTGAGCTTCCGGCCTTTGAAGATGCCAAATACCTATCAAGACTCAATTGGCAAAGGTGCTCCCGCTACTCAGAAGTGCCCTCT

GCTGGACAGTCCTCTGGAGGTGGAGAAAGGAGCTGAAACACCATCAGCAACATGGCTCTTGTACTCACATCCAACTAGCAAGAGG

AAGAGGATTAACCTAGGCATCTACTACAACCGGAACCCCTTGGAGGTGAACTGCTGGTCCCGCCCGTGGATCTTGAACCGTGGGC

CCAGTGGCTACTCTGATCTGGCTGTTGTGGAAGAACAGGACTTGGTGGCGTGTTTGTTTGAGTGTGGGGAGAAGAATGAGTATGA

GCGGATTGACTTCTGTCTGTTTTCAGACCATGAGGTCCTGAGCTGTGAAGACTGTACCAGCCCTAGTAGCGACTAAAGCCAAATC

AAGACGGATGAGTGAGGCCCAGCTTCCCACAGAAAGGAATGGCAGCTACAGCCAGGGTAACAGAGGTCTCTGATGTCTAGAGAAA

ACTCTAAAAACTAATAATCTGCTCCTTGAATTTTTTCACTTTTCCCTTCAATGAGCATGGTGAAAATTGTGCCATATCTTACATA

ACGAGGCTCTTGAACTGGGAGTTTGAATCTCTTCTCTTCCCATTAAAAGGAGAGGCCATGTGCTCGCTTCGCGTTCGACAAAGCC

TGGATTCTGATCTTGAGTGGAAGCCACAGGCTTGTCTTTTCCAATGGTTCACTGCTCACCTGAGTATTAGGTGATGTGTAGGTGC

CTTGGCCAGAAGAAAGATCTGTGTTGTTGTATTTTTTTAAATTTATTTATTTACTATATGTAAGTACACTGCAGCTGTCTTCAGA

CACACCAGAAGAGGGCGTCAGATCTCATTAGAGATGGTTGTGAGCCACCATGTGGTTGCTGGGATTTGAACTCAGGACCTTCAGA

SEQUENCE LISTING

AGAGCAGTCAGTGCTCTTAACTACTGAGCCATCTCTCAAGCCCCGCATTGCTGTATTTTTAATAAGAAAAATGCCCTTATCCTTC

CAATAATGCCTGGAGCTGTACAAATTCTCTGTCTTAGAAGACTTGAGAAAGCAGAACTGTAAGGTCAGATGCTTTCTCCAGCCTT

GATGCTGTGTTCCACCTTCCCTTCCTCATCCAGAAAACAGTTACTAGGGAGAAAATGAGAAACCCATGCCAGCTGCCCTTGATGA

TGGTTGATAACGGTGCTTATTGCTTTTGATGTCATTACCTCTGTTAGAGATGAATCAGAGTCAGAGGTCCTTAGCTGCATCCACC

CATTTCCAGGGGGACATTCTAACACTGCTGAACAGTCAGCTAAAATGAGAGCTGTGTGTCCTAGCCTGATTCCAGGTTAGTCATG

ATGCTTCCTGGAGCTGGGCTTTTATCTAATCCCAGGAGCCATCTAGGGGAGGCTCAGAGCTAGCAGGTGATCTTCCTGAGATGGT

TTCACCGTGACAGGTGAACCATGAGCCCTTCCAAGCAAGGCCAAAGGACAACATTATAGGAAAGATTTCTAGTATTAATATGCCT

TTTCTCTGTGTGTGTACTGTCTTGTAGTGATGCTATATAGACAAATAGATGATTTCTTATTTTTTGTTTGTTTGTTTGTTTTTTT

GTTTTTCTGTAGCCCTAGCTGTCCTGGAACTCACTTTGTAAACCAGGCTGGCCTCGATCTCAGAAATCCGCCTGCCTCTGCCTCC

CGAGTGCTGGGATTAAAGGTGTGCACCACCACACCTTAATGATGATCCTATAAGTATTCCTAAAATTATACTAGTAATTATTAAC

TCCTTTATAATAGGACTGCTATTAAAGCCCTCGCTGATATGAAAACTACAGTGAGAACTCTGCCAGTCTTCACATGTCATAATTA

CTTCTGAGATAGAAAGCAGGCATTTACAACTTAGAACACATTTCTTAGAGCTGTAAAACAATTAACTAGAGGTCATAAAAGGGAA

TGAAAGATTTATTGTAGGTGCTAGGACAGAACATAAAATATTGACTGGGCTTATCTATATGAAACTTCATTGTTAACTTTTACAC

AAGAATTATGGTTTTTAACTTTCAGTGAACCTGCGGAGCTAGTGACAGAAGAGAAATGTCTAGTTAGATAACTACTCTTAATGGA

AATTCACATAAACATCTGTTGCCATCTTCTTTTTGAATTTATGTTTAAACTTGTGAATGTTTGAATTAGACACTACGCGAGCACA

TAGAAAATAAAGAACTAAGCGTGAA

SEQ ID NO: 90:
GGACAGTGTGCATCACGGAGCTTGTGGCCCAGACTGTGCCTGGCAGACCCAGAGGACCTAAGGCTTGGCTCTAGTGGTGGTCAGC

ACAGCCCTCGGTGGTCTGCGGAGCCTGATATTGCTTTACGTAAGGGCTGTTCTGCTGTGCATCTCCTGTGTCTGAAGCTATTCGC

CATGGAGACTGCTGGAGCTCCCTTCTGCTTCCATGTGGACTCCCTGGTACCTTGCTCCTACTGGAAGGTTATGGGGCCCACGCGT

GTTCCCAGGAGAACGGTGCTCTTCCAGAGGGAAAGGACGGGCCTGACCTACCGTGTGCCTGCGTTACTCTGTGTGCCTCCCAGGC

CTACTCTGCTGGCCTTCGCGGAACAGCGACTTAGCCCTGATGACTCCCATGCCCACCGCCTGGTGCTACGGAGGGGCACGCTGAC

CAGGGGCTCAGTGCGGTGGGGCACTCTGAGTGTACTGGAGACTGCAGTACTGGAGGAGCACAGGTCTATGAACCCTTGCCCGGTG

CTGGATGAGCACTCTGGTACCATCTTCCTCTTCTTCATTGCCGTGCTGGGCCACACACCGGAGGCCGTGCAAATCGCCACTGGCA

AGAACGCTGCTCGCCTCTGCTGTGTGACCAGCTGTGACGCTGGCCTCACCTGGGGCAGTGTTCGAGATCTCACTGAGGAAGCCAT

TGGTGCTGCATTGCAGGACTGGGCCACCTTTGCTGTGGGTCCGGGCCATGGAGTTCAGCTGCGCTCGGGTCGCCTGCTTGTTCCT

GCTTACACCTATCATGTGGACCGACGGGAATGTTTTGGCAAGATCTGCTGGACCAGTCCCCACTCCTTGGCATTCTACAGTGATG

ATCATGGGATCTCCTGGCATTGTGGAGGCCTTGTGCCCAACCTACGCTCTGGAGAGTGCCAACTGGCTGCGGTAGATGGAGACTT

TCTCTACTGTAATGCTCGAAGCCCTCTGGGTAACCGTGTGCAGGCACTGAGTGCTGATGAAGGCACGTCCTTCCTACCAGGGGAG

CTGGTGCCTACATTGGCAGAGACGGCTCGTGGTTGCCAGGGTAGCATTGTGGGCTTCCTAGCTCCACCCTCAATCGAGCCTCAGG

ATGACCGGTGGACAGGGAGTCCTAGGAACACCCCACATTCCCCATGCTTCAATCTCAGAGTACAGGAGTCTTCGGGGGAAGGTGC

CAGAGGTCTTCTTGAACGTTGGATGCCCAGGTTGCCTCTCTGCTACCCACAGTCCCGGAGCCCAGAGAATCATGGCCTAGAGCCT

GGGTCAGATGGAGATAAGACATCCTGGACTCCGGAATGTCCTATGTCCTCTGATTCCATGCTTCAGAGCCCCACATGGCTACTAT

ATTCCCACCCAGCAGGGCGTAGAGCTCGGCTCCACATGGGAATCTACCTGAGCCGATCCCCCTTGGATCCCCACAGCTGGACAGA

GCCCTGGGTGATCTATGAGGGCCCCAGTGGCTACTCTGACCTTGCCTTTCTTGGGCCTATGCCTGGGGCATCCCTGGTTTTTGCC

TGTCTGTTTGAGAGCGGGACCAGGACTTCCTATGAAGACATTTCTTTTTGCTTGTTCTCACTGGCGGATGTCCTGGAGAATGTGC

CCACTGGCTTAGAGATGCTAAGTCTCAGGGATAAGGCTCAGGGGCATTGCTGGCCCTCTTGATGGCCTCACCCTCTCGTAGCCGC

CTGGAGAGGAAGGGTAGACTATATAGAGGAGGTTAGGGGTAGGTCAGCATGATGCTAGGATGGAGAGAGCTCTGTCCCCTCGTGG

ATGGTGGTGGTGACTCACCCGGGGGGCCAGCTGCTTTCTGAGTGCAAATGAGAAAAATAAAGAGCTGCGCTGTGACTTTTCTTTC

SEQUENCE LISTING

CACATCAAAGCTTGGGTGTCAGTGCTTTAGCTTGATGCTCTGATCACCATGCAAATCTTCCACCGGCGCCTTGCTCAGCTTTCAT

ATCCCAAGGGTGCCTGGGAGGAAGGCAACAGGGACAGTGGACATCACTGCACCACTTTCCACGACCCTGTGTGCCAACCTCAGCC

ACTTTGAAACATGCTGATGACTGAGGTCTGTTCACTTTCTTAATTTCAAGCAGGAGAAGCAGGTTGGGGAGCCAGCCTCCCCAGC

TAGAGGGGACAGAACTTGACTTGAGCAGGGGGGTACCTCCTAGGACCTGCTCCATGTGCCTACTTCTTTACCCTTCTCTAGAGAG

GGCTCTTGTCCTGTCAGAGCTGTTTTCTCCCTTCTCTTGTTTTTTCTTTTTCAAGACTGTTTCTCTGTGTTAGCCCTGGCTGTCC

TGGATCTCACTCTGTAGATCAGGCTGACCTTGAGTTCAAAGCTCCATCTGCCTCTACTTCTCACATTACTGTGATTAAAGGCATA

TACTACCACTGCCTGGTGCCCTTTTGTATTTCTTATTAAAGTCCTAATGTCTGATTATAAAAACAGTCTGTGTGGGCTGGAGTGA

TGGCTTACTCAGTAAAGCACTTGCCATGGAATCTGGGCAATCTGAGTTTCATTTTTAGCATCCTGTAAAAATCCCAATTTGATGG

TGTACTTGTAATGTCAGCATGGAGAGGCAGAGATAGGTAAGTTCCCCAAGACTCTTTGAACCGACAGCTTGGCCTCACTGGCACA

TTCCAGGTCTCAGTGAGAGACCCTGCCTCAAAATACAAAGAAAGAGCTGCTGAAGAGTGGGTCAGAGTTGACCTCTGATCTCCGG

AAGTATATGATACACACCCGTGCATGCACTCTTCCTTACAAAATAAAAAGCAAAACAAAACCCCAACAGGTATATGGCCATTTTA

GAAAAATTAGAAGATTTAGAAAGCTATACATAAAAAAAAATGACCTAAAGAAAAATCTTTACTGTTCTGGGCACTATCCCTATCA

AACCACTGTGTTCTTTGGCCAAGCCTTGGGGTGGACACTGTTTTGAGGTGGGTCCTGTTATCTCCACTAGGTAGTGGAGTTTTGT

GTCAGACTAACTGGGTCTTAAAGCTGTCTTTAAGGCCATCAGGAGCTACTGACTTGCCTGCCTCAGCAGAGCATATCCTGAAGGT

CGGGGTTAAGTCTCCTTCCCGAGCGAGTTGCCTTCCAGTGGGCCCCTGGACTCCTAGGTCCTCAGCGCTCATCAGCTGCCAAGGA

CTCTGAGGGAATGTCCTCTGACTGTGGCCCCGAAAGGTAGGGGAGGGGGATGTGCTTAGGCTTAGGACAGGGTCCTGTTTCAGTC

TGCCTTCACTGTTAGTAGCACTGTGCCACATGGCACAGACTGGGCGAGCTTTAAAGGAAGGAGGTTGATATTGGTTCCCACTTCT

GGGGATCATGGTTGAGCAGCCTTGTCTGATGATGGTTGTCTTGATGGTAGATCGTGAGGTAGTTGATGAAGGTATGACATGGTGA

GAAACTCTGTGTGTGTGTGTTATTTTCTCTGTGTTCTACCTATACATCTATCTATGTATATATGTATCTATCTATCTACCTGGAG

GCTGGAGAGATAGCTTAGTGGTTAAGAACATTTGTTGTTCTTGCATAGTCCTGGATTTAAATTTTCAGCACCCACATGGCAGCTC

ACAACAACCCATAAATCCAGTTTCAGAGGATCCAACCTCTGATATACCATGTCAGCCAGAGCAGACACGGCTGAAGGTGGTTTGA

TCCCCGTATGGAGAGGTGACAATTGGGAAGAGAGAAAGATCAACTTAACCATGCAAGGAACAGGAAGTTAAATACTGAACAGGGA

AGGTAAAGGCAGGAAGTAGATGTAGAGGGCAAATCAATGAAACCCAAACATACCCAAATTACGCTAAACACACACTGACATGCCA

ATTAAAAGGACAAATTGGCTCCACTGGCAAAACCAAAACAGACACTGAAGATCCAAACAGTCACATGCCAACTACCGCGGAGGGA

GACAGACACAGAGAAGACCGTGACAGACACTTGGACACTCTTGAGAGTGGATGTGCAGGAAGAGAGCTCTGCCAGTGGAGAAGAA

AGCACTCAGAAGAAAGTGACAGCAGCTGTAAATTTGTATTCTGCTAATGTTATGTTCCAAAGTTGAAAGCAAAATTGTACCAATT

CATAAGAACAAACAGGCTGACTCTCAGTTGTGACTGAACGTCTCTCAGTAACTGACGGGGCGAGCAGGCCAAAGGAGAGTCGGCT

CAGAAGGGTGCATAGCCACGCCAAATCAAATAAGCAAGTACAACCGGCAGGCTCTATTTCTAGCACAAAGGGGTCTGTGCCTCAT

TCTGTGCTTGGGTCAGAGCTTGGGTCTCTCATTTGGATGTAAGTGGTGTAGTGGAGAAGCAGGAAATAATCCGGAGCGCATATTT

TGATTTTAACATAAGTGCTGATTTGGGAGGGAGTTTTGTCAAATTGTGTTTTTACAATGTTTTTTTTTTTTTAAATGATGCTTTT

TTGTAAAGTGTACAAATGTGATATAAGATTGGTTCTGCTACATTCAGTTTCTATAAAAGTGGTTCTAAAATATTGTACTGTCAAT

CATCTCATGATTATTCTACTGTACACATTACTGACTTTGTATGTAATAATTAATATTAGAAGAAAATATAATTTATTTGAATATA
AAA

SEQ ID NO: 91:
X₁ASLPX₂LQKESVFQSGAHAYRIPALLYLPGQQSLLAFAEQRASKKDEHAELIVLRRGDYDAPTHQVQWQAQEVVAQARLDGHR

SMNPCPLYDAQTGTLFLFFIAIPGQVTEQQQLQTRANVTRLCQVTSTDHGRTWSSPRDLTDAAIGPAYREWSTFAVGPGHCLQLH

DRARSLVVPAYAYRKLHPX₃QRPIPSAFCFLSHDHGRTWARGHFVAQDTLECQVAEVETGEQRVVTLNARSHLRARVQAQSTNDG

LDFQESQLVKKLVEPPPQGCQGSVISFPSPRSGPGSPAQWLLYTHPTHSWQRADLGAYLNPRPPAPEAWSEPVLLAKGSX₄AYSD

LQSMGTGPDGSPLFGCLYEANDYEEIVFLMFTLKQAFPAEYLPQ

SEQUENCE LISTING

SEQ ID NO: 92:
X$_1$ASLPX$_2$LQKESVFQSGAHAYRIPALLYLPGQQSLLAFAEQRASKKDEHAELIVLRRGDYDAPTHQVQWQAQEVVAQARLDGHR

SMNPCPLYDAQTGTLFLFFIAIPGQVTEQQQLQTRANVTRLCQVTSTDHGRTWSSPRDLTDAAIGPAYREWSTFAVGPGHCLQLH

DRARSLVVPAYAYRKLHPX$_3$QRPIPSAFCFLSHDHGRTWARGHFVAQDTLECQVAEVETGEQRVVTLNARSHLRARVQAQSTNDG

LDFQESQLVKKLVEPPPQGCQGSVISFPSPRSGPGSPAQWLLYTHPTHSWQRADLGAYLNPRPPAPEAWSEPVLLAKGSX$_4$AYSD

LQSMGTGPDGSPLFGCLYEANDYEEIVFLMFTLKQAFPAEYLPQGGGGSGGGGSDKTHTCPPCPAPELLGGPSVFLFPPKPKDTL

MISRTPEVTCVVVDVSHEDPEVKFNWYVDGVEVHNAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQPENNYKTTPPVLDSDGSFFLTSKLTVDKSRWQQGN

VFSCSVMHEALHNHYTQKSLSLSPGK

SEQ ID NO: 93:
X$_1$ASLPX$_2$LQKESVFQSGAHAYRIPALLYLPGQQSLLAFAEQRASKKDEHAELIVLRRGDYDAPTHQVQWQAQEVVAQARLDGHR

SMNPCPLYDAQTGTLFLFFIAIPGQVTEQQQLQTRANVTRLCQVTSTDHGRTWSSPRDLTDAAIGPAYREWSTFAVGPGHCLQLH

DRARSLVVPAYAYRKLHPX$_3$QRPIPSAFCFLSHDHGRTWARGHFVAQDTLECQVAEVETGEQRVVTLNARSHLRARVQAQSTNDG

LDFQESQLVKKLVEPPPQGCQGSVISFPSPRSGPGSPAQWLLYTHPTHSWQRADLGAYLNPRPPAPEAWSEPVLLAKGSX$_4$AYSD

LQSMGTGPDGSPLFGCLYEANDYEEIVFLMFTLKQAFPAEYLPQGGGGSGGGGSDKTHTCPPCPAPELLGGPSVFLFPPKPKDTL

MISRTPEVTCVVVDVSHEDPEVKFNWYVDGVEVHNAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQPENNYKTTPPVLDSDGSFFLYSKLTVDKSRWQQGN

VFSCSVMHEALHNHYTQKSLSLSPGKGGGGSGGGGSGGGGSEVQLVESGGGLVQPGGSLRLSCAASGFNIKDTYIHWVRQAPGKG

LEWVARIYPTNGYTRYADSVKGRFTISADTSKNTAYLQMNSLRAEDTAVYYCSRWGGDGFYAMDYWGQGTLVTVSSGGGGSGGGG

SGGGGSDIQMTQSPSSLSASVGDRVTITCRASQDVNTAVAWYQQKPGKAPKLLIYSASFLYSGVPSRFSGSRSGTDFTLTISSLQ

PEDFATYYCQQHYTTPPTFGQGTKVEIK

SEQ ID NO: 94:
ELVLTQPASVSGSPGQSITISCTGTSSDVGGYNYVSWYQQHPGKAPKLMIYDVSKRPSGVSNRFSGSKSGNTASLTISGLQAEDE

ADYYCSSYTSSSTLVFGGGTKLTVLGQPKAAPSVTLFPPSSEELQANKATLVCLISDFYPGAVTVAWKADSSPVKAGVETTTPSK

QSNNKYAASSYLSLTPEQWKSHRSYSCQVTHEGSTVEKTVAPTECS

SEQ ID NO: 95:
GAGCTCGTGTTGACTCAGCCTGCCTCCGTGTCTGGGTCTCCTGGACAGTCGATCACCATCTCCTGCACTGGAACCAGCAGTGACG

TTGGTGGTTATAACTATGTCTCCTGGTACCAACAGCACCCAGGCAAAGCCCCCAAACTCATGATTTATGATGTCAGTAAGCGGCC

CTCAGGGGTTTCTAATCGCTTCTCTGGCTCCAAGTCTGGCAACACGGCCTCCCTGACCATCTCTGGGCTCCAGGCTGAGGACGAG

GCTGATTATTACTGCAGCTCATATACAAGCAGCAGCACTTTGGTATTCGGCGGAGGGACCAAGCTGACCGTCCTAGGTCAGCCCA

AGGCGGCGCCCTCGGTCACTCTGTTCCCGCCCTCCTCTGAGGAGCTTCAAGCCAACAAGGCCACACTGGTGTGTCTCATAAGTGA

CTTCTACCCGGGAGCCGTGACAGTGGCCTGGAAGGCAGATAGCAGCCCCGTCAAGGCGGGAGTGGAGACCACCACACCCTCCAAA

CAAAGCAACAACAAGTACGCGGCCAGCAGCTACCTGAGCCTGACGCCTGAGCAGTGGAAGTCCCACAGAAGCTACAGCTGCCAGG

TCACGCATGAAGGGAGCACCGTGGAGAAGACAGTGGCCCCTACAGAATGTTCA

SEQ ID NO: 96:
EVQLLESGGGLVQPGGSLRLSCTTSGFTFNTYAMSWVRQAPGKGLEWLSGINNNGRTAFYADSVKGRFTISRDNSKNTLYLQINS

LRADDTAVYFCAKDVRFIAVPGDSWGQGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCPPCPAPELLGGPSVFLFPPKPKDTLM

ISRTPEVTCVVVDVSHEDPEVKFNWYVDGVEVHNAKTKPREEQYNSTYRVVSVLTVLHQDWLNGKEYKCKVSNKALPAPIEKTIS

KAKGQPREPQVYTLPPSREEMTKNQVSLYCLVKGFYPSDIAVEWESNGQPENNYKTTPPVLDSDGSFFLYSKLTVDKSRWQQGNV

FSCSVMHEALHNHYTQKSLSLSPGK

-continued

| SEQUENCE LISTING |
| --- |

SEQ ID NO: 97:
GAGGTGCAGCTGCTCGAGTCAGGGGGAGGCTTGGTACAGCCGGGGGGGTCCCTGAGACTCTCCTGTACAACCTCTGGATTCACCT

TTAACACGTATGCCATGAGTTGGGTCCGCCAGGCTCCAGGGAAGGGGCTGGAATGGCTCTCAGGTATTAATAACAATGGTCGGAC

TGCATTCTACGCAGACTCCGTGAAGGGCCGCTTCACCATCTCCAGAGACAACTCCAAAAACACACTTTATCTGCAAATTAATAGT

CTGAGAGCGGACGACACGGCCGTTTATTTCTGTGCGAAAGATGTCAGATTTATCGCAGTGCCTGGTGACTCCTGGGGCCAGGGAA

CCCTGGTCACCGTCTCCTCAGCTAGCACCAAGGGCCCATCCGTCTTCCCCCTGGCACCCTCCTCCAAGAGCACCTCTGGGGGCAC

AGCGGCCCTGGGCTGCCTGGTCAAGGACTACTTCCCCGAACCGGTGACGGTGTCCTGGAACTCAGGCGCTCTGACCAGCGGCGTG

CACACCTTCCCGGCTGTCCTACAGTCCTCAGGACTCTACTCCCTCAGCAGCGTGGTGACCGTGCCCTCCAGCAGCTTGGGCACCC

AGACCTACATCTGCAACGTGAATCACAAGCCCAGCAACACCAAGGTGGACAAGAAAGTTGAGCCCAAATCTTGTGACAAAACTCA

CACATGCCCACCGTGCCCAGCACCTGAACTCCTGGGGGGACCGTCAGTCTTCCTCTTCCCCCCAAAACCCAAGGACACCCTCATG

ATCTCCCGGACCCCTGAGGTCACATGCGTGGTGGTGGACGTGAGCCACGAAGACCCTGAGGTCAAGTTCAACTGGTACGTGGACG

GCGTGGAGGTGCATAATGCCAAGACAAAGCCGCGGGAGGAGCAGTACAACAGCACGTACCGTGTGGTCAGCGTCCTCACCGTCCT

GCACCAGGACTGGCTGAATGGCAAGGAGTACAAGTGCAAGGTCTCCAACAAAGCCCTCCCAGCCCCCATCGAGAAAACCATCTCC

AAAGCCAAAGGGCAGCCCCGAGAACCACAGGTCTACACCCTGCCCCCATCCCGGGAGGAGATGACCAAGAACCAGGTCAGCCTGT

ACTGCCTGGTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGTAAA

SEQ ID NO: 98:
GACGCCTCTTTACCCTATTTACAGAAGGAGAGCGTCTTTCAGTCCGGCGCTCACGCCTATAGGATCCCCGCTTTACTGTATTTAC

CCGGTCAGCAGTCTTTACTGGCTTTCGCCGAGCAGCGGGCTTCCAAGAAGGACGAGCACGCTGAGCTGATCGTGTTACGTAGGGG

AGACTACGACGCCCCCACCCATCAAGTTCAATGGCAAGCTCAAGAAGTGGTGGCTCAAGCTCGGCTCGATGGCCATCGGAGCATG

AACCCTTGTCCCCTCTACGACGCCCAAACCGGCACTTTATTTCTGTTCTTCATCGCCATCCCCGGTCAAGTTACCGAGCAGCAAC

AGCTGCAGACCCGGGCTAACGTGACAAGGCTGTGCCAAGTTACCTCCACCGACCACGGAAGGACTTGGTCCTCCCCTCGTGATCT

GACCGATGCCGCTATCGGCCCCGCTTACCGGGAGTGGTCCACCTTTGCCGTGGGACCCGGCCATTGTCTGCAGCTGCATGATAGG

GCTCGGTCTTTAGTGGTGCCCGCTTACGCCTACCGGAAGCTGCACCCCAAGCAGCGGCCTATCCCCTCCGCTTTTTGTTTTTTAA

GCCATGACCATGGTCGTACTTGGGCTCGTGGCCATTTTGTGGCCCAAGATACTTTAGAGTGCCAAGTTGCCGAGGTGGAGACTGG

TGAGCAGCGGGTGGTGACTTTAAATGCCCGGTCCCATTTAAGGGCTAGGGTGCAAGCCCAGTCCACCAACGACGGACTGGATTTC

CAAGAATCCCAGCTGGTGAAGAAGCTCGTCGAACCTCCCCCCCAAGGTTGCCAAGGAAGCGTGATCTCCTTCCCCTCCCCTAGGA

GCGGACCCGGTTCCCCCGCTCAGTGGCTGCTCTACACCCATCCCACCCATTCTTGGCAGAGGGCTGATTTAGGCGCCTATTTAAA

CCCTCGTCCTCCCGCTCCCGAAGCTTGGAGCGAGCCCGTGCTGCTCGCTAAGGGCAGCGCCGCCTACAGCGATTTACAGTCCATG

GGAACCGGACCCGATGGCAGCCCTCTGTTCGGCTGTTTATATGAGGCTAACGACTACGAGGAGATCGTGTTTCTCATGTTCACTT

TAAAGCAAGCTTTTCCCGCTGAGTATCTGCCCCAAGGTGGAGGCGGCAGCGGCGGCGGCGGCTCCGACAAAACTCACACATGCCC

ACCGTGCCCAGCACCTGAACTCCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGACGGCGTGGAGG

TGCATAATGCCAAGACAAAGCCGCGGGAGGAGCAGTACAACAGCACGTACCGTGTGGTCAGCGTCCTCACCGTCCTGCACCAGGA

CTGGCTGAATGGCAAGGAGTACAAGTGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACCACGCCTCCCGT

GCTGGACTCCGACGGCTCCTTCTTCCTCACCAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCTCCGGGTAAATGA

SEQUENCE LISTING

SEQ ID NO: 99:
ATGGCCTCTTTACCCTATTTACAGAAGGAGAGCGTCTTTCAGTCCGGCGCTCACGCCTATAGGATCCCCGCTTTACTGTATTTAC

CCGGTCAGCAGTCTTTACTGGCTTTCGCCGAGCAGCGGGCTTCCAAGAAGGACGAGCACGCTGAGCTGATCGTGTTACGTAGGGG

AGACTACGACGCCCCCACCCATCAAGTTCAATGGCAAGCTCAAGAAGTGGTGGCTCAAGCTCGGCTCGATGGCCATCGGAGCATG

AACCCTTGTCCCCTCTACGACGCCCAAACCGGCACTTTATTTCTGTTCTTCATCGCCATCCCCGGTCAAGTTACCGAGCAGCAAC

AGCTGCAGACCCGGGCTAACGTGACAAGGCTGTGCCAAGTTACCTCCACCGACCACGGAAGGACTTGGTCCTCCCCTCGTGATCT

GACCGATGCCGCTATCGGCCCCGCTTACCGGGAGTGGTCCACCTTTGCCGTGGGACCCGGCCATTGTCTGCAGCTGCATGATAGG

GCTCGGTCTTTAGTGGTGCCCGCTTACGCCTACCGGAAGCTGCACCCCAAGCAGCGGCCTATCCCCTCCGCTTTTTGTTTTTAA

GCCATGACCATGGTCGTACTTGGGCTCGTGGCCATTTTGTGGCCCAAGATACTTTAGAGTGCCAAGTTGCCGAGGTGGAGACTGG

TGAGCAGCGGGTGGTGACTTTAAATGCCCGGTCCCATTTAAGGGCTAGGGTGCAAGCCCAGTCCACCAACGACGGACTGGATTTC

CAAGAATCCCAGCTGGTGAAGAAGCTCGTCGAACCTCCCCCCCAAGGTTGCCAAGGAAGCGTGATCTCCTTCCCCTCCCCTAGGA

GCGGACCCGGTTCCCCCGCTCAGTGGCTGCTCTACACCCATCCCCACCCATTCTTGGCAGAGGGCTGATTTAGGCGCCTATTTAAA

CCCTCGTCCTCCCGCTCCCGAAGCTTGGAGCGAGCCCGTGCTGCTCGCTAAGGGCAGCTGCGCCTACAGCGATTTACAGTCCATG

GGAACCGGACCCGATGGCAGCCCTCTGTTCGGCTGTTTATATGAGGCTAACGACTACGAGGAGATCGTGTTTCTCATGTTCACTT

TAAAGCAAGCTTTTCCCGCTGAGTATCTGCCCCAAGGTGGAGGCGGCAGCGGCGGCGGCGGCTCCGACAAAACTCACACATGCCC

ACCGTGCCCAGCACCTGAACTCCTGGGGGGACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGACGGCGTGGAGG

TGCATAATGCCAAGACAAAGCCGCGGGAGGAGCAGTACAACAGCACGTACCGTGTGGTCAGCGTCCTCACCGTCCTGCACCAGGA

CTGGCTGAATGGCAAGGAGTACAAGTGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGAGATGACCAAGAACCAGGTCAGCCTGACCTGCCTGG

TCAAAGGCTTCTATCCCAGCGACATCGCCGTGGAGTGGGAGAGCAATGGGCAGCCGGAGAACAACTACAAGACCACGCCTCCCGT

GCTGGACTCCGACGGCTCCTTCTTCCTCTACAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCTCCGGGTAAAGGAGGTGGCGGCAGCGGCG

GCGGAGGCAGCGGAGGAGGAGGCAGCGAGGTGCAGCTGGTGGAGTCCGGAGGAGGACTGGTGCAGCCCGGAGGATCTTTAAGGCT

GAGCTGTGCCGCCAGCGGCTTCAACATCAAGGACACCTACATCCACTGGGTGAGGCAAGCTCCCGGCAAAGGACTCGAGTGGGTG

GCTCGTATCTACCCCACCAACGGCTATACTCGTTACGCCGACTCCGTCAAGGGTCGTTTCACCATTTCCGCCGACACCTCCAAGA

ACACCGCCTATTTACAGATGAATTCTTTACGGGCCGAAGACACAGCTGTCTACTACTGCTCCCGGTGGGGCGGAGACGGATTCTA

CGCCATGGACTACTGGGGACAAGGTACACTGGTGACAGTGTCCAGCGGCGGAGGAGGATCTGGCGGCGGCGGAAGCGGCGGTGGC

GGTAGCGATATCCAGATGACCCAGAGCCCTTCCTCTTTAAGCGCTTCCGTGGGCGATCGTGTCACCATCACTTGTAGGGCCTCCC

AAGATGTGAACACCGCTGTGGCTTGGTACCAGCAGAAGCCCGGCAAGGCTCCCAAGCTGCTGATCTACTCCGCCAGCTTTCTGTA

TTCCGGAGTGCCTTCTCGTTTCAGCGGCTCTCGTAGCGGCACCGACTTCACTTTAACCATCAGCTCTTTACAGCCCGAGGACTTC

GCCACCTACTACTGCCAGCAGCATTACACCACACCCCCCCACCTTCGGACAAGGTACCAAAGTGGAGATCAAGTGA

SEQ ID NO: 100:
$X_1X_2SX_3PX_4$LQKESVFQSGAHAYRIPALLYLPGQQSLLAFAEQRASKKDEHAELIVLRRGDYDAPTHQVQWQAQEVVAQARLDG

HRSMNPCPLYDAQTGTLFLFFIAIPGQVTEQQQLQTRANVTRLX$_5$QVTSTDHGRTWSSPRDLTDAAIGPAYREWSTFAVGPGHCL

QLHDRARSLVVPAYAYRKLHPX$_6$QRPIPSAFX$_7$FLSHDHGRTWARGHFVAQDTLECQVAEVETGEQRVVTLNARSHLRARVQAQS

TNDGLDFQX$_8$SQLVKKLVEPPPQGX$_9$QGSVISFPSPRSGPGSPAQWLLYTHPTHSWQRADLGAYLNPRPPAPEAWSEPX$_{10}$LLAK

GSX$_{11}$AYSDLQSMGTGPDGSPLFGX$_{12}$LYEANDYEEIVFLMFTLKQAFPAEYLPQ

-continued

SEQUENCE LISTING

SEQ ID NO: 101:
X$_1$X$_2$SX$_3$PX$_4$LQKESVFQSGAHAYRIPALLYLPGQQSLLAFAEQRASKKDEHAELIVLRRGDYDAPTHQVQWQAQEVVAQARLDG

HRSMNPCPLYDAQTGTLFLFFIAIPGQVTEQQQLQTRANVTRLX$_5$QVTSTDHGRTWSSPRDLTDAAIGPAYREWSTFAVGPGHCL

QLHDRARSLVVPAYAYRKLHPX$_6$QRPIPSAFX$_7$FLSHDHGRTWARGHFVAQDTLECQVAEVETGEQRVVTLNARSHLRARVQAQS

TNDGLDFQX$_8$SQLVKKLVEPPPQGX$_9$QGSVISFPSPRSGPGSPAQWLLYTHPTHSWQRADLGAYLNPRPPAPEAWSEPX$_{10}$LLAK

GSX$_{11}$AYSDLQSMGTGPDGSPLFGX$_{12}$LYEANDYEEIVFLMFTLKQAFPAEYLPQGGGGSGGGGSDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYKCKVSN

KALPAPIEKTISKAKGQPREPQVYTLPPSREEMTKNQVSLTCLVKGFYPSDIAVEWESNGQPENNYKTTPPVLDSDGSFFLTSKL

TVDKSRWQQGNVFSCSVMHEALHNHYTQKSLSLSPGK

SEQ ID NO: 102:
X$_1$X$_2$SX$_3$PX$_4$LQKESVFQSGAHAYRIPALLYLPGQQSLLAFAEQRASKKDEHAELIVLRRGDYDAPTHQVQWQAQEVVAQARLDG

HRSMNPCPLYDAQTGTLFLFFIAIPGQVTEQQQLQTRANVTRLX$_5$QVTSTDHGRTWSSPRDLTDAAIGPAYREWSTFAVGPGHCL

QLHDRARSLVVPAYAYRKLHPX$_6$QRPIPSAFX$_7$FLSHDHGRTWARGHFVAQDTLECQVAEVETGEQRVVTLNARSHLRARVQAQS

TNDGLDFQX$_8$SQLVKKLVEPPPQGX$_9$QGSVISFPSPRSGPGSPAQWLLYTHPTHSWQRADLGAYLNPRPPAPEAWSEPX$_{10}$LLAK

GSX$_{11}$AYSDLQSMGTGPDGSPLFGX$_{12}$LYEANDYEEIVFLMFTLKQAFPAEYLPQGGGGSGGGGSDKTHTCPPCPAPELLGGPSVF

LFPPKPKDTLMISRTPEVTCVVVDVSHEDPEVKFNWYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSDIAVEWESNGQPENNYKTTPPVLDSDGSFFLYSKLT

VDKSRWQQGNVFSCSVMHEALHNHYTQKSLSLSPGKGGGGSGGGGSGGGGSEVQLVESGGGLVQPGGSLRLSCAASGFNIKDTYI

HWVRQAPGKGLEWVARIYPTNGYTRYADSVKGRFTISADTSKNTAYLQMNSLRAEDTAVYYCSRWGGDGFYAMDYWGQGTLVTVS

SGGGGSGGGGSGGGGSDIQMTQSPSSLSASVGDRVTITCRASQDVNTAVAWYQQKPGKAPKLLIYSASFLYSGVPSRFSGSRSGT

DFTLTISSLQPEDFATYYCQQHYTTPPTFGQGTKVEIK

SEQ ID NO: 103:
TVEKSVVFKAEGEHFTDQKGNTIVGSGSGGTTKYFRIPAMCTTSKGTIVVFADARHNTASDQSFIDTAAARSTDGGKTWNKKIAI

YNDRVNSKLSRVMDPTCIVANIQGRETILVMVGKWNNNDKTWGAYRDKAPDTDWDLVLYKSTDDGVTFSKVETNIHDIVTKNGTI

SAMLGGVGSGLQLNDGKLVFPVQMVRTKNITTVLNTSFIYSTDGITWSLPSGYCEGFGSENNIIEFNASLVNNIRNSGLRRSFET

KDFGKTWTEFPPMDKKVDNRNHGVQGSTITIPSGNKLVAAHSSAQNKNNDYTRSDISLYAHNLYSGEVKLIDDFYPKVGNASGAG

YSCLSYRKNVDKETLYVVYEANGSIEFQDLSRHLPVIKSYNGGGGSGGGGSDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSDGSFFLYSKLTVDKSRWQQGNVFS

CSVMHEALHNHYTQKSLSLSPGKGGGGSGGGGSGGGGSEVQLVESGGGLVQPGGSLRLSCAASGFNIKDTYIHWVRQAPGKGLEW

VARIYPTNGYTRYADSVKGRFTISADTSKNTAYLQMNSLRAEDTAVYYCSRWGGDGFYAMDYWGQGTLVTVSSGGGGSGGGGSGG

GGSDIQMTQSPSSLSASVGDRVTITCRASQDVNTAVAWYQQKPGKAPKLLIYSASFLYSGVPSRFSGSRSGTDFTLTISSLQPED

FATYYCQQHYTTPPTFGQGTKVEIK

SEQ ID NO: 104:
ACAGTGGAAAAGTCCGTGGTGTTCAAGGCCGAGGGCGAGCACTTCACCGACCAGAAAGGCAATACCATCGTCGGCTCTGGCAGCG

GCGGCACCACCAAGTACTTTAGAATCCCCGCCATGTGCACCACCAGCAAGGGCACCATTGTGGTGTTCGCCGACGCCAGACACAA

CACCGCCAGCGATCAGAGCTTCATCGATACCGCTGCCGCCAGATCTACCGATGGCGGCAAGACCTGGAACAAGAAGATCGCCATC

TACAACGACCGCGTGAACAGCAAGCTGAGCAGAGTGATGGACCCTACCTGCATCGTGGCCAACATCCAGGGCAGAGAAACCATCC

TGGTCATGGTCGGAAAGTGGAACAACAACGATAAGACCTGGGGCGCCTACAGAGACAAGGCCCCTGATACCGATTGGGACCTCGT

GCTGTACAAGAGCACCGATGACGGCGTGACCTTCAGCAAGGTGGAAACAAACATCCACGACATCGTGACCAAGAACGGCACCATC

-continued

---

SEQUENCE LISTING

---

TCTGCCATGCTCGGCGGCGTTGGATCTGGCCTGCAACTGAATGATGGCAAGCTGGTGTTCCCCGTGCAGATGGTCCGAACAAAGA

ATATCACCACCGTGCTGAATACCAGCTTCATCTACAGCACCGACGGCATCACATGGTCCCTGCCTAGCGGCTACTGTGAAGGCTT

TGGCAGCGAGAACAACATCATCGAGTTCAACGCCAGCCTGGTCAACAACATCCGGAACAGCGGCCTGCGGAGAAGCTTCGAGACA

AAGGACTTCGGAAAGACGTGGACCGAGTTTCCTCCAATGGACAAGAAGGTGGACAACCGGAACCACGGCGTGCAGGGCAGCACAA

TCACAATCCCTAGCGGCAACAAACTGGTGGCCGCTCACTCTAGCGCCCAGAACAAGAACAACGACTACACCAGAAGCGACATCAG

CCTGTACGCCCACAACCTGTACAGCGGCGAAGTGAAGCTGATCGACGACTTCTACCCCAAAGTGGGCAATGCCAGCGGAGCCGGC

TACAGCTGTCTGAGCTACCGGAAAAATGTGGACAAAGAAACCCTGTACGTGGTGTACGAGGCCAACGGCAGCATCGAGTTTCAGG

ACCTGAGCAGACATCTGCCCGTGATCAAGAGCTACAACGGCGGAGGTGGAAGTGGCGGAGGCGGATCcGACAAAACTCACACATG

CCCACCGTGCCCAGCACCTGAACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCAACTGGTACGTGGACGGCGTGG

AGGTGCATAATGCCAAGACAAAGCCGCGGGAGGAGCAGTACAACAGCACGTACCGTGTGGTCAGCGTCCTCACCGTCCTGCACCA

GGACTGGCTGAATGGCAAGGAGTACAAGTGCAAGGTCTCCAACAAAGCCCTCCCAGCCCCCATCGAGAAAACCATCTCCAAAGCC

AAAGGGCAGCCCCGAGAACCACAGGTcTACACCCTGCCCCCATCCCGGGAGGAGATGACCAAGAACCAGGTCAGCCTGACCTGCC

TGGTCAAAGGCTTCTATCCCAGCGACATCGCCGTGGAGTGGGAGAGCAATGGGCAGCCGGAGAACAACTACAAGACCACGCCTCC

CGTGCTGGACTCCGACGGCTCCTTCTTCCTCTATAGCAAGCTCACCGTGGACAAGAGCAGGTGGCAGCAGGGGAACGTCTTCTCA

TGCTCCGTGATGCATGAGGCTCTGCACAACCACTACACGCAGAAGAGCCTCTCCCTGTCTCCGGGTAAAGGAGGCGGAGGATCTG

GCGGAGGTGGAAGTGGCGGAGGCGGATCTGAGGTGCAGCTGGTTGAATCTGGCGGAGGACTGGTTCAGCCTGGCGGATCTCTGAG

ACTGTCTTGTGCCGCCAGCGGCTTCAACATCAAGGACACCTACATCCACTGGGTCCGACAGGCCCCTGGCAAAGGACTTGAATGG

GTCGCCAGAATCTACCCCACCAACGGCTACACCAGATACGCCGACTCTGTGAAGGGCAGATTCACCATCAGCGCCGACACCAGCA

AGAACACCGCCTACCTGCAGATGAACAGCCTGAGAGCCGAGGACACCGCCGTGTACTACTGTTCTAGATGGGGAGGCGACGGCTT

CTACGCCATGGATTATTGGGGCCAGGGCACCCTGGTCACCGTTTCTTCTGGCGGAGGAGGATCTGGCGGAGGCGGAAGTGGCGGA

GGCGGATCTGACATCCAGATGACACAGAGCCCTAGCAGCCTGTCTGCCAGCGTGGGAGACAGAGTGACCATCACCTGTAGAGCCA

GCCAGGACGTGAACACAGCCGTGGCTTGGTATCAGCAGAAGCCTGGCAAGGCCCCTAAGCTGCTGATCTACAGCGCCAGCTTTCT

GTACTCCGGCGTGCCCAGCAGATTCAGCGGCTCTAGAAGCGGCACCGACTTCACCCTGACCATAAGCAGTCTGCAGCCCGAGGAC

TTCGCCACCTACTACTGTCAGCAGCACTACACCACACCTCCAACCTTTGGCCAGGGCACCAAGGTGGAAATCAAG

---

SEQUENCE LISTING

---

Sequence total quantity: 109
SEQ ID NO: 1                 moltype = AA  length = 380
FEATURE                      Location/Qualifiers
source                       1..380
                             mol_type = protein
                             organism = Homo sapiens
SEQUENCE: 1
MASLPVLQKE SVFQSGAHAY RIPALLYLPG QQSLLAFAEQ RASKKDEHAE LIVLRRGDYD     60
APTHQVQWQA QEVVAQARLD GHRSMNPCPL YDAQTGTLFL FFIAIPGQVT EQQQLQTRAN    120
VTRLCQVTST DHGRTWSSPR DLTDAAIGPA YREWSTFAVG PGHCLQLHDR ARSLVVPAYA    180
YRKLHPIQRP IPSAFCFLSH DHGRTWARGH FVAQDTLECQ VAEVETGEQR VVTLNARSHL    240
RARVQAQSTN DGLDFQESQL VKKLVEPPPQ GCQGSVISFP SPRSGPGSPA QWLLYTHPTH    300
SWQRADLGAY LNPRPPAPEA WSEPVLLAKG SCAYSDLQSM GTGPDGSPLF GCLYEANDYE    360
EIVFLMFTLK QAFPAEYLPQ                                                380

SEQ ID NO: 2                 moltype = AA  length = 385
FEATURE                      Location/Qualifiers
source                       1..385
                             mol_type = protein
                             organism = Mus sp.
SEQUENCE: 2

```
MEDLRPMATC PVLQKETLFR TGVHAYRIPA LLYLKKQKTL LAFAEKRASK TDEHAELIVL    60
RRGSYNEATN RVKWQPEEVV TQAQLEGHRS MNPCPLYDKQ TKTLFLFFIA VPGRVSEHHQ   120
LHTKVNVTRL CCVSSTDHGR TWSPIQDLTE TTIGSTHQEW ATFAVGPGHC LQLRNPAGSL   180
LVPAYAYRKL HPAQKPTPFA FCFISLDHGH TWKLGNFVAE NSLECQVAEV GTGAQRMVYL   240
NARSFLGARV QAQSPNDGLD FQDNRVVSKL VEPPHGCHGS VVAFHNPISK PHALDTWLLY   300
THPTDSRNRT NLGVYLNQMP LDPTAWSEPT LLAMGICAYS DLQNMGQGPD GSPQFGCLYE   360
SGNYEEIIFL IFTLKQAFPT VFDAQ                                         385

SEQ ID NO: 3            moltype = AA  length = 5
FEATURE                 Location/Qualifiers
source                  1..5
                        mol_type = protein
                        organism = Mus sp.
SEQUENCE: 3
EDLRP                                                                 5

SEQ ID NO: 4            moltype = AA  length = 6
FEATURE                 Location/Qualifiers
source                  1..6
                        mol_type = protein
                        organism = Mus sp.
SEQUENCE: 4
MEDLRP                                                                6

SEQ ID NO: 5            moltype = AA  length = 380
FEATURE                 Location/Qualifiers
REGION                  1..380
                        note = Description of Artificial Sequence: Synthetic
                         polypeptide
source                  1..380
                        mol_type = protein
                        organism = synthetic construct
SEQUENCE: 5
MASLPVLQKE SVFQSGAHAY RIPALLYLPG QQSLLAFAEQ RASKKDEHAE LIVLRRGDYD    60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPIQRP IPSAFCFLSH DHGRTWARGH FVAQDTLECQ VAEVETGEQR VVTLNARSHL   240
RARVQAQSTN DGLDFQESQL VKKLVEPPPQ GCQGSVISFP SPRSGPGSPA QWLLYTHPTH   300
SWQRADLGAY LNPRPPAPEA WSEPVLLAKG SAAYSDLQSM GTGPDGSPLF GLLYEANDYE   360
EIVFLMFTLK QAFPAEYLPQ                                               380

SEQ ID NO: 6            moltype = AA  length = 386
FEATURE                 Location/Qualifiers
REGION                  1..386
                        note = Description of Artificial Sequence: Synthetic
                         polypeptide
source                  1..386
                        mol_type = protein
                        organism = synthetic construct
SEQUENCE: 6
MEDLRPMASL PVLQKESVFQ SGAHAYRIPA LLYLPGQQSL LAFAEQRASK KDEHAELIVL    60
RRGDYDAPTH QVQWQAQEVV AQARLDGHRS MNPCPLYDAQ TGTLFLFFIA IPGQVTEQQQ   120
LQTRANVTRL CQVTSTDHGR TWSSPRDLTD AAIGPAYREW STFAVGPGHC LQLHDRARSL   180
VVPAYAYRKL HPIQRPIPSA FCFLSHDHGR TWARGHFVAQ DTLECQVAEV ETGEQRVVTL   240
NARSHLRARV QAQSTNDGLD FQESQLVKKL VEPPPQGCQG SVISFPSPRS GPGSPAQWLL   300
YTHPTHSWQR ADLGAYLNPR PPAPEAWSEP VLLAKGSCAY SDLQSMGTGP DGSPLFGCLY   360
EANDYEEIVF LMFTLKQAFP AEYLPQ                                        386

SEQ ID NO: 7            moltype = AA  length = 364
FEATURE                 Location/Qualifiers
source                  1..364
                        mol_type = protein
                        organism = Homo sapiens
SEQUENCE: 7
ENDFGLVQPL VTMEQLLWVS GRQIGSVDTF RIPLITATPR GTLLAFAEAR KMSSSDEGAK    60
FIALRRSMDQ GSTWSPTAFI VNDGDVPDGL NLGAVVSDVE TGVVFLFYSL CAHKAGCQVA   120
STMLVWSKDD GVSWSTPRNL SLDIGTEVFA PGPGSGIQKQ REPRKGRLIV CGHGTLERDG   180
VFCLLSDDHG ASWRYGSGVS GIPYGQPKQE NDFNPDECQP YELPDGSVVI NARNQNNYHC   240
HCRIVLRSYD ACDTLRPRDV TFDPELVDPV VAAGAVVTSS GIVFFSNPAH PEFRVNLTLR   300
WSFSNGTSWR KETVQLWPGP SGYSSLATLE GSMDGEEQAP QLYVLYEKGR NHYTESISVA   360
KISV                                                               364

SEQ ID NO: 8            moltype = AA  length = 428
FEATURE                 Location/Qualifiers
source                  1..428
                        mol_type = protein
                        organism = Homo sapiens
SEQUENCE: 8
MEEVTTCSFN SPLFRQEDDR GITYRIPALL YIPPTHTFLA FAEKRSTRRD EDALHLVLRR    60
```

```
GLRIGQLVQW GPLKPLMEAT LPGHRTMNPC PVWEQKSGCV FLFFICVRGH VTERQQIVSG    120
RNAARLCFIY SQDAGCSWSE VRDLTEEVIG SELKHWATFA VGPGHGIQLQ SGRLVIPAYT    180
YYIPSWFFCF QLPCKTRPHS LMIYSDDLGV TWHHGRLIRP MVTVECEVAE VTGRAGHPVL    240
YCSARTPNRC RAEALSTDHG EGFQRLALSR QLCEPPHGCQ GSVVSFRPLE IPHRCQDSSS    300
KDAPTIQQSS PGSSLRLEEE AGTPSESWLL YSHPTSRKQR VDLGIYLNQT PLEAACWSRP    360
WILHCGPCGY SDLAALEEEG LFGCLFECGT KQECEQIAFR LFTHREILSH LQGDCTSPGR    420
NPSQFKSN                                                             428

SEQ ID NO: 9                   moltype = AA   length = 461
FEATURE                        Location/Qualifiers
source                         1..461
                               mol_type = protein
                               organism = Homo sapiens
SEQUENCE: 9
MRPADLPPRP MEESPASSSA PTETEEPGSS AEVMEEVTTC SFNSPLFRQE DDRGITYRIP     60
ALLYIPPTHT FLAFAEKRST RRDEDALHLV LRRGLRIGQL VQWGPLKPLM EATLPGHRTM    120
NPCPVWEQKS GCVFLFFICV RGHVTERQQI VSGRNAARLC FIYSQDAGCS WSEVRDLTEE    180
VIGSELKHWA TFAVGPGHGI QLQSGRLVIP AYTYYIPSWF FCFQLPCKTR PHSLMIYSDD    240
LGVTWHHGRL IRPMVTVECE VAEVTGRAGH PVLYCSARTP NRCRAEALST DHGEGFQRLA    300
LSRQLCEPPH GCQGSVVSFR PLEIPHRCQD SSSKDAPTIQ QSSPGSSLRL EEEAGTPSES    360
WLLYSHPTSR KQRVDLGIYL NQTPLEAACW SRPWILHCGP CGYSDLAALE EEGLFGCLFE    420
CGTKQECEQI AFRLFTHREI LSHLQGDCTS PGRNPSQFKS N                       461

SEQ ID NO: 10                  moltype = AA   length = 484
FEATURE                        Location/Qualifiers
source                         1..484
                               mol_type = protein
                               organism = Homo sapiens
SEQUENCE: 10
MGVPRTPSRT VLFERERTGL TYRVPSLLPV PPGPTLLAFV EQRLSPDDSH AHRLVLRRGT     60
LAGGSVRWGA LHVLGTAALA EHRSMNPCPV HDAGTGTVFL FFIAVLGHTP EAVQIATGRN    120
AARLCCVASR DAGLSWGSAR DLTEEAIGGA VQDWATFAVG PGHGVQLPSG RLLVPAYTYR    180
VDRRECFGKI CRTSPHSFAF YSDDHGRTWR CGGLVPNLRS GECQLAAVDG GQAGSFLYCN    240
ARSPLGSRVQ ALSTDEGTSF LPAERVASLP ETAWGCQGSI VGFPAPAPNR PRDDSWSVGP    300
GSPLQPPLLG PGVHEPPEEA AVDPRGGQVP GGPFSRLQPR GDGPRQPGPR PGVSGDVGSW    360
TLALPMPFAA PPQSPTWLLY SHPVGRRARL HMGIRLSQSP LDPRSWTEPW VIYEGPSGYS    420
DLASIGPAPE GGLVFACLYE SGARTSYDEI SFCTFSLREV LENVPASPKP PNLGDKPRGC    480
CWPS                                                                 484

SEQ ID NO: 11                  moltype = AA   length = 496
FEATURE                        Location/Qualifiers
source                         1..496
                               mol_type = protein
                               organism = Homo sapiens
SEQUENCE: 11
MMSSAAFPRW LSMGVPRTPS RTVLFERERT GLTYRVPSLL PVPPGPTLLA FVEQRLSPDD     60
SHAHRLVLRR GTLAGGSVRW GALHVLGTAA LAEHRSMNPC PVHDAGTGTV FLFFIAVLGH    120
TPEAVQIATG RNAARLCCVA SRDAGLSWGS ARDLTEEAIG GAVQDWATFA VGPGHGVQLP    180
SGRLLVPAYT YRVDRRECFG KICRTSPHSF AFYSDDHGRT WRCGGLVPNL RSGECQLAAV    240
DGGQAGSFLY CNARSPLGSR VQALSTDEGT SFLPAERVAS LPETAWGCQG SIVGFPAPAP    300
NRPRDDSWSV GPGSPLQPPL LGPGVHEPPE EAAVDPRGGQ VPGGPFSRLQ PRGDGPRQPG    360
PRPGVSGDVG SWTLALPMPF AAPPQSPTWL LYSHPVGRRA RLHMGIRLSQ SPLDPRSWTE    420
PWVIYEGPSG YSDLASIGPA PEGGLVFACL YESGARTSYD EISFCTFSLR EVLENVPASP    480
KPPNLGDKPR GCCWPS                                                    496

SEQ ID NO: 12                  moltype = AA   length = 5
FEATURE                        Location/Qualifiers
source                         1..5
                               mol_type = protein
                               organism = Homo sapiens
SEQUENCE: 12
MASLP                                                                  5

SEQ ID NO: 13                  moltype = AA   length = 4
FEATURE                        Location/Qualifiers
source                         1..4
                               mol_type = protein
                               organism = Homo sapiens
SEQUENCE: 13
ASLP                                                                   4

SEQ ID NO: 14                  moltype = AA   length = 8
FEATURE                        Location/Qualifiers
REGION                         1..8
                               note = Description of Artificial Sequence: Synthetic peptide
source                         1..8
                               mol_type = protein
                               organism = synthetic construct
SEQUENCE: 14
```

-continued

```
TVEKSVVF                                                        8

SEQ ID NO: 15          moltype = AA   length = 12
FEATURE                Location/Qualifiers
source                 1..12
                       mol_type = protein
                       organism = Homo sapiens

SEQUENCE: 15
GDYDAPTHQV QW                                                   12

SEQ ID NO: 16          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct

SEQUENCE: 16
SMDQGSTW                                                        8

SEQ ID NO: 17          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct

SEQUENCE: 17
STDGGKTW                                                        8

SEQ ID NO: 18          moltype = AA   length = 8
FEATURE                Location/Qualifiers
source                 1..8
                       mol_type = protein
                       organism = Homo sapiens

SEQUENCE: 18
PRPPAPEA                                                        8

SEQ ID NO: 19          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct

SEQUENCE: 19
QTPLEAAC                                                        8

SEQ ID NO: 20          moltype = AA   length = 9
FEATURE                Location/Qualifiers
source                 1..9
                       mol_type = protein
                       organism = Homo sapiens

SEQUENCE: 20
NPRPPAPEA                                                       9

SEQ ID NO: 21          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct

SEQUENCE: 21
SQNDGES                                                         7

SEQ ID NO: 22          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct

SEQUENCE: 22
LSHSLST                                                         7

SEQ ID NO: 23          moltype = DNA   length = 1092
FEATURE                Location/Qualifiers
source                 1..1092
```

```
                        mol_type = other DNA
                        organism = Homo sapiens
SEQUENCE: 23
gagaacgact ttggactggt gcagcctctg gtcaccatgg aacagctgct gtgggtttcc    60
ggcagacaga tcggcagcgt ggacaccttc agaatccctc tgatcaccgc cacacctaga   120
ggcaccctgc tggcctttgc cgaggccaga aagatgagca gctctgacga gggcgccaag   180
tttattgccc tgaggcggtc tatggaccag ggctctacat ggtcccctac cgccttcatc   240
gtgaacgatg cgacgtgcc cgatggcctg aatctgggag ctgtggtgtc cgatgtggaa    300
accggcgtg tgttcctgtt ctacagcctg tgtgcccaca aggccggttg tcaggtggcc    360
agcacaatgc tcgtgtggtc caaggacgac ggcgtgtcct ggtctacccc tagaaacctg   420
agcctggaca tcggcaccga agtgtttgct ccaggacctg gctctggcat ccagaagcag   480
agagagccca gaaagggcag actgatcgtg tgtggccacg gcacccttga gagagatggc   540
gttttctgcc tgctgagcga cgatcatggc gcctcttgga gatacggcag cggagtgtct   600
ggaatccctt acggccagcc taagcaagag aacgatttca accccgacga gtgccagcct   660
tacgagctgc ctgatggcag cgtcgtgatc aacgcccgga accagaacaa ctaccactgc   720
cactgccgga tcgtgctgag aagctacgac gcctgcgata ccctgcggcc tagagatgtg   780
accttcgatc ctgagctggt ggaccctgtt gttgccgctg gtgccgtcgt gacatctagc   840
ggcatcgtgt tcttcagcaa ccctgctcac cccgagttca gagtgaatct gaccctgcgg   900
tggtccttca gcaatggcac aagctggcgg aaagaaaccg tgcagctttg gcctggacct   960
agcggctact cttctctggc tacactggaa ggcagcatgg acggcgaaga acaggcccct  1020
cagctgtacg tgctgtacga gaagggcaga aaccactaca ccgagagcat cagcgtggcc  1080
aagatcagcg tt                                                       1092
```

```
SEQ ID NO: 24             moltype = DNA  length = 1140
FEATURE                   Location/Qualifiers
source                    1..1140
                          mol_type = other DNA
                          organism = Homo sapiens
SEQUENCE: 24
atggccagcc tgcctgtgct gcagaaagaa agcgtgttcc agtctggcgc ccacgcctac    60
agaattcccg ctctgctgta tctgccaggc cagcagtctc tgctggcttt cgctgaacag   120
cgggccagca agaaggatga gcacgccgaa ctgatcgtgc tgcggagagg cgattacgac   180
gcccctacac atcaggtgca gtggcaggct caagaggtgg tggctcaggc tagactggac   240
ggccacagat ctatgaaccc ctgtcctctg tacgatgccc agaccggcac actgtttctg   300
ttctttatcg ctatccccgg ccaagtgacc gagcagcagc agctgcagac aagagccaac   360
gtgaccagac tgtgtcaagt gacctccacc gaccacggca gaacctggtc tagccctaga   420
gatctgaccg acgccgccat cggacctgcc tatagagagt ggtccacctt cgccgttgga   480
cctggacact gtctccagct gcacgacagg gctagatctc tggtggtgcc tgcctacgcc   540
tatagaaagc tgcaccccat ccagcggcct attcctagcg ccttctgctt tctgagccac   600
gatcacggca ggacatgggc cagaggacat ttcgtggccc aggacacact ggaatgccac   660
gtggccgaag tggaaaccgg cgagcagaga gtcgtgaccc tgaacgccag atctcacctg   720
agagccagag tgcaggccca gagcacaaac gacggcctgg atttccaaga gagccagctg   780
gtcaagaaac tggtggaacc tcctccacag ggctgtccag gaagcgtgat cagctttcca   840
tctcctagaa gcggccctgg ctctcctgct cagtggctgc tgtatacaca ccccacacac   900
agctggcaga gagccgatct gggcgcctac ctgaatccta gacctcctgc tcctgaggct   960
tggagcgaac ctgttctgct ggccaagggc agctgtgcct acagcgatct gcagtctatg  1020
ggcacaggcc ctgatggcag ccctctgttt ggctgtctgt acgaggccaa cgactacgaa  1080
gagatcgtgt tcctgatgtt caccctgaag caggcctttc cagccgagta cctgcctcaa  1140
```

```
SEQ ID NO: 25             moltype = DNA  length = 1284
FEATURE                   Location/Qualifiers
source                    1..1284
                          mol_type = other DNA
                          organism = Homo sapiens
SEQUENCE: 25
atggaggaag tgaccacctg tagcttcaac agccctctgt ccggcaaga ggacgaccgg    60
ggcatcacct acagaatccc tgctctgctg tacatccctc ctacacacac ctttctggcc   120
ttcgccgaga agcggagcac cagacgagat gaagatgccc tgcacctggt gctgagaaga   180
ggcctgagaa tcggacagct ggtgcagtgg ggacctctga agcctctgat ggaagccaca   240
ctgcccggcc acagaaccat gaatccttgt cctgtgtggg agcagaaaag cggctgcgtg   300
ttcctgttct tcatctgcgt gcggggccac gtgaccgaga gacagcaaat cgtgtccggc   360
agaaacgccg ccagactgtg cttcatctac agccaggatg ccggctgctc ttggagcgaa   420
gttcgggatc tgaccgaaga agtgatcggc agcgagctga agcactgggc cacatttgct   480
gttggccctg gccacggaat ccagctgcaa tctggcagac tggtcatccc cgcctcacac   540
tactatatcc ccagctggtt cttctgcttc caactgcctt gcaagacccg gcctcacagc   600
ctgatgatct cacgcgacga tctgggccgt acatggcacc acggcagact gatcagaccc   660
atggtcaccg tggaatgcga ggtggccgaa gtgacaggca gagctggaca ccctgtgctg   720
tactgctctg ccagaacacc caaccggtgt agagccgagg ctctgtctac agatcacggc   780
gagggctttc agagactggc cctctctaga cagctgtcag aacttcctca tggctgtcag   840
ggcagcgtgg tgtccttcag acctctggaa atccctcacc ggtgccagga cagcagctct   900
aaggatgccc ctaccatcca gcagtctagc cctggcagca gcctggagact ggaagaggaa   960
gccgaacac ctagcgagag ctggctgctg tactctcacc ccaccagcag aaagcagaga  1020
gtggacctgg gcatctacct gaatcagacc cctctggaag ccgcctgttg gagcagacct  1080
tggattctgt actgtggccc ttgcgcctac tctgatctgg aagaagagggc  1140
ctgttcggct gcctgtttga gtgcggcaca aagcaagagt gcgagcagat cgccttccgg  1200
ctgttcaccc cacagagagat cctgagccat ctgcagggcg actgcacaag cccaggcaga  1260
aatcccagcc agttcaagag caac                                          1284
```

```
SEQ ID NO: 26             moltype = DNA  length = 1452
```

```
FEATURE              Location/Qualifiers
source               1..1452
                     mol_type = other DNA
                     organism = Homo sapiens
SEQUENCE: 26
atgggcgtgc ccagaacacc cagcagaacc gtgctgttcg agagagagag gaccggcctg   60
acctacagag tgccttctct gctgcctgtg cctcctggac ctacactgct ggccttcgtg  120
gaacagagac tgagccccga tgattctcac gcccacagac tggtgctgag aagaggaaca  180
ctggctggcg gctctgttag atggggagca ctgcatgtgc tgggcacagc tgctcttgcc  240
gagcacagat ccatgaatcc ctgtcctgtg cacgacgccg gaaccggcac agtgtttctg  300
ttctttatcg ccgtgctggg ccacacacct gaggccgttc aaattgccac cggcagaaat  360
gccgccagac tgtgttgtgt ggcctccaga gatgccggcc tgtcttgggg atctgccaga  420
gatctgaccg aggaagccat tggcggagcc gttcaggatt gggccacatt tgctgttgga  480
cctggacacg gcgtgcagct gccaagtggt agactgctgg tgcctgccta cacatacaga  540
gtggatcgga gagagtgctt cggaaagatc tgccggacaa gccctcacag cttcgccttc  600
tactccgacg atcacggccg gacttggaga tgtggtggcc tggtgcctaa tctgagaagc  660
ggcgaatgtc aactggccgc cgttgatggt ggacaggctg gcagcttcct gtactgcaac  720
gccagatctc ctctgggctc tagagtgcag gccctgtcta ccgatgaggg caccagtttt  780
ctgcccgccg aaagagttgc ctctctgcct gaaacagcct ggggctgtca gggctctatc  840
gtgggatttc ctgctcctgc tccaaacaga ccccgggacg attcttggag tgtcggccct  900
ggatctccac tgcagcctcc attgcttgga ccaggcgttc acgagccacc tgaagaggct  960
gccgttgatc ctagaggcgg acaagttcct ggcggcctct ttagcagact gcagccaaga 1020
ggcgacggcc ctagacaacc tggaccaaga cctggcgtca gcggagatgt tggctcttgg 1080
acactggccc tgcctatgcc ttttgccgct cctcctcagt ctcctacctg gctgctgtac 1140
tctcaccctg ttggcagacg ggccagactg cacatgggca tcagactgtc tcagagccct 1200
ctggacccca gaagctggac agagccttgg gtcatctatg agggccctag cggctacagc 1260
gatctggcct ctattggccc agctcctgaa ggcggactgg tgttcgcttg tctgtatgag 1320
agcggcgcca gaaccagcta cgacgagatc agcttctgca ccttcagcct gcgcgaggtg 1380
ctggaaaatg tgcccgcctc tcctaagcct cctaacctgg gcgataagcc tagaggctgt 1440
tgctggccat ct                                                     1452

SEQ ID NO: 27         moltype = AA  length = 47
FEATURE              Location/Qualifiers
source               1..47
                     mol_type = protein
                     organism = Homo sapiens
SEQUENCE: 27
MTGERPSTAL PDRRWGPRIL GFWGGCRVWV FAAIFLLLSL AASWSKA              47

SEQ ID NO: 28         moltype = AA  length = 22
FEATURE              Location/Qualifiers
REGION               1..22
                     note = Description of Artificial Sequence: Synthetic peptide
source               1..22
                     mol_type = protein
                     organism = synthetic construct
SEQUENCE: 28
MDMRVPAQLL GLLLLWLPGA RC                                         22

SEQ ID NO: 29         moltype = AA  length = 4
FEATURE              Location/Qualifiers
source               1..4
                     mol_type = protein
                     organism = Homo sapiens
SEQUENCE: 29
YGTL                                                            4

SEQ ID NO: 30         moltype = AA  length = 382
FEATURE              Location/Qualifiers
source               1..382
                     mol_type = protein
                     organism = Salmonella typhimurium
SEQUENCE: 30
MTVEKSVVFK AEGEHFTDQK GNTIVGSGSG GTTKYFRIPA MCTTSKGTIV VFADARHNTA   60
SDQSFIDTAA ARSTDGGKTW NKKIAIYNDR VNSKLSRVMD PTCIVANIQG RETILVMVGK  120
WNNNDKTWGA YRDKAPDTDW DLVLYKSTDD GVTFSKVETN IHDIVTKNGT ISAMLGGVGS  180
GLQLNDGKLV FPVQMVRTKN ITTVLNTSFI YSTDGITWSL PSGYCEGFGS ENNIIEFNAS  240
LVNNIRNSGL RRSFETKDFG KTWTEFPPMD KKVDNRNHGV QGSTITIPSG NKLVAAHSSA  300
QNKNNDYTRS DISLYAHNLY SGEVKLIDDF YPKVGNASGA GYSCLSYRKN VDKETLYVVY  360
EANGSIEFQD LSRHLPVIKS YN                                         382

SEQ ID NO: 31         moltype = AA  length = 232
FEATURE              Location/Qualifiers
source               1..232
                     mol_type = protein
                     organism = Homo sapiens
SEQUENCE: 31
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
```

```
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK           232

SEQ ID NO: 32           moltype = AA  length = 227
FEATURE                 Location/Qualifiers
REGION                  1..227
                        note = Description of Artificial Sequence: Synthetic
                        polypeptide
source                  1..227
                        mol_type = protein
                        organism = synthetic construct
SEQUENCE: 32
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLTSKL TVDKSRWQQG NVFSCSVMHE ALHNHYTQKS LSLSPGK              227

SEQ ID NO: 33           moltype = AA  length = 232
FEATURE                 Location/Qualifiers
REGION                  1..232
                        note = Description of Artificial Sequence: Synthetic
                        polypeptide
source                  1..232
                        mol_type = protein
                        organism = synthetic construct
SEQUENCE: 33
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL YCLVKGFYPS DIAVEWESNG QPENNYKTTP  180
PVLDSDGSFF LYSKLTVDKS RWQQGNVFSC SVMHEALHNH YTQKSLSLSP GK           232

SEQ ID NO: 34           moltype = DNA  length = 1383
FEATURE                 Location/Qualifiers
source                  1..1383
                        mol_type = other DNA
                        organism = Homo sapiens
SEQUENCE: 34
atgagacctg cggacctgcc cccgcgcccc atggaagaat ccccggccgtc cagctctgcc  60
ccgacagaga cggaggagcc ggggtccagt gcagaggtca tggaagaagt gacaacatgc  120
tccttcaaca gccctctgtt ccggcaggaa gatgacagag ggattaccta ccggatccca  180
gccctgctct acatacccc cacccacacc ttcctggcct ttgcagagaa gcgttctacg  240
aggagagatg aggatgctct ccacctggtg ctgaggcgag ggttgaggat tgggcagttg  300
gtacagtggg ggccctgaa gccactgatg gaagccacac taccggggca tcggaccatg  360
aaccctgtc ctgtatggga gcagaagagt ggttgtgtgt tcctgttctt catctgtgtg  420
cggggccatg tcacagagcg tcaacagatt gtgtcaggca ggaatgctgc ccgcctttgc  480
ttcatctaca gtcaggatgc tggatgttca tggagtgagg tgagggactt gactgaggag  540
gtcattggct cagagctgaa gcactgggcc acatttgcat tgggcccagg tcatggcatc  600
cagctgcagt cagggagact ggtcatccct gcgtatacct actacatccc ttcctggttc  660
ttttgcttcc agctaccatg taaaaccagg cctcattctc tgatgatcta cagtgatgac  720
ctaggggtca catggcacca tggtagactc attaggccca tggttacagt agaatgtgaa  780
gtggcagagg tgactgggag ggctggccac cctgtgctat attgcagtgc ccggacacca  840
aacaggtgcc gggcagaggc gctcagcact gaccatggtg aaggctttca gagactggcc  900
ctgagtcgac agctctgtga gcccccacat ggttgccaag ggagtgtggt aagtttccgg  960
cccctggaga tcccacatag gtgccaggac tctagcagca aagatgcacc caccattcag  1020
cagagctctc caggcagttc actgaggctg gaggaggaag ctggaacacc gtcagaatca  1080
tggctcttgt actcacaccc aaccagtagg aaacagaggg ttgacctagg tatctatctc  1140
aaccagaccc ccttggaggc tgcctgctgg tcccgcccct ggatcttgca ctgtgggccc  1200
tgtggctact ctgatctggc tgctctggag gaggaggggt tgtttgggtg tttgtttgaa  1260
tgtgggacca agcaagagtg tgagcagatt gccttccgcc tgtttacaca ccgggagatc  1320
ctgagtcacc tgcaggggga ctgcaccagc cctggtagga acccaagcca attcaaaagc  1380
aat                                                               1383

SEQ ID NO: 35           moltype = DNA  length = 1488
FEATURE                 Location/Qualifiers
source                  1..1488
                        mol_type = other DNA
                        organism = Homo sapiens
SEQUENCE: 35
atgatgagct ctgcagcctt cccaaggtgg ctgagcatgg gggtccctcg taccccttca  60
cggacagtgc tcttcgagcg ggagaggacg ggcctgacct accgcgtgcc ctcgctgctc  120
cccgtgcccc ccgggcccac cctgctggcc tttgtggagc agcggctcag ccctgacgac  180
tcccacgccc accgcctggt gctgaggagg ggcacgctgg ccggggggctc cgtgcggtgg  240
ggtgccctgc acgtgctggg gacagcagcc ctggcggagc accggtccat gaaccccctgc  300
cctgtgcacg atgctggcac gggcaccgtc ttcctcttct tcatcgcgt gctgggccac  360
acgcctgagg ccgtgcagat cgccacggga aggaacgccg cgcgcctctg ctgtgtggcc  420
agccgtgacg ccgcctctc gtggggcagc gcccgggacc tcaccgagga ggccatcggt  480
ggtgccgtgc aggactgggc cacattcgct gtgggtcccg ccacggtgt gcagctgccc  540
tcaggccgc tgctggtacc cgcctacacc taccgcgtgg accgccgaga gtgttttggc  600
aagatctgcc ggaccagccc tcactccttc gccttctaca gcgatgacca cggccgcacc  660
```

```
tggcgctgtg gaggcctcgt gcccaacctg cgctcaggcg agtgccagct ggcagcggtg   720
gacggtgggc aggccggcag cttcctctac tgcaatgccc ggagcccact gggcagccgt   780
gtgcaggcgc tcagcactga cgagggcacc tccttcctgc ccgcagagcg cgtggcttcc   840
ctgcccgaga ctgcctgggg ctgccagggc agcatcgtgg gcttccagc ccccgccccc    900
aacaggccac gggatgacag ttggtcagtg ggccccggga gtcccctcca gcctccactc   960
ctcggtcctg gagtccacga accccccagg gaggctgctg tagaccccg tggaggccaa    1020
gtgcctggtg ggcccttcag ccgtctgcag cctcgggggg atggccccag gcagcctggc   1080
cccaggcctg gggtcagtgg ggatgtgggg tcctggaccc tggcactccc catgcccttt   1140
gctgccccgc cccagagccc cacgtggctg ctgtactccc acccagtggg gcgcagggct   1200
cggctacaca tgggtatccg cctgagccag tccccgctgg acccgcgcag ctggacagag   1260
ccctgggtga tctacgaggg ccccagccgc tactccgacc tggcgtccat cgggccggcc   1320
cctgaggggg gcctggtttt tgcctgcctg tacgagagcg gggccaggac ctcctatgat   1380
gagatttcct tttgtacatt ctccctgcgt gaggtcctga agaacgtgcc cgccagcccc   1440
aaaccgccca accttgggga caagcctcgg gggtgctgct ggccctcc                1488
```

SEQ ID NO: 36                 moltype = AA    length = 379
FEATURE                       Location/Qualifiers
REGION                        1..379
                              note = Description of Artificial Sequence: Synthetic
                              polypeptide
source                        1..379
                              mol_type = protein
                              organism = synthetic construct SEQUENCE: 36
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV   120
TRLCQVTSTD HGRTWSSPRD LTDAAIGPAY REWSTFAVGP GHCLQLHDRA RSLVVPAYAY   180
RKLHPKQRPI PSAFCFLSHD HGRTWARGHF VAQDTLECQV AEVETGEQRV VTLNARSHLR   240
ARVQAQSTND GLDFQESQLV KKLVEPPPQG CQGSVISFPS PRSGPGSPAQ WLLYTHPTHS   300
WQRADLGAYL NPRPPAPEAW SEPVLLAKGS CAYSDLQSMG TGPDGSPLFG CLYEANDYEE   360
IVFLMFTLKQ AFPAEYLPQ                                                 379

SEQ ID NO: 37                 moltype = AA    length = 379
FEATURE                       Location/Qualifiers
REGION                        1..379
                              note = Description of Artificial Sequence: Synthetic
                              polypeptide
source                        1..379
                              mol_type = protein
                              organism = synthetic construct SEQUENCE: 37
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV   120
TRLCQVTSTD HGRTWSSPRD LTDAAIGPAY REWSTFAVGP GHCLQLHDRA RSLVVPAYAY   180
RKLHPKQRPI PSAFCFLSHD HGRTWARGHF VAQDTLECQV AEVETGEQRV VTLNARSHLR   240
ARVQAQSTND GLDFQESQLV KKLVEPPPQG CQGSVISFPS PRSGPGSPAQ WLLYTHPTHS   300
WQRADLGAYL NPRPPAPEAW SEPVLLAKGS AAYSDLQSMG TGPDGSPLFG CLYEANDYEE   360
IVFLMFTLKQ AFPAEYLPQ                                                 379

SEQ ID NO: 38                 moltype = AA    length = 380
FEATURE                       Location/Qualifiers
REGION                        1..380
                              note = Description of Artificial Sequence: Synthetic
                              polypeptide
source                        1..380
                              mol_type = protein
                              organism = synthetic construct SEQUENCE: 38
AASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPKQRP IPSAFCFLSH DHGRTWARGH FVAQDTLECQ VAEVETGEQR VVTLNARSHL   240
RARVQAQSTN DGLDFQESQL VKKLVEPPPQ GCQGSVISFP SPRSGPGSPA QWLLYTHPTH   300
SWQRADLGAY LNPRPPAPEA WSEPVLLAKG SAAYSDLQSM GTGPDGSPLF GCLYEANDYE   360
EIVFLMFTLK QAFPAEYLPQ                                                380

SEQ ID NO: 39                 moltype = AA    length = 380
FEATURE                       Location/Qualifiers
REGION                        1..380
                              note = Description of Artificial Sequence: Synthetic
                              polypeptide
source                        1..380
                              mol_type = protein
                              organism = synthetic construct SEQUENCE: 39
DASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPKQRP IPSAFCFLSH DHGRTWARGH FVAQDTLECQ VAEVETGEQR VVTLNARSHL   240
```

```
RARVQAQSTN DGLDFQESQL VKKLVEPPPQ GCQGSVISFP SPRSGPGSPA QWLLYTHPTH    300
SWQRADLGAY LNPRPPAPEA WSEPVLLAKG SAAYSDLQSM GTGPDGSPLF GCLYEANDYE    360
EIVFLMFTLK QAFPAEYLPQ                                                380

SEQ ID NO: 40           moltype = AA   length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 40
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLYC LVKGFYPSDI AVEWESNGQP ENNYKTTPPV LDSDGSFFLY SKLTVDKSRW    420
QQGNVFSCSV MHEALHNHYT QKSLSLSPGK                                     450

SEQ ID NO: 41           moltype = AA   length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 41
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 42           moltype = AA   length = 242
FEATURE                 Location/Qualifiers
REGION                  1..242
                        note = Description of Artificial Sequence: Synthetic
                         polypeptide
source                  1..242
                        mol_type = protein
                        organism = synthetic construct
SEQUENCE: 42
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS    120
GGGGSGGGGS GGGGSDIQMT QSPSSLSASV GDRVTITCRA SQDVNTAVAW YQQKPGKAPK    180
LLIYSASFLY SGVPSRFSGS RSGTDFTLTI SSLQPEDFAT YYCQQHYTTP PTFGQGTKVE    240
IK                                                                  242

SEQ ID NO: 43           moltype = AA   length = 873
FEATURE                 Location/Qualifiers
REGION                  1..873
                        note = Description of Artificial Sequence: Synthetic
                         polypeptide
source                  1..873
                        mol_type = protein
                        organism = synthetic construct
SEQUENCE: 43
ASLPYLQKES VFQSGAHAYR IPALLYLPGQ QSLLAFAEQR ASKKDEHAEL IVLRRGDYDA    60
PTHQVQWQAQ EVVAQARLDG HRSMNPCPLY DAQTGTLFLF FIAIPGQVTE QQQLQTRANV    120
TRLCQVTSTD HGRTWSSPRD LTDAAIGPAY REWSTFAVGP GHCLQLHDRA RSLVVPAYAY    180
RKLHPKQRPI PSAFCFLSHD HGRTWARGHF VAQDTLECQV AEVETGEQRV VTLNARSHLR    240
ARVQAQSTND GLDFQESQLV KKLVEPPPQG CQGSVISFPS PRSGPGSPAQ WLLYTHPTHS    300
WQRADLGAYL NPRPPAPEAW SEPVLLAKGS CAYSDLQSMG TGPDGSPLFG CLYEANDYEE    360
IVFLMFTLKQ AFPAEYLPQG GGSGGGGSD KTHTCPPCPA PELLGGPSVF LFPPKPKDTL    420
MISRTPEVTC VVVDVSHEDP EVKFNWYVDG VEVHNAKTKP REEQYNSTYR VVSVLTVLHQ    480
DWLNGKEYKC KVSNKALPAP IEKTISKAKG QPREPQVYTL PPSREEMTKN QVSLTCLVKG    540
FYPSDIAVEW ESNGQPENNY KTTPPVLDSD GSFFLYSKLT VDKSRWQQGN VFSCSVMHEA    600
LHNHYTQKSL SLSPGKGGGG SGGGGSGGGG SEVQLVESGG GLVQPGGSLR LSCAASGFNI    660
KDTYIHWVRQ APGKGLEWVA RIYPTNGYTR YADSVKGRFT ISADTSKNTA YLQMNSLRAE    720
DTAVYYCSRW GGDGFYAMDY WGQGTLVTVS SGGGGSGGGG SGGGGSDIQM TQSPSSLSAS    780
VGDRVTITCR ASQDVNTAVA WYQQKPGKAP KLLIYSASFL YSGVPSRFSG SRSGTDFTLT    840
ISSLQPEDFA TYYCQQHYTT PPTFGQGTKV EIK                                 873

SEQ ID NO: 44           moltype = AA   length = 873
FEATURE                 Location/Qualifiers
REGION                  1..873
```

```
                            note = Description of Artificial Sequence: Synthetic
                             polypeptide
source                      1..873
                            mol_type = protein
                            organism = synthetic construct
SEQUENCE: 44
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV  120
TRLCQVTSTD HGRTWSSPRD LTDAAIGPAY REWSTFAVGP GHCLQLHDRA RSLVVPAYAY  180
RKLHPKQRPI PSAFCFLSHD HGRTWARGHF VAQDTLECQV AEVETGEQRV VTLNARSHLR  240
ARVQAQSTND GLDFQESQLV KKLVEPPPQG CQGSVISFPS PRSGPGSPAQ WLLYTHPTHS  300
WQRADLGAYL NPRPPAPEAW SEPVLLAKGS AAYSDLQSMG TGPDGSPLFG CLYEANDYEE  360
IVFLMFTLKQ AFPAEYLPQG GGGSGGGGSD KTHTCPPCPA PELLGGPSVF LFPPKPKDTL  420
MISRTPEVTC VVVDVSHEDP EVKFNWYVDG VEVHNAKTKP REEQYNSTYR VVSVLTVLHQ  480
DWLNGKEYKC KVSNKALPAP IEKTISKAKG QPREPQVYTL PPSREEMTKN QVSLTCLVKG  540
FYPSDIAVEW ESNGQPENNY KTTPPVLDSD GSFFLYSKLT VDKSRWQQGN VFSCSVMHEA  600
LHNHYTQKSL SLSPGKGGGG SGGGGSGGGG SEVQLVESGG GLVQPGGSLR LSCAASGFNI  660
KDTYIHWVRQ APGKGLEWVA RIYPTNGYTR YADSVKGRFT ISADTSKNTA YLQMNSLRAE  720
DTAVYYCSRW GGDGFYAMDY WGQGTLVTVS SGGGGSGGGG SGGGGSDIQM TQSPSSLSAS  780
VGDRVTITCR ASQDVNTAVA WYQQKPGKAP KLLIYSASFL YSGVPSRFSG SRSGTDFTLT  840
ISSLQPEDFA TYYCQQHYTT PPTFGQGTKV EIK                               873

SEQ ID NO: 45               moltype = AA  length = 874
FEATURE                     Location/Qualifiers
REGION                      1..874
                            note = Description of Artificial Sequence: Synthetic
                             polypeptide
source                      1..874
                            mol_type = protein
                            organism = synthetic construct
SEQUENCE: 45
AASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                              874

SEQ ID NO: 46               moltype = AA  length = 874
FEATURE                     Location/Qualifiers
REGION                      1..874
                            note = Description of Artificial Sequence: Synthetic
                             polypeptide
source                      1..874
                            mol_type = protein
                            organism = synthetic construct
SEQUENCE: 46
DASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                              874

SEQ ID NO: 47               moltype = AA  length = 874
FEATURE                     Location/Qualifiers
REGION                      1..874
                            note = Description of Artificial Sequence: Synthetic
                             polypeptide
source                      1..874
                            mol_type = protein
```

```
                        organism = synthetic construct
SEQUENCE: 47
AASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ GGGGSGGGGS DKTHTCPPCP APELLGGPSV FLFPPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                             874

SEQ ID NO: 48            moltype = AA  length = 874
FEATURE                  Location/Qualifiers
REGION                   1..874
                         note = Description of Artificial Sequence: Synthetic
                          polypeptide
source                   1..874
                         mol_type = protein
                         organism = synthetic construct
SEQUENCE: 48
DASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ GGGGSGGGGS DKTHTCPPCP APELLGGPSV FLFPPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                             874

SEQ ID NO: 49            moltype = AA  length = 213
FEATURE                  Location/Qualifiers
REGION                   1..213
                         note = Description of Artificial Sequence: Synthetic
                          polypeptide
source                   1..213
                         mol_type = protein
                         organism = synthetic construct
SEQUENCE: 49
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRTV APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 50            moltype = AA  length = 450
FEATURE                  Location/Qualifiers
REGION                   1..450
                         note = Description of Artificial Sequence: Synthetic
                          polypeptide
source                   1..450
                         mol_type = protein
                         organism = synthetic construct
SEQUENCE: 50
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLYC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 51            moltype = AA  length = 616
FEATURE                  Location/Qualifiers
REGION                   1..616
                         note = Description of Artificial Sequence: Synthetic
```

-continued

```
                         polypeptide
source                   1..616
                         mol_type = protein
                         organism = synthetic construct
SEQUENCE: 51
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV  120
TRLCQVTSTD HGRTWSSPRD LTDAAIGPAY REWSTFAVGP GHCLQLHDRA RSLVVPAYAY  180
RKLHPKQRPI PSAFCFLSHD HGRTWARGHF VAQDTLECQV AEVETGEQRV VTLNARSHLR  240
ARVQAQSTND GLDFQESQLV KKLVEPPPQG CQGSVISFPS PRSGPGSPAQ WLLYTHPTHS  300
WQRADLGAYL NPRPPAPEAW SEPVLLAKGS CAYSDLQSMG TGPDGSPLFG CLYEANDYEE  360
IVFLMFTLKQ AFPAEYLPQG GGGSGGGGSD KTHTCPPCPA PELLGGPSVF LFPPKPKDTL  420
MISRTPEVTC VVVDVSHEDP EVKFNWYVDG VEVHNAKTKP REEQYNSTYR VVSVLTVLHQ  480
DWLNGKEYKC KVSNKALPAP IEKTISKAKG QPREPQVYTL PPSREEMTKN QVSLTCLVKG  540
FYPSDIAVEW ESNGQPENNY KTTPPVLDSD GSFFLTSKLT VDKSRWQQGN VFSCSVMHEA  600
LHNHYTQKSL SLSPGK                                                  616

SEQ ID NO: 52            moltype = AA   length = 616
FEATURE                  Location/Qualifiers
REGION                   1..616
                         note = Description of Artificial Sequence: Synthetic
                         polypeptide
source                   1..616
                         mol_type = protein
                         organism = synthetic construct
SEQUENCE: 52
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV  120
TRLCQVTSTD HGRTWSSPRD LTDAAIGPAY REWSTFAVGP GHCLQLHDRA RSLVVPAYAY  180
RKLHPKQRPI PSAFCFLSHD HGRTWARGHF VAQDTLECQV AEVETGEQRV VTLNARSHLR  240
ARVQAQSTND GLDFQESQLV KKLVEPPPQG CQGSVISFPS PRSGPGSPAQ WLLYTHPTHS  300
WQRADLGAYL NPRPPAPEAW SEPVLLAKGS AAYSDLQSMG TGPDGSPLFG CLYEANDYEE  360
IVFLMFTLKQ AFPAEYLPQG GGGSGGGGSD KTHTCPPCPA PELLGGPSVF LFPPKPKDTL  420
MISRTPEVTC VVVDVSHEDP EVKFNWYVDG VEVHNAKTKP REEQYNSTYR VVSVLTVLHQ  480
DWLNGKEYKC KVSNKALPAP IEKTISKAKG QPREPQVYTL PPSREEMTKN QVSLTCLVKG  540
FYPSDIAVEW ESNGQPENNY KTTPPVLDSD GSFFLTSKLT VDKSRWQQGN VFSCSVMHEA  600
LHNHYTQKSL SLSPGK                                                  616

SEQ ID NO: 53            moltype = AA   length = 617
FEATURE                  Location/Qualifiers
REGION                   1..617
                         note = Description of Artificial Sequence: Synthetic
                         polypeptide
source                   1..617
                         mol_type = protein
                         organism = synthetic construct
SEQUENCE: 53
AASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLTSKL TVDKSRWQQG NVFSCSVMHE  600
ALHNHYTQKS LSLSPGK                                                 617

SEQ ID NO: 54            moltype = AA   length = 617
FEATURE                  Location/Qualifiers
REGION                   1..617
                         note = Description of Artificial Sequence: Synthetic
                         polypeptide
source                   1..617
                         mol_type = protein
                         organism = synthetic construct
SEQUENCE: 54
DASLPYLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLTSKL TVDKSRWQQG NVFSCSVMHE  600
ALHNHYTQKS LSLSPGK                                                 617
```

-continued

```
SEQ ID NO: 55          moltype = AA   length = 618
FEATURE                Location/Qualifiers
REGION                 1..618
                       note = Description of Artificial Sequence: Synthetic
                        polypeptide
source                 1..618
                       mol_type = protein
                       organism = synthetic construct
SEQUENCE: 55
TVEKSVVFKA EGEHFTDQKG NTIVGSGSGG TTKYFRIPAM CTTSKGTIVV FADARHNTAS    60
DQSFIDTAAA RSTDGGKTWN KKIAIYNDRV NSKLSRVMDP TCIVANIQGR ETILVMGKW    120
NNNDKTWGAY RDKAPDTDWD LVLYKSTDDG VTFSKVETNI HDIVTKNGTI SAMLGGVGSG    180
LQLNDGKLVF PVQMVRTKNI TTVLNTSFIY STDGITWSLP SGYCEGFGSE NNIIEFNASL    240
VNNIRNSGLR RSFETKDFGK TWTEFPPMDK KVDNRNHGVQ GSTITIPSGN KLVAAHSSAQ    300
NKNNDYTRSD ISLYAHNLYS GEVKLIDDFY PKVGNASGAG YSCLSYRKNV DKETLYVVYE    360
ANGSIEFQDL SRHLPVIKSY NGGGGSGGGG SDKTHTCPPC PAPELLGGPS VFLFPPKPKD    420
TLMISRTPEV TCVVVDVSHE DPEVKFNWYV DGVEVHNAKT KPREEQYNST YRVVSVLTVL    480
HQDWLNGKEY KCKVSNKALP APIEKTISKA KGQPREPQVY TLPPSREEMT KNQVSLTCLV    540
KGFYPSDIAV EWESNGQPEN NYKTTPPVLD SDGSFFLTSK LTVDKSRWQQ GNVFSCSVMH    600
EALHNHYTQK SLSLSPGK                                                  618

SEQ ID NO: 56          moltype = DNA   length = 1854
FEATURE                Location/Qualifiers
misc_feature           1..1854
                       note = Description of Artificial Sequence: Synthetic
                        polynucleotide
source                 1..1854
                       mol_type = other DNA
                       organism = synthetic construct
SEQUENCE: 56
acagtggaaa agtccgtggt gttcaaggcc gagggcgagc acttcaccga ccagaaaggc     60
aataccatcg tcggctctgg cagcggcggc accaccaagt actttagaat ccccgccatg    120
tgcaccacca gcaagggcac cattgtggtg ttcgccgacg cccagacacaa caccgccagc    180
gatcagagct tcatcgatac cgctgccgcc agatctaccg atggcggcaa gacctggaac    240
aagaagatcg ccatctacaa cgaccgcgtg aacagcaagc tgagcagagt gatggaccct    300
acctgcatcg tggccaacat ccagggcaga gaaaccatcc tggtcatggt cggaaagtgg    360
aacaacaacg ataagacctg gggcgcctac agagacaagg ccctgatac cgattgggac    420
ctcgtgctgt acaagagcac cgatgacggc gtgacctca gcaaggtgga aacaaacatc    480
cacgacatcg tgaccaagaa cggcaccatc tctgccatgc tcggcggcgt tggatctggc    540
ctgcaactga atgatggcaa gctggtgttc ccgtgcaga tggtccgaac aaagaatatc    600
accaccgtgc tgaataccag cttcatctac agcaccgacg gcatcacatg gtccctgcct    660
agcggctact gtgaaggctt tggcagcgag aacaacatca tcgagttcaa cgccagcctg    720
gtcaacaaca tccggaacag cggcctgcgc agaagcttcg agacaaagga cttcggaaag    780
acgtggaccg agtttcctcc aatggacaag aaggtggaca accggaacca cggcgtgcag    840
ggcagcacaa tcacaatccc tagcggcaac aaactggtgg ccgctcactc tagcgcccag    900
aacaagaaca acgactacac cagaagcgac atcagcctgt acgcccacaa cctgtacagc    960
ggcgaagtga agctgatcga cgacttctac cccaaagtgg gcaatgccag cggagccggc   1020
tacagctgtc tgagctaccg gaaaaatgtg gacaaagaaa ccctgtacgt ggtgtacgag   1080
gccaacggca gcatcgagtt tcaggacctg agcagacatc tgcccgtgat caagagctac   1140
aacggcggag gtggaagtgg cggaggcgga tccgacaaaa ctcacacatg cccaccgtgc   1200
ccagcacctg aactcctggg gggaccgtca gtcttcctct tccccccaaa acccaaggac   1260
accctcatga tctcccggac ccctgaggtc acatgcgtgg tggtggacgt gagccacgaa   1320
gaccctgagg tcaagttcaa ctggtacgtg gacggcgtgg aggtgcataa tgccaagaca   1380
aagccgcggg aggagcagta caacagcacg taccgtgtgg tcagcgtcct caccgtcctg   1440
caccaggact ggctgaatgg caaggagtac aagtgcaagg tctccaacaa agccctccca   1500
gcccccatcg agaaaaccat ctccaaagcc aaagggcagc cccgagaacc acaggtctac   1560
accctgcccc catcccggga ggagatgacc aagaaccagg tcagcctgac ctgcctggtc   1620
aaaggcttct atcccagcga catcgccgtg gagtgggaga gcaatgggca gccggagaag   1680
aactacaaga ccacgcctcc cgtgctggac tccgacggct ccttcttcct cactacgaag   1740
ctcaccgtgg acaagagcag gtggcagcag gggaacgtct tctcatgctc cgtgatgcat   1800
gaggctctgc acaaccacta cacgcagaag agcctctccc tgtctccggg taaa         1854

SEQ ID NO: 57          moltype = AA   length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 57
EVQLVESGGG LVQPGGSLRL SCAASGFNIK DTYIHWVRQA PGKGLEWVAR IYPTNGYTRY     60
ADSVKGRFTI SADTSKNTAY LQMNSLRAED TAVYYCSRWG GDGFYAMDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLYC LVKGFYPSDI AVEWESNGQP ENNYKTTPPV LDSDGSFFLY SKLTVDKSRW    420
```

QQGNVFSCSV MHEALHNHYT QKSLSLSPGK                                        450

SEQ ID NO: 58              moltype = DNA   length = 1350
FEATURE                    Location/Qualifiers
misc_feature               1..1350
                           note = Description of Artificial Sequence: Synthetic
                            polynucleotide
source                     1..1350
                           mol_type = other DNA
                           organism = synthetic construct SEQUENCE: 58
gaggtgcagc tggttgaatc tggcggagga ctggttcagc ctggcggatc tctgagactg   60
tcttgtgccg ccagcggctt caacatcaag gacacctaca tccactgggt ccgacaggcc   120
cctggcaaag gacttgaatg ggtcgccaga atctacccca ccaacggcta caccagatac   180
gccgactctg tgaagggcag attcaccatc agcgccgaca ccagcaagaa caccgcctac   240
ctgcagatga acagcctgag agccgaggac accgccgtgt actactgttc tagatgggga   300
ggcgacggct tctacgccat ggattattgg ggccagggca ccctggtcac cgtttcttct   360
gctagcacca agggcccatc cgtcttcccc ctggcaccct cctccaagag cacctctggg   420
ggcacagcgg ccctgggctg cctggtcaag gactacttcc ccgaaccggt gacggtgtcc   480
tggaactcag gcgctctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaactca cacatgccca ccgtgcccag cacctgaact cctgggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc   1020
aaagccaaag ggcagccccg agaaccacag gtctacaccc tgcccccatc ccgggaggag   1080
atgaccaaga accaggtcag cctgtactgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                     1350

SEQ ID NO: 59              moltype = AA   length = 846
FEATURE                    Location/Qualifiers
REGION                     1..846
                           note = Description of Artificial Sequence: Synthetic
                            polypeptide
source                     1..846
                           mol_type = protein
                           organism = synthetic construct SEQUENCE: 59
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSTVEKS VVFKAEGEHF   480
TDQKGNTIVG SGSGGTTKYF RIPAMCTTSK GTIVVFADAR HNTASDQSFI DTAAARSTDG   540
GKTWNKKIAI YNDRVNSKLS RVMDPTCIVA NIQGRETILV MVGKWNNNDK TWGAYRDKAP   600
DTDWDLVLYK STDDGVTFSK VETNIHDIVT KNGTISAMLG GVGSGLQLND GKLVFPVQMV   660
RTKNITTVLN TSFIYSTDGI TWSLPSGYCE GFGSENNIIE FNASLVNNIR NSGLRRSFET   720
KDFGKTWTEF PPMDKKVDNR NHGVQGSTIT IPSGNKLVAA HSSAQNKNND YTRSDISLYA   780
HNLYSGEVKL IDDFYPKVGN ASGAGYSCLS YRKNVDKETL YVVYEANGSI EFQDLSRHLP   840
VIKSYN                                                              846

SEQ ID NO: 60              moltype = DNA   length = 2538
FEATURE                    Location/Qualifiers
misc_feature               1..2538
                           note = Description of Artificial Sequence: Synthetic
                            polynucleotide
source                     1..2538
                           mol_type = other DNA
                           organism = synthetic construct SEQUENCE: 60
gaggtgcagc tggttgaatc tggcggagga ctggttcagc ctggcggatc tctgagactg   60
tcttgtgccg ccagcggctt caacatcaag gacacctaca tccactgggt ccgacaggcc   120
cctggcaaag gacttgaatg ggtcgccaga atctacccca ccaacggcta caccagatac   180
gccgactctg tgaagggcag attcaccatc agcgccgaca ccagcaagaa caccgcctac   240
ctgcagatga acagcctgag agccgaggac accgccgtgt actactgttc tagatgggga   300
ggcgacggct tctacgccat ggattattgg ggccagggca ccctggtcac cgtttcttct   360
gctagcacca agggcccatc cgtcttcccc ctggcaccct cctccaagag cacctctggg   420
ggcacagcgg ccctgggctg cctggtcaag gactacttcc ccgaaccggt gacggtgtcc   480
tggaactcag gcgctctgac cagcggcgtg cacaccttcc cggctgtcct acagtcctca   540
ggactctact ccctcagcag cgtggtgacc gtgccctcca gcagcttggg cacccagacc   600

```
tacatctgca acgtgaatca caagcccagc aacaccaagg tggacaagaa agttgagccc   660
aaatcttgtg acaaaactca cacatgccca ccgtgcccag cacctgaact cctgggggga   720
ccgtcagtct tcctcttccc cccaaaaccc aaggacaccc tcatgatctc ccggacccct   780
gaggtcacat gcgtggtggt ggacgtgagc cacgaagacc ctgaggtcaa gttcaactgg   840
tacgtggacg gcgtggaggt gcataatgcc aagacaaagc cgcgggagga gcagtacaac   900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc  1020
aaagccaaag ggcagccccg agaaccacag gtctacaccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa ggtggcggag gatctggcgg aggtggaagc  1380
ggcggaggcg gatctacagt ggaaaagtcc gtggtgttca aggccgaggg cgagcacttc  1440
accgaccaga aaggcaatac catcgtcggc tctggcagcg gcggcaccac caagtacttt  1500
agaatccccg ccatgtgcac caccagcaag ggcaccattg tggtgttcgc cgacgccaga  1560
cacaacaccg ccagcgatca gagcttcatc gataccgctg ccgccagaag tacagacggc  1620
ggcaagacct ggaacaagaa gatcgccatc tacaacgacc gcgtgaacag caagctgagc  1680
agagtgatgg accctacctg catcgtggcc aacatccagg gcagagaaac catcctggtc  1740
atggtcggaa agtggaacaa caacgataag acctggggcg cctacagaga caaggcccct  1800
gataccgatt gggacctcgt gctgtataag agcaccgacg acggcgtgac cttcagcaag  1860
gtggaaacaa acatccacga catcgtgacc aagaacggca catctctgc catgctcggc  1920
ggcgttggat ctggcctgca actgaatgat ggcaagctgg tgttccccgt gcagatggtc  1980
cgaacaaaga acatcaccac cgtgctgaat accagcttca tctactccac cgacggcatc  2040
acatggtccc tgcctagcgg ctactgtgaa ggctttggca gcgagaacaa catcatcgag  2100
ttcaacgcca gcctggtcaa caacatccgg aacagcggcc tgcggagaag cttcgagaca  2160
aaggacttcg gaaagacgtg gaccgagttt cctccaatgg acaagaaggt ggacaaccgg  2220
aaccacggcg tgcagggcag cacaatcaca atccctagcg gcaacaaact ggtggccgct  2280
cactctagcg cccagaacaa gaacaacgat tacaccagaa gcgacatcag cctgtacgcc  2340
cacaacctgt actccggcga agtgaagctg atcgacgact tctaccccaa agtgggcaat  2400
gccagcggag ccggctacag ctgtctgagc taccgtgaaa atgtggacaa agaaaccctg  2460
tacgtggtgt acgaggccaa cggcagcatc gagtttcagg acctgagcag acatctgccc  2520
gtgatcaaga gctacaat                                                2538
```

```
SEQ ID NO: 61          moltype = AA  length = 618
FEATURE                Location/Qualifiers
REGION                 1..618
                       note = Description of Artificial Sequence: Synthetic
                       polypeptide
source                 1..618
                       mol_type = protein
                       organism = synthetic construct
SEQUENCE: 61
TVEKSVVFKA EGEHFTDQKG NTIVGSGSGG TTKYFRIPAM CTTSKGTIVV FADARHNTAS   60
DQSFIDTAAA RSTDGGKTWN KKIAIYNDRV NSKLSRVMVP TCIVANIQGR ETILVMVGKW  120
NNNDKTWGAY RDKAPDTDWD LVLYKSTDDG VTFSKVETNI HDIVTKNGTI SAMLGGVGSG  180
LQLNDGKLVF PVQMVRTKNI TTVLNTSFIY STDGITWSLP SGYCEGFGSV NNIIEFNASL  240
VNNIRNSGLR RSFETKDFGK TWTEFPPMDK KVDNRNHGVQ GSTITIPSGN KLVAAHSSAQ  300
NKNNDYTRSD ISLYAHNLYS GEVKLIDDFY PKVGNASGAG YSCLSYRKNV DKETLYVVYE  360
ANGSIEFQDL SRHLPVIKSY NGGGGSGGGG SDKTHTCPPC PAPELLGGPS VFLFPPKPKD  420
TLMISRTPEV TCVVVDVSHE DPEVKFNWYV DGVEVHNAKT KPREEQYNST YRVVSVLTVL  480
HQDWLNGKEY KCKVSNKALP APIEKTISKA KGQPREPQVY TLPPSREEMT KNQVSLTCLV  540
KGFYPSDIAV EWESNGQPEN NYKTTPPVLD SDGSFFLTSK LTVDKSRWQQ GNVFSCSVMH  600
EALHNHYTQK SLSLSPGK                                                618
```

```
SEQ ID NO: 62          moltype = DNA  length = 1854
FEATURE                Location/Qualifiers
misc_feature           1..1854
                       note = Description of Artificial Sequence: Synthetic
                       polynucleotide
source                 1..1854
                       mol_type = other DNA
                       organism = synthetic construct
SEQUENCE: 62
acagtggaaa agtccgtggt gttcaaggcc gagggcgagc acttcaccga ccagaaaggc   60
aataccatcg tcggctctgg cagcggcggc accaccaagt actttagaat ccccgccatg  120
tgcaccacca gcaagggcac cattgtggtg ttcgccgacg ccagacacaa caccgccagc  180
gatcagagct tcatcgatac cgctgccgcc agaagtacag acggcggcaa gacctggaac  240
aagaagatcg ccatctacaa cgaccgcgtg aacagcaagc tgagcagagt gatggtgcct  300
acctgcatcg tggccaacat ccagggcaga gaaaccatcc tggtcatggt cggaaagtgg  360
aacaacaacg ataagacctg gggcgcctac agagacaagg ccctgatac cgattgggac  420
ctcgtgctgt ataagagcac cgacgacggc gtgaccttca gcaaggtgga aacaaacatc  480
cacgacatcg tgaccaagaa cggcaccatc tctgccatgc tcggcggcgt tggatctggc  540
ctgcaactga atgatggcaa gctggtgttc cccgtgcaga tggtccgaac aaagaacatc  600
accaccgtgc tgaataccag cttcatctac tccaccgacg gcatcacatg gtccctgcct  660
agcggctact gtgaaggctt tggcagcgtg aacaacatca tcgagttcaa cgccagcctg  720
gtcaacaaca tccggaacag cggcctgcgg agaagcttcg agacaaagga cttcggaaag  780
acgtggaccg agtttcctcc aatggacaag aaggtggaca accggaacca ccgcgtgcag  840
ggcagcacaa tcacaatccc tagcggcaac aaactggtgg ccgctcactc tagcgcccag  900
```

```
aacaagaaca acgattacac cagaagcgac atcagcctgt acgcccacaa cctgtactcc   960
ggcgaagtga agctgatcga cgacttctac cccaaagtgg gcaatgccag cggagccggc  1020
tacagctgtc tgagctaccg gaaaaatgtg gacaaagaaa ccctgtacgt ggtgtacgag  1080
gccaacggca gcatcgagtt tcaggacctg agcagacatc tgcccgtgat caagagctac  1140
aatggcggag gtggaagtgg cggaggcgga tccgacaaaa ctcacacatg cccaccgtgc  1200
ccagcacctg aactcctggg gggaccgtca gtcttcctct tccccccaaa acccaaggac  1260
accctcatga tctcccggac ccctgaggtc acatgcgtgg tggtggacgt gagccacgaa  1320
gaccctgagg tcaagttcaa ctggtacgtg gacggcgtgg aggtgcataa tgccaagaca  1380
aagccgcggg aggagcagta caacagcacg taccgtgtgg tcagcgtcct caccgtcctg  1440
caccaggact ggctgaatgg caaggagtac aagtgcaagg tctccaacaa agccctccca  1500
gcccccatcg agaaaaccat ctccaaagcc aaagggcagc cccgagaacc acaggtctac  1560
accctgcccc catcccggga ggagatgacc aagaaccagg tcagcctgac ctgcctggtc  1620
aaaggcttct atcccagcga catcgccgtg gagtgggaga gcaatgggca gccggagaac  1680
aactacaaga ccacgcctcc cgtgctggac tccgacggct ccttcttcct cactacaag  1740
ctcaccgtgg acaagagcag gtggcagcag gggaacgtct tctcatgctc cgtgatgcat  1800
gaggctctgc acaaccacta cacgcagaag agcctctccc tgtctccggg taaa        1854
```

```
SEQ ID NO: 63              moltype = AA  length = 386
FEATURE                    Location/Qualifiers
REGION                     1..386
                           note = Description of Artificial Sequence: Synthetic
                           polypeptide
source                     1..386
                           mol_type = protein
                           organism = synthetic construct
SEQUENCE: 63
MEDLRPMASL PVLQKESVFQ SGAHAYRIPA LLYLPGQQSL LAFAEQRASK KDEHAELIVL   60
RRGDYDAPTH QVQWQAQEVV AQARLDGHRS MNPCPLYDAQ TGTLFLFFIA IPGQVTEQQQ  120
LQTRANVTRL CQVTSTDHGR TWSSPRDLTD AAIGPAYREW STFAVGPGHC LQLHDRARSL  180
VVPAYAYRKL HPIQRPIPSA FCFLSHDHGR TWARGHFVAQ DTLECQVAEV ETGEQRVVTL  240
NARSHLRARV QAQSTNDGLD FQESQLVKKL VEPPPQGCQG SVISFPSPRS GPGSPAQWLL  300
YTHPTHSWQR ADLGAYLNPR PPAPEAWSEP VLLAKGSCAY SDLQSMGTGP DGSPLFGCLY  360
EANDYEEIVF LMFTLKQAFP AEYLPQ                                       386
```

```
SEQ ID NO: 64              moltype = DNA  length = 1158
FEATURE                    Location/Qualifiers
misc_feature               1..1158
                           note = Description of Artificial Sequence: Synthetic
                           polynucleotide
source                     1..1158
                           mol_type = other DNA
                           organism = synthetic construct
SEQUENCE: 64
atggaagatc tcaggcccat ggcatctctg cctgtgctgc agaaagaaag cgtgttccag   60
tctggcgccc acgcctacag aattcccgct ctgctgtatc tgccaggcca gcagtctctg  120
ctggctttcg ctgaacagcg ggccagcaag aaggatgagc acgccgaact gatcgtgctg  180
cggagaggcg attacgacgc ccctacacat caggtgcagt ggcaggctca agaggtggtg  240
gctcaggcta gactggacgg ccacagatct atgaacccct gtcctctgta cgatgcccag  300
accggcacac tgtttctgtt ctttatcgct atccccggcc aagtgaccga gcagcagcag  360
ctgcagacaa gagccaacgt gaccagactg tgtcaagtga cctccaccga ccacggcaga  420
acctggtcta gccctagaga tctgaccgac gccgccatcg gacctgccta tagagagtgg  480
tccaccttcg ccgttggacc tggacactgt ctccagctgc acgacagggc tagatctctg  540
gtggtgcctg cctacgccta tagaaagctg caccccatcc agcggcctat tcctagcgcc  600
ttctgctttc tgagccacga tcacggcagg acatgggcca gaggacattt cgtggcccag  660
gacacactgg aatgccaggt ggccgaagtg gaaaccggcg agcagagagt cgtgaccctg  720
aacgccagat ctcacctgag agccagagtg caggcccaga gcacaaacga cggcctggat  780
ttccaagaga gccagctggt caagaaactg gtggaacctc ctccacaggg ctgtcaggga  840
agcgtgatca gctttccatc tcctagaagc ggccctggct ctcctgctca gtggctgctg  900
tatacacacc ccacacacag ctggcagaga gccgatctgg gcgcctacct gaatcctaga  960
cctcctgctc ctgaggcttg gagcgaacct gttctgctgg ccaagggcag ctgtgcctac  1020
agcgatctgc agtctatggg cacaggccct gatggcagcc ctctgtttgg ctgtctgtac  1080
gaggccaacg actacgaaga gatcgtgttc ctgatgttca ccctgaagca ggcctttcca  1140
gccgagtacc tgcctcaa                                                1158
```

```
SEQ ID NO: 65              moltype = AA  length = 873
FEATURE                    Location/Qualifiers
REGION                     1..873
                           note = Description of Artificial Sequence: Synthetic
                           polypeptide
source                     1..873
                           mol_type = protein
                           organism = synthetic construct
SEQUENCE: 65
ASLPYLQKES VFQSGAHAYR IPALLYLPGQ QSLLAFAEQR ASKKDEHAEL IVLRRGDYDA   60
PTHQVQWQAQ EVVAQARLDG HRSMNPCPLY DAQTGTLFLF FIAIPGQVTE QQQLQTRANV  120
TRLCQVTSTD HGRTWSSPRD LTDAAIGPAY REWSTFAVGP GHCLQLHDRA RSLVVPAYAY  180
RKLHPKQRPI PSAFCFLSHD HGRTWARGHF VAQDTLECQV AEVETGEQRV VTLNARSHLR  240
ARVQAQSTND GLDFQESQLV KKLVEPPPQG CQGSVISFPS PRSGPGSPAQ WLLYTHPTHS  300
WQRADLGAYL NPRPPAPEAW SEPVLLAKGS CAYSDLQSMG TGPDGSPLFG CLYEANDYEE  360
```

```
IVFLMFTLKQ AFPAEYLPQG GGGSGGGGSD KTHTCPPCPA PELLGGPSVF LFPPKPKDTL   420
MISRTPEVTC VVVDVSHEDP EVKFNWYVDG VEVHNAKTKP REEQYNSTYR VVSVLTVLHQ   480
DWLNGKEYKC KVSNKALPAP IEKTISKAKG QPREPQVYTL PPSREEMTKN QVSLTCLVKG   540
FYPSDIAVEW ESNGQPENNY KTTPPVLDSD GSFFLYSKLT VDKSRWQQGN VFSCSVMHEA   600
LHNHYTQKSL SLSPGKGGGG SGGGGSGGGG SEVQLVESGG GLVQPGGSLR LSCAASGFNI   660
KDTYIHWVRQ APGKGLEWVA RIYPTNGYTR YADSVKGRFT ISADTSKNTA YLQMNSLRAE   720
DTAVYYCSRW GGDGFYAMDY WGQGTLVTVS SGGGGSGGGG SGGGGSDIQM TQSPSSLSAS   780
VGDRVTITCR ASQDVNTAVA WYQQKPGKAP KLLIYSASFL YSGVPSRFSG SRSGTDFTLT   840
ISSLQPEDFA TYYCQQHYTT PPTFGQGTKV EIK                               873

SEQ ID NO: 66            moltype = DNA  length = 2619
FEATURE                  Location/Qualifiers
misc_feature             1..2619
                         note = Description of Artificial Sequence: Synthetic
                          polynucleotide
source                   1..2619
                         mol_type = other DNA
                         organism = synthetic construct
SEQUENCE: 66
gcatctctgc cttacctgca gaaagaaagc gtgttccagt ctggcgccca cgcctacaga   60
attcccgctc tgctgtatct gccaggccag cagtctctgc tggctttcgc tgaacagcgg   120
gccagcaaga aggatgagca cgccgaactg atcgtgctgc ggagaggcga ttacgacgcc   180
cctacacatc aggtgcagtg gcaggctcaa gaggtggtgg ctcaggctag actggacggc   240
cacagatcta tgaacccctg tcctctgtac gatgcccaga ccggcacact gtttctgttc   300
tttatcgcta tccccggcca agtgaccgag cagcagcagc tgcagacaag agccaacgtg   360
accagatgt gtcaagtgac ctccaccgac cacggcaaga cctggtctag ccctagagat   420
ctgaccgacg ccgccatcgg acctgcctat agagagtggt ccaccttcgc cgttggacct   480
ggacactgtc tccagctgca cgacagggct agatctctgg tggtgcctgc ctacgcctat   540
agaaagctgc accccaaaca gcggcctatt cctagcgcct tctgctttct gagccacgat   600
cacggcagga catgggccag aggacatttc gtggtgccag acacactgga atgccaggtg   660
gccgaagtgg aaaccggcga gcagagagtc gtgaccctga acgccagatc tcacctgaga   720
gccagagtgc aggcccagag cacaaacgac ggcctggatt ccaagagag ccagctggtc   780
aagaaactgg tggaacctcc tccacagggc tgtcagggaa gcgtgatcag ctttccatct   840
cctagaagcg gccctggctc tcctgctcag tggctgctgt atacacaccc cacacacgac   900
tggcagagag ccgatctggg cgcctacctg aatcctagac ctcctgctcc tgaggcttgg   960
agcgaacctg ttctgctggc caagggcagc tgtgcctaca gcgatctgca gtctatgggc   1020
acaggccctg atggcagccc tctgtttggc tgtctgtacg aggccaacga ctacgaagag   1080
atcgtgttcc tgatgttcac cctgaagcag gcctttccag ccgagtacct gcctcaaggc   1140
ggaggtggaa gtggcggagg cggatccgac aaaactcaca catgcccacc gtgcccagca   1200
cctgaactcc tggggggacc gtcagtcttc ctcttccccc caaaacccaa ggacaccctc   1260
atgatctccc ggacccctga ggtcacatgc gtggtggtgg acgtgagcca cgaagaccct   1320
gaggtcaagt tcaactggta cgtggacggc gtggaggtgc ataatgccaa gacaaagccg   1380
cgggaggagc agtacaacag cacgtaccgt gtggtcagcg tcctcaccgt cctgcaccag   1440
gactggctga atggcaagga gtacaagtgc aaggtctcca acaaagccct cccagccccc   1500
atcgagaaaa ccatctccaa agccaaaggg cagccccgag aaccacaggt ctacaccctg   1560
cccccatccc gggaggagat gaccaagaac caggtcagcc tgacctgcct ggtcaaaggc   1620
ttctatccca gcgacatcgc cgtggagtgg gagagcaatg ggcagccgga gaacaactac   1680
aagaccacgc ctcccgtgct ggactccgac ggctccttct tcctctatag caagctcacc   1740
gtggacaaga gcaggtggca gcaggggaac gtcttctcat gctccgtgat gcatgaggct   1800
ctgcacaacc actacacgca gaagagcctc tccctgtctc cgggtaaagg aggcggagga   1860
tctggcggag gtggaagtgg cggaggcgga tctgaggtgc agctggttga atctggcgga   1920
ggactggttc agcctggcgg atctctgaga ctgtcttgtg ccgccagcgg cttcaacatc   1980
aaggacacct acatccactg ggtccgacag gcccctggca aaggacttga atgggtcgcc   2040
agaatctacc ccaccaacgg ctacaccaga tacgccgact ctgtgaaggg cagattcacc   2100
atcagcgacg acaccagcaa gaacaccgcc tacctgcaga tgaacagcct gagagccgag   2160
gacaccgccg tgtactactg ttctagatgg ggaggcgacg gcttctacgc catggattat   2220
tggggccagg gcaccctggt caccgtttct tctggcggag gaggatctgg cggaggcgga   2280
agtggcggag gcggatctga catccagatg acacagagcc ctagcagcct gtctgccagc   2340
gtgggagaca gagtgaccat cacctgtaga gccagccagg acgtgaacac agccgtggct   2400
tggtatcagc agaagcctgg caaggcccct aagctgctga tctcagcgc cagctttctg   2460
tactccggcg tgcccagcag attcagcggc tctagaagcg gcaccgactt caccctgacc   2520
ataagcagtc tgcagcccga ggacttcgcc acctactact gtcagcagca ctacaccaca   2580
cctccaacct ttggccaggg caccaaggtg gaaatcaag                         2619

SEQ ID NO: 67            moltype = AA  length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 67
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 68            moltype = DNA  length = 642
```

```
FEATURE              Location/Qualifiers
misc_feature         1..642
                     note = Description of Artificial Sequence: Synthetic
                      polynucleotide
source               1..642
                     mol_type = other DNA
                     organism = synthetic construct
SEQUENCE: 68
gacatccaga tgacacagag ccctagcagc ctgtctgcca gcgtgggaga cagagtgacc  60
atcacctgta gagccagcca ggacgtgaac acagccgtgg cttggtatca gcagaagcct  120
ggcaaggccc ctaagctgct gatctacagc gccagctttc tgtactccgg cgtgcccagc  180
agattcagcg gctctagaag cggcaccgac ttcaccctga ccataagcag tctgcagccc  240
gaggacttcg ccacctacta ctgtcagcag cactacacca cacctccaac ctttggccag  300
ggcaccaagg tggaaatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 69         moltype = AA  length = 227
FEATURE              Location/Qualifiers
source               1..227
                     mol_type = protein
                     organism = Homo sapiens
SEQUENCE: 69
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 70         moltype = AA  length = 380
FEATURE              Location/Qualifiers
REGION               1..380
                     note = Description of Artificial Sequence: Synthetic
                      polypeptide
source               1..380
                     mol_type = protein
                     organism = synthetic construct
SEQUENCE: 70
MASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ                                            380

SEQ ID NO: 71         moltype = AA  length = 380
FEATURE              Location/Qualifiers
REGION               1..380
                     note = Description of Artificial Sequence: Synthetic
                      polypeptide
source               1..380
                     mol_type = protein
                     organism = synthetic construct
SEQUENCE: 71
MASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ                                            380

SEQ ID NO: 72         moltype = AA  length = 380
FEATURE              Location/Qualifiers
REGION               1..380
                     note = Description of Artificial Sequence: Synthetic
                      polypeptide
source               1..380
                     mol_type = protein
                     organism = synthetic construct
SEQUENCE: 72
AASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
```

-continued

```
SWQRADLGAY LNPRPPAPEA WSEPVLLAKG SCAYSDLQSM GTGPDGSPLF GCLYEANDYE  360
EIVFLMFTLK QAFPAEYLPQ                                               380

SEQ ID NO: 73            moltype = AA  length = 380
FEATURE                  Location/Qualifiers
REGION                   1..380
                         note = Description of Artificial Sequence: Synthetic
                          polypeptide
source                   1..380
                         mol_type = protein
                         organism = synthetic construct
SEQUENCE: 73
DASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ                                               380

SEQ ID NO: 74            moltype = AA  length = 874
FEATURE                  Location/Qualifiers
REGION                   1..874
                         note = Description of Artificial Sequence: Synthetic
                          polypeptide
source                   1..874
                         mol_type = protein
                         organism = synthetic construct
SEQUENCE: 74
MASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SCAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                               874

SEQ ID NO: 75            moltype = AA  length = 874
FEATURE                  Location/Qualifiers
REGION                   1..874
                         note = Description of Artificial Sequence: Synthetic
                          polypeptide
source                   1..874
                         mol_type = protein
                         organism = synthetic construct
SEQUENCE: 75
MASLPYLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPKQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SAAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                               874

SEQ ID NO: 76            moltype = AA  length = 617
FEATURE                  Location/Qualifiers
REGION                   1..617
                         note = Description of Artificial Sequence: Synthetic
                          polypeptide
source                   1..617
                         mol_type = protein
                         organism = synthetic construct
SEQUENCE: 76
```

```
AASLPYLQKE SVFQSGAHAY RIPALLYLPG QQSLLAFAEQ RASKKDEHAE LIVLRRGDYD      60
APTHQVQWQA QEVVAQARLD GHRSMNPCPL YDAQTGTLFL FFIAIPGQVT EQQQLQTRAN     120
VTRLCQVTST DHGRTWSSPR DLTDAAIGPA YREWSTFAVG PGHCLQLHDR ARSLVVPAYA     180
YRKLHPKQRP IPSAFCFLSH DHGRTWARGH FVAQDTLECQ VAEVETGEQR VVTLNARSHL     240
RARVQAQSTN DGLDFQESQL VKKLVEPPPQ GCQGSVISFP SPRSGPGSPA QWLLYTHPTH     300
SWQRADLGAY LNPRPPAPEA WSEPVLLAKG SCAYSDLQSM GTGPDGSPLF GCLYEANDYE     360
EIVFLMFTLK QAFPAEYLPQ GGGGSGGGGS DKTHTCPPCP APELLGGPSV FLFPPKPKDT     420
LMISRTPEVT CVVVDVSHED PEVKFNWYVD GVEVHNAKTK PREEQYNSTY RVVSVLTVLH     480
QDWLNGKEYK CKVSNKALPA PIEKTISKAK GQPREPQVYT LPPSREEMTK NQVSLTCLVK     540
GFYPSDIAVE WESNGQPENN YKTTPPVLDS DGSFFLTSKL TVDKSRWQQG NVFSCSVMHE     600
ALHNHYTQKS LSLSPGK                                                    617

SEQ ID NO: 77            moltype = AA   length = 617
FEATURE                  Location/Qualifiers
REGION                   1..617
                         note = Description of Artificial Sequence: Synthetic
                          polypeptide
source                   1..617
                         mol_type = protein
                         organism = synthetic construct
SEQUENCE: 77
DASLPYLQKE SVFQSGAHAY RIPALLYLPG QQSLLAFAEQ RASKKDEHAE LIVLRRGDYD      60
APTHQVQWQA QEVVAQARLD GHRSMNPCPL YDAQTGTLFL FFIAIPGQVT EQQQLQTRAN     120
VTRLCQVTST DHGRTWSSPR DLTDAAIGPA YREWSTFAVG PGHCLQLHDR ARSLVVPAYA     180
YRKLHPKQRP IPSAFCFLSH DHGRTWARGH FVAQDTLECQ VAEVETGEQR VVTLNARSHL     240
RARVQAQSTN DGLDFQESQL VKKLVEPPPQ GCQGSVISFP SPRSGPGSPA QWLLYTHPTH     300
SWQRADLGAY LNPRPPAPEA WSEPVLLAKG SCAYSDLQSM GTGPDGSPLF GCLYEANDYE     360
EIVFLMFTLK QAFPAEYLPQ GGGGSGGGGS DKTHTCPPCP APELLGGPSV FLFPPKPKDT     420
LMISRTPEVT CVVVDVSHED PEVKFNWYVD GVEVHNAKTK PREEQYNSTY RVVSVLTVLH     480
QDWLNGKEYK CKVSNKALPA PIEKTISKAK GQPREPQVYT LPPSREEMTK NQVSLTCLVK     540
GFYPSDIAVE WESNGQPENN YKTTPPVLDS DGSFFLTSKL TVDKSRWQQG NVFSCSVMHE     600
ALHNHYTQKS LSLSPGK                                                    617

SEQ ID NO: 78            moltype = AA   length = 617
FEATURE                  Location/Qualifiers
REGION                   1..617
                         note = Description of Artificial Sequence: Synthetic
                          polypeptide
source                   1..617
                         mol_type = protein
                         organism = synthetic construct
SEQUENCE: 78
MASLPYLQKE SVFQSGAHAY RIPALLYLPG QQSLLAFAEQ RASKKDEHAE LIVLRRGDYD      60
APTHQVQWQA QEVVAQARLD GHRSMNPCPL YDAQTGTLFL FFIAIPGQVT EQQQLQTRAN     120
VTRLCQVTST DHGRTWSSPR DLTDAAIGPA YREWSTFAVG PGHCLQLHDR ARSLVVPAYA     180
YRKLHPKQRP IPSAFCFLSH DHGRTWARGH FVAQDTLECQ VAEVETGEQR VVTLNARSHL     240
RARVQAQSTN DGLDFQESQL VKKLVEPPPQ GCQGSVISFP SPRSGPGSPA QWLLYTHPTH     300
SWQRADLGAY LNPRPPAPEA WSEPVLLAKG SCAYSDLQSM GTGPDGSPLF GCLYEANDYE     360
EIVFLMFTLK QAFPAEYLPQ GGGGSGGGGS DKTHTCPPCP APELLGGPSV FLFPPKPKDT     420
LMISRTPEVT CVVVDVSHED PEVKFNWYVD GVEVHNAKTK PREEQYNSTY RVVSVLTVLH     480
QDWLNGKEYK CKVSNKALPA PIEKTISKAK GQPREPQVYT LPPSREEMTK NQVSLTCLVK     540
GFYPSDIAVE WESNGQPENN YKTTPPVLDS DGSFFLTSKL TVDKSRWQQG NVFSCSVMHE     600
ALHNHYTQKS LSLSPGK                                                    617

SEQ ID NO: 79            moltype = AA   length = 617
FEATURE                  Location/Qualifiers
REGION                   1..617
                         note = Description of Artificial Sequence: Synthetic
                          polypeptide
source                   1..617
                         mol_type = protein
                         organism = synthetic construct
SEQUENCE: 79
MASLPYLQKE SVFQSGAHAY RIPALLYLPG QQSLLAFAEQ RASKKDEHAE LIVLRRGDYD      60
APTHQVQWQA QEVVAQARLD GHRSMNPCPL YDAQTGTLFL FFIAIPGQVT EQQQLQTRAN     120
VTRLCQVTST DHGRTWSSPR DLTDAAIGPA YREWSTFAVG PGHCLQLHDR ARSLVVPAYA     180
YRKLHPKQRP IPSAFCFLSH DHGRTWARGH FVAQDTLECQ VAEVETGEQR VVTLNARSHL     240
RARVQAQSTN DGLDFQESQL VKKLVEPPPQ GCQGSVISFP SPRSGPGSPA QWLLYTHPTH     300
SWQRADLGAY LNPRPPAPEA WSEPVLLAKG SAAYSDLQSM GTGPDGSPLF GCLYEANDYE     360
EIVFLMFTLK QAFPAEYLPQ GGGGSGGGGS DKTHTCPPCP APELLGGPSV FLFPPKPKDT     420
LMISRTPEVT CVVVDVSHED PEVKFNWYVD GVEVHNAKTK PREEQYNSTY RVVSVLTVLH     480
QDWLNGKEYK CKVSNKALPA PIEKTISKAK GQPREPQVYT LPPSREEMTK NQVSLTCLVK     540
GFYPSDIAVE WESNGQPENN YKTTPPVLDS DGSFFLTSKL TVDKSRWQQG NVFSCSVMHE     600
ALHNHYTQKS LSLSPGK                                                    617

SEQ ID NO: 80            moltype = DNA   length = 1143
FEATURE                  Location/Qualifiers
source                   1..1143
                         mol_type = other DNA
```

```
                           organism = Salmonella typhimurium
SEQUENCE: 80
acagtggaaa agtccgtggt gttcaaggcc gagggcgagc acttcaccga ccagaaaggc    60
aataccatcg tcggctctgg cagcggcggc accaccaagt actttagaat ccccgccatg   120
tgcaccacca gcaagggcac cattgtggtg ttcgccgacg ccagacacaa caccgccagc   180
gatcagagct tcatcgatac cgctgccgcc agatctaccg atggcggcaa gacctggaac   240
aagaagatcg ccatctacaa cgaccgcgtg aacagcaagc tgagcagagt gatggaccct   300
acctgcatcg tggccaacat ccagggcaga gaaaccatcc tggtcatggt cggaaagtgg   360
aacaacaacg ataagacctg gggccgcctac agagacaagg ccctgatac cgattgggac   420
ctcgtgctgt acaagagcac cgatgacggc gtgaccttca gcaaggtgga aacaaacatc   480
cacgacatcg tgaccaagaa cggcaccatc tctgccatgc tcggcggcgt tggatctggc   540
ctgcaactga atgatggcaa gctggtgttc cccgtgcaga tggtccgaac aaagaatatc   600
accaccgtgc tgaataccag cttcatctac agcaccgacg gcatcacatg gtccctgcct   660
agcggctact gtgaaggctt tggcagcgag aacaacatca tcgagttcaa cgccagcctg   720
gtcaacaaca tccggaacag cggcctgcgg agaagcttcg agacaaagga cttcggaaag   780
acgtggaccg agtttcctcc aatggacaag aaggtggaca accggaacca cggcgtgcag   840
ggcagcacaa tcacaatccc tagcggcaac aaactggtgg ccgctcactc tagcgcccag   900
aacaagaaca acgactacac cagaagcgac atcagcctgt acgcccacaa cctgtacgac   960
ggcgaagtga agctgatcga cgacttctac cccaaagtgg gcaatgccag cggagccggc  1020
tacagctgtc tgagctaccg gaaaaatgtg gacaaagaaa ccctgtacgt ggtgtacgag  1080
gccaacggca gcatcgagtt tcaggacctg agcagacatc tgcccgtgat caagagctac  1140
aac                                                                1143

SEQ ID NO: 81            moltype = AA   length = 781
FEATURE                 Location/Qualifiers
source                  1..781
                        mol_type = protein
                        organism = Vibrio cholera
SEQUENCE: 81
MRFKNVKKTA LMLAMFGMAT SSNAALFDYN ATGDTEFDSP AKQGWMQDNT NNGSGVLTNA    60
DGMPAWLVQG IGGRAQWTYS LSTNQHAQAS SFGWRMTTEM KVLSGGMITN YYANGTQRVL   120
PIISLDSSGN LVVEFEGQTG RTVLATGTAA TEYHKFELVF LPGSNPSASF YPDGKLIRDN   180
IQPTASKQNM IVWGNGSSNT DGVAAYRDIK FEIQGDVIFR GPDRIPSIVA SSVTPGVVTA   240
FAEKRVGGGD PGALSNTNDI ITRTSRDGGI TWDTELNLTE QINVSDEFDF SDPRPIYDPS   300
SNTVLVSYAR WPTDAAQNGD RIKPWMPNGI FYSVYDVASG NWQAPIDVTD QVKERSFQIA   360
GWGGSELYRR NTSLNSQQDW QSNAKIRIVD GAANQIQVAD GSRKYVVTLS IDESGGLVAN   420
LNGVSAPIIL QSEHAKVHSF HDYELQYSAL NHTTTLFVDG QQITTWAGEV SQENNIQFGN   480
ADAQIDGRLH VQKIVLTQQG HNLVEFDAFY LAQQTPEVEK DLEKLGWTKI KTGNTMSLYG   540
NASVNPGPGH GITLTRQQNI SGSQNGRLIY PAIVLDRFFL NVMSIYSDDG GSNWQTGSTL   600
PIPFRWKSSS ILETLEPSEA DMVELQNGDL LLTARLDFNQ IVNGVNYSPR QQFLSKDGGI   660
TWSLLEANNA NVFSNISTGT VDASITRFEQ SDGSHFLLFT NPQGNPAGTN GRQNLGLWFS   720
FDEGVTWKGP IQLVNGASAY SDIYQLDSEN AIVIVETDNS NMRILRMPIT LLKQKLTLSQ   780
N                                                                   781

SEQ ID NO: 82            moltype = DNA   length = 2424
FEATURE                 Location/Qualifiers
source                  1..2424
                        mol_type = other DNA
                        organism = Vibrio cholera
SEQUENCE: 82
ttgtcaatca agatgacttc acaacgaaga agagcatcga ttcacaagga aacagattct    60
aatataaagg gagtagatat gcgtttcaaa aacgtaaaga aaaccgcttt aatgcttgca   120
atgttcggta tggcgacaag ctcaaacgcc gcacttttg actataacgc aacgggtgac   180
actgagtttg acagtccagc caaacaggga tggatgcaag acaacacgaa taatggcagc   240
ggcgttttaa ccaatgcaga tggaatgccc gcttggttgg tgcaaggtat tggagggaga   300
gctcaatgga catattctct ctctactaat caacatgccc aagcatcaag tttcggttgg   360
cgaatgacga cagaaatgaa agtgctcagt ggtggaatga tcacaaacta ctacgccaac   420
ggcactcagc gtgtcttacc catcatttca ttagatagca gtggtaactt agttgttgag   480
tttgaagggc aaactggacg caccgttttg gcaaccggca cagcagcaac ggaatatcat   540
aaatttgaat tggtattcct tcctggaagt aacccatccg ctagcttta cttcgatggt   600
aaactcattc gtgacaacat ccagccgact gcatcaaaac aaaatatgat cgtatggggg   660
aatggctcat caaatacgga tggtgtcgcc gcttatcgtg atattaagtt tgaaattcaa   720
ggcgacgtca tcttcagagg cccagaccgt ataccgtcca ttgtagcaag tagcgtaaca   780
ccaggggtgg taaccgcatt tgcagagaaa cgtgtggggg gaggagatcc cggtgctctg   840
agtaatacca atgacataat cactcgtacc tcacgagatg gcggtataac ttgggatacc   900
gagctcaacc tcactgagca aatcaatgtc agtgatgagt ttgatttctc cgatcctcgg   960
cctatctatg atccttcctc caatacggtt cttgtctctt atgctcgatg gccgaccgat  1020
gccgctcaaa acggagatcg aataaaacca tggatgccaa acggtatttt ttacagcgtc  1080
tatgatgttg catcaggga ctggcaagcg cctatcgatg ttaccgatca ggtgaaagaa  1140
cgcagtttcc aaatcgctgg ttggggtggt tcagagctgt atcgccgaaa taccagccta  1200
aatagccagc aagactggca atcaaacgct aagatccgaa ttgttgatgg tgcagcgaac  1260
cagatacaag ttgccgatgg tagccgaaaa tatgttgtca cactgagtat tgatgaatca  1320
ggtggtctag tcgctaatct aaacggtgtt agtgctccga ttatcctgca atctgaacac  1380
gcaaaggtac actctttcca tgactacgaa cttcaatatt cggcgttaaa ccacaccaca  1440
acgttattcg tggatggtca gcaaatcaca acttgggctg gcgaagtatc gcaggagaac  1500
aacattcagt ttggtaatgc ggatgcccaa attgacggca gactgcatgt gcaaaaaatt  1560
gttctcacac agcaaggcca taaccctgtg agtttgatg ctttctattt agcacagcaa  1620
accccctgaag tagagaaaga ccttgaaaag cttggttgga caaaaattaa aacgggcaac  1680
accatgagtt tgtatggaaa tgccagtgtc aacccaggac cgggtcatgg catcaccctt  1740
```

```
actcgacaac aaaatatcag tggcagccaa aacggccgct tgatctaccc agcgattgtg    1800
cttgatcgtt tcttcttgaa cgtcatgtct atttacagtg atgatggcgg ttcaaactgg    1860
caaaccggtt caacactccc tatccccttt cgctggaaga gttcgagtat cctagaaact    1920
ctcgaaccta gtgaagctga tatggttgaa ctccaaaacg tgatctact  ccttactgca    1980
cgccttgatt ttaaccaaat cgttaatggt gtgaactata gcccacgcca gcaatttttg    2040
agtaaagatg tgtggaatcac gtggagccta cttgaggcta acaacgctaa cgtctttagc    2100
aatatcagta ctggtaccgt tgatgcttct attactcggt tcgagcaaag tgacggtagc    2160
catttcttac tctttactaa cccacaagga aaccctgcgg ggacaaatgg caggcaaaat    2220
ctaggcttat ggtttagctt cgatgaaggg gtgacatgga aaggaccaat tcaacttgtt    2280
aatggtgcat cggcatattc tgatatttat caattggatt cggaaaatgc gattgtcatt    2340
gttgaaacgg ataattcaaa tatgcgaatt cttcgtatgc ctatcacatt gctaaaacag    2400
aagctgacct tatcgcaaaa ctaa                                           2424
```

```
SEQ ID NO: 83              moltype = AA  length = 409
FEATURE                    Location/Qualifiers
source                     1..409
                           mol_type = protein
                           organism = Mus sp.
SEQUENCE: 83
MVGADPTRPR GPLSYWAGRR GQGLAAIFLL LVSAAESEAR AEDDFSLVQP LVTMEQLLWV    60
SGKQIGSVDT FRIPLITATP RGTLLAFAEA RKKSASDEGA KFIAMRRSTD QGSTWSSTAF    120
IVDDGEASDG LNLGAVVNDV DTGIVFLIYT LCAHKVNCQV ASTMLVWSKD DGISWSPPRN    180
LSVDIGTEMF APGPGSGIQK QREPGKGRLI VCGHGTLERD GVFCLLSDDH GASWHYGTGV    240
SGIPFGQPKH DHDFNPDECQ PYELPDGSVI INARNQNNYH CRCRIVLRSY DACDTLRPRD    300
VTFDPELVDP VVAAGALATS SGIVFFSNPA HPEFRVNLTL RWSFSNGTSW LKERVQVWPG    360
PSGYSSLTAL ENSTDGKKQP PQLFVLYEKG LNRYTESISM VKISVYGTL               409
```

```
SEQ ID NO: 84              moltype = AA  length = 393
FEATURE                    Location/Qualifiers
source                     1..393
                           mol_type = protein
                           organism = Mus sp.
SEQUENCE: 84
MTVQPSPWFS DLRPMATCPV LQKETLFRTG VHAYRIPALL YLKKQKTLLA FAEKRASKTD    60
EHAELIVLRR GSYNEATNRV KWQPEEVVTQ AQLEGHRSMN PCPLYDKQTK TLFLFFIAVP    120
GRVSEHHQLH TKVNVTRLCC VSSTDHGRTW SPIQDLTETT IGSTHQEWAT FAVGPGHCLQ    180
LRNPAGSLLV PAYAYRKLHP AQKPTPFAFC FISLDHGHTW KLGNFVAENS LECQVAEVGT    240
GAQRMVYLNA RSFLGARVQA QSPNDGLDFQ DNRVVSKLVE PPHGCHGSVV AFHNPISKPH    300
ALDTWLLYTH PTDSRNRTNL GVYLNQMPLD PTAWSEPTLL AMGICAYSDL QNMGQGPDGS    360
PQFGCLYESG NYEEIIFLIF TLKQAFPTVF DAQ                                  393
```

```
SEQ ID NO: 85              moltype = AA  length = 418
FEATURE                    Location/Qualifiers
source                     1..418
                           mol_type = protein
                           organism = Mus sp.
SEQUENCE: 85
MEEVPPYSLS STLFQQEEQS GVTYRIPALL YLPPTHTFLA FAEKRTSVRD EDAACLVLRR    60
GLMKGRSVQW GPQRLLMEAT LPGHRTMNPC PVWEKNTGRV YLFFICVRGH VTERCQIVWG    120
KNAARLCFLC SEDAGCSWGE VKDLTEEVIG SEVKRWATFA VGPGHGIQLH SGRLIIPAYA    180
YYVSRWFLCF ACSVKPHSLM IYSDDFGVTW HHGKFIEPQV TGECQVAEVA GTAGNPVLYC    240
SARTPSRFRA EAFSTDSGGC FQKPTLNPQL HEPRTGCQGS VVSFRPLKMP NTYQDSIGKG    300
APATQKCPLL DSPLEVEKGA ETPSATWLLY SHPTSKRKRI NLGIYYNRNP LEVNCWSRPW    360
ILNRGPSGYS DLAVVEEQDL VACLFECGEK NEYERIDFCL FSDHEVLSCE DCTSPSSD      418
```

```
SEQ ID NO: 86              moltype = AA  length = 501
FEATURE                    Location/Qualifiers
source                     1..501
                           mol_type = protein
                           organism = Mus sp.
SEQUENCE: 86
METAGAPFCF HVDSLVPCSY WKVMGPTRVP RRTVLFQRER TGLTYRVPAL LCVPPRPTLL    60
APAEQRLSPD DSHAHRLVLR RGTLTRGSVR WGTLSVLETA VLEEHRSMNP CPVLDEHSGT    120
IFLFFIAVLG HTPEAVQIAT GKNAARLCCV TSCDAGLTWG SVRDLTEEAI GAALQDWATF    180
AVGPGHGVQL RSGRLLVPAY TYHVDRRECF GKICWTSPHS LAFYSDDHGI SWHCGGLVPN    240
LRSGECQLAA VDGDFLYCNA RSPLGNRVQA LSADEGTSFL PGELVPTLAE TARGCQGSIV    300
GFLAPPSIEP QDDRWTGSPR NTPHSPCFNL RVQESSGEGA RGLLERWMPR LPLCYPQSRS    360
PENHGLEPGS DGDKTSWTPE CPMSSDSMLQ SPTWLLYSHP AGRRARLHMG IYLSRSPLDP    420
HSWTEPWVIY EGPSGYSDLA FLGPMPGASL VFACLFESGT RTSYEDISFC LFSLADVLEN    480
VPTGLEMLSL RDKAQGHCWP S                                              501
```

```
SEQ ID NO: 87              moltype = DNA  length = 3850
FEATURE                    Location/Qualifiers
source                     1..3850
                           mol_type = other DNA
                           organism = Mus sp.
SEQUENCE: 87
gggtcacatg ctgatggact aattggagtc gcggcagcgc gggctgcggc ccccaagggg    60
aggggtcgga gtgacgtgcg cgcttttaaa gggccgaggt cagctgacgg cttgccaccg    120
```

```
gtgaccagtt cctggacagg gatcgccggg agctatggtg ggggcagacc cgaccagacc  180
ccggggaccg ctgagctatt gggcgggccg tcggggtcag gggctcgcag cgatcttcct  240
gctcctggtg tccgcggcgg aatccgaggc cagggcagag gatgacttca gcctggtgca  300
gccgctggtg accatggagc agctgctgtg ggtgagcggg aagcagatcg gctctgtaga  360
cactttccgc atcccgctca tcacagccac ccctcgggcg acgctcctgg ccttcgctga  420
ggccaggaaa aaatctgcat ccgatgaggg ggccaagttc atcgccatga ggaggtccac  480
ggaccagggt agcacgtggt cctctacagc cttcatcgta gacgatgggg aggcctccga  540
tggcctgaac ctgggcgctg tggtgaacga tgtagacaca gggatagtgt tccttatcta  600
taccctctgt gctcacaagg tcaactgcca ggtggcctct accatgttgg tttggagtaa  660
ggacgacggc atttcctgga gcccacccg gaatctctct gtggatattg gcacagagat  720
gtttgcccct ggacctggct caggcattca gaaacagcgg gagcctggga agggccggct  780
cattgtgtgt ggacacggga cgctggagcg agatggggtc ttctgtctcc tcagtgatga  840
ccacggtgcc tcctggcact acggcactgg agtgagcggc attccctttg gccagcccaa  900
acacgatcac gatttcaacc ccgacgagtg ccagccctac gagcttccag atggctcggt  960
catcatcaac gcccggaacc agaataacta ccattgccgc tgcaggatcg tcctccgcag  1020
ctatgacgcc tgtgacaccc tcaggccccg ggatgtgacc ttcgaccctg agctcgtgga  1080
ccctgtggta gctgcaggag cactagccac cagctccggc attgtcttct tctccaatcc  1140
agcccaccct gagttccgag tgaacctgac cctgcgctgg agtttcagca atggtacatc  1200
ctggcagaag gagagggtcc aggtgtggcc gggacccagc ggctactcgt ccctgacagc  1260
cctgaaaac agcacggatg gaaagaagca gcccccgcag ctgttcgttc tgtacgagaa  1320
aggcctgaac cggtacaccg agagcatctc catggtcaaa atcagcgtct acggcacgct  1380
ctgagcccg tgcccaaagg acaccaagtc ctggtcgatg acttcacagc tctctggacc  1440
atctgcagag ggtgcctgaa acacagctct tcctctgaac tctgaccttt tgcaacttct  1500
catcaacagg gaagtctctt cgttatgact taacacccag cttcctctcg gggcaggaag  1560
tccctccgtc accaagagca cttttttcca gtatgctggg gatggcccct gtccattctc  1620
ttccaggaca acggagctgt gcctttctgg gacaggatgg gggaggggct ccccctggag  1680
agatgaacag atacgaactc agggaactga gaaggcccgg tgtcctaggg tacaaaggca  1740
ggtactagat gtgattgctg aaagtcccca gggcagagtg tcctttcaga gcaaggataa  1800
gcacacctac gtgtgcacct ttgattattt atgaatcgaa atatttgtaa cttaaaattt  1860
ttgatgcaga aaaagcgttt gtggagtctg tggttctgtc tgctcacgcc ttcccaattg  1920
cctcctggag agacaggaag gcagctggaa gaggagccga tgtacttact gggaagcaga  1980
aaccccctaga ttccatcctg gctgctgctg tttgcaagtg tcaaagatgg gggggcgtgt  2040
ttatattta tatttctaag atggggtggc ataggaaata gggaacagat gtgtaaaacc  2100
agatgggaag gacagtctgt gagaaaggag caagcagttg ctgcaggtgt gggagagcaa  2160
agcccttctc cacgtggaaa gagcccagat ggacgctaag catgttgggc acctgtaacc  2220
ccgcactcgc tggactgacg gtgtagctca gtggtggagc tagtacttgg aacgcctaag  2280
actctgggtt cagtccttgg gggggggggt atgtgtttat tgagaggaag gtgtacgtac  2340
tgtaggtcag aggacagctt actggagttg tctctctcct tcacgctgtg agtcctgtgg  2400
aatgacctca ggtgtcagag ttggggggcag gtgcctttgc cagctgagcc atcttgctgt  2460
ctctgcttta atttaaaaaa aaaaaaaaaa aagaatatta aggtctgagg gattcgggct  2520
gcgttcattt caattagagg gtcatatttc ttttgacatt tcttctctaa gaaatgttaa  2580
gatcatttgt tctgtgtgat agaggtatag ctccattgta tgtcagcagt gagggatcct  2640
gtgcatttta tccagagttt gtacggtgtt ctaggggctg ctagtgcagc ccagtgctaa  2700
acacttcagc atgcacaagg cctcaatcag tgcatgcatg tgcacacaca cacagacaca  2760
cacgtacaca ctgacacagg tacacaaata cacactggcc cacatgtaca catcgactca  2820
caggtacaca gacccacttt gacacacata tacacagaca caaacgcact ggcacacaca  2880
tatacacagg cacacatgga tagatgacac cacgtgtaca catacacaca cacagaaa  2940
tacaaatgtt caggttttct aaaaaaaaaa aaattagaga cgtgttgact tcatttttag  3000
caaaaatcct gtcatgtatc ttaaagtgga ttgaacccac tatgtagccc aggctggcct  3060
ccaaatgggc atccttctgc ctcagtctcc cgagggctag gataacagga gtatgccatc  3120
acacctggct aatagaaatt ttcaaaattg tttgtttgaa ggtgactctt actatattgt  3180
ctaactgatc tccagttcgt gaaatcctcc tgcctcagaa ccaggactgt caatataacc  3240
caccaagaca ggccaacatt cacaattgat tgttagtttg tggtctgaat caaggtctta  3300
tactgtagcc caggctagcc cggaatacac gatatctcca gtgcttcaga tcctcagttc  3360
taactaagca tggccacatc catgtttaac tgcaaatttg atgttaccat ggtttggttt  3420
ggtttggttt ggtttggttt ggtttggttt ggttttttgg ccatttttt tttctcatgc  3480
tgaggccttg tgctctcaag ttggggagac agcatggagg gtagctgcaa ctgtaaccc  3540
agttccaggg gacctgacac cctctggcct ccacaagtat taggcacatc tgtggtgcac  3600
agacatacaa tcaggcaaaa tattcataca cataaaataa aataatttaa aacaaaagca  3660
aaaatcagga cctaagaaaa aaatctattc ctgattcttt tatgtttttgt ttgtatttta  3720
tcaagacagg gttgtttctc tgtatagccc tggctgtctt ggaattcact ctgtagacca  3780
ggctggcctc aaactcagaa atcctcctgc ctttgccttc caagtgctgg aattaaaggc  3840
atgcgccacc                                                         3850
```

```
SEQ ID NO: 88          moltype = DNA  length = 1722
FEATURE                Location/Qualifiers
source                 1..1722
                       mol_type = other DNA
                       organism = Mus sp.
SEQUENCE: 88
gacatgaccc aaacggcccc tggctgcaag gtaatatcgg aagttgacta agaatggacg  60
ccccaccact gactgacccg cccctgagt ctgagattgg acttgtctct ggatacagtc  120
atactttgag gtactacaag ttagaaactg ttaggttact cagttcagtc catgacagtc  180
caaccttctc catggttttc cgatctcagg cccatggcga cctgccctgt cctgcagaag  240
gagacactgt tccgcacagg cgtccatgct tacagaatcc ctgctctgct ctacctgaag  300
aagcagaaga ccctgctggc cttttgcggaa aagcgagcca gcaagacgga tgagcacgca  360
gagttgattg tcctgagaag aggaagctac aacgaagcca ccaaccgtgt caagtggcag  420
cctgaggaag tggtgaccca agcccagctg gaaggccacc gctccatgaa tccatgtccc  480
ttgtatgaca agcaaacaaa gaccctcttc ctttttcttca tcgctgtccc tgggcgtgta  540
```

-continued

```
tcagaacatc atcagctcca cactaaggtt aatgtcacac ggctgtgctg tgtcagcagc     600
actgaccatg ggaggacctg gagccccatc caggacctca cagagaccac cattggcagc     660
actcatcagg aatgggccac atttgctgtg ggtcctgggc attgtctgca gctgcggaac     720
ccagctggga gcctgctggt acctgcttat gcctaccgga aactgcaccc tgctcagaag     780
cctacccct  ttgccttctg cttcatcagc cttgaccatg ggcacacatg gaaactaggc     840
aactttgtgg ctgaaaactc actggagtgc caggtggctg aggttggcac tggagctcag     900
aggatggtat atctcaatgc taggagcttc ctgggagcca gggtccaggc acaaagtcct     960
aatgatggtc tggatttcca ggacaaccgg gtagtgagta agcttgtaga gccccccac     1020
gggtgtcag gaagtgtggt tgccttccac aaccccatct ctaagccaca tgccttagac     1080
acatggcttc tttatacaca ccctacagac tccaggaata gaaccaacct gggtgtgtac     1140
ctaaaccaga tgccactaga tcccacagcc tggtcagagc ccaccctgct ggccatgggc     1200
atctgtgcct actcagactt acagaacatg gggcaaggcc ctgatggctc cccacagttt     1260
gggtgtctgt atgaatcagg taactatgaa gagatcattt tcctcatatt caccctgaag     1320
caagctttcc ccactgtatt tgatgcccag tgatctcagt gcacgtggcc caaagggctt     1380
ccttgtgctt caaaacaccc atctctcttt gcttccagca tcctctggac tcttgagtcc     1440
agctcttggg taacttcctc aggaggatgc agagaatttg gtctcttgac tctctgcagg     1500
ccttattgtt tcagcctctg gttctctttt cagcccagaa atcaaaggag cctggctttc     1560
ctcagcctgt tggcagggca ggtggggaca gtatatatag aggctgccat tctgcatgtc     1620
ggttgtcact atgctagttt aacctgcctg tttccccatg cctagtgttt gaatgagtat     1680
taataaaata tccaacccag cccatttctt cctggaaaaa aa                        1722
```

```
SEQ ID NO: 89          moltype = DNA  length = 3340
FEATURE                Location/Qualifiers
source                 1..3340
                       mol_type = other DNA
                       organism = Mus sp.
SEQUENCE: 89
actgcgcggt gaaggggcgt ggcctggccg gggaggttga cacccagacg ctgctctcag      60
tcctctggcg cctgctcccc agcgcattcc ttctgctcct gggatatttg tctcattact     120
gccagttctt gcgcagcggt cactgggttc gtttcagcgt ctgtggtttc tgtcgctgtt     180
atccagtctc catcgcccca gctcagcttc aggccttctt ccgagactcc acgggagagc     240
ccagagagcc tccggagccg aagccatgga ggaagtccca ccctactccc tcagcagcac     300
cctgttccag caggaagaac agagtggggt gacctaccgg atcccagccc tgctgtacct     360
tcctcccacc cacaccttcc tggcctttgc agagaagcgg acctcagtca gagatgagga     420
tgctgcctgc ctggtgctca gacgagggct gatgaagggg cgctctgtac agtggggccc     480
ccaacggcta ctgatggagg ccacattacc tgggcatcgc accatgaacc cctgccctgt     540
gtgggagaaa aatactggcc gtgtgtacct gttttttcatc tgtgtgcggg gccatgttac     600
tgagaggtgc cagattgtgt ggggcaaaaa tgccgcccgt ctctgcttcc tttgcagtga     660
agatgccggc tgctcttggg gtgaagtgaa agacttgaca ggaggggtca ttggctcaga     720
ggtgaagcgc tgggccacat ttgctgtggg cccaggtcat ggcatccagc tacactcggg     780
aaggctgatc atccccgcct atgcctacta tgtctcacgt tggtttctct gctttgcgtg     840
ttcagtcaag ccccattccc tgatgatcta cagtgatgac tttggagtca catggcacca     900
tggcaagttc attgagcccc aggtgacagg ggagtgccaa ggtggccgaag tggctgggac     960
ggctggtaac cctgtgctca ctgcagtgcc cgaacaccaa gccgatttcg agcagaggct    1020
tttagtactg atagtggtgg ctgctttcag aagccaaccc tgaacccaca actccatgag    1080
cctcgaaccg gctgccaagg tagtgtagtg agcttccggc ctttgaagat gccaaatacc    1140
tatcaagact caattggcaa aggtgctccc gctactcaga agtgccctct gctggacagt    1200
cctctggagg tggagaaagg agctgaaaca ccatcagcaa catggctctt gtactcacat    1260
ccaactagca agaggaagag gattaaccta ggcatctact acaacggaa ccccttggag     1320
gtgaactgct ggtcccgccc gtggatcttg aaccgtgggc ccagtggcta ctctgatctg    1380
gctgttgtgg aagaacagga cttggtggcg tgtttgtttg agtgtgggga gaagaatgag    1440
tatgagcgga ttgacttctg tctgttttca gaccatgagg tcctgagctg tgaagactgt    1500
accagcccta gtagcgacta aagccaaatc aagacggatg agtgaggccc agcttcccac    1560
agaaaggaat ggcagctaca gccagggtaa cagaggtctc tgatgtctag agaaaactct    1620
aaaaactaat aatctgctcc ttgaatttt  tcactttttcc cttcaatgag catggtgaaa   1680
attgtgccat atcttacata acgaggctct tgaactggga gtttgaatct cttctcttcc    1740
cattaaaagg agaggccatg tgctcgcttc gcgttcgaca aagcctggat tctgatcttg    1800
agtggaagcc acaggcttgt cttttccaat ggttcactgc tcacctgagt attaggtgat    1860
gtgtaggtgc cttggccaga agaaagatct gtgttgttgt atttttttaa atttatttat    1920
ttactatatg taagtacact gcagctgtct tcagacacac cagaagaggg cgtcagatct    1980
cattagagat ggttgtgagc caccatgtgg ttgctgggat ttgaactcag gaccttcaga    2040
agagcagtca gtgctcttaa ctactgagcc atctctcaag ccccgcattg ctgtattttt    2100
aataagaaaa atgcccttat ccttccaata atgcctggag ctgtacaaat tctctgtctt    2160
agaagacttg agaaagcaga actgtaaggt cagatgcttt ctccagcctt gatgctgtgt    2220
tccaccttcc cttcctcatc cagaaaacag ttactaggga gaaaatgaga aacccatgcc    2280
agctgccctt gatgatggtt gataacggtg cttattgctt ttgatgtcat tacctctgtt    2340
agagatgaat cagagtcaga ggtccttagc tgcatccacc catttccagg gggacattct    2400
aacactgctg aacagtcagc taaaatgaga gctgtgtgtc ctagcctgat tccaggttag    2460
tcatgatgct tcctggagct gggctttat  ctaatcccag gagccatcta ggggaggctc    2520
agagctagca ggtgatcttc ctgagatggt ttcaccgtga caggtgaacc atgagccctt    2580
ccaagcaagg ccaaaggaca acattatagg aaagatttct agtattaata tgccttttct    2640
ctgtgtgtgt actgtcttgt agtgatgcta tatagacaaa tagatgattt cttattttttt   2700
gtttgtttgt ttgtttttttt gttttttctgt agccctagct gtcctggaac tcactttgta    2760
aaccaggctg gcctcgatct cagaaatccg cctgcctctg cctcccgagt gctgggatta    2820
aaggtgtgca ccaccacacc ttaatgatga tcctataagt attcctaaaa ttatactagt    2880
aattattaac tcctttataa taggactgct attaaagccc tcgctgatat gaaaactaca    2940
gtgagaactc tgccagtctt cacatgtcat aattacttct gagatagaaa gcaggcattt    3000
acaacttaga acacatttct tagagctgta aaacaattaa ctagaggtca taaaaggaa     3060
tgaaagattt attgtaggtg ctaggacaga acataaaata ttgactgggc ttatctatat    3120
```

-continued

```
gaaacttcat tgttaacttt tacacaagaa ttatggtttt taacttttcag tgaacctgcg   3180
gagctagtga cagaagagaa atgtctagtt agataaactac tcttaatgga aattcacata   3240
aacatctgtt gccatcttct tttttgaattt atgtttaaac ttgtgaatgt ttgaattaga   3300
cactacgcga gcacatagaa aataaagaac taagcgtgaa                          3340
```

SEQ ID NO: 90            moltype = DNA   length = 4608
FEATURE                  Location/Qualifiers
source                   1..4608
                         mol_type = other DNA
                         organism = Mus sp.
SEQUENCE: 90

```
ggacagtgtg catcacggag cttgtggccc agactgtgcc tggcagaccc agaggaccta   60
aggcttggct ctagtggtgg tcagcacagc cctcggtggt ctgcggagcc tgatattgct   120
ttacgtaagg gctgttctgc tgtgcatctc ctgtgtctga agctattcgc catggagact   180
gctggagctc ccttctgctt ccatgtggac tccctggtac cttgctccta ctggaaggtt   240
atggggccca cgcgtgttcc caggagaacg gtgctcttcc agagggaaag gacgggcctg   300
acctaccgtg tgcctgcgtt actctgtgtg cctcccaggc ctactctgct ggccttcgcg   360
gaacagcgac ttagccctga tgactcccat gcccaccgcc tggtgctacg gaggggcacg   420
ctgaccaggg gctcagtgcg gtggggcact ctgagtgtac tggagactgc agtactggag   480
gagcacaggt ctatgaaccc ttgcccggtg ctggatgagc actctggtac catcttcctc   540
ttcttcattg ccgtgctggg ccacacaccg gaggccgtgc aaatcgccac tggcaagaac   600
gctgctcgcc tctgctgtgt gaccagctgt gacgctggcc tcacctgggg cagtgttcga   660
gatctcactg aggaagccat tggtgctgca ttgcaggact gggccacctt tgctgtgggt   720
ccgggccatg gagttcagct gcgctcgggt cgcctgcttg ttcctgctta cacctatcat   780
gtggaccgac gggaatgttt tggcaagatc tgctggacca gtcccactc cttggcattc    840
tacagtgatg atcatgggat ctcctggcat tgtggaggcc ttgtgcccaa cctacgctct   900
ggagagtgcc aactggctgc ggtagatgga gactttctct actgtaatgc tcgaagccct   960
ctgggtaacc gtgtgcaggc actgagtgct gatgaaggca cgtccttcct accaggggag   1020
ctggtgccta cattggcaga gacggctcgt ggttgccagg gtagcattgt gggcttccta   1080
gctccaccct caatcgagcc tcaggatgac cggtggacag ggagtcctag gaacacccca   1140
cattccccat gcttcaatct cagagtacag gagtcttcgg gggaaggtgc cagaggtctt   1200
cttgaacgtt ggatgcccag gttgcctctc tgctacccac agtcccggag cccagagaat   1260
catggcctag agcctgggtc agatggagat aagacatcct ggactccgga atgtcctatg   1320
tcctctgatt ccatgcttca gagccccaca tggctactat attcccaccc agcagggcgt   1380
agagctcggc tccacatggg aatctacctg agccgatccc ccttggatcc ccacagctg    1440
acagagccct gggtgatcta tgagggcccc agtggctact ctgaccttgc ctttcttggg   1500
cctatgcctg gggcatccct ggtttttgcc tgtctgtttg agagcgggac caggacttcc   1560
tatgaagaca tttctttttg cttgttctca ctggcggatg tcctggagaa tgtgcccact   1620
ggcttagaga tgctaagtct cagggataag gctcagggc attgctggcc ctcttgatgg    1680
cctcacccct tcgtagccgc ctggagagga agggtagact atatagagga ggttgaggggt  1740
aggtcagcat gatgctagga tggagagagc tctgtcccct cgtggatggt ggtggtgact   1800
cacccggggg gccagctgct ttctgagtgc aaatgagaaa aataaagagc tgcgctgtga   1860
ctttttcttc cacatcaaag cttgggtgtc agtgctttag gttgatgctc tgatcaccat   1920
gcaaatcttc caccggcgcc ttgctcagct ttcatatccc aagggtgcct gggaggaagg   1980
caacagggac agtggacatc actgcaccac tttccacgac cctgtgtgcc aacctcagcc   2040
actttgaaac atgctgatga ctgaggtctg ttcactttct taatttcaag caggagaagc   2100
aggttgggga gccagcctcc ccagctagag gggacagaac ttgacttgag caggggggta   2160
cctcctagga cctgctccat gtgcctactt ctttaccctt ctctagagag ggctcttgtc   2220
ctgtcagagc tgtttttctcc cttctcttgt tttttctttt tcaagactgt ttctctgtgt   2280
tagccctggc tgtcctggat ctcactctgt agatcaggct gaccttgagt tcaaagctcc   2340
atctgcctct acttctcaca ttactgtgat taaaggcata tactaccact gcctggtgcc   2400
cttttgtatt tcttattaaa gtcctaatgt ctgattataa aaacagtctg tgtgggctga   2460
agtgatggct tactcagtaa agcacttgcc atggaatctg ggcaatctga gtttcatttt   2520
tagcatcctg taaaaatccc aatttgatgg tgtacttgta atgtcagcat ggagaggcag   2580
agataggtaa gttccccaag actctttgaa ccgacagctt ggcctcactg gcacattcca   2640
ggtctcagtg agagaccctg cctcaaaata caaagaaaga gctgctgaag agtgggtcag   2700
agttgacctc tgatctccgg aagtatatga tacacacccg tgcatgcact cttccttaca   2760
aaataaaaag caaaacaaaa ccccaacagg tatatggcca ttttagaaaa attagaagat   2820
ttagaaagct atacataaaa aaaaatgacc taaagaaaaa tctttactgt tctgggcact   2880
atccctatca aaccactgtg ttctttggcc aagccttggg gtggacactg ttttgaggtg   2940
ggtcctgtta tctccactag gtagtggagt tttgtgtcag actaactggg tcttaaagct   3000
gtctttaagg ccatcaggag ctactgactt gcctgcctca gcagagcata tcctgaaggt   3060
cggggttaag tctccttccc gagcgagttg ccttccagtg ggccctgga ctcctaggtc    3120
ctcagcgctc atcagctgcc aaggactctg agggaatgtc ctctgactgt ggcccccgaaa  3180
ggtaggggag ggggatgtgc ttaggcttag gacaggggtcc tgtttcagtc tgccttcact   3240
gttagtagca ctgtgccaca tggcacagac tgggcgagct ttaaaggaag gaggttgata   3300
ttggttccca cttctgggga tcatggttga gcagccttgt ctgatgatgg ttgtcttgat   3360
ggtagatcgt gaggtagttg atgaaggtat gacatggtga gaaactctgt gtgtgtgtgt   3420
tattttctct gtgttctacc tatacatcta tctatgtata tatgtatcta tctatctacc   3480
tggaggctgg agagatagct tagtggttaa gaacatttgt tgttcttgca tagtcctgga   3540
tttaaatttt cagcacccac atggcagctc acaacaaccc ataaatccag tttcagagga   3600
tccaacctct gatataccat gtcagccaga gcagacacgg ctgaaggtgg tttgatcccc   3660
gtatggagag gtgacaattg ggaagagaga aagatcaact taaccatgca aggaacagga   3720
agttaaatac tgaacaggga aggtaaaggc aggaagtaga tgtagagggc aaatcaatga   3780
aacccaaaca tacccaaatt acgctaaaca cacactgaca tgccaattaa aaggacaaat   3840
tggctccact ggcaaaacca aaacagacac tgaagatcca aacagtcaca tgccaactac   3900
cgcggaggga gacagacaca gagaagaccg tgacagacac ttggacactc ttgagagtgg   3960
atgtgcagga agagagctct gccagtggag aagaaagcac tcagaagaaa gtgacagcag   4020
ctgtaaattt gtattctgct aatgttatgt tccaaagttg aaagcaaaat tgtaccaatt   4080
```

```
cataagaaca aacaggctga ctctcagttg tgactgaacg tctctcagta actgacgggg   4140
cgagcaggcc aaaggagagt cggctcagaa gggtgcatag ccacgccaaa tcaaataagc   4200
aagtacaacc ggcaggctct atttctagca caaaggggtc tgtgcctcat tctgtgcttg   4260
ggtcagagct tgggtctctc atttggatgt aagtggtgta gtggagaagc aggaaataat   4320
ccggacgca tattttgatt ttaacataag tgctgatttg ggagggagtt ttgtcaaatt   4380
gtgtttttac aatgtttttt ttttttttaaa tgatgcttttt ttgtaaagtg tacaaatgtg   4440
atataagatt ggtctgcta cattcagttt ctataaaagt ggttctaaaa tattgtactg   4500
tcaatcatct catgattatt ctactgtaca cattactgac tttgtatgta ataattaata   4560
ttagaagaaa atataattta tttgaatata aaaaaaaaaa aaaaaaaa              4608
```

```
SEQ ID NO: 91            moltype = AA  length = 380
FEATURE                  Location/Qualifiers
REGION                   1..380
                         note = Description of Artificial Sequence: Synthetic
                          polypeptide
MOD_RES                  1
                         note = Ala, Arg, Asn, Asp, Gln, Glu, Gly, His, Leu, Lys,
                          Met, Phe, Thr, Val, or not present
MOD_RES                  6
                         note = Phe, Trp, Tyr or Val
MOD_RES                  187
                         note = Arg, Ile or Lys
MOD_RES                  332
                         note = Ala, Cys, Ser or Val
source                   1..380
                         mol_type = protein
                         organism = synthetic construct
SEQUENCE: 91
XASLPXLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPXQRP IPSAFCFLSH DHGRTWARGH FVAQDTLECQ VAEVETGEQR VVTLNARSHL   240
RARVQAQSTN DGLDFQESQL VKKLVEPPPQ GCQGSVISFP SPRSGPGSPA QWLLYTHPTH   300
SWQRADLGAY LNPRPPAPEA WSEPVLLAKG SXAYSDLQSM GTGPDGSPLF GCLYEANDYE   360
EIVFLMFTLK QAFPAEYLPQ                                               380
```

```
SEQ ID NO: 92            moltype = AA  length = 617
FEATURE                  Location/Qualifiers
REGION                   1..617
                         note = Description of Artificial Sequence: Synthetic
                          polypeptide
MOD_RES                  1
                         note = Ala, Arg, Asn, Asp, Gln, Glu, Gly, His, Leu, Lys,
                          Met, Phe, Thr, Val, or not present
MOD_RES                  6
                         note = Phe, Trp, Tyr or Val
MOD_RES                  187
                         note = Arg, Ile or Lys
MOD_RES                  332
                         note = Ala, Cys, Ser or Val
source                   1..617
                         mol_type = protein
                         organism = synthetic construct
SEQUENCE: 92
XASLPXLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN   120
VTRLCQVTST DHGRTWSSPR DLTDAAIGPA YREWSTFAVG PGHCLQLHDR ARSLVVPAYA   180
YRKLHPXQRP IPSAFCFLSH DHGRTWARGH FVAQDTLECQ VAEVETGEQR VVTLNARSHL   240
RARVQAQSTN DGLDFQESQL VKKLVEPPPQ GCQGSVISFP SPRSGPGSPA QWLLYTHPTH   300
SWQRADLGAY LNPRPPAPEA WSEPVLLAKG SXAYSDLQSM GTGPDGSPLF GCLYEANDYE   360
EIVFLMFTLK QAFPAEYLPQ GGGGSGGGGS DKTHTCPPCP APELLGGPSV FLFPPKPKDT   420
LMISRTPEVT CVVVDVSHED PEVKFNWYVD GVEVHNAKTK PREEQYNSTY RVVSVLTVLH   480
QDWLNGKEYK CKVSNKALPA PIEKTISKAK GQPREPQVYT LPPSREEMTK NQVSLTCLVK   540
GFYPSDIAVE WESNGQPENN YKTTPPVLDS DGSFFLTSKL TVDKSRWQQG NVFSCSVMHE   600
ALHNHYTQKS LSLSPGK                                                  617
```

```
SEQ ID NO: 93            moltype = AA  length = 874
FEATURE                  Location/Qualifiers
REGION                   1..874
                         note = Description of Artificial Sequence: Synthetic
                          polypeptide
MOD_RES                  1
                         note = Ala, Arg, Asn, Asp, Gln, Glu, Gly, His, Leu, Lys,
                          Met, Phe, Thr, Val, or not present
MOD_RES                  6
                         note = Phe, Trp, Tyr or Val
MOD_RES                  187
                         note = Arg, Ile or Lys
MOD_RES                  332
```

```
                        note = Ala, Cys, Ser or Val
source                  1..874
                        mol_type = protein
                        organism = synthetic construct
SEQUENCE: 93
XASLPXLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLCQVTST DHGRTWSSPR DLTDAAIGPA YREWSTFAVG PGHCLQLHDR ARSLVVPAYA  180
YRKLHPXQRP IPSAFCFLSH DHGRTWARGH FVAQDTLECQ VAEVETGEQR VVTLNARSHL  240
RARVQAQSTN DGLDFQESQL VKKLVEPPPQ GCQGSVISFP SPRSGPGSPA QWLLYTHPTH  300
SWQRADLGAY LNPRPPAPEA WSEPVLLAKG SXAYSDLQSM GTGPDGSPLF GCLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                             874

SEQ ID NO: 94            moltype = AA  length = 216
FEATURE                  Location/Qualifiers
REGION                   1..216
                         note = Description of Artificial Sequence: Synthetic
                          polypeptide
source                   1..216
                         mol_type = protein
                         organism = synthetic construct
SEQUENCE: 94
ELVLTQPASV SGSPGQSITI SCTGTSSDVG GYNYVSWYQQ HPGKAPKLMI YDVSKRPSGV   60
SNRFSGSKSG NTASLTISGL QAEDEADYYC SSYTSSSTLV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 95            moltype = DNA  length = 648
FEATURE                  Location/Qualifiers
misc_feature             1..648
                         note = Description of Artificial Sequence: Synthetic
                          polynucleotide
source                   1..648
                         mol_type = other DNA
                         organism = synthetic construct
SEQUENCE: 95
gagctcgtgt tgactcagcc tgcctccgtg tctgggtctc ctggacagtc gatcaccatc   60
tcctgcactg gaaccagcag tgacgttggt ggttataact atgtctcctg gtaccaacag  120
cacccaggca aagcccccaa actcatgatt tatgatgtca gtaagcggcc ctcaggggtt  180
tctaatcgct tctctggctc caagtctggc aacacggcct ccctgaccat ctctgggctc  240
caggctgagg acgaggctga ttattactgc agctcatata caagcagcag cactttggta  300
ttcggcggag ggaccaagct gaccgtccta ggtcagccca aggcggcgcc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca caagtacgc ggccagcagc  540
tacctgagcc tgacgcctga gcagtggaag tcccacagaa gctacagctg ccaggtcacg  600
catgaaggga gcaccgtgga agacagtg gcccctacag aatgttca                 648

SEQ ID NO: 96            moltype = AA  length = 450
FEATURE                  Location/Qualifiers
REGION                   1..450
                         note = Description of Artificial Sequence: Synthetic
                          polypeptide
source                   1..450
                         mol_type = protein
                         organism = synthetic construct
SEQUENCE: 96
EVQLLESGGG LVQPGGSLRL SCTTSGFTFN TYAMSWVRQA PGKGLEWLSG INNNGRTAFY   60
ADSVKGRFTI SRDNSKNTLY LQINSLRADD TAVYFCAKDV RFIAVPGDSW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLYC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 97            moltype = DNA  length = 1350
FEATURE                  Location/Qualifiers
misc_feature             1..1350
                         note = Description of Artificial Sequence: Synthetic
                          polynucleotide
```

```
source                  1..1350
                        mol_type = other DNA
                        organism = synthetic construct
SEQUENCE: 97
gaggtgcagc tgctcgagtc aggggggaggc ttggtacagc cggggggggtc cctgagactc  60
tcctgtacaa cctctggatt caccttaac acgtatgcca tgagttgggt ccgccaggct  120
ccagggaagg ggctggaatg gctctcaggt attaataaca atggtcggac tgcattctac  180
gcagactccg tgaagggccg cttcaccatc tccagagaca actccaaaaa cacactttat  240
ctgcaaatta atagtctgag agcggacgac acggccgttt atttctgtgc gaaagatgtc  300
agatttatcg cagtgcctgg tgactcctgg ggccaggaa ccctggtcac cgtctcctca  360
gctagcacca agggcccatc cgtcttcccc ctggcaccct cctccaagag cacctctggg  420
ggcacagcgg ccctgggctg cctggtcaag gactacttcc ccgaaccggt gacggtgtcc  480
tggaactcag gcgctctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagaa agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag ggcagccccg agaaccacag gtctacaccc tgcccccatc ccgggaggag  1080
atgaccaaga accaggtcag cctgtactgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggtaaa                                   1350

SEQ ID NO: 98            moltype = DNA  length = 1854
FEATURE                 Location/Qualifiers
misc_feature            1..1854
                        note = Description of Artificial Sequence: Synthetic
                        polynucleotide
source                  1..1854
                        mol_type = other DNA
                        organism = synthetic construct
SEQUENCE: 98
gacgcctctt taccctattt acagaaggag agcgtctttc agtccggcgc tcacgcctat  60
aggatcccg ctttactgta tttacccggt cagcagtctt tactggcttt cgccgagcag  120
cgggcttcca agaaggacga gcacgctgag ctgatcgtgt tacgtagggg agactacgac  180
gcccccaccc atcaagttca atggcaagct caagaagtgg tggctcaagc tcggctcgat  240
ggccatcgga gcatgaaccc ttgtcccctc tacgacgccc aaaccggcac tttatttctg  300
ttcttcatcg ccatccccgg tcaagttacc gagcagcaac agctgcagac ccgggctaac  360
gtgacaaggc tgtgccaagt tacctccacc gaccacggaa ggacttggtc ctcccctcgt  420
gatctgaccg atgccgctat cggccccgct taccgggagt ggtccacctt tgccgtggga  480
cccggccatt gtctgcagct gcatgatagg gctcggtctt tagtggtgcc cgcttacgcc  540
taccggaagc tgcaccccaa gcagcggcct atcccctccg ctttttgttt tttaagccat  600
gaccatggtc gtacttgggc tcgtggccat tttgtggccc aagatacttt agagtgccaa  660
gttgccgagt tggagactgg tgagcagcgg gtggtgactt aaatgcccg gtcccattta  720
agggctaggg tgcaagccca gtccaccaac gacggactgg atttccaaga atcccagctg  780
gtgaagaagc tcgtcgaacc tccccccaa ggttgccaag gaagcgtgat ctccttccca  840
tcccctagga gcggaccgg ttccccgct cagtggctgc tctacaccca tcccacccat  900
tcttggcaga gggctgattt aggcgcctat ttaaaccctc gtcctcccgc tcccgaagct  960
tggagcgagc ccgtgctgct cgctaagggc agcgccgcct acagcgattt acagtccatg  1020
ggaaccggac ccgatggcag ccctctgttc ggctgtttat atgaggctaa cgactacgag  1080
gagatcgtgt ttctcatgtt cactttaaag caagcttttc ccgctgagta tctgcccaa  1140
ggtgaggcg gcagcggcgg cggcggctcc gacaaaactc acacatgccc accgtgccca  1200
gcacctgaac tcctgggggg accgtcagtc ttcctcttcc ccccaaaacc caaggacacc  1260
ctcatgatct cccggacccc tgaggtcaca tgcgtggtgg tggacgtgag ccacgaagac  1320
cctgaggtca agttcaactg gtacgtggac ggcgtggagg tgcataatgc caagacaaag  1380
ccgcgggagg agcagtacaa cagcacgtac cgtgtggtca gcgtcctcac cgtcctgcac  1440
caggactggc tgaatggcaa ggagtacaag tgcaaggtct ccaacaaagc cctcccagcc  1500
cccatcgaga aaaccatctc caaagccaaa gggcagcccc gagaaccaca ggtgtacacc  1560
ctgcccccat cccgggagga tgaccaagaa ccaggtcagc ctgacctg cctggtcaaa  1620
ggcttctatc ccagcgacat cgccgtggag tgggagagca atgggcagcc ggagaacaac  1680
tacaagacca cgcctcccgt gctggactcc gacggctcct tcttcctcac cagcaagctc  1740
accgtggaca agagcaggtg gcagcagggg aacgtcttct catgctccgt gatgcatgag  1800
gctctgcaca accactacac gcagaagagc ctctccctgt ctccgggtaa atga         1854

SEQ ID NO: 99            moltype = DNA  length = 2625
FEATURE                 Location/Qualifiers
misc_feature            1..2625
                        note = Description of Artificial Sequence: Synthetic
                        polynucleotide
source                  1..2625
                        mol_type = other DNA
                        organism = synthetic construct
SEQUENCE: 99
atggcctctt taccctattt acagaaggag agcgtctttc agtccggcgc tcacgcctat  60
```

```
aggatccccg ctttactgta tttacccggt cagcagtctt tactggcttt cgccgagcag   120
cgggcttcca agaaggacga gcacgctgag ctgatcgtgt tacgtagggg agactacgac   180
gcccccaccc atcaagttca atggcaagct caagaagtgg tggctcaagc tcggctcgat   240
ggccatcgga gcatgaaccc ttgtcccctc tacgacgccc aaaccggcac tttatttctg   300
ttcttcatcg ccatcccgg tcaagttacc gagcagcaac agctgcagac ccgggctaac   360
gtgacaaggc tgtgccaagt tacctccacc gaccacggaa ggacttggtc ctcccctcgt   420
gatctgaccg atgccgctat cggccccgct taccgggagt ggtccacctt tgccgtggga   480
cccggccatt gtctgcagct gcatgatagg gctcggtctt tagtggtgcc cgcttacgcc   540
taccggaagc tgcacccaa gcagcggcct atccccctccg ctttttgttt tttaagccat   600
gaccatggtc gtacttgggc tcgtggccat tttgtggccc aagatacttt agagtgccaa   660
gttgccgagg tggagactgg tgagcagcgg gtggtgactt aaatgcccg gtcccattta   720
agggctaggg tgcaagccca gtccaccaac gacggactgg atttccaaga atcccagctg   780
gtgaagaagc tcgtcgaacc tcccccccaa ggttgccaag gaagcgtgat ctccttcccc   840
tccctagga gcggaccgg ttcccccgct cagtggctgc tctacaccca tcccacccat   900
tcttggcaga gggctgattt aggcgcctat ttaaaccctc gtcctcccgc tcccgaagct   960
tggagcgagc ccgtgctgct cgctaagggc agctgcgcct acagcgattt acagtccatg   1020
ggaaccggac ccgatggcag ccctctgttc ggctgtttat atgaggctaa cgactacgag   1080
gagatcgtgt ttctcatgtt cactttaaag caagcttttc ccgctgagta tctgccccaa   1140
ggtggaggcg gcagcggcgg cggcggctcc gacaaaactc acacatgccc accgtgccca   1200
gcacctgaac tcctggggggg accgtcagtc ttcctcttcc ccccaaaacc caaggacacc   1260
ctcatgatct cccggacccc tgaggtcaca tgcgtggtgg tggacgtgag ccacgaagac   1320
cctgaggtca agttcaactg gtacgtggac ggcgtggaag tgcataatgc caagacaaag   1380
ccgcgggagg agcagtacaa cagcacgtac cgtgtggtca gcgtcctcac cgtcctgcac   1440
caggactggc tgaatggcaa ggagtacaag tgcaaggtct ccaacaaagc cctcccagcc   1500
cccatcgaga aaaccatctc caaagccaaa gggcagcccc gagaaccaca ggtgtacacc   1560
ctgcccccat cccgggagga gatgaccaag aaccaggtca gcctgacctg cctggtcaaa   1620
ggcttctatc ccagcgacat cgccgtggag tgggagagca atgggcagcc ggagaacaac   1680
tacaagacca cgcctcccgt gctggactcc gacggctcct tcttcctcta cagcaagctc   1740
accgtggaca gagcaggtg gcagcagggg aacgtcttct catgctccgt gatgcatgag   1800
gctctgcaca accactacac gcagaagagc ctctccctg ctccgggtaa aggaggtggc   1860
ggcagcggcg gcggaggcag cggaggagga ggcagcgagg tgcagctggt ggagtccgga   1920
ggaggactgg tgcagcccgg aggatcttta aggctgagct gtgccgccag cggcttcaac   1980
atcaaggaca cctacatcca ctgggtgagg caagctcccg gcaaaggact cgagtgggtg   2040
gctcgtatct accccaccaa cggctatact cgttacgccg atccgtcaa gggtcgtttc   2100
accatttccg ccgacacctc caagaacacc gcctatttac agatgaattc tttacgggcc   2160
gaagacacag ctgtctacta ctgctcccgg tggggcggag acggattcta cgccatggac   2220
tactggggac aaggtacact ggtgacagtg tccagcggcg gaggaggatc tggcggcggc   2280
ggaagcggcg gtggcggtag cgatatccag atgacccaga gcccttcctc tttaagcgct   2340
tccgtgcaca tcgtgtcac catcacttgt agggcctccc aagatgtgaa caccgctgtg   2400
gcttggtacc agcagaagcc cggcaaggct cccaagctgc tgatctactc cgccagcttt   2460
ctgtattccg gagtgccttc tcgtttcagc ggctctcgta gcggcaccga cttcacttta   2520
accatcagct ctttacagcc cgaggacttc gccacctact actgccagca gcattacacc   2580
acacccccca ccttcggaca aggtaccaaa gtggagatca agtga   2625
```

SEQ ID NO: 100              moltype = AA   length = 380
FEATURE                    Location/Qualifiers
REGION                     1..380
                           note = Description of Artificial Sequence: Synthetic
                            polypeptide
MOD_RES                    1
                           note = Ala, Arg, Asn, Asp, Gln, Glu, Gly, His, Leu, Lys,
                            Met, Phe, Thr, Val, or not present
MOD_RES                    2
                           note = Ala or Lys
MOD_RES                    4
                           note = Asn or Leu
MOD_RES                    6
                           note = Phe, Trp, Tyr or Val
MOD_RES                    125
                           note = Ala, Cys, Ile, Ser or Val
MOD_RES                    187
                           note = Arg, Ile or Lys
MOD_RES                    196
                           note = Ala, Cys, Leu or Val
MOD_RES                    257
                           note = Glu or Lys
MOD_RES                    272
                           note = Cys or Val
MOD_RES                    325
                           note = Lys or Val
MOD_RES                    332
                           note = Ala, Cys, Ser or Val
MOD_RES                    352
                           note = Cys, Leu or Val
source                     1..380
                           mol_type = protein
                           organism = synthetic construct
SEQUENCE: 100
XXSXPXLQKE SVFQSGAHAY RIPALLYLPG QQSLLAFAEQ RASKKDEHAE LIVLRRGDYD   60

```
APTHQVQWQA QEVVAQARLD GHRSMNPCPL YDAQTGTLFL FFIAIPGQVT EQQQLQTRAN  120
VTRLXQVTST DHGRTWSSPR DLTDAAIGPA YREWSTFAVG PGHCLQLHDR ARSLVVPAYA  180
YRKLHPXQRP IPSAFXFLSH DHGRTWARGH FVAQDTLECQ VAEVETGEQR VVTLNARSHL  240
RARVQAQSTN DGLDFQXSQL VKKLVEPPPQ GXQGSVISFP SPRSGPGSPA QWLLYTHPTH  300
SWQRADLGAY LNPRPPAPEA WSEPXLLAKG SXAYSDLQSM GTGPDGSPLF GXLYEANDYE  360
EIVFLMFTLK QAFPAEYLPQ                                            380

SEQ ID NO: 101            moltype = AA  length = 617
FEATURE                   Location/Qualifiers
REGION                    1..617
                          note = Description of Artificial Sequence: Synthetic
                           polypeptide
MOD_RES                   1
                          note = Ala, Arg, Asn, Asp, Gln, Glu, Gly, His, Leu, Lys,
                           Met, Phe, Thr, Val, or not present
MOD_RES                   2
                          note = Ala or Lys
MOD_RES                   4
                          note = Asn or Leu
MOD_RES                   6
                          note = Phe, Trp, Tyr or Val
MOD_RES                   125
                          note = Ala, Cys, Ile, Ser or Val
MOD_RES                   187
                          note = Arg, Ile or Lys
MOD_RES                   196
                          note = Ala, Cys, Leu or Val
MOD_RES                   257
                          note = Glu or Lys
MOD_RES                   272
                          note = Cys or Val
MOD_RES                   325
                          note = Lys or Val
MOD_RES                   332
                          note = Ala, Cys, Ser or Val
MOD_RES                   352
                          note = Cys, Leu or Val
source                    1..617
                          mol_type = protein
                          organism = synthetic construct
SEQUENCE: 101
XXSXPXLQKE SVFQSGAHAY RIPALLYLPG QQSLLAFAEQ RASKKDEHAE LIVLRRGDYD  60
APTHQVQWQA QEVVAQARLD GHRSMNPCPL YDAQTGTLFL FFIAIPGQVT EQQQLQTRAN  120
VTRLXQVTST DHGRTWSSPR DLTDAAIGPA YREWSTFAVG PGHCLQLHDR ARSLVVPAYA  180
YRKLHPXQRP IPSAFXFLSH DHGRTWARGH FVAQDTLECQ VAEVETGEQR VVTLNARSHL  240
RARVQAQSTN DGLDFQXSQL VKKLVEPPPQ GXQGSVISFP SPRSGPGSPA QWLLYTHPTH  300
SWQRADLGAY LNPRPPAPEA WSEPXLLAKG SXAYSDLQSM GTGPDGSPLF GXLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLTSKL TVDKSRWQQG NVFSCSVMHE  600
ALHNHYTQKS LSLSPGK                                               617

SEQ ID NO: 102            moltype = AA  length = 874
FEATURE                   Location/Qualifiers
REGION                    1..874
                          note = Description of Artificial Sequence: Synthetic
                           polypeptide
MOD_RES                   1
                          note = Ala, Arg, Asn, Asp, Gln, Glu, Gly, His, Leu, Lys,
                           Met, Phe, Thr, Val, or not present
MOD_RES                   2
                          note = Ala or Lys
MOD_RES                   4
                          note = Asn or Leu
MOD_RES                   6
                          note = Phe, Trp, Tyr or Val
MOD_RES                   125
                          note = Ala, Cys, Ile, Ser or Val
MOD_RES                   187
                          note = Arg, Ile or Lys
MOD_RES                   196
                          note = Ala, Cys, Leu or Val
MOD_RES                   257
                          note = Glu or Lys
MOD_RES                   272
                          note = Cys or Val
MOD_RES                   325
                          note = Lys or Val
```

```
MOD_RES              332
                     note = Ala, Cys, Ser or Val
MOD_RES              352
                     note = Cys, Leu or Val
source               1..874
                     mol_type = protein
                     organism = synthetic construct
SEQUENCE: 102
XXSXPXLQKE SVFQSGAHAY RIPALLYLPG QQSLLAFAEQ RASKKDEHAE LIVLRRGDYD   60
APTHQVQWQA QEVVAQARLD GHRSMNPCPL YDAQTGTLFL FFIAIPGQVT EQQQLQTRAN  120
VTRLXQVTST DHGRTWSSPR DLTDAAIGPA YREWSTFAVG PGHCLQLHDR ARSLVVPAYA  180
YRKLHPXQRP IPSAFXFLSH DHGRTWARGH FVAQDTLECQ VAEVETGEQR VVTLNARSHL  240
RARVQAQSTN DGLDFQXSQL VKKLVEPPPQ GXQGSVISFP SPRSGPGSPA QWLLYTHPTH  300
SWQRADLGAY LNPRPPAPEA WSEPXLLAKG SXAYSDLQSM GTGPDGSPLF GXLYEANDYE  360
EIVFLMFTLK QAFPAEYLPQ GGGGSGGGGS DKTHTCPPCP APELLGGPSV FLFPPKPKDT  420
LMISRTPEVT CVVVDVSHED PEVKFNWYVD GVEVHNAKTK PREEQYNSTY RVVSVLTVLH  480
QDWLNGKEYK CKVSNKALPA PIEKTISKAK GQPREPQVYT LPPSREEMTK NQVSLTCLVK  540
GFYPSDIAVE WESNGQPENN YKTTPPVLDS DGSFFLYSKL TVDKSRWQQG NVFSCSVMHE  600
ALHNHYTQKS LSLSPGKGGG GSGGGGSGGG GSEVQLVESG GGLVQPGGSL RLSCAASGFN  660
IKDTYIHWVR QAPGKGLEWV ARIYPTNGYT RYADSVKGRF TISADTSKNT AYLQMNSLRA  720
EDTAVYYCSR WGGDGFYAMD YWGQGTLVTV SSGGGGSGGG GSGGGGSDIQ MTQSPSSLSA  780
SVGDRVTITC RASQDVNTAV AWYQQKPGKA PKLLIYSASF LYSGVPSRFS GSRSGTDFTL  840
TISSLQPEDF ATYYCQQHYT TPPTFGQGTK VEIK                              874

SEQ ID NO: 103       moltype = AA  length = 875
FEATURE              Location/Qualifiers
REGION               1..875
                     note = Description of Artificial Sequence: Synthetic
                     polypeptide
source               1..875
                     mol_type = protein
                     organism = synthetic construct
SEQUENCE: 103
TVEKSVVFKA EGEHFTDQKG NTIVGSGSGG TTKYFRIPAM CTTSKGTIVV FADARHNTAS   60
DQSFIDTAAA RSTDGGKTWN KKIAIYNDRV NSKLSRVMDP TCIVANIQGR ETILVMVGKW  120
NNNDKTWGAY RDKAPDTDWD LVLYKSTDDG VTFSKVETNI HDIVTKNGTI SAMLGGVGSG  180
LQLNDGKLVF PVQMVRTKNI TTVLNTSFIY STDGITWSLP SGYCEGFGSE NNIIEFNASL  240
VNNIRNSGLR RSFETKDFGK TWTEFPPMDK KVDNRNHGVQ GSTITIPSGN KLVAAHSSAQ  300
NKNNDYTRSD ISLYAHNLYS GEVKLIDDFY PKVGNASGAG YSCLSYRKNV DKETLYVVYE  360
ANGSIEFQDL SRHLPVIKSY NGGGGSGGGG SDKTHTCPPC PAPELLGGPS VFLFPPKPKD  420
TLMISRTPEV TCVVVDVSHE DPEVKFNWYV DGVEVHNAKT KPREEQYNST YRVVSVLTVL  480
HQDWLNGKEY KCKVSNKALP APIEKTISKA KGQPREPQVY TLPPSREEMT KNQVSLTCLV  540
KGFYPSDIAV EWESNGQPEN NYKTTPPVLD SDGSFFLYSK LTVDKSRWQQ GNVFSCSVMH  600
EALHNHYTQK SLSLSPGKGG GGSGGGGSGG GGSEVQLVES GGGLVQPGGS LRLSCAASGF  660
NIKDTYIHWV RQAPGKGLEW VARIYPTNGY TRYADSVKGR FTISADTSKN TAYLQMNSLR  720
AEDTAVYYCS RWGGDGFYAM DYWGQGTLVT VSSGGGGSGG GGSGGGGSDI QMTQSPSSLS  780
ASVGDRVTIT CRASQDVNTA VAWYQQKPGK APKLLIYSAS FLYSGVPSRF SGSRSGTDFT  840
LTISSLQPED FATYYCQQHY TTPPTFGQGT KVEIK                             875

SEQ ID NO: 104       moltype = DNA  length = 2625
FEATURE              Location/Qualifiers
misc_feature         1..2625
                     note = Description of Artificial Sequence: Synthetic
                     polynucleotide
source               1..2625
                     mol_type = other DNA
                     organism = synthetic construct
SEQUENCE: 104
acagtggaaa agtccgtggt gttcaaggcc gagggcgagc acttcaccga ccagaaaggc   60
aataccatcg tcggctctgg cagcggcggc accaccaagt actttagaat ccccgccatg  120
tgcaccacca gcaagggcac cattgtggtt ttcgccgacg ccagacacaa caccgccagc  180
gatcagagct tcatcgatac cgctgccgcc agatctaccg atggcggcaa gacctggaac  240
aagaagatcg ccatctacaa cgaccgcgtg aacagcaagc tgagcagagt gatggaccct  300
acctgcatcg tggccaacat ccagggcaga gaaaccctc tggtcatggt cggaaagtgg  360
aacaacaacg ataagacctg gggcgcctac agagacaagg ccctgatac cgattgggac  420
ctcgtgctgt acaagagcac cgatgacggc gtgaccttca gcaaggtgga aacaaacatc  480
cacgacatcg tgaccaagaa cggcaccatc tctgccatgc tcgcggcgt tggatctggc  540
ctgcaactga tgatggcaa gctggtgttc cccgtgcaga tggtccgaac aaagaatatc  600
accaccgtgc tgaataccag cttcatctac agcaccgacg gcatcacatg gtccctgcct  660
agcggctact gtgaaggctt ggcagcgag aacaacatca tcgagttcaa cgccagcctg  720
gtcaacaaca tccggaacag cggcctgcgg agaagcttcg agacaaagga cttcggaaag  780
acgtggaccg agtttcctcc aatggacaag aaggtggaca accggaacca cggcgtgcag  840
ggcagcacaa tcacaatccc tagcggcaac aaactggtgg ccgctcactc tagcgcccag  900
aacaagaaca acgactacac cagaagcgac atcagcctgt acgctcacaa cctgtacagc  960
ggcgaagtga agctgatcga cgacttctac cccaaagtgg gcaatgccag cggagccggc 1020
tacagctgtc tgagctaccg aaaaatgtg gacaaagaaa ccctgtacgt ggtgtacgag 1080
gccaacggca gcatcgagtt tcaggacctg agcagacatc tgcccgtgat caagagctac 1140
aacggcggag tggaagtggg cggaggcgga tccgacaaaa ctcacacatg cccaccgtgc 1200
ccagcacctg aactcctggg gggaccgtca gtcttcctct tccccccaaa acccaaggac 1260
```

```
accctcatga tctcccggac ccctgaggtc acatgcgtgg tggtggacgt gagccacgaa   1320
gaccctgagg tcaagttcaa ctggtacgtg gacggcgtgg aggtgcataa tgccaagaca   1380
aagccgcggg aggagcagta caacagcacg taccgtgtgg tcagcgtcct caccgtcctg   1440
caccaggact ggctgaatgg caaggagtac aagtgcaagg tctccaacaa agccctccca   1500
gcccccatcg agaaaaccat ctccaaagcc aaagggcagc cccgagaacc acaggtctac   1560
accctgcccc catcccggga ggagatgacc aagaaccagg tcagcctgac ctgcctggtc   1620
aaaggcttct atcccagcga catcgccgtg gagtgggaga gcaatgggca gccggagaac   1680
aactacaaga ccacgcctcc cgtgctggac tccgacggct ccttcttcct ctatagcaag   1740
ctcaccgtgg acaagagcag gtggcagcag gggaacgtct tctcatgctc cgtgatgcat   1800
gaggctctgc acaaccacta cacgcagaag agcctctccc tgtctccggg taaaggaggc   1860
ggaggatctg gcggaggtgg aagtggcgga ggcggatctg aggtgcagct ggttgaatct   1920
ggcggaggac tggttcagcc tggcggatct ctgagactgt cttgtgccgc cagcggcttc   1980
aacatcaagg acacctacat ccactgggtc cgacaggccc ctggcaaagg acttgaatgg   2040
gtcgccagaa tctaccccac caacggctac accagatacg ccgactctgt gaagggcaga   2100
ttcaccatca gcgccgacac cagcaagaac accgcctacc tgcagatgaa cagcctgaga   2160
gccgaggaca ccgccgtgta ctactgttct agatggggag gcgacggctt ctacgccatg   2220
gattattggg gccagggcac cctggtcacc gtttcttctg cggaggagg atctggcgga   2280
ggcggaagtg gcggaggcgg atctgacatc cagatgacac agagccctag cagcctgtct   2340
gccagcgtgg gagacagagt gaccatcacc tgtagagcca gccaggacgt gaacacagcc   2400
gtggcttggt atcagcagaa gcctggcaag gcccctaagc tgctgatcta cagcgccagc   2460
tttctgtact ccggcgtgcc cagcagattc agcggctcta gaagcggcac cgacttcacc   2520
ctgaccataa gcagtctgca gcccgaggac ttcgccacct actactgtca gcagcactac   2580
accacacctc caacctttgg ccagggcacc aaggtggaaa tcaag         2625
```

SEQ ID NO: 105            moltype = AA   length = 10
FEATURE                   Location/Qualifiers
REGION                    1..10
                          note = Description of Artificial Sequence: Synthetic 10xHis
                          tag
source                    1..10
                          mol_type = protein
                          organism = synthetic construct
SEQUENCE: 105
HHHHHHHHHH                                                                10

SEQ ID NO: 106            moltype = AA   length = 15
FEATURE                   Location/Qualifiers
REGION                    1..15
                          note = Description of Artificial Sequence: Synthetic peptide
REGION                    1..15
                          note = MISC_FEATURE - This sequence may encompass 1-5 "Gly
                          Gly Pro" repeating units
source                    1..15
                          mol_type = protein
                          organism = synthetic construct
SEQUENCE: 106
GGPGGPGGPG GPGGP                                                          15

SEQ ID NO: 107            moltype = AA   length = 25
FEATURE                   Location/Qualifiers
REGION                    1..25
                          note = Description of Artificial Sequence: Synthetic peptide
REGION                    1..25
                          note = MISC_FEATURE - This sequence may encompass 1-5 "Gly
                          Gly Gly Gly Ser" repeating units
source                    1..25
                          mol_type = protein
                          organism = synthetic construct
SEQUENCE: 107
GGGGSGGGGS GGGGSGGGGS GGGGS                                               25

SEQ ID NO: 108            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 108
GGGGSGGGGS                                                                10

-continued

```
SEQ ID NO: 109      moltype = AA  length = 6
FEATURE             Location/Qualifiers
REGION              1..6
                    note = Description of Artificial Sequence: Synthetic 6xHis
                     tag
source              1..6
                    mol_type = protein
                    organism = synthetic construct
SEQUENCE: 109
HHHHHH                                                               6
```

What is claimed is:

1. A recombinant mutant human sialidase enzyme comprising an amino acid sequence having at least 90% sequence identity to SEQ ID NO: 1; a substitution of the methionine residue at position 1 of SEQ ID NO: 1; and sialidase enzymatic activity.

2. The recombinant mutant human sialidase enzyme of claim 1, wherein the methionine residue at position 1 is substituted by arginine (M1R), histidine (M1H), lysine (M1K), aspartic acid (M1D), threonine (M1T), asparagine (M1N), glutamine (M1Q), glycine (M1G), alanine (M1A), valine (M1V), leucine (M1L), phenylalanine (M1F), or tyrosine (M1Y).

3. The recombinant mutant human sialidase enzyme of claim 2, wherein the methionine residue at position 1 is substituted by histidine (M1H).

4. The recombinant mutant human sialidase enzyme of claim 2, wherein the methionine residue at position 1 is substituted by leucine (M1L).

5. The recombinant mutant human sialidase enzyme of claim 2, wherein the methionine residue at position 1 is substituted by phenylalanine (M1F).

6. The recombinant mutant human sialidase enzyme of claim 2, wherein the methionine residue at position 1 is substituted by asparagine (M1N).

7. The recombinant mutant human sialidase enzyme of claim 2, wherein the methionine residue at position 1 is substituted by alanine (M1A).

8. The recombinant mutant human sialidase enzyme of claim 2, wherein the methionine residue at position 1 is substituted by threonine (M1T).

9. The recombinant mutant human sialidase enzyme of claim 1, further comprising one or more of (a) a substitution of the valine residue at position 6 of SEQ ID NO: 1; (b) a substitution of the isoleucine residue at position 187 of SEQ ID NO: 1 with a lysine (I187K); and (c) a substitution of the cysteine residue at position 332 of SEQ ID NO: 1.

10. The recombinant mutant human sialidase enzyme of claim 9, wherein the valine residue at position 6 is substituted by tyrosine (V6Y) and/or the cysteine residue at position 332 is substituted by alanine (C332A).

11. A fusion protein comprising:
(a) the recombinant mutant human sialidase enzyme of claim 1; and (b) an immunoglobulin Fc domain and/or an immunoglobulin antigen-binding domain;
wherein the recombinant mutant human sialidase enzyme and the immunoglobulin Fc domain and/or the immunoglobulin antigen-binding domain are linked by a peptide bond or an amino acid linker.

12. An antibody conjugate comprising the fusion protein of claim 11.

13. The antibody conjugate of claim 12, wherein the antibody conjugate comprises:
(a) a first polypeptide comprising an immunoglobulin light chain;
(b) a second polypeptide comprising an immunoglobulin heavy chain; and
(c) a third polypeptide comprising the immunoglobulin Fc domain and the recombinant mutant human sialidase enzyme;
wherein the first and second polypeptides are covalently linked together and the second and third polypeptides are linked together, and wherein the first polypeptide and the second polypeptide together define the immunoglobulin antigen-binding domain.

14. An isolated nucleic acid comprising a nucleotide sequence encoding the recombinant mutant human sialidase enzyme of claim 1.

15. An expression vector comprising the nucleic acid of claim 14.

16. A host cell comprising the expression vector of claim 15.

17. A pharmaceutical composition comprising the recombinant mutant human sialidase enzyme of claim 1.

18. A method of treating cancer in a subject in need thereof, the method comprising administering to the subject an effective amount of the recombinant mutant human sialidase enzyme of claim 1.

19. A method of treating cancer in a subject in need thereof, the method comprising administering to the subject an effective amount of the antibody conjugate of claim 13.

20. A method of increasing expression of HLA-DR, CD86, CD83, IFNγ, IL-1b, IL-6, TNFα, IL-17A, IL-2, or IL-6 in a cell or tissue, the method comprising contacting the cell or tissue with an effective amount of the recombinant mutant human sialidase enzyme of claim 1.

* * * * *